US007799523B2

(12) United States Patent
Paeper et al.

(10) Patent No.: US 7,799,523 B2

(45) Date of Patent: Sep. 21, 2010

(54) **ASSOCIATION OF POLYMORPHISMS IN THE *SOST* GENE REGION WITH BONE MINERAL DENSITY**

(75) Inventors: Bryan W. Paeper, Seattle, WA (US); Sean Proll, Seattle, WA (US); Patrick R. Charmley, Seattle, WA (US); Mary E. Brunkow, Seattle, WA (US); Andreas Gerardus Uitterlinden, Poortugaal (NL)

(73) Assignee: Celltech R & D, Inc., Bothell, WA (US)

( * ) Notice: Subject to any disclaimer, the term of this patent is extended or adjusted under 35 U.S.C. 154(b) by 782 days.

(21) Appl. No.: 10/408,168

(22) Filed: Apr. 3, 2003

(65) Prior Publication Data

US 2003/0235847 A1 Dec. 25, 2003

Related U.S. Application Data

(60) Provisional application No. 60/370,088, filed on Apr. 3, 2002.

(51) Int. Cl.

*C12Q 1/68* (2006.01)
*C12P 19/34* (2006.01)
*C07H 21/02* (2006.01)
*C07H 21/04* (2006.01)

(52) U.S. Cl. ........................ 435/6; 435/91.1; 435/91.2; 536/23.1; 536/24.3

(58) Field of Classification Search ...................... None
See application file for complete search history.

(56) References Cited

U.S. PATENT DOCUMENTS 4,331,647 A 5/1982 Goldenberg (Continued)

FOREIGN PATENT DOCUMENTS

JP 4-141095 5/1992

(Continued)

OTHER PUBLICATIONS

GenBank accession No. ACO55813.7, Jul. 11, 2001, available 1997.*

(Continued)

*Primary Examiner*—Jehanne S Sitton
(74) *Attorney, Agent, or Firm*—Marshall, Gerstein & Borun LLP

(57) ABSTRACT

Compositions and methods are provided for determining in a subject a risk for having, or presence of, altered bone mineral density such as osteoporosis or osteopenia or other conditions characterized by decreased or increased bone density. Specifically, the invention relates to determination of a sclerostin gene region nucleotide polymorphism (SRP) in DNA of the sclerostin gene region of human chromosome 17. In certain embodiments, SRPs that indicate an increased risk for altered bone mineral density occur as gender-associated polymorphisms. Isolated polynucleotides comprising representative SRPs are also provided.

9 Claims, 1 Drawing Sheet

U.S. PATENT DOCUMENTS

Figure 1:
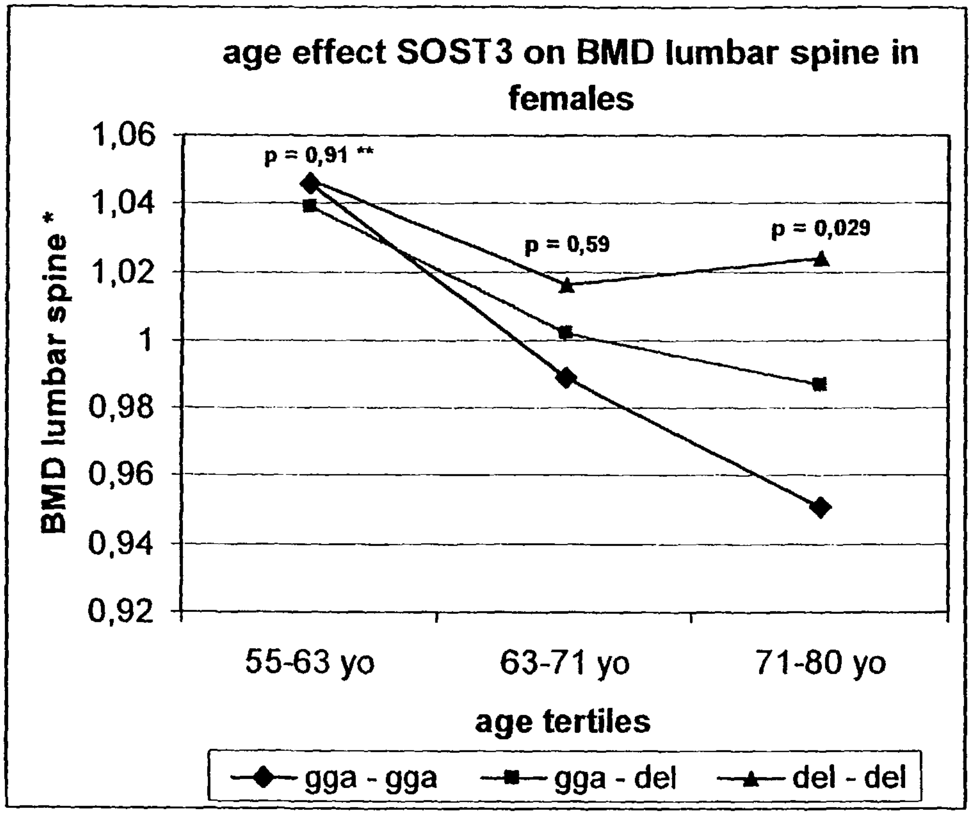

| | | | |
|---|---|---|---|
| 4,376,110 A | 3/1983 | Davis et al. | |
| 4,411,993 A | 10/1983 | Gillis | |
| 4,427,115 A | 1/1984 | Laipply | |
| 4,543,439 A | 9/1985 | Frackelton, Jr. et al. | |
| RE32,011 E | 10/1985 | Zimmerman et al. | |
| 4,837,440 A | 6/1989 | Burtscher et al. | |
| 4,902,614 A | 2/1990 | Wakabayashi et al. | |
| 5,070,108 A | 12/1991 | Margolis | |
| 5,145,684 A | 9/1992 | Liversidge et al. | |
| 5,223,409 A | 6/1993 | Ladner et al. | |
| 5,399,363 A | 3/1995 | Liversidge et al. | |
| 5,453,492 A | 9/1995 | Butzow et al. | |
| 5,466,468 A | 11/1995 | Schneider et al. | |
| 5,543,158 A | 8/1996 | Gref et al. | |
| 5,552,157 A | 9/1996 | Yagi et al. | |
| 5,565,213 A | 10/1996 | Nakamori et al. | |
| 5,567,434 A | 10/1996 | Szoka, Jr. | |
| 5,627,052 A | 5/1997 | Schrader et al. | |
| 5,641,515 A | 6/1997 | Ramtoola et al. | |
| 5,698,426 A | 12/1997 | Huse | |
| 5,738,868 A | 4/1998 | Shinkarenko et al. | |
| 5,780,263 A | 7/1998 | Hastings et al. | |
| 5,795,587 A | 8/1998 | Gao et al. | |
| 5,811,238 A | 9/1998 | Stemmer et al. | |
| 5,830,721 A | 11/1998 | Stemmer et al. | |
| 5,837,458 A | 11/1998 | Minshull et al. | |
| 5,877,397 A | 3/1999 | Lonberg et al. | |
| 5,968,747 A * | 10/1999 | Hillman et al. | 435/6 |
| 6,054,561 A | 4/2000 | Ring | |
| 6,057,421 A | 5/2000 | Muller et al. | |
| 6,077,673 A * | 6/2000 | Chenchik et al. | 435/6 |
| 6,117,911 A | 9/2000 | Grainger et al. | |
| 6,133,426 A | 10/2000 | Gonzalez et al. | |
| 6,180,370 B1 | 1/2001 | Queen et al. | |
| 6,207,153 B1 | 3/2001 | Dan et al. | |
| 6,395,511 B1 | 5/2002 | Brunkow et al. | |
| 6,489,445 B1 | 12/2002 | Brunkow et al. | 530/350 |
| 6,495,736 B1 | 12/2002 | Galas et al. | 800/18 |
| 6,703,199 B1 | 3/2004 | Koide | |
| 6,803,453 B1 | 10/2004 | Brunkow et al. | |
| 6,806,055 B2 | 10/2004 | Berman et al. | |
| 6,815,201 B2 | 11/2004 | Pinter | |
| 6,818,748 B2 | 11/2004 | Fulton et al. | |
| 7,192,583 B2 | 3/2007 | Brunkow et al. | |
| 2003/0165410 A1 | 9/2003 | Taylor | |
| 2003/0186915 A1 | 10/2003 | Pan et al. | |
| 2004/0009535 A1 | 1/2004 | Brunkow et al. | |
| 2004/0058321 A1 | 3/2004 | Brunkow et al. | |
| 2004/0141875 A1 | 7/2004 | Doshi | |
| 2004/0146888 A1 | 7/2004 | Paszty et al. | |
| 2004/0158045 A1 | 8/2004 | Brunkow et al. | |
| 2005/0106683 A1 | 5/2005 | Winkler et al. | |
| 2005/0228172 A9 * | 10/2005 | Wang | 536/24.3 |
| 2005/0238646 A1 | 10/2005 | Ledbetter et al. | |
| 2006/0233801 A1 | 10/2006 | Brunkow et al. | |
| 2007/0110747 A1 | 5/2007 | Paszty et al. | |

FOREIGN PATENT DOCUMENTS

| | | |
|---|---|---|
| WO | WO 91/13152 | 9/1991 |
| WO | WO-92/02551 | 2/1992 |
| WO | WO 92/06693 | 4/1992 |
| WO | WO-95/30003 | 11/1995 |
| WO | WO-98/21335 | 5/1998 |
| WO | WO-99/03996 | 1/1999 |
| WO | WO 99/06554 A2 | 2/1999 |
| WO | WO-99/15556 | 4/1999 |
| WO | WO-00/32773 | 6/2000 |
| WO | WO 00/61720 * | 10/2000 |
| WO | WO-00/75317 | 12/2000 |
| WO | WO-01/64885 | 9/2001 |
| WO | WO-01/92308 | 12/2001 |
| WO | WO 01/98491 A2 * | 12/2001 |
| WO | WO-03/106657 | 12/2003 |
| WO | WO-2005/003158 | 1/2005 |
| WO | WO-2005/014650 | 2/2005 |

OTHER PUBLICATIONS

GenBank accession No. AC073954.3, Nov. 17, 2000.*
GenBank accession No. AF326736.1, Feb. 28, 2001.*
GenBank accession No. AC003098.1, Jan. 29, 1998.*
Result #2 of SEQ ID No. 9 in GenEmbl.*
Result #4 of SEQ ID No. 9 in GenEmbl.*
Result #6 of SEQ ID No. 1 in Published patents database.*
Result #1 of SEQ ID No. 1 in GenEmbl database.*
Result # 4 of SEQ ID No. 1 in GenEmbl database.*
Result #2 of SEQ ID No. 8 in GenEmbl database.*
Result #12 of SEQ ID No. 8 in GenEmbl database.*
email from Peter De Jong.*
Brunkow et al; Am. J. Hum. Genet. vol. 68, pp. 577-589; 2001.*
Annotated alignment of Genbank Accession No. AC003098 (1998) and nucleotides 10001-11100 of SEQ ID No. 1.*
Hegele ; Arterioscler. Thromb. Vasc. Biol.; 2002, vol. 22, pp. 1058-1061.*
Balemans et al; Bone; vol. 31, pp. 515-519; 2002.*
Lucentini (The Scientist; 2004, vol. 24, p. 20).*
Juppner (Bone, vol. 17; 39S-40S; 1995).*
Genbank Accession No. AA393768, Apr. 24, 1997.
Genbank Accession No. AA393939, May 19, 1997.
Genbank Accession No. AAB33865, May 27, 1995.
Genbank Accession No. BAA19765, Feb. 7, 1999.
Genbank Accession No. CAA88759, Jan. 8, 1997.
Genbank Accession No. D38082, Feb. 8, 1999.
Genbank Accession No. D79813, Feb. 9, 1996.
Genbank Accession No. D89675, Feb. 7, 1999.
Genbank Accession No. S75359, Jun. 20, 2000.
Genbank Accession No. U25110, Feb. 2, 1996.
Genbank Accession No. Z48923, Jan. 8, 1997.
Balemans et al., "Extracellular Regulation of BMP Signaling in Vertebrates: A Cocktail of Modulators," Developmental Biology (2002), 250:231-250.
Bendayan, M., "Possibilities of False Immunocytochemical Results Generated by the Use of Monoclonal Antibodies: The Example of the Anti-proinsulin Antibody," J. of Histochem. Cytochem. (1995) 43(9): 881-886.
Berman et al., "The Protein Data Bank," Acta Cryst. (2002) 58(1):899-907.
Birren et al., EMBL Sequence Database, Accession No. AC003098, Nov. 14, 1997.
Bonaldo et al., "Normalizaton and Subtraction: Two Approaches to Facilitate Gene Discovery," Genome Res. (1996) 6(9):791-806.
Bonaldo et al. EMBL Sequence Database, Accession No. AI113131, Sep. 4, 1998.
Bost et al., "Antibodies Against a Peptide Sequence within the HIV Envelope Protein Crossreacts with Human Interleukin-2," Immunol. Invest. (1988)17(6&7):577-586.
Bradley et al., "Modifying The Mouse: Design and Desire," Bio/Technology (1992) 10:534-539.
Brunkow et al., "Bone Dysplasia Schlerosteois Results from Loss of the SOST Gene Product, a Novel Cysteine Knot-Containing Protein." Am. J. Hum. Genet. (2001) 68:577-589.
Campbell et al., "Totipotency or Multipotentiality of Cultured Cells: Applications and Progress," Theriogenology (1997) 47:63-72.
Colman, P., "Effects of Amino Acid Sequence Changes on Antibody-Antigen Interactions," Research in Immunology (1994) 145:33-36.
Durham et al., "Alterations in Insulin-Like Growth Factor (IGF)-Dependent IGF-Binding Protein-4 Proteolysis in Transformed Osteobla . . . ," Endocrinology (1995) 136(4):1374-1380.
Groppe et al., "Structural Basis of BMP Signalling Inhibition by the Cystine Knot Protein Noggin," Nature (2002) 420:636-642.
Harlow et. al., "Antibodies: A Laboratory Manual," (1988) pp. 141-157, Cold Spring Harbor Laboratory, Cold Spring Harbor, NY.

Hart et al., "Crystal Structure of the Human TBR2 Ectodomain-TGF-B3 Complex," Nat. Struc. Biol. (2002) 9(3):203-208.
Hay et al., "ATCC Cell Lines and Hybridomas," American Type Culture Collection 8th ed., (1994) pp. 149, 258 and 428, Rockville, MD.
Hoffman et al., "BMP Signaling Pathways in Cartilage and Bone Formation," Critical Review in Eukaryotic Gene Expression (2001) 11(1-3):23-45.
Lian et al., "Bone Formation: Osteoblast Lineage Cells, Growth Factors, Matrix Proteins, and the Mineralization Process," Primer on the Metabolic Bone Diseases and Disorders of Mineral Metabolism, $4^{th}$ Edition (1999) 14-29.
Hsu et al., "The Xenopus Dorsalizing Factor Gremlin IDentifies a Novel Family of Secreted Proteins that Antagonize BMP Activities," Molecular Cell (1998) 1:673-683.
Iemura et al., "Direct Binding of follistatin to a complex of bone-morphogenetic protein and its receptor inhibits ventral and epidermal cell fates in early Xenopus embryo," Proc. Natl. Acad. Sci. USA (1998) 95:9337-9342.
Innis et al, "Evolutionary Trace Analysis of TGF-B and Related Growth Factors: Implications for Stie-Directed Mutagenesis," Protein Engineering (2000)13(12):839-847.
Kawabata et al., "Signal Transduction by Bone Morphogenetic Proteins," Cytokine and Growth Factor Reviews (1998) 9(1):49-61.
Khosla et al., "Concise Review for Primary-Care Physicians. Treatment Options for Osteoporosis," Mayo Clin. Proc. (1995) 70:978-982.
Miyazono et al., "TGF-B Signaling by Smad Proteins," Advances in Immunology (2000) 75:115-157.
Mullins et al., "Molecular Medicine in Genetically Engineered Animals," J. Clin. Invest (1996) 97(7):1557-1560.
Nickel et al., "The Crystal Structure of the BMP-2:BMPR:IA Complex and the Generation of BMP-2 An . . . ," J. of Bone and Joint Surgery 83-A (2001) [Suppl. 1 part 1]:S1-7-S1-14.
Nicolas et al., "An Age-Related Decrease in the Concentration of Insulin-Like Growth Factor Binding Protein-5 in Human Cortical Bone," Calcif. Tissue Int. (1995) 57:206-212.
Oshima et al., "Rapid Communication TGF-β Receptor Type II Deficiency Results in Defects of Yolk.Sac Hematopoiesis and Vasculogenesis," Developmental Biology (1996) 179:297-302.
Pittenger et al., "Multilineage Potential of Adult Human Mesenchymal Stem Cells," Science (1999) 284:143-147.
Pockwinse et al., "Expression of Cell Growth and Bone Specific Genes at Single Cell Resolution During Development of Bone Tissue-Like Organization in Primary Osteoblast Cultures," Journal of Cellular Biochemistry (1992) 49:310-323.
Reddi, A. Hari, "Interplay between bone morphogenetic proteins and cognate binding proteins in bone and cartilage development: noggin, chordin and DAN," Center for tissue Regeneration and Repair, Dept. of Ortho. Surgery, U.C. Davis, School of Medicine, Sacramento, CA (2000) (http://arthritis-research.com/content/3/1/001).
Riggs, "Overview of Osteoporosis," West J. Med. (1991) 154:63-77.
Sali et al., "Comparative Protein Modelling by Satisfaction of Spatial Restraints," J. Mol. Biol. (1993) 234(3):779-815.
Schmitt et al., "Bone Morphogenetic Proteins: An Update on Basic Biology and Clinical Relevance," Journal of Orthopaedic Research (1999) 17:269-278.
Scheufler et al. "Crystal Structure of Human Bone Morphogenetic Protein-2 at 2.7 Å Resolution," J. Mol. Biol. (1999) 287(1):103-115.
Schlunegger et al., "Refined Crystal Structure of Human Transforming Growth Factor β2 at 1.95 Å Resolution," J. Mol. Biol. (1993) 231(2):445-458.
Serra et al., "Expression of a Truncated, Kinase-Defective TGF-β Type II Receptor in Mouse Skeletal Tissue Promotes Terminal Chondroocyte Differentiation and Osteoarthritis," J Cell Biol. (1997) 139(2):541-552.
Sigmund, "Viewpoint: Are Studies in Genetically Altered Mice Out of Control?," Arterioscler. Thromb. Vasc. Biol. (2000) 20:1425-1429.
Smith, "TGF β Inhibitors: New and Unexpected Requirements in Vertebrate Development," TIG (1999) 15(1):3-5.
Wall, "Trangenic Livestock: Progress and Prospects for the Future," Theriogenology (1996) 45:57-68.
Zimmerman et al., "The Spemann Organizer Signal Noggin Binds and Inactives Bone Morphogenetic Protein 4," Cell (1996) 86(4):599-606.
Alting-Mees et al., "Monoclonal Antibody Expression Libraries: A Rapid Alternative to Hybridomas" *Strategies in Molecular Biology*, 3:1-9 (1990).
Alves et al., "Sclerosteosis: A Marker of Dutch Ancestry?" *Rev. Bras. Genet.*, 4:825-834 (1982).
Angal et al., "A Single Amino Acid Substitution Abolishes the Heterogeneity of Chimeric Mouse/Human (IgG4) Antibody," *Mol. Immunol.*, 30(1):105-108 (1993).
Avsian-Kretcher et al., "Comparative Genomic Analysis of the Eight-Membered Ring Cystine Knot-Containing Bone Morphogenetic Protein Antagonists," *Mol. Endo.*, 18(1):1-12 (2004).
Babcook et al., "A Novel Strategy for Generating Monoclonal Antibodies from Single, Isolated Lymphocytes Producing Antibodies of Defined Specificities," *Proc. Natl. Acad. Sci.* (*USA*), 93:7843-7848 (1996).
Baines et al., "Purification of Immunoglobulin G (IgG)," Methods in Molecular Biology, 10:79-104, The Humana Press, Inc. (1992).
Balemans et al., "Increased Bone Density in Sclerosteosis is due to the Deficiency of a Novel Secreted Protein (SOST)," *Hum. Mol. Genet.*, 10:537-543 (2001).
Beighton et al., "The Clinical Features of Sclerosteosis," *Annals of Internal Medicine*, 84:393-397 (1976).
Beighton et al., "The Syndromic Status of Sclerosteosis and van Buchem Disease," *Clinical Genetics*, 25:175-181 (1984).
Bird et al., "Single-Chain Antigen-Binding Proteins," *Science*, 242:423-426 (1988).
Black et al., "A Somatic Cell Hybrid Map of the Long Arm of Human Chromosome 17, Containing the Familial Breast Cancer Locus (BRCAI)," *Am. J. Hum. Genet.*, 52:702-710 (1993).
Boden et al., "Glucocorticoid-Induced Differentiation of Fetal Rat Calvarial Osteoblasts is Mediated by Bone Morphogenetic Protein-6," *Endocrinology*, 138(7):2820-2828 (1997).
Boerner et al., "Production of Antigen-Specific Human Monoclonal Antibodies from in Vitro-Primed Human Splenocytes," *J. Immunol.*, 147:86-95 (1991).
Bondestam, "Ligands & Signaling Components of the Transforming Growth Factor," Helsinki University Biomedical Dissertations (2002).
Bostrom et al., "Immunolocalization and Expression of Bone Morphogenetic Proteins 2 and 4 in Fracture Healing," *J. Orth. Res.*, 13:357-367 (1995).
Bowie et al., "A Method to Identify Protein Sequences that Fold into a Known Three-Dimensional Structure," *Science*, 253:164-170 (1991).
Bowie et al., "Deciphering the Message in Protein Sequences: Tolerance to Amino Acid Substitutions," *Science* 247:1306-1310 (1990).
Brenner et al., "Population Statistics of Protein Structures: Lessons from Structural Classifications," *Curr. Op. Struct. Biol.*, 7(3):369-376 (1997).
Brown, T., "Hybridization Analysis of DNA Blots," 2.10.1-2.10.16 (2000).
Bruggemann et al., "Production of Human Antibody Repertoires in Transgenic Mice," *Curr. Opin. Biotechnol.*, 8:455-458 (1997).
Burton et al., "Human Antibodies from Combinatorial Libraries," *Adv. Immunol.*, 57:191-280 (1994).
Byrne et al., "CD4+CD45RBHi T Cell Transfer Induced Colitis in Mice is Accompanied by Osteopenia which is Treatable with Recombinant Human Osteoprotegerin," *Gut*, 54:78-86 (2005).
Chandran et al.,"Recent Trends in Drug Delivery Systems: Liposomal Drug Delivery System—Preparation and Characterisation," *Indian J. Exp. Biol.*, 35(8):801-809 (1997).
Chou et al., "Empirical Predication of Protein Conformation," *Ann. Rev. Biochem.*, 47:251-276 (1979).
Chou et al., "Prediction of the Secondary Structure of Proteins from their Amino Acid Sequence," *Adv. Enzymol. Relat. Areas Mol. Biol.*, 47:45-148 (1978).
Clark, "Antibody Humanization: A Case of the 'Emperor's New Clothes'?," *Immunology Today*, 21(8):397-402 (2000).
Coleman, "A Structural View of Immune Recognition by Antibodies," *Research in Immunology*, 145:33-36 (1994).

Collins, "Identifying Human Disease Genes by Positional Cloning," *The Harvey Lectures*, Series 86:149-164 (1992).
Collins, "Positional Cloning Moves from Perditional to Traditional," *Nature Genetics*, 9:347-350 (1995).
Cook et al., "Structural Basis for a Functional Antagonist in the Transforming Growth Factor β Superfamily," *Biological Chemistry* 280(48):40177-40186 (2005).
Cormier, "Markers of Bone Metabolism," *Curr. Opin. in Rheu.*, 7:243 (1995).
Couvreur et al., "Polyalkylcyanoacrylates as Colloidal Drug Carriers," *Crit. Rev. Ther. Drug Carrier Syst.*, 5(1):1-20 (1988).
Crameri et al., "DNA Shuffling of a Family of Genes from Diverse Species Accelerates Directed Evolution," *Nature*, 391:288-291 (1998).
Dall'Acqua et al., "Antibody Humanization by Framework Shuffling," *Methods*, 36(1):43-60 (2005).
Ebara et al., "Mechanism for the Action of Bone Morphogenetic Proteins and Regulation of Their Activity," *Spine*, 27(165):S10-S15 (2002).
EMBL Accession No. AA393939, 2000.
EMBL Accession No. AI113131, 2000.
Epstein et al., "Endocrine Function in Sclerosteosis," *S. Afr. Med. J.*, 55:1105-1110 (1979).
Frost et al., "On the Rat Model of Human Osteopenias and Osteoporoses," *Bone and Mineral*, 18:227-236 (1992).
Fujiwara et al., "Accession No. D79813," *EMBL Sequence Database* (1996).
Gazzerro et al., "Bone Morphogenetic Proteins Induce the Expression of Noggin, Which Limits Their Activity in Cultured Rat Osteoblasts," *J. Clin. Invest.*, 102(12):2106-2114 (1998).
Genbank Accession No. NM_001203, 2008.
Genbank Accession No. NM_001204, 2007.
Genbank Accession No. NM_004329, 2007.
Genbank Accession No. NM_030849, 2006.
Genbank Accession No. NM_033346, 2005.
Genbank Accession No. NP_001194, 2008.
Geysen et al., "Cognitive Features of Continuous Antigenic Determinants," *Molecular Recognition* 1(1):32-41 (1988).
Gitelman et al., "Vgr-1/BMP-6 Induces Osteoblastic Differentiation of Pluripotential Mesenchymal Cells," *Cell Growth & Differentiation*, 6:827-836 (1995).
Glasky et al., "Stability of Specific Immunoglobulin Secretion by EBV-Transformed Lymphoblastoid Cells and Human-Murine Heterohybridomas," *Hybridoma*, 8:377-389 (1989).
Green et al., "Antigen-Specific Human Monoclonal Antibodies from Mice Engineered with Human Ig Heavy and Light Chain YACs," *Nature Genet.*, 7:13 (1994).
Greene et al., "Screening Recombinant DNA Libraries," *Current Protocols in Molecular Biology*, Ch. 6(1) (1990).
Gribskov et al., "Profile Analysis," *Meth. Enzym.*, 183:146-159 (1990).
Gribskov et al., "Profile Analysis: Detection of Distantly Related Proteins," *Proc. Nat. Acad. Sci.* (*USA*), 84(13):4355-4358 (1987).
Groeneveld et al., "Bone Morphogenetic Proteins in Human Bone Regeneration," *Eur. J. Endocrinol.*, 142:9-21 (2000).
Guinness-Hey, "Increased Trabecular Bone Mass in Rats Treated with Human Synthetic Parathyroid Hormone," *Metab. Bone Dis. Relat. Res.*, 5:177-181 (1984).
Harris, "Processing of C-Terminal Lysine and Arginine Residues of Proteins Isolated from Mammalian Cell Culture," *Journal of Chromatography*, 705:129-134 (1995).
Hill et al., "Multiple Extracellular Signals Promote Osteoblast Survival and Apoptosis," *Endocrinology*, 138(9):3849-3858 (1997).
Hillier et al., "WashU-Merck EST Project 1997," *EMBL Sequence Database*, AA393768.1 (1997).
Hillier et al., "WashU-Merck EST Project 1997," *EMBL Sequence Datatbase*, AA393939.1 (1997).
Hock et al., "Perspective: Osteoblast Apoptosis and Bone Turnover," *J. Bone Miner. Res.*, 16(6):975-984 (2001).
Hollinger et al., "Engineered Antibody Fragments and the Rise of Single Domains," *Nature Biotech.*, 23(9):1126-1136 (2005).
Holm et al., "Protein Folds and Families: Sequence and Structure Alignments," *Nucl. Acid Res.*, 27(1):244-247 (1999).
Hoogenboom et al., "By-Passing Immunisation: Human Antibodies from Synthetic Repertoires of Germline $V_H$ Gene Segmens Rearranged in Vitro," *J. Molec. Biol.*, 227:381-388 (1992).
Huse et al., "Generation of a Large Combinatorial Library of the Immunoglobulin Repertoire in Phage Lambda," *Science*, 246:1275-1281 (1989).
Hwang et al., "Use of Human Germline Genes in a CDR Homoloy-Based Approach to Antibody Humanization," *Methods*, 36(1):35-42 (2005).
Jakobovits et al., "Production of Antigen-Specific Human Antibodies from Mice Engineered with Human Heavy and Light Chain YACs[a]," *Ann. N.Y. Acad. Sci.*, 764:525-535 (1995).
Jee et al., "Overview: Animal Models of Osteopenia and Osteoporosis," *J. Musculoskel. Neuron. Interact.*, 1:193-207 (2001).
Jilka et al., "Increased Bone Formation by Prevention of Osteoblast Apoptosis with Parathyroid Hormone," *J. Clin. Invest.*, 104:439-446 (1999).
Jones, "Progress in Protein Structure Predication," *Curr. Opin. Struct. Biol.*, 7(3):377-387 (1997).
Kabat et al., "Sequences of Proteins of Immunological Interest," U.S. Department of Health and Human Services, NIH, USA (1987) (Table of Contents).
Kalu, The Ovariectomized Rat Model of Postmenopausal Bone Loss, *Bone and Mineral*, 15:175-192 (1991).
Kang et al., "Linkage of Recognition and Replication Functions by Assembling Combinatorial Antibody Fab Libraries Along Phage Surfaces," *Proc. Natl. Acad. Sci.* (*USA*), 88:4363-4366 (1991).
Katagiri et al., "The Non-Osteogenic Mouse Pluripotent Cell Line, C3H10T1/2, is Induced to Differentiate into Osteoblastic Cells by Recombinant Human Bone Morphogenetic Protein-2," *Biochem. Biophys. Res. Comm.*, 172(1):295-299 (1990).
Keller et al., "Molecular recognition of BMP-2 and BMP receptor IA," *Nature Structural & Molecular Biolody* 11(5):481-488 (2004).
Khalil, TGF-β: From Latent to Active, *Microbes and Infection*, 1(15):1255-1263 (1999).
Kohler et al., "Continuous Cultures of Fused Cells Secreting Antibody of Predefined Specificity," *Nature*, 256:495 (1975).
Koli et al., "Latency, Activation, and Binding Proteins of TGF-β,"*Microscopy Res. Tech.*, 52:354-362 (2001).
Koreth et al., "Microsatellites and PCR Genomic Analysis," *J. Pathology*, 178:239-248 (1996).
Kramer et al., "The Gapped Duplex DNA Approach to Oligonucleotide-Directed Mutation Construction," *Nucleic Acids Res.*, 12:9441 (1984).
Kunkel et al., "Rapid and Efficient Site-Specific Mutagenesis without Phenoypic Selection," *Methods in Enzymol.*, 154:367-382 (1987).
Kunkel, "Rapid and Efficient Site-Specific Mutagenesis without Phenotypic Selection," *Proc. Natl. Acad. Sci.* (*USA*), 82:488-492 (1985).
Kusu et al., "Sclerostin is a Novel Secreted Osteoclast-Dervied Bone Morphogenetic Protein Antagonist with Unique Ligand Specificity," *J. Biol. Chem.*, 278:24113-24117 (2003).
Lasic, "Novel Applications of Liposomes," *Trends Biotechnol.*, 16(7):307-321 (1998).
Latham, "The Biochemical and Cellular Characterization of Sclerostin, The Causative Gene for Sclerosteosis,"*Calcified Tissue International*, 70(4):244 (2002).
Liu et al., "Human Type II Receptor for Bone Morphogenic Proteins (BMPs): Extension of the Two-Kinase Receptor Model to the BMPs," *Molecular and Cellular Biology*, 15(7):3479-3486 (1995).
Lonberg et al., "Antigen-Specific Human Antibodies from Mice Comprising Four Distinct Genetic Modifications," *Nature*, 368:856 (1994).
Low et al., "Mimicking Somatic Hypermutation: Affinity Maturation of Antibodies Displayed on Bacteriophage using a Bacterial Mutator Strain," *J. Mol. Biol.*, 250:350-368 (1996).
Margalit, "Liposome-Mediated Drug Targeting in Topical and Regional Therapies," *Crit. Rev. Ther. Drug Carrier Syst.*, 12(2-3):233-261 (1995).
Marks et al., "By-Passing Immunization: Building High Affinity Human Antibodies by Chain Shuffling," *Bio/Technology*, 10:779-783 (1992).
Miyazono et al., "Divergence and Convergence of TGF-β/BMP Signaling," *J. Cell. Physiol.*, 187:265-276 (2001).

Moult, "The Current State of the Art in Protein Structure Predicion," *Curr. Opin. Biotech*., 7(4):422-427 (1996).
Nakase et al., "Transient and Localized Expression of Bone Morphogenetic Protein 4 Messenger RNA During Fracture Healing," *J. Bone Miner. Res*., 9(5):651-659 (1994).
Nelson, "Positional Cloning Reaches Maturity," *Current Opinion in Genetics and Development*, 5:298-303 (1995).
Nifuji et al., "Coordinated Expression of Noggin and Bone Morphogenetic Proteins (BMPs) During Early Skeletogenesi and Induction of Noggin Expression by BMP-7," *J. Bone Miner. Res*., 14(12):2057-2066 (1999).
Nisonoff et al., "Separation of Univalent Fragments from the Bivalent Rabbit Antidody Molecule by Reduction of Disulfide Bonds," *Arch. Biochem. Biophys*., 89:230-244 (1960).
Nygren et al., "Scaffolds for Engineering Novel Binding Sites in Proteins," *Curr. Opin. Struct. Biol*., 7:463-469 (1997).
Oelgeschlager et al., "The Evolutionarily Conserved BMP-Binding Protein Twisted Gastrulation Promotes BMP Signalling," *Nature*, 105:757-763 (2000).
Oreffo et al., "Human Bone Marrow Osteoprogenitors Express Estrogen Receptor-Alpha and Bone Morphogenetic Proteins 2 and 4 mRNA During Osteoblastic Differentiation," *J. Cell. Biochem*., 75:382-392 (1999).
Patten et al., "Applications of DNA Shuffling to Pharmaceuticals and Vaccines," *Curr. Opin. Biotechnol*., 8:724-733 (1997).
Piek et al., "Specificity, Diversity, and Regulation of TGF-β Superfamily Signaling," *FASEB J*., 13:2105-2124 (1999).
Pietromonaco et al., "Protein Kinase C-0 Phosphorylation of Moesin in the Actin-Binding Sequence," *J. Biol. Chem*., 273:7594-7603 (1998).
Pignatti et al., "Tracking Disease Genes by Reverse Genetics," *J. Psychiar. Res*., 26(4):287-298 (1992).
Pluckthun et al., "Expression of Functional Anitbody Fv and Fab Fragments in *Escherichia coli," Methods Enzymol*., 178:497-515 (1989).
Porter, "The Hydrolysis of Rabbit γ-Globulin and Antibodies with Crystalline Papain," *Biochem. J*., 73:119-126 (1959).
Quintanar-Guerrero et al., "Preparation Techniques and Mechanisms of Formation of Biodegradable Nanoparticles from Preformed Polymers," *Drug Dev. Ind. Pharm*., 24(12):1113-1128 (1998).
Rosenzweig et al., "Cloning and characterization of a human type II receptor for bone morphogenetic proteins," *Proc. Natl. Acad. Sci, USA*, 92:7632-7636 (1995).
Sambrook et al., "Synthetic Oligonucleotide Probes," *Molecular Cloning—A Laboratory Manual*, Ch.11:11.1-11.19 and 11.58-11.61 (1989).
Sanger et al., "DNA Sequencing with Chain-Terminating Inhibitors," *PNAS*, 74:5463-5467 (1997).
Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci*. (*USA*), 86:5728-5732 (1989).
Scatchard et al., "The Attractions of Proteins for Small Molecules and Ions," *Ann. N. Y. Acad. Sci*., 51:660-672 (1949).
Schlebusch et al., "Production of a Single-Chain Fragment of the Murine Anti-Idiotypic Antibody ACA125 as Phage-Displayed and Soluble Antibody by Recombinant Phage Antibody Technique," *Hybridoma*, 16:47-52 (1997).
Sippl et al., "Threading Thrills and Threats," *Structure*, 4(1):15-19 (1996).
Sivakumar et al., "New Insights into Extracellular Matrix Assembly and Reorganization from Dynamic Imaging of Extracellular Matrix Proteins in Living Osteoblasts," *J. Cell. Sci*., 119(7):1350-1360 (2006).
Smith et al., "Glucocorticoids Inhibit Development Stage-Specific Osteoblast Cell Cycle," *J. Biol. Chem*., 275:19992-20001 (2000).
Sudo et al., "In Vitro Differentiation and Calcification in a New Clonal Osteogenic Cell Line Derived from Newborn Mouse Calvaria," *J. Cell Biol*., 96:191-198 (1983).
Sutherland et al., "Sclerostin Promotes the Apoptosis of Human Osteoblastic Cells: A Novel Regulation of Bone Formation," *Bone*, 35:828-835 (2004).
Suzawa et al., "Extracellular Matrix-Associated Bone Morphogenetic Proteins are Essential for Differentiation of Murine Osteoblastic Cells in Vitro," *Endocrinology*, 140:2125-2133 (1999).
Takakura, "Drug Delivery Systems in Gene Therapy," *Nippon Rinsho*, 56(3):691-695 (1998) (Abstract Only).
Tam et al., "TGF-β Receptor Expression on Human Keratinocytes: A 150 kDa GPI-Anchored TGF-β1 Binding Protein Forms a Heteromeric Complex with Type I and Type II Receptors," *J. Cellular Biochem*., 70:573-586 (1998).
Taylor et al., "Human Immunoglobulin Transgenes Undergo Rearrangement, Somatic Mutation and Class Switching in Mice That Lack Endogenous IgM," *Int. Immun*., 6:579 (1994).
The Merck Manual-Second Home Edition, Ch. 61:1-3 (2005).
Thompson et al., "Affinity Maturation of a High-Affinity Human Monoclonal Antibody Against the Third Hypervariable Loop of Human Immunodeficiency Virus: Use of Phage Display to Improve Affinity and Broaden Strain Reactivity," *J. Mol. Biol*., 256:77-88 (1996).
Thornton et al., "Prediction of Progress at Last," *Nature*, 354:105-106 (1991).
Van Hul et al., "Van Buchem Disease (Hyperostosis Corticalis Generalisata) Maps to Chromosome 17q12-a21," *Am. J. Hum. Genet*., 2:391-399 (1998).
von Bubnoff et al., "Intracellular BMP Signaling Regulation in Vertebrates: Pathway or Network?" *Dev. Biol*., 239:1-14 (2001).
Wang, "Bone Morphogenetic Proteins (BMPs): Therapeutic Potential in Healing Bony Defects," *TIBTECH*, 11:379-383 (1993).
Warmington et al., "Sclerostin Antagonism in Adult Rodents, via Monoclonal Antibody Mediated Blockade, Increases Bone Mineral Density and Implicates Sclerostia as a Key Regulator of Bone Mass During Adulthood," *J. Bone Min. Res*., 19:S56-S57 (2004).
Winter et al., "Making Antibodies by Phase Display Technology," *Annu. Rev. Immunol*., 12:433-455 (1994).
Wolff et al., "Monoclonal Antibody Homodimers: Enhanced Antitumor Activity in Nude Mice," Cancer Res., 53:2560-2565 (1993).
Yang et al., "CDR Walking Mutagenesis for the Affinity Maturation of a Potent Human Anti-HIV-1 Antibody into the Picomolar Range," *J. Mol. Biol*., 254:392-403 (1995).
Zambaux et al., "Influence of Experimental Parameters on the Characteristics of Poly(Lactic Acid) Nanoparticles Prepared by a Double Emulsion Method," *J. Controlled Release*, 50(1-3):31-40 (1998).
Zhang et al., "Humanization of an Anti-Human TNF-α Antibody by Variable Region Resurfacing with the Aid of Molecular Modeling," *Molecular Immunology*, 42(12):1445-1451 (2005).
zur Muhlen et al., "Solid Lipid Nanoparticles (SLN) for Controlled Drug Delivery—Drug Release and Release Mechanism," *Eur. J. Pharm. Biopharm*., 45(2):149-155 (1998).
Notice of Opposition, European Patent No. 1 133 558.
Genbank Accession No. AC003098, Jan. 29, 1998.
NCBI Online Mendelian Inheritance in Man database of human genes and genetic disorders, [online] www.ncbi.nlm.nih.gov/omim, MIM 269500; 17q12-q21, 2008.
Burger, H. et al., "The Association Between Age and Bone Mineral Density in Men and Women Aged 55 years and Over: The Rotterdam Study," *Bone and Mineral 25*(1):1-13, Apr. 1994.
Hofman, A. et al., "Determinants of Disease and Disability in the Elderly: The Rotterdam Elderly Study," *Eur. J. Epidemiology* 7(4):403-422, Jul. 1991.

* cited by examiner

SEQUENCE LISTING

```
<160> NUMBER OF SEQ ID NOS: 42

<210> SEQ ID NO 1
<211> LENGTH: 130320
<212> TYPE: DNA
<213> ORGANISM: Homo sapiens
<220> FEATURE:
```

-continued

<221> NAME/KEY: misc_feature
<222> LOCATION: 100722, 100754, 102080, 117731, 124408, 124532, 124585,
124955, 124956, 124963, 124964, 124965, 124967
<223> OTHER INFORMATION: n = A,T,C or G

<400> SEQUENCE: 1

```
caccccccatc cccagctccc agggcctctg ccacgcgggc ttcttttttt ttttgagaca     60

gagtctcgct ctgtcaccca ggctggagca caatctcagc acaatctcac ctcaccgcaa    120

cctctgcctc ctgggttcaa gcaattctct ggcctcagcc tcctgagtag ctgggattat    180

aggctcgcgc caccacaccc agctattttt ttgtatcttt agtaaagacg ggatttcact    240

atgttggcca gtctggtctc gaactcctga ccttgtgatc cagttgcctt ggcctcccaa    300

agtgctggga ttacaggcgt gagccactgt gcccagcccc ttgcaggctt ctgacagcac    360

agatggtttt gcccgctttc ctactctgtg ggctcatcca cctcatatgt gtgtgctgcc    420

tccgtgttgc ttctgctaag tggcagtctg gtcattcttt gtatttgtcc tttctactgt    480

ggatgggcct ttgggggttt ctaactgtgg gccatgatgt gcagtgttgc ctgtgaacat    540

tctggcccat gttcgtgaat gtgaatgcgt atctctattg gacctgggcc tgggagtggg    600

attgctgggc cagaggggat gcacgtgttc agcttgagga gataccgccg tgccgcacag    660

ctttccaaag tggttgtgcc aattcacgcc tcacctcccc cagccacgca gaagagttcc    720

agttgcccca tatcttcacc agcactttgg gttttccatc cttttcattt tagccattct    780

gacaggcaca cagtggcgtg acattgtgct tttaagtggc acttcacgga agagtcttga    840

ccaacgccat ggtgtgatgg gacgccccca gctcaccacg tctcccctgt ttcttacagg    900

ccgggtgctc gtccactgcc gggaaggtta tagccgctcc ccaacgctag ttatcgccta    960

cctcatgatg cggcagaaga tggacgtcaa gtctgccctg agcatcgtga ggcagaaccg   1020

tgagatcggc cccaacgatg gcttcctggc ccagctctgc cagctcaatg acagactagc   1080

caaggagggg aagttgaaac cctagggcac ccccaccgcc tctgctcgag aggtccgtgg   1140

gggaggccgt gggcaaaggt gtcccgagct gccatgttta ggaaacacac tgtaccctgc   1200

tcccagcatc acaaggcact tgtctacaag tgtgtcccaa cacagtcctg ggccactttc   1260

cccaccctgg ggagcacata aagaagcttg ccaagggggg cgtccttgct ccccagttgt   1320

cctgtttctg taacttatga tgtcttttcc ctgagatggg ggctcagagg gggaaggcct   1380

gtggcctgca tgcttcccga tggcccacgg caggaggtgt gtggaagtgt aaggcctaag   1440

atgctcacag aggtccctca tgacctccct tccccaactc ccgaatcctc tcttgagtgt   1500

ggacctcaac accttgagcc ctagtaaagg aactatgcaa atgcaggcca ctctccccac   1560

cacgtctgtg ccccgcactg tccccacagc cttccacacc ctgtgcatag gcagccctct   1620

cacgtcttga ggtccgaagc tggggtgggg gtgtccgtca gttattagtg gatggagatt   1680

cccacagcaa ggctgcattt gaatgatttc cttaggatga atggtcccta cacaaagagg   1740

ccttgtgggc aaacctggag aaccctccta aatccataga gttttcaaaa tgtgaatctt   1800

tggaagcctt gagttcagaa tctgctgctc tggaatattt cccttcgatc ttatctcagt   1860

cacttcgttt ttgagaagag tgatgccttg ggcatgcttt tttttttttc ttttttagaa   1920

aacagggagt tgaagtccaa cctatttaaa aaccccacca tttggagaat tacaagggtt   1980

ttgtcctgaa ttgtagtgtt ggcaagccca agccactcgt gctaactgct ttttgtctcg   2040

gttgctattc caagaacaga aggaggaagt tggccaatta cagcgtgtgt gcatggatgt   2100

gtgtgggggg cgtgcctctc agaaacgcgg ccagaagaca agcagggaag tgaaaggtcc   2160
```

-continued

```
caggcacaca ccctgcccat tgcaggtggc tcttacagct ctctggtgcc agcacgggat   2220
ccctgaagtg actcagccag gcagacatga gacatggcgg agtgtccaaa tggatccttt   2280
attggtggta gagcaaaaaa acccaaacac gataaacctt tcaaaagact ttctaaggat   2340
gatattggaa tgcaccagcc ctcacatgtg tatgcacatt tgccagaata taagagtttt   2400
gttttaaata cagtcttgtt aggattttac gttattgtta ttatggaaag tgattgtgat   2460
gctatttatc ttcagggtca ctctgggcaa agagaaggtc ctcagccatg cccccagcac   2520
cttgcacata ggtgtctgat aaaagtttaa gaaattaaac actttttgag caccaaatat   2580
atatagggca ttgttctggt gggtgtgtca cgctcccaga agactgaatt tatggtagga   2640
tcactcgcaa ggccttgtga aggagtctta cctaaaacaa aagaaatatc agggactttt   2700
gttgactatt tacaactcag ttttacattt aaattcaggc agtgttaata tgccaaggta   2760
gggaatgtgc ctttttcaga gttggccagg agctcctggc tgggacacgg agaggcaggt   2820
gtggcgtaag gcctcactcc cggctgtgaa ggtctctgat cacacagaag cagccctgcc   2880
cagcctggtc atttgctgtc cgcttttctc tgtgaccaca gcagccctga acaaccagta   2940
tgtgtcttct tctccagata gtgaaaaagg tgtccagata aacccaccta agtgaaatgg   3000
ccatcctcta aactgggtac ctcactgcac agcttctagg tagccttcca acttaatcta   3060
acttgagcct cacagtaacc ctgtaaagtt agtagagctt gttcttgtat tgtgaccttt   3120
tttaaaaaaa aggaactgag gttcagaatg attaagggcc tggcccccag ggttgtccag   3180
ctccataagg tggagctggg caagattttg ggtttgctgc tccctgaagc tggattcttt   3240
catacgatac tctttctcaa gaagggggct ccctgggatc tccaggtgta ctgcacttac   3300
cctcaatcca gccccggaga agcaagtgaa aagggtgggt ccctcatagg ctagaatgtg   3360
cagctctttc tccaggtggg atgtagcacc ccaaagtaga gctttctgct ctgctcctgg   3420
aaaaggctag ggagctgggg ctggggctcc cctcccatga ccaggcagtg gtcaccccat   3480
gggacaggca cagctactta cgcgaacaca gcaggttggt gtggctggct aactaggacc   3540
tctcgaaagt ctctgtgggg gcatgaggga gaaaaggcca ttgggagaat tactgccttt   3600
actttgggac tacttttatg ctgataactt gggatttctt gatagtcctt cacccctgaa   3660
accccgtatt tacttaacaa gatttagctc ttagttcttc aagtaaaatt aaagtctctt   3720
gtgtaagagc caacacatgc ccagctgcgg atgggagctg ttcctggaca gccttctact   3780
gcctgggaag tgatggaaca ggaactcagg gtgcccttac cccctcccca gacctgttcc   3840
ctttctttga ctgacagagc accatccagg caaaattaga gcgccaaatg gttttcttct   3900
caatcttaaa gcagtatacc tttccacagg ctcgtctgtg tccctgccac tctgagttat   3960
ccagaaacca ccacctacaa atgaggggac tcatctagaa gacctctaag gtcccctttt   4020
ggctctgagg ggtctctaat aatccccact tggaattcag caccgcaagg aaattatggg   4080
tatgtgagcc ataatatgat ggccagcagg tggcgctgcc ttccacccat ggtgatggat   4140
ggtttggaaa gggaatgttg gtgccttttg tgccacaagt taagatgcta ctgttttaaa   4200
ggaaaaaaaa aaaaaaaagt actgatcttc aatatgaaga catgagcttt tctcgcagga   4260
aattttcttt ttcacagaac tggtgtcagg aatcactgaa gggctaaccg tgatagtcct   4320
tgcaagtaag tcaaggtttt atcctgattg gaaatagaag acatttccgg ttgagagaac   4380
agattcgttg gaagcttaac ttttgttgcc tcttaacgcc accaaatttt agggtaattt   4440
gattatgaaa gagtgaattt ttctggacag aaaagggaga gctaccaaat tgttttttc    4500
tttttaaaag gaagtttaat gtccgttgta tcacaaatca gtgttaaaac accagaactt   4560
```

-continued

```
tagccaaaat aaatgtctta cattacaaag gtattgtttt tttgtccttc ttatcacagt   4620
tggtattctt ttacgttttt atgcttagct ttttttgttt gggcttagct tttatatttg   4680
cgatttctaa ctttttaaaa ataatcatct aaaacatagc cgttctgagc tagttatagg   4740
ttccatgatg gcactgttta tgcagtagat attgatgaac acctttccag taccagaaat   4800
gttctggtag gaatattctt aggtagaatg gccataatgg tcctgaatga aggaggtaag   4860
gtttgtgctt ctaagaaagc aggggactag ggtgttcatc tcaaggtagc ctcacgtgat   4920
gactgggtga cattttgaga tttgagtgat cctgcaaatg aacagtccct aaacatatcc   4980
ccttccccca gatgccttaa attccactat tggtgctatg ttcctttgaa taaaaaacct   5040
tagagaaagt aggtgccttt tcctcccaga cagaagtctg ggcagagaaa gcctctcgag   5100
gttcccattc cctctatcac atgaagcaat tggactcgct tcctatttgt caagactctg   5160
acaatgtaat ctttatggtt ctacacaaaa tcttaaggca gagcactaaa atataaaaca   5220
ggtaaaagtt tttaagtata atttttaaaa aatttttcat taaaaataat actatatgta   5280
catagtaata cacttaaaca atgcaaaagg cttatacgga aaagtgagtc acttgctcct   5340
tcaatctatc tccccataag cgtcatatcc ttaaaggaaa atgtcaagca tatataagca   5400
cacatatgtg catacgtgtg tatatacaga gatatctctg ctttgttgtt tgttttgctt   5460
agcttatatt atggttattg tttttattgc tctacccct tcatcttaac agctacatag   5520
cattccattg tgtatggatg tgtaaataaa gacaaggtga tttggacatc cctcaatgca   5580
gggtactgcc taaaagcaga agtttgccct cctaatccag atatttcctt tttaccacct   5640
acaagtggga gcaaaatctg ttttaaaatg cagccaataa ggagaatcct cagtttccat   5700
taattagaga taggggcctc ctccagaacc aagtagagaa tgaaaccgga tgacctttga   5760
gagtccttcc agatcaaaga ttctatgatc ccaaggagtc aaaggagcat aatatacttt   5820
ccaaatttgg cctgtcattc aaagtctggt ccaaatgcca catcttacca taaggatccc   5880
agatcctccc caggggaaag agattgttct ctcctttgaa ggcccataag aaaattgtcc   5940
ttttgaaaaa atgcatctgg tgaggatgtg gaacaacagg aactctttgt ttcagtgggg   6000
aatgcaaaat ggtacagcca ctttggagga cagtttgcag tttagtttct tgcaaaacta   6060
cacatacttt tattgcacaa tccagcagtc atgctccttg gtatttattc aaatgatttg   6120
aaaacttaac gttcgtataa aaacctgcac acagctgggc atggtggctc atgcctgtaa   6180
tcccagcact ttgggaggct gaggtgggca gatcacttga ggttaggagt ttgagaccat   6240
actggccaac atggggaaac cccttctcta ctaaaaatac aaaaattagc caggtgtggt   6300
ggtgctcacc tgtaatccca cctactcggg aggctgagcc aggagaatca cttgaaccca   6360
ggaggcggag gttgcagtga gctgagatca cggcactgca ccccagcctg ggagacagag   6420
taagactccg tcttaagaca aaacaaaaca aaaaacctgt acaaaatgtt tataccacct   6480
ctattaataa ttgccagagc ttgaaagcaa ccaagatgtc cttcagtaga tgacagtagg   6540
tgactagata aaccgtgata catcaagacg atggagtatt actcagtgct aaaaaaaaaa   6600
ataagctgtt catgccatga aaagacatgg aggaacccca aatgaatatt actaactgaa   6660
agaagccaat ctgaaaagac tatgtatggg tatattccaa ctctatatga catcctggaa   6720
aaggcaaaaa taaaggtaca gtaaaaagat cagtggttgc caggggttgg ggaaagtcgg   6780
ggagggatga ataggcagag cagatagttt ttttggacaa tgaaaatact gcccatctgt   6840
atgatactat aatggtagat gtatgtcatt atacatttgt ccaaagccat aggatgtaca   6900
```

-continued

```
acactagtgc tgtgatgtaa accatggact tcaggtgata atgatgtgtc atgtaggctc   6960
atcaatcata gcaaatgcac cactctggtg gcgggatgtt gataacgggg gcagctgtac   7020
atgtgtgggc acaggacata aatgagaaat ctctgtacca tccactcagt tttgctgtga   7080
acctaaaagt gctccagaaa aaaaataaag tttttttag aaaaaagcat ctgaaccttt   7140
ttttcagtgg cattgatcac cttccatctg gtagtggagt tgtttggatg cggaaattat   7200
ttcttccatg gtatgcgagc tcctggagag ggagtgcgtg tccccccttgc tttattaaac   7260
gtttggcgag tgaacatcag aagaagcaac tcgacagaaa caaaagctgg taaataatca   7320
catggaaaag cagcttttct ggaaattaag tttcaactgt taaattcaat gtttaaaaaa   7380
atcggctggg tgcggtggct cccgcctgca atcccagcac tttatgggat tgtgggaaca   7440
cctgatgtca ggagttcaag accagcctgg ccgacatggc gaaaccccat ctctacaaaa   7500
caaacaaaaa aaaatgcaaa aattagctgg gtgtggtggc gggagtctgt agtcctagct   7560
actcgggagg ctgaggcagg agaactgctt gaacccagga ggtggaggtt atatgagcca   7620
agatcacacc actgcactcc cgcctgggtg acagagcgag actctgtctc aaaaaaaaaa   7680
aaaaaaatca acatcccaaa cccagtgttg acagtcttat ttatgggttg aactgcattc   7740
ctcccaaatg catatattga agtcctaagt cacagtacct gagaatgtga ccttatttgg   7800
aaatagggct attacagatg taactcgtta agatgaggtc attaggctgg gcctaatcta   7860
atatgcctga cctccttaga aaaaagggaa aattcgaaca cagagagaac accatgtgaa   7920
gatgaaggca gggattgggg gtgacacttc tgcaagccag tgaatgccac agcttgtcag   7980
cagccagcag aaggcaggta aaaggccttc ctcactgtcc tcgaaggaac caactctgcc   8040
aatgtcttga acttgcactc ctaacctcca gctctgtgag acgacttctg ttgtttatgc   8100
cacccaattt gtggtactta gttacggcag cctcatcaaa gtaccaccta tgggagcctc   8160
tattttgcag gtgagggcgg ggactgggct gagttttctg gaaaacagcc ctgcaatacc   8220
ctcatcagac caccaaactc ttcacactcc ctcagacaca gcattcactt ccagaaataa   8280
ctctaaagtt ttgttttgtt tttttaaact ttgtggaata ctactcagcc aaaaaaaaaa   8340
aaaaagaaaa gaaaaaggaa catgttactg atatgtacaa cttggataat ggaaataatg   8400
ctgagtgaaa aaaaaatccc caaaggctac atactaattg attccattta tataaccttt   8460
ttttttttt tttgagacag tctcactctg tcacccaggc tggagcacag tggcgcgatc   8520
tcagctcact gcaacttccg cctcctgagt tcaagcgatt ctcttgcctt agcttcccaa   8580
gtagctggga ttacaggtgc gtgccaccat gcccagctaa tttttgtatt tttagtagag   8640
acagggtttc gccatgttgg ccaggctggt ctcgaactcc tgacctcaag tgatctgcct   8700
gccttggctt cccaaagtgc tgggattaca tgagtgagcc accgcacctg gtcgcattta   8760
tgtaacaatt ttgaagtgaa aaaaaaaatg acagaaatgg agattagatg agtagttgcc   8820
aggggttagt tgtgggaggg agggaaaagg agggaaggag gtgggcaaca ggagaaagac   8880
ttgtggtcac agagctgtgc tttatcttga ctgtggtgga tccccaaatt tacccgtgac   8940
aagattgcat agaactaagt atacacacac gtgaatgcgt gtgcacgcac acagtagagg   9000
ttaagccacg ggagatgtgg gtaagattgg taaattgtgt caatatcaat atcctagttg   9060
tgatattgtc ctatagtttc gcaaggtgtt attgttgtgg gaaactggat aaaggataca   9120
cggagtctgc attttctttt ttttattttt attttttgag acggggtctc actctgtcaa   9180
ccaggctgga gtgcagtggc ccaagtatgg ctcactgcag cctcgacctc aacctcaagt   9240
gaacctccca cctcagcctc ccaagtagct aagaccacag gcgtgcgacc ccatgcccag   9300
```

-continued ctaattttta aattttttgt agagactagg cctcaccatg ttgcccaggc ttttatttct 9360
tataagtata tttaaattta taattatatc cacattttaa aattttaatt taaaaaatta 9420
ctctgaggcc gggcattgtg gctcatgcct ctaatcccca gcaccttggg aggccgagtt 9480
gggcagatca cccgaggtca gaagttcgag accagcctga gtaacatgga gaaacccccg 9540
tctctactaa aaatacaaaa ttggccgggc gtggtggtgc attcctgtaa tcccagctac 9600
tcgggaggct gaggcaggag aattgcttga acccaggagg tggaggttgc agtgagccaa 9660
gattgtgcca ctgcactgca gcctgggcca cagagagaat ctgccaaaaa aagaaaaaaa 9720
aaaaaatttc agccgtacaa ggatgttcat agcaaccctg ctggaaatag gaaaaaaaat 9780
tggaaataac ctaaactact cacaatagga atcagctaaa accctggggg tttaattcca 9840
gggaatactg tgaacaatga caagtttgtg gactgagtaa aaataaacag ctgtcaatga 9900
cttaacatta aatgaaacag cagaagatgt cacagcaggt tctcgctgag ccattcagag 9960
gggtgtggat catttagagg ttcaagtcca ctggattctt ctttttcctt ttaatattac 10020
ttcacttcca aataaggaaa ggaaaggaaa ggaaatcacg tccagtcctg agacttgcca 10080
tcctgcagtc accccctcctt ttgtctccag caggtggcag acgcgttcca gggatgaatc 10140
ccactgcctc tgtttaatgc agacggtcca gccgctccca acagcaggtg gggctataag 10200
catccatcct acctgctcaa ggaacccagg catcagaact gctctctccc aagtccattg 10260
caagaaggca gtcgtctggt catgagaggg ttaacagtcc acattccaga gcaagggaaa 10320
aggaggctgg agggtcatag acaaggggag gtggtgcgga gggccagctt ctcacaacac 10380
taccggctct gctgggagag atagatcacc cccaacaatg gccacagctg ttttcatctg 10440
ccctgaagga aactgactta ggaagcaggt atcagagagg gcccttcctg agggggcttc 10500
tgtctggctt gtaaaactgt cagagcagct gcattcatgt gtcggatgat ggatgatgga 10560
aaggacagtc ggctgcagat ggacacagcg acttgcaagt tgaggcaggt ggcaaaggac 10620
ttgcagaggc tctgcaggtg gggcatgctg attcattgcc cagttaaaat accagaggat 10680
ctgggcagcc tcttcacagg agctgcttgt cctcaaacaa tctgtcttca atgaaagatt 10740
cctctggcct tcctttctct tcttgcacct caggtgtgaa tccttctccc ccacgcctct 10800
acctgcgccc ccgccccccg ccccggccct gtgtggctca ttatatgcag ggccaaggca 10860
gcattttctc ttagcttctt tgtgaccagt tggtcctggg atggcttcat ggaacacatc 10920
ctgtggtgtg caccaatgaa gctttccata caggactcaa aactgttttt gaaaaatgta 10980
accagctgga agacaagaaa ataaaatgtc agcactaaaa acgctggctg tggcttttgc 11040
taaggaaagg aatttggtgt tgtcttctca cacacacaga ctggttgggg aaatgactgt 11100
cttcagcaca tcaccctgcg agccacagtg agtgccctgg ctcagaagtg cctgtcacag 11160
tgcacaggat ccctgaggag catgagctgg gatttcctct gtgctgtcca tcacaggagc 11220
ctgagtgacc agcgcatcct cgatttgtaa ccagaatcct gccctctctc ccaagcgggc 11280
acccttgctc tgaccctcta gttctctctc ttgccttcca gagaatacca agagaggctt 11340
tcttggttag gacaatgaat gctgagactt gtggagttgg gaccaatggg atttctttaa 11400
aagcatcttt ttgcctctgg ctgggtctat gggggtcaaa cagaaacacc ttgggccatt 11460
tgttggtggg gtgacaaatg aacttggcct gagaaatgga ataggccggg ctcagccccg 11520
cgaagcactc agaactgcac attttctttg ttgagcgggt ccacagtttg ttttgagaat 11580
gcccgagggc ccagggagac agacaattaa aagccggagc tcattttgat atctgaaaac 11640

-continued

```
cacagccgcc agcacgtggg aggtgccgga gagcaggctt gggccttgcc tcacacgccc  11700
cctctctctg ggtcacctgg gagtgccagc agcaatttgg aagtttgctg agctagagga  11760
gaagtctttg gggagggttt gctctgagca cacccctttc cctccctccg gggctgaggg  11820
aaacatggga ccagccctgc cccagcctgt cctcattggc tggcatgaag cagagagggg  11880
ctttaaaaag gcgaccgtgt ctcggctgga gaccagagcc tgtgctactg gaaggtggcg  11940
tgccctcctc tggctggtac catgcagctc ccactggccc tgtgtctcgt ctgcctgctg  12000
gtacacacag ccttccgtgt agtggagggc caggggtggc aggcgttcaa gaatgatgcc  12060
acggaaatca tccccgagct cggagagtac cccgagcctc caccggagct ggagaacaac  12120
aagaccatga accgggcgga gaacggaggg cggcctcccc accacccctt tgagaccaaa  12180
ggtatggggt ggaggagaga attcttagta aaagatcctg gggaggtttt agaaacttct  12240
ctttgggagg cttggaagac tggggtagac ccagtgaaga ttgctggcct ctgccagcac  12300
tggtcgagga acagtcttgc ctggaggtgg gggaagaatg gctcgctggt gcagccttca  12360
aattcaggtg cagaggcatg aggcaacaga cgctggtgag agcccagggc agggaggacg  12420
ctggggtggt gagggtatgg catcagggca tcagaacagg ctcaggggct cagaaaagaa  12480
aaggtttcaa agaatctcct cctgggaata taggagccac gtccagctgc tggtaccact  12540
gggaagggaa caaggtaagg gagcctccca tccacagaac agcacctgtg gggcaccgga  12600
cactctatgc tggtggtggc tgtccccacc acacagaccc acatcatgga atccccagga  12660
ggtgaacccc cagctcgaag gggaagaaac aggttccagg cactcagtaa cttggtagtg  12720
agaagagctg aggtgtgaac ctggtttgat ccaactgcaa gatagccctg gtgtgtgggg  12780
gggtgtgggg gacagatctc cacaaagcag tggggaggaa ggccagagag gcacccctgc  12840
agtgtgcatt gcccatggcc tgcccaggga gctggcactt gaaggaatgg gagttttcgg  12900
cacagtttta gcccctgaca tgggtgcagc tgagtccagg ccctggaggg gagagcagca  12960
tcctctgtgc aggagtaggg acatctgtcc tcagcagcca ccccagtccc aaccttgcct  13020
cattccaggg gagggagaag gaagaggaac cctgggttcc tggtcaggcc tgcacagaga  13080
agcccaggtg acagtgtgca tctggctcta taattggcag gaatcctgag gccatggggg  13140
cgtctgaaat gacacttcag actaagagct tccctgtcct ctggccatta tccaggtggc  13200
agagaagtcc actgcccagg ctcctggacc ccagccctcc ccgcctcaca acctgttggg  13260
actatggggt gctaaaaagg gcaactgcat gggaggccag ccaggaccct ccgtcttcaa  13320
aatggaggac aagggcgcct ccccccacag ctccccttct aggcaaggtc agctgggctc  13380
cagcgactgc ctgaagggct gtaaggaacc caaacacaaa atgtccacct tgctggactc  13440
ccacgagagg ccacagcccc tgaggaagcc acatgctcaa aacaaagtca tgatctgcag  13500
aggaagtgcc tggcctaggg gcgctattct cgaaaagccg caaaatgccc ccttccctgg  13560
gcaaatgccc ccctgaccac acacacattc cagccctgca gaggtgagga tgcaaaccag  13620
cccacagacc agaaagcagc cccagacgat ggcagtggcc acatctcccc tgctgtgctt  13680
gctcttcaga gtgggggtgg ggggtggcct tctctgtccc ctctctggtt tggtcttaag  13740
actatttttc attctttctt gtcacattgg aactatcccc atgaaacctt tgggggtgga  13800
ctggtactca cacgacgacc agctatttaa aaagctccca cccatctaag tccaccatag  13860
gagacatggt caaggtgtgt gcaggggatc aggccaggcc tcggagccca atctctgcct  13920
gcccagggag tatcaccatg aggcgcccat tcagataaca cagaacaaga aatgtgccca  13980
gcagagagcc aggtcaatgt ttgtggcagc tgaacctgta ggttttgggt cagagctcag  14040
```

-continued

```
ggcccctatg gtaggaaagt aacgacagta aaaagcagcc ctcagctcca tcccccagcc  14100
cagcctccca tggatgctcg aacgcagagc ctccactctt gccggagcca aaaggtgctg  14160
ggaccccagg gaagtggagt ccggagatgc agcccagcct tttgggcaag ttcttttctc  14220
tggctgggcc tcagtattct cattgataat gagggggttg gacacactgc ctttgattcc  14280
tttcaagtct aatgaattcc tgtcctgatc acctcccctt cagtccctcg cctccacagc  14340
agctgccctg atttattacc ttcaattaac ctctactcct ttctccatcc cctgtccacc  14400
cctcccaagt ggctggaaaa ggaatttggg agaagccaga gccaggcaga aggtgtgctg  14460
agtacttacc ctgcccaggc cagggaccct gcggcacaag tgtggcttaa atcataagaa  14520
gaccccagaa gagaaatgat aataataata cataacagcc gacgctttca gctatatgtg  14580
ccaaatggta ttttctgcat tgcgtgtgta atggattaac tcgcaatgct tggggcggcc  14640
cattttgcag acaggaagaa gagagaggtt aaggaacttg cccaagatga cacctgcagt  14700
gagcgatgga gccctggtgt ttgaacccca gcagtcattt ggctccgagg ggacagggtg  14760
cgcaggagag ctttccacca gctctagagc atctgggacc ttcctgcaat agatgttcag  14820
gggcaaaagc ctctggagac aggcttggca aaagcagggc tggggtggag agagacgggc  14880
cggtccaggg caggggtggc caggcgggcg gccaccctca cgcgcgcctc tctccacaga  14940
cgtgtccgag tacagctgcc gcgagctgca cttcacccgc tacgtgaccg atgggccgtg  15000
ccgcagcgcc aagccggtca ccgagctggt gtgctccggc cagtgcggcc cggcgcgcct  15060
gctgcccaac gccatcggcc gcggcaagtg gtggcgacct agtgggcccg acttccgctg  15120
catccccgac cgctaccgcg cgcagcgcgt gcagctgctg tgtcccggtg gtgaggcgcc  15180
gcgcgcgcgc aaggtgcgcc tggtggcctc gtgcaagtgc aagcgcctca cccgcttcca  15240
caaccagtcg gagctcaagg acttcgggac cgaggccgct cggccgcaga agggccggaa  15300
gccgcggccc cgcgcccgga gcgccaaagc caaccaggcc gagctggaga acgcctacta  15360
gagcccgccc gcgcccctcc ccaccggcgg gcgccccggc cctgaacccg cgccccacat  15420
ttctgtcctc tgcgcgtggt ttgattgttt atatttcatt gtaaatgcct gcaacccagg  15480
gcagggggct gagaccttcc aggccctgag gaatcccggg cgccggcaag gccccccctca  15540
gcccgccagc tgaggggtcc cacggggcag gggagggaat tgagagtcac agacactgag  15600
ccacgcagcc ccgcctctgg ggccgcctac ctttgctggt cccacttcag aggaggcaga  15660
aatggaagca ttttcaccgc cctggggttt taagggagcg gtgtgggagt gggaaagtcc  15720
agggactggt taagaaagtt ggataagatt ccccccttgca cctcgctgcc catcagaaag  15780
cctgaggcgt gcccagagca caagactggg ggcaactgta gatgtggttt ctagtcctgg  15840
ctctgccact aacttgctgt gtaaccttga actacacaat tctccttcgg gacctcaatt  15900
tccactttgt aaaatgaggg tggaggtggg aataggatct cgaggagact attggcatat  15960
gattccaagg actccagtgc cttttgaatg ggcagaggtg agagagagag agagaaagag  16020
agagaatgaa tgcagttgca ttgattcagt gccaaggtca cttccagaat tcagagttgt  16080
gatgctctct tctgacagcc aaagatgaaa aacaaacaga aaaaaaaaag taaagagtct  16140
atttatggct gacatattta cggctgacaa actcctggaa gaagctatgc tgcttcccag  16200
cctggcttcc ccggatgttt ggctacctcc acccctccat ctcaaagaaa taacatcatc  16260
cattggggta gaaaaggaga gggtccgagg gtggtgggag ggatagaaat cacatccgcc  16320
ccaacttccc aaagagcagc atccctcccc cgacccatag ccatgtttta aagtcacctt  16380
```

-continued

```
ccgaagagaa gtgaaaggtt caaggacact ggccttgcag gcccgaggga gcagccatca  16440
caaactcaca gaccagcaca tccctttga gacaccgcct tctgcccacc actcacggac  16500
acatttctgc ctagaaaaca gcttcttact gctcttacat gtgatggcat atcttacact  16560
aaaagaatat tattggggga aaaactacaa gtgctgtaca tatgctgaga aactgcagag  16620
cataatagct gccacccaaa aatctttttg aaaatcattt ccagacaacc tcttactttc  16680
tgtgtagttt ttaattgtta aaaaaaaaaa gttttaaaca gaagcacatg acatatgaaa  16740
gcctgcagga ctggtcgttt ttttggcaat tcttccacgt gggacttgtc cacaagaatg  16800
aaagtagtgg tttttaaaga gttaagttac atatttattt tctcacttaa gttatttatg  16860
caaaagtttt tcttgtagag aatgacaatg ttaatattgc tttatgaatt aacagtctgt  16920
tcttccagag tccagagaca ttgttaataa agacaatgaa tcatgaccga aaggatgtgg  16980
tctcattttg tcaaccacac atgacgtcat ttctgtcaaa gttgacaccc ttctcttggt  17040
cactagagct ccaaccttgg acacaccttt gactgctctc tggtggccct tgtggcaatt  17100
atgtcttcct ttgaaaagtc atgtttatcc cttcctttcc aaacccagac cgcatttctt  17160
cacccagggc atggtaataa cctcagcctt gtatcctttt agcagcctcc cctccatgct  17220
ggcttccaaa atgctgttct cattgtatca ctcccctgct caaaagcctt ccatagctcc  17280
cccttgccca ggatcaagtg cagtttccct atctgacatg ggaggccttc tctgcttgac  17340
tcccacctcc cactccacca agcttcctac tgactccaaa tggtcatgca gatccctgct  17400
tccttagttt gccatccaca cttagcaccc ccaataacta atcctctttc tttaggattc  17460
acattacttg tcatctcttc ccctaacctt ccagagatgt tccaatctcc catgatccct  17520
ctctcctctg aggttccagc cccttttgtc tacaccacta ctttggttcc taattctgtt  17580
ttccatttga cagtcattca tggaggacca gcctggccaa gtcctgctta gtactggcat  17640
agacaacaca aagccaagta caattcagga ccagctcaca ggaaacttca tcttcttcga  17700
agtgtggatt tgatgcctcc tgggtagaaa tgtaggatct tcaaaagtgg gccagcctcc  17760
tgcacttctc tcaaagtctc gcctccccaa ggtgtcttaa tagtgctgga tgctagctga  17820
gttagcatct tcagatgaag agtaacccta aagttactct tcagttgccc taaggtggga  17880
tggtcaactg gaaagcttta aattaagtcc agcctacctt gggggaaccc acccccacaa  17940
agaaagctga ggtccctcct gatgacttgt cagtttaact accaataacc cacttgaatt  18000
aatcatcatc atcaagtctt tgataggtgt gagtgggtat cagtggccgg tcccttcctg  18060
gggctccagc ccccgaggag gcctcagtga gcccctgcag aaaatccatg catcatgagt  18120
gtctcagggc ccagaatatg agagcaggta ggaaacagag acatcttcca tccctgagag  18180
gcagtgcggt ccagtgggtg gggacacggg ctctgggtca ggtttgtgtt gtttgtttgt  18240
ttgttttgag acagagtctc gctctattgc ccaggctgga gtgcagtgtc acaatctcgg  18300
cttactgcaa cttctgcctt cccggattca agtgattctc ctgcctcagc ctccagagta  18360
gctgggatta caggtgcgtg ccaccacgcc tggctaattt ttgtattttt gatagagacg  18420
gggtttcacc atgttggcca ggctagtctc gaactcttga cctcaagtga tctgcctgcc  18480
tcggcctccc aaagtgctgg gattacaggc gtgagccacc acacccagcc ccaggttggt  18540
gtttgaatct gaggagactg aagcaccaag gggttaaatg ttttgcccac agccatactt  18600
gggctcagtt ccttgcccta cccctcactt gagctgctta gaacctggtg ggcacatggg  18660
caataaccag gtcacactgt tttgtaccaa gtgttatggg aatccaagat aggagtaatt  18720
tgctctgtgg aggggatgag ggatagtggt tagggaaagc ttcacaaagt gggtgttgct  18780
```

-continued

```
tagagatttt ccaggtggag aagggggctt ctaggcagaa ggcatagccc aagcaaagac  18840
tgcaagtgca tggctgctca tgggtagaag agaatccacc attcctcaac atgtaccgag  18900
tccttgccat gtgcaaggca acatgggggt accaggaatt ccaagcaatg tccaaaccta  18960
gggtctgctt tctgggacct gaagatacag gatggatcag cccaggctgc aatcccatta  19020
ccacgagggg gaaaaaaacc tgaaggctaa attgtaggtc gggttagagg ttatttatgg  19080
aaagttatat tctacctaca tggggtctat aagcctggcg ccaatcagaa aaggaacaaa  19140
caacagacct agctgggagg ggcagcattt tgttgtaggg ggcggggcac atgttctggg  19200
ggtacagcca gactcagggc ttgtattaat agtctgagag taagacagac agagggatag  19260
aaggaaatag gtccctttct ctctctctct ctctctctct ctcactctct ctctctctca  19320
cacacacaca cagacacaca cacacgctct gtaggggtct acttatgctc caagtacaaa  19380
tcaggccaca tttacacaag gaggtaaagg aaaagaacgt tggaggagcc acaggacccc  19440
aaaattccct gttttccttg aatcaggcag gacttacgca gctgggaggg tggagagcct  19500
gcagaagcca cctgcgagta agccaagttc agagtcacag acaccaaaag ctggtgccat  19560
gtcccacacc cgcccacctc ccacctgctc cttgacacag ccctgtgctc cacaacccgg  19620
ctcccagatc attgattata gctctggggc ctgcaccgtc cttcctgcca catccccacc  19680
ccattcttgg aacctgccct ctgtcttctc ccttgtccaa gggcaggcaa gggctcagct  19740
attgggcagc tttgaccaac agctgaggct ccttttgtgg ctggagatgc aggaggcagg  19800
ggaatattcc tcttagtcaa tgcgaccatg tgcctggttt gcccagggtg gtctcgttta  19860
cacctgtagg ccaagcgtaa ttattaacag ctcccacttc tactctaaaa aatgacccaa  19920
tctgggcagt aaattatatg gtgcccatgc tattaagagc tgcaacttgc tgggcgtggt  19980
ggctcacacc tgtaatccca gtactttggg acgtcaaggc gggtggatca cctgaggtca  20040
cgagttagag actggcctgg ccagcatggc aaaaccccat ctttactaaa aatacaaaaa  20100
ttagcaaggc atggtggcat gcacctgtaa tcccaggtac tcgggaggct gagacaggag  20160
aatggcttga acccaggagg cagaggttgc agtgagccaa gattgtgcca ctgccctcca  20220
gccctggcaa cagagcaaga cttcatctca aaagaaaaag gatactgtca atcactgcag  20280
gaagaaccca ggtaatgaat gaggagaaga gaggggctga gtcaccatag tggcagcacc  20340
gactcctgca ggaaaggcga gacactgggt catgggtact gaagggtgcc ctgaatgacg  20400
ttctgcttta gagaccgaac ctgagccctg aaagtgcatg cctgttcatg ggtgagagac  20460
taaattcatc attccttggc aggtactgaa tcctttctta cggctgccct ccaatgccca  20520
atttccctac aattgtctgg ggtgcctaag cttctgccca ccaagagggc cagagctggc  20580
agcgagcagc tgcaggtagg agagataggt acccataagg gaggtgggaa agagagatgg  20640
aaggagaggg gtgcagagca cacacctccc ctgcctgaca acttcctgag ggctggtcat  20700
gccagcagat ttaaggcgga ggcaggggag atggggcggg agaggaagtg aaaaaggaga  20760
gggtggggat ggagaggaag agagggtgat cattcattca ttccattgct actgactgga  20820
tgccagctgt gagccaggca ccaccctagc tctgggcatg tggttgtaat cttggagcct  20880
catggagctc acagggagtg ctggcaagga gatggataat ggacggataa caaataaaca  20940
tttagtacaa tgtccgggaa tggaaagttc tcgaaagaaa aataaagctg gtgagcatat  21000
agacagccct gaaggcggcc aggccaggca tttctgagga ggtggcattt gagctaagac  21060
caaaatgtgg tgggagaggg agccacacaa ggatctgggg gtgtgtgcac tgggaggggg  21120
```

-continued

```
agcagcaagt gcaaagggcc tgaaggtatg tagggggtgg agaagggaca ccactaattg  21180
ccttgggtgc ctttcaggcg tctccatgcc aaggctctaa cccctgatgt ggaagccaac  21240
atagtaatta taattatagt gaagaggggt gtgtgtgtgt gtgtgtgtgt gtgtgtgtgt  21300
gtgattgaaa gagagagaga atgagtctct gtaccttctc ttgggtctgt atgttgaaaa  21360
cctaagtgac cctaaagaag aatatttgca tattattaat tatgtagcta tacatgtttt  21420
ttttgagaca aagtcttgct ttgtcaccca gactggagtg cagtggcagc aatcatggct  21480
cactgcagcc tctgcctccc aggctcaagc catcctcctg tctcactctc ctgagtagct  21540
gggctacagg cagttgccac catgcccggc taatttttgt atttttttag agatggggct  21600
tcactttgtt gcccaagctg gtgcacatct ttattctttt tttttttttt ttttgagaca  21660
gagtctcact ctgtcgccca ggctggagtg cagtggtgcg atctcacggc tcactgcaac  21720
ctctgcctcc tggcttcaag tgattctcct gcctcagcct cctgagtagc cgggactaca  21780
ggcacgtgcc accacgcccg gctaatttgt ttttgtattt ttagtagaga cggggtttca  21840
ctgtgttagc caggatggtc tcaatctcct gacctcgtga ttcccccgcc tcggcctccc  21900
aaagtgttgg gattacaggt gtgagccact gcaccccgcc acatctttat tctttaggct  21960
tttgataggt ttgcttaagt aatgctgcta gcactgggca gatgtattac aataggaata  22020
ttgatgccct tgaactcctt ctagcacata cagatgtgac acaattcata tgcagttgcg  22080
gaaatgcctg tagttttctt taatggatgc ctataagatc caggctgtaa tctataagat  22140
cctataggct gtgtgcctat aagatcctgc tgtgaattct tccctgctgt ggctctaagc  22200
cagatgtata aatatatgta gatggataca ggtttatgct attcagccga gactctaggt  22260
caggcgatgg agatctgaaa ggtaagaagg agtctagaaa tgaattcctt ctggaaagat  22320
tcatgattca ttcttacttc tctgaactat agaagagcat cctcatcagt gaatgtattc  22380
gtcactgcat ccactgcaaa ccccccttggg gaacactcac cttcactgtg cttctggatt  22440
tgcacatgtg cttgcatatg cacacacaca ctcacacaca cacattcaca ccatctttac  22500
tctgaatata caatgccaag ctttcccagg tattctaaaa tcctcctgtt tctgaccctt  22560
ggttggcaga tgtccaaaaa tgatactgac atcccaggtc agaatggtcg ccagttccga  22620
tcaagacaga gccccgtatc ttccagggac actagacaag atgccaggac cacgcctccg  22680
ctctgcccag aggccaaaag cagcccaaca aggtgaagtg ttctctgcat gcattactcc  22740
ctgggtcccc caagatcggc ctccagctct cctccaccca ggagctgctg tgtggagaca  22800
gagactggct cggggtccca ttccccaatc ccctcccttc catctgctat gccgctgcca  22860
gatggatttt actttctctg tttttttaaa aagcaaagtt caaaaaaatat tttaaacaca  22920
ggaaatttaa tacgttagca ttttagctcc atctacagta tttctttatt ttttacacag  22980
ggtttcactc tgttgcccag actgcagtac agtggcacaa tcatagctca ctgcagcctc  23040
tatctcctgg gctcaagtgg tcttcctacc tcagcctccc aagaagctga gactacaggt  23100
gtgcaccact acacctagct aatgtttttt atttttatta gagacaaggt ctcactatgt  23160
ttcccaggct ggtcttaaac tcctgagctc aagtgatcct cctgccttgg cctcccaaag  23220
tgctgggatt ataggtgtaa gccaccatgc cccgcccata tttcttttag atataaaacc  23280
aatagaaaaa ttctatgtat ttctctttcc atgcctttcc ctccatggat tgtttccaaa  23340
ggcaacaatc catgttttca taccatccta catatattat ttataatcaa tatacaaacg  23400
tgcgttttta aatttcacat gcattttatc ataccataca tatgctgaaa ctcacctttt  23460
tttttactc aaaattatgc ttttaagatc tagccatgtt ggattatttt aaaatcttga  23520
```

-continued

```
atggtattat attttatgac tataccacta tttgcttatc tatttttctt tttttttttt  23580
ttttgagaca gagtctcgct ctgtcaccca ggctggagtg caatggcgca atgttggctc  23640
actgcaactt ctgcctcctg agttcaagca attctcctgc ctcagcttcc tgagtagctg  23700
gaactacagg tatgtgccac cacacccagc taattttttg tatttgtagt agagacgagg  23760
tttcaccatg ttggccaggc tggtctcgaa ctcctggcct caggtgatcc acctgcctcg  23820
gcctcccaaa gtgctgagat tacaggcgtg agccactgcg cctggcctgc ttatctattt  23880
ttctactgat ttagtttgtt tccagtgttt tcaccatcaa acccaatgca ctaaggaaga  23940
tgcccgaatt tgtctcctga cgcgacatat gctagagttt cttcaggaca gagaggagtg  24000
agtgttctaa tacaaaaatc taatcatgct atttccccgc tcaaattcct ccatggaatt  24060
tattacctaa aaggtcaact ctaaactcct tagcttacaa gtacatgatc tggtatccat  24120
ctacctgtcc agccacgcat ttgaccgctg acttccttag cactttgttc tctgcaatat  24180
cgtatttctc ttaatttcta aatcgcccag gggtttcaa gcctctgctt ttgcacattc  24240
tccttagtct gtctaggatc ccctcctcca actcctctgg cctggaaatt ccccttcaag  24300
tctccttttg aggagactgc ctcctccaca gagctgacca ccacgccaca tccaggctgt  24360
gttacaagat tgacacacag gctgaacgtg gccgtctccc ctctggacta tgaggctatt  24420
gaggacagga ccccagcctc tgcacatttg tagcctcagt gcttttgcac agggcttggc  24480
cagaatccgg gctccataaa tatttgttga attaatggat gtttggctgc tggggcatga  24540
tttgagcagc agaaatgaaa agcccagctt cctcccagct cagcagcagg caagaacttt  24600
gggacaactt ttccaaagca cttatttcat tcaagaccct ctgtagcttt gcaaccatgg  24660
cggggaacgg ggcccttccc aagaaaccaa gtccatgatt gtttaccctg gacattatta  24720
aacacccaca ttacaggtat ctctgtcatt tggccaacaa tttggtgtgt gatgttaggt  24780
tatttctatg tctgaagaaa acagctcagc tctgactaaa gaaataaatg ataccatttt  24840
tctttcaggc aaccagattc cttggtacaa aaggctccct ggggagaaat gccgggacag  24900
tgtggctcct ctgaggctat ttacatctgt cagcttctct aatctcttgc cttccttcct  24960
ctgtctgttt ccttcccttt gcacagagcc cggcattgag cctggtactt acagggaggg  25020
tggtggagcc atcgtcctca cgtatgcgct ggggatcggg gttggtgggg ggtggccagt  25080
ggcatttggt gggttttttt ttgttgttag aaaccagcct taatttaaga taataactct  25140
ccttgtttgc cagtgatcgc tatttgtagg cacctatttt ccctggtcaa tttggctaag  25200
ataaatcgaa tctaaaaggg aacattttct aaaaatgctg cggggcagtt tgcagaaact  25260
ggaccaagga acatcttcca ggtcacctgt tccatgatgg cctggatgcc cccctcttta  25320
aatgagattg ggggcataga aacagactcc ccagcctttt acgacaacac ctttaaagtg  25380
tcattgaaac ctgggggaac aaggaccctg aagaatcatt tggtctggac tttactgaaa  25440
gattccaatt cctgcatggt cagccccccgc cccctctcca actggtctct tgtcagtgtc  25500
ctcacaaccc ccagcccagc cctggctccc accctccacc caccctgcct gtctgttagt  25560
tcctcgaaag caccagctcc caattatgac gatgctgttc cctctgccag ggacactctt  25620
cttgcattct ctgccatcca tctgatgtcg gctcaaatat cacctcctca gaggccttcc  25680
ctgaccatcc catctaaaac aggattccac tattcttttt cctaaccctt gtcacaagtt  25740
gtcattttat atttgtctca tggcaggtct gcctccgctg cccagttgta agctctatta  25800
gacagggact gagctggctt gttcttgaga tctgagacca cagagcctgg cctgcagcag  25860
```

-continued

```
gtgctcagta tatcagtata tgttggcaac tgagtgaacc agcaaggggt cggtgggccc  25920
tggcacaatt gctctgctac cgctaacacc accactaaga atgtcattta aataccagat  25980
cataagcacc aactttagtt ccaggcagcc ctcctcctgg agtgggagca agagactctc  26040
tccacctcat cccccaggcc tggaaaaatg ttttgagctt tcagttgctt attctttgct  26100
tctttatgca caagttgttt tcctttcctc aatcgcttta tttccctttt ttctagtagt  26160
cacatcttca ttagagattt tatattacaa tatcattcat agactccctt ttaaatttcc  26220
ctggtccttc tgttgctgtc tggggagaca gaggtgcaca ctctgaagtc ggtactggac  26280
ccattcacac tgcccagctt ctgtgtggct gaccagccgt gtgtcattta ataccagact  26340
gtgtggctga ccagctgggt gtctccaacc cctcaggggc tccaccagac ccttggaatc  26400
aacccccctat ggttctccct tgggccccta tctcctgcat gcattcaact caccaaccac  26460
cacgtgcgcg gtttctgttt tctgtccatt tgcctaacgt ctcttgaatc catccatttc  26520
tctccagtgc cacttccctg gtttggccgc cgtctccctt gtcctggcct ctgatattct  26580
cctggcctct ggactcacct cctctaagcc agtcttcctc tgggcgcaga atctgatcct  26640
gtccctcctc tgcttcctgt ggccttagga tggagagcac tcacctcagc caggccccca  26700
ggctaaaccc gatctgatgc tcccagctct ccaagccctt ctcttctcag atgcctctct  26760
gggctcctct tagttcctgc aagtcccgca ctctctccca cctccggcct ttgggcagcg  26820
agtctttcag ctaagtggtt ttcctacatc accttctact ccctcctcgg ctctcataca  26880
tcctcctgga tgccccgctg aacctcctgg gccagttagg gccttcccct gtgttttcct  26940
gacagattgt agtttccctc atattgcctt ggtgaagtgc cctctaactg ccaatttatt  27000
attattattt tattattatt attattttga gataataatc tcagagtctt gctctgtcac  27060
ccaggctgga gggcagtggc atgatcttgg ctcactgcaa cctctgcctc ccaggttcca  27120
gcgattctcc tgcctcagcc tcctgagtag ctgggactac aggcacatgc caccacgcct  27180
ggctaatttt tgtattgtta gtagagatgg ggtttcacca tgttgtccag gctggtctcg  27240
aactcccgac ctcaagtgat ctgcccacct tggcctccca aagtgctggg attataggca  27300
tgagccacta tgcccggcca ccaatttatt atttcttccc ttagactggg agcttcatga  27360
gggcagaggc tggctgtcat gctcaggggt gcagagaaga tcctgactta aaattcctgt  27420
gacttggaca tgcaggagaa gccagacgtg aaggatataa attgaaccaa cttggactga  27480
agatcccagc caggaggatc tgctccccca ggaagggaac tgatttgtcc tcgaggcccc  27540
tgggatagga gaagccacag catcctgttg tttgatcttc ttatcttcaa gcaggcatga  27600
ctcggttcca gaaatacaag ccataagata gacctccaga ctcctagaga cgatctgaag  27660
ctgcagaagc cctccactga aagaccggac ccactgccta ctcctcctgg caggtgccct  27720
ggacaagggc acagacttca cagcgttcaa gtgtgaaggg attgtccttc tccagccctg  27780
gatattaaaa ggtctacccc gatgagccat ggagggactc tgagtgtgtg tgtgtgtgtg  27840
tgtgtgtgtg tgtgtgtgtg tgttggagga gttgcttatg gaaaatattt ttcctgctct  27900
taaaaaggga ctcctgccag gcatggtggc tcatgcctgt aatccaagca gtttgggagg  27960
ccgaggcagg tggatcacct gaggtcagga attcgagacc agcctgacca acatggagaa  28020
accctgtctc taataaaaat acaaaattag ccgggcatgg tggcacatgc ctgtaatccc  28080
agctactcgg gaggctgagg caggagaatt gcttgaaccc aggaggcaga ggttgcggtg  28140
agccgagatc gctccactac cctccagccg gggcaacaag agtgaaactc tgtctaaaat  28200
aaaatttaaa aaaagaacaa aaagggactc ctggctgggc atggtggctc atgcttgtaa  28260
```

-continued

```
ttccaatact ttaggaggct gagtcaggtg gatcacttta gcccaggagt tcaagaccag  28320
cctggtcaac atggcaaaaa atacaaaaaa aaaaaaatta gccaggaatg gtggtgtgca  28380
cctgtagtcc cagctactag gcagactgag gtgggaggat cacctgagcc tgggagtttg  28440
aggctgcagt gagctgtggt tgcaccaccg caccccagcc tgggtgacag agcaagaccc  28500
tgtctaagaa aaaaaaaggc gtgtagcact tccctcctct cccccattat ctcccttgct  28560
ccccctctcc atgtgaggtg ctggcttccc ccttcacctt ttgacatgat tggaagcttc  28620
ctgaggcctc cccagaaacc cagcagatgc ccagcaccat gcttcctgta ccgcctgcag  28680
gaccacaagc caattaaacc tcttttcttt ataaattacc cagactcagg tcagtcagcc  28740
ttccttcctt ccttctttta aattttttaa ttttgagaca gagttttcct ctgttgccca  28800
ggctggagtg tagtggtgca atcttggctc actgcaactt cctcttccta ggcttaagtg  28860
atcctcctgc cttgggctcc caaactgctg ggatcagagg catgagccac cgcatctggt  28920
ctcagatatt tctttatagc aatgcaagaa tggcctaata cgggtgacaa gtcagagttt  28980
gcagggaagc ccaagaagca agcacatcag ctgcctgagt gaggccgtga agggagccgg  29040
tggacaggtc tgcgggcagc tgtagctcag caagcccagc tggccagaac acgggccaga  29100
ccgggagcca gcagcccgag aggtggattg gccaggcata tctctgcctc agtgtcatca  29160
cggcacatga ccgtgacaac cccctgagag tcaggatgct gcttcacttt tattttccaa  29220
atctcatgca agctcctctt ttgaccaact ctaccctaga cccctctgga gaaggggttt  29280
ctgggaagta ttattcccag attagccaaa tggacaaaac acaaaccagc aggaagacca  29340
gccccactca tctctctggc ctcctcccct ctactcccta cctgtgccca ggccctaaac  29400
tgtttacagc tccccattgt gcctctgccc atgctatgtc ctcaatttgg gatacctctg  29460
ctctcttctt tagctagtca atgctactga gccctcagga tctggcccca gagactcatt  29520
ccctgagaca tcttccctct ctgagaactc ccctctcctc tgtgctcccc aagaactggg  29580
tacaaaccca cattgcaact cctgttaccc accgagtctt cctcctcgcc agggctagga  29640
atctcttggg aaggaggact gtgtctgtgc tggccagcct cccagcagct agtgctggga  29700
aggcagggtt ctcaaggagg gcgcaatgcc ctcctggcat ggaaaccact aaaccaccgg  29760
tgcagtgtgc ttcagaatca cgtagggaac gtgttacaca ttcagattcc cagtcctcac  29820
ctccccgaga ttttgatttg gtagttctgg agctagactc aggaacctgc atttttcttt  29880
tttttaaatt gggcagcctc tagagccaga gtaggctcag agactcccag gaaccagcat  29940
tttttagcaa acactgtgag taattcatga gcaatttgtc taccacatca ggctgactct  30000
gacagagctg aatctttttt tattttttta agagtttaag tctaactctt ttcatttttt  30060
ttaaccttag tttctagtta gattagaagg tctgtctctt ttatagataa aagctctatt  30120
aagtccttat aggtcttatt ctgcttttat tggaggccct gaagcccaga ctatgggatt  30180
taaaagtctc tgaagggtga cagagaggac cagagagaag gcagtagagt cgaggcatgg  30240
agcttgccga gggcctggcc gggacagaga ggcccagcaa cgccttggcc ccaagaaaat  30300
cttcttgtct ttctggaatg ccgagaagcc ctgaggaggt cctgggtggg aagagctaag  30360
ccatagtagg tgtgctgagg cccatgggag gggactcagc atgtgcctca gtagcccgtg  30420
acgcgggacc tcccacgcgg gtctcctgag gagctggaga gaagcagatt attcctccaa  30480
catatcagtg agggcacctt gggcccaact ggctggggag gtggggatgt gtggggtggg  30540
gacgggatga cagcagagga gctggcacta ggacaggagc cacagcaggc tgggtaccac  30600
```

-continued agagtggggc cttgccagtt tcgacatctg tccccagtcc ctgcctggtc acccaaggaa 30660
tgtggcttta gatttgtggc tcgggacccc aggagaggga gagggagcct ctcagcctgt 30720
ctagatcttc ttggccaggt ggtgggaggt ggcttctccc aggggccccg ggggctgctg 30780
gatgagacgc tgactcagtt atcttctgag ttgagccatt gttttattta aaaatacaga 30840
gcaaataaac ccacaatatc actccacccc atggacacaa gcactactta tatttaggtg 30900
taacccottc cagtcttgtt tcctctgtgt atgtgtgtgt gtgtgtgtgt gtgtgtgtgt 30960
gcaggcacat gcatgtgttt gtttgtacca taggtccata aagttctgta ttctgtatga 31020
caccattagc attttctatg ttgccacaga gtctttgtga ccatcattcc caaaggctgc 31080
ctggtctact gagatgatgg gccatagttt ccttaaggat cctttgttgt cttctgaccc 31140
acacaatgac actaagtttt acctggggcc agactcccgc tccctgaagt cagccctgtt 31200
caaaccccaa atcttggccc tctcaatcca gtccttcact ccctgacctc ttcctgcatt 31260
cttctgcctg ctccagactt tttgatttac ctcccaattt atgtatcaca ctcaccaccc 31320
ccctagatct gacagcttag ataatgcctt cttgaatact ggaaaaacct gaattgccat 31380
cagtttttga ggttcctaat atactataaa atgtaaatat gcctaaagag ggttataaag 31440
attgtcagct attttaggct gggtgtggtg gctcacacct gtaatcccag cactttggga 31500
ggccaagggg ggtggatttc ttgagcccaa gagttcagga ccaaccttgg caacatggta 31560
aaatcccacc tctacccaaa atacaaatat tagccaatct cttaacccag tctcaaaaca 31620
aataaataga ttaaaattaa aaataaaaga ttgtcagcta tttcagtgtt tacactgaac 31680
aaattaatat tcctttcacc agtaatgtgg tataacattg ttatgaaccc ccaagaaatg 31740
tacaaataag gtaccacacg tgataccaac tctccagatg tggagacaag gtcaaggcca 31800
aatgacaaat gttctctttg ggtcttgtca gagtcactct ctgagactaa atatgcaatt 31860
gcacttgaag aaaaaaatag cagaagtcta aatttgagac ccattgagac ctgagccaat 31920
ggctttccat actccccttg tgtctgcacc caattaaaaa caaaataaaa caggttatcc 31980
tggctgcttc tctagaactg tcccttggcc taccttgtca ggctgagcct ggcacctgtc 32040
ctcagatctg atgccttgtt gcctggagtg cctcccccac ccactcaacc ctagctcctg 32100
ggatcctgcc ttgggtcagc ccccttggct ggtaccagag gtgtttggaa cattggatgg 32160
cttctaatgt tttcactatc gtaaatgtgg tggatgggat tctctggttc tgtcagctcc 32220
ttttccctct ctatgctcat ccttactgag gagggaacat tttaagctca cccctactga 32280
ggagggagtc ttttaacctc ataaatcatt agagtgatac atcaagaatc cactctaagc 32340
agagaagtgg attatctcaa ggcccctcca ctcagaagat gggaggatgt ggagcaggtg 32400
gttctatttg ccttgagcac aagggccaca gggagcaatc cagatttgct ggctactgac 32460
caaaggggat gaagctcctt ttctaagaga agaaggttag acaaggaagg agatgagaga 32520
gatcaaggga aacagagatt actgggcatc atggaagctg ttttctggaa ggcaacccag 32580
tgggaagggt ggggacgctc tgcatcatga atgagtggag gtgatacttg ctggcagtag 32640
attcagcttt tatccatttc tggccacgga agggcagaat gtggccatga atgactttgc 32700
tcaaatacat ttttctctac ttaggattat ttcttttccc caagggggca catttctatg 32760
gctcttctca tatattgctg gattggtttc tagaagatgg gtatcacttt acaatagggc 32820
aagagaggat cccatttttg gcacatataa gtatgcaata agtaagtgat taatagcaag 32880
cagaacagaa aatccccagg ctgtggggca gtggtgctgt tgctggaggg agaacatcca 32940
gatctttaac ctctggggcc acttcaaata cacttgccca ggatttaagc atcattagta 33000

-continued

```
gatgttgctg agccaaatcg ataaatggat atggcaaagg ctgtgtagat tttagagcag 33060
ggcagatggg atgcaatttt caggaatcct acaaggccta gatgtaacag tgtgatcctc 33120
agggcaggac ttaattcagg accctgccat cagaagtgaa atgaagcact aatatatccc 33180
acgacatgga tgaaccttga aagcatgcta agtaaagaag ccagaccaaa agaccacata 33240
ttatatgact ccacttatat gaagattcct gcagcctcta cgctccacca ctgataactc 33300
cctccagatt caaattcctg tgggcctgcc tgctctagct ggggccggga tgggaggtac 33360
cagaacccca caactgacac ccccaacagg gctgtcagga gagaggtaat ttgctcaaag 33420
aaaaatttag atggaggcaa aagccacagc tctccactaa ccacgctgct aaaactttgg 33480
gggctgctat gcaccagaac tagttgaaac catagagcca caggccaaat ctggcccacg 33540
gcttattact ttacagccca tgaaggaaga atggtttttg ttggtgttgt agttttgaga 33600
cagagttttg ctcttgttgc ccaggctgga gtgcaatggc gcaatctcag ctcactgcaa 33660
cctccacctc ccgcgttcaa atgattctcc tgcctcagct cccaagtagc tgggattaca 33720
ggcatgcacc accacgccca gctaattttg tatttttagt agaaacgggg tttctccatg 33780
ttggtcaggc tggtctcaga ctccctgcat caggtgatcc gcccgcctcg gcctcccaaa 33840
gtgctgggat tacaggcatg agccactgcg ctggccggaa gaatggtttt tacagatgaa 33900
tatctgcaat tgatttgatg acagggaaca ccaactttga atcccaatta agtaaaatgt 33960
tgccctccca atcctgcaaa aaacaaaaca aagcaaaaaa caaacaaaca aaaaaacaaa 34020
aaaaccaaac acattcttct cattagtaaa cctgcattac aaaaaactgt tcctggcagg 34080
actcagtgac tcatgcctat aatcccagca ctttgggaag ctgaagtggg aggatcgcat 34140
gagcccagaa gtttgagacc agcctgggcg acacagggag acctcatctt tacaaaaaat 34200
gtaaaaagta gccagtgtgc tggtgcatgc ctgtagctcc aagttacttg ggaggatcac 34260
ttgagcccag gaggtcaagg ctgcagtgag ctatgcattc aagcctggga gacagagtga 34320
gaccatgtct caaaaaacca aaaaccaaca aacagaaaca accctgttac caattattat 34380
tattatattt ttcaatttgt caataaaaat gtttggaaat ttgtttaccg tcttatcaag 34440
taagtgctta cctaacatcc tcagttttga ctcttggcct gcaaacccca atatttacta 34500
tctagctgtt tactgcccct tactctaggg cagtgcctct caaattgtgg tgatcataga 34560
atcacctgga gagctgttaa aacagattgc tgggccgtag tcccagatac tctaattcag 34620
taggttaaac atagagttta ctatatgaca cgtcaattcc actcctaggt atatacccaa 34680
gagatttgaa aatatgtcag tacaaaaact tgcacatgaa tgttcatagc agcattattc 34740
ataatagcca aaaattggaa acaatccaat atccatcaat tgatgaatgg atatacacat 34800
tattgtatat ccatatgagg taggaagtga gactcgactc cagagatgaa gtcagacacc 34860
aaactgcgga ctagctaaaa caaggaaggg gcagaaccag ctttccataa gatatgccca 34920
ccagtgagcc atgtcagttt accattgcca tgacaacacc tgggagttac cactcctttc 34980
catggcaatg acccgctgac ccaaaagtga ctaccccttc cctagaaatt tctgcataaa 35040
ccacccctta atccatatgt aattaaaagt ggtataaata tgactgcaaa ataccctgag 35100
ctgctactct ttgcctatgg ggtagccctg ttctgcagga gcagtcacag agctgtaacc 35160
actgctgctt caataaagct gtcttctacc tctggcttgc ccttgaattc cttcctgggc 35220
aaagccaaaa atcctcatgg actaagtccc aatttggggt tcatctgccc tgcatcacat 35280
acaatagagt attatgcaat tctgaagtga aatgaagtac tgatatatcg cacgacatgg 35340
```

-continued

```
atgaaccttg aaaacatgct aagtgaaaga agccagacca aaaggccaca tattatatga  35400
ctccacttat atgaaatgtc cagaataggc aagtacatag agatggaaga gagattagtt  35460
gttgtcaggg aatgtaagac agtggaagtg gagagtgact gctaatgagg acgaagtttc  35520
ttttttctgt catgaaaatg ttctggaagt agtggtgatg gttgtacagt cttttgaata  35580
tactaaaacc actgaattgt acactttaaa atggtaaatt ttacggtatg tgaattatat  35640
ctcaatgaga aaataaataa ataagacaca caacccatga cattggacgc aatctggaac  35700
tagttctcag aaaatgattt tgcttgatgc ataatatata ttaaagaaaa aagattgcta  35760
cttctttgag ggcaattaaa ttttttcgct agcatctctc tacattttct ttctcatcaa  35820
agtcaatgag aaaacagaat tcctgaaaag aaactttgct actaacaatt aagacctaaa  35880
actatcagta agttaaggac acgacaatgg ggctcttgga atcaatgaca gactcggacc  35940
ggctgtttta actgacttat catgaaatga atgatgacag aaacaataca atggaaatta  36000
tttttcatgg aaagaattca tggcaccctt tgtgtttgtg actggaatga ccacggatgt  36060
ggttcagtct gaatgtgtat ctgcagccac aaaacagatt tgagcttttg tcttgcaaaa  36120
tccatctgaa catattggct gcattcgctc agcccagaga ttaagtcatc atcttgggca  36180
gggtttcagt gaaggctaaa tcagatccag ggagagagag agcaggcagt gccggtgcct  36240
atcttgcagg ggatgcccca gaaaggctga aatacaatgc cccagtggct agctgttgct  36300
ggaaagaagc aagctggagg gcacagaagg tttaaaaaag gggctcctg aatgtcactg  36360
ggttccccaa acctccaaga ggaagctgta cccagattct actgccatcc tcttacggtg  36420
gaaagcaaag gcttgggctg tgtatccctc caggactcct ccatgagccc tagtgtctgc  36480
agagggtgtg gtccaggaag aagcaactga ccttctgctt ccagaagtga ggatttcctg  36540
tagctcctag gcctggcctg ccctgggatg gctccaaccc taccaatata tgtgagttcc  36600
tttatagctg ctgtttattt ttgaaaggaa gcatctttgg tgaccagcat cacatgtcaa  36660
agttgagagt gcatgaccaa aagatcctgt gactcaggga gagctctaga tagcctttat  36720
ctctgcccaa ttattcttcc agaatctcag ttagtgatcc tgtcattcat cttctcataa  36780
accttctatg gctccccacc accaaccaaa ttaaatccaa gtctggaaac aggcattcat  36840
gaatccagct ctgcaataca gcagtatata cttttgcagt gtcaactacc tggagttagt  36900
acagactcca caggttaagg acatagtctt caacaagact gccctcactt cagagacccc  36960
acataatatg gggtccccag gctacctgca tttctgatca actggctaca aatttggggg  37020
ttcccacaac ccctcatatt tgataatttg ctacaatgac tcacataact cagcaaagtg  37080
ctatacttac cattacactt ttattataaa gggtacaaat caggaccagc caaatgaaga  37140
gatccatagg gtgaggtctg ggaggatccc aaacacagag cttccatatc ttctccccat  37200
ggagtcagga tgtatcaccc tcctagcaca ctggtgttca cccaccagga ggctcaattg  37260
agccttgagg tccagagttt ttattggtgt ttcatcacga ggcatgattg atcaaataat  37320
tggccatgtg attgaactca atctctaacc tccctggaag tcaggctgat ataatctggc  37380
tcaaaacccc aaccctctaa tcatttggtt ggttcctaat ggctagtccc catcttgaaa  37440
ctatctaggg gcccaccatg agtcaccttg ttagtatgaa ctcaggcatg gtcccagtgg  37500
ctcactatga ataacaaaga cattcctatc acttgggaaa ttccaagggt ttagaagcta  37560
cctctcagaa acccaagaca actggagaaa ttattatgca acaaatgcca gcctatcttc  37620
accacagtgt gccccatgac cccttttcta tgctcttggc ttaggtcagg cagagcagct  37680
tgcggctctc catgtggacc tggagatttt tcacctcgct tcctttgctt gcactgattc  37740
```

-continued

```
ctttgtctgg aattgcctcc atgagggtac ccatccttcg tgtagatata actgtcctca  37800
ttttagatga gaaagttgag gactagaaga tgaagtcact tttcaaagac aattggatct  37860
atatgataaa accaggccat aaatccaggc ctatctgaag ccccaacctg tgtgatccca  37920
cttccccatg ggcagtagga ttggctgata ttattgaaat cccttaaaga tcattctgta  37980
attattctcc catgaaaaaa tggcttaaag ggggcaaaac ttgccatcac taacaatgcc  38040
accttgggga agctaaactc ccaaattaac agataccctc aactgcaagt aatagaaagg  38100
cccacaaaaa gacccttaga ccaggagctg gcaaactttt tctgcaaagg gccaagggcc  38160
agagagtaaa tatttgaggc tttgcaggcc ataaggtctc tgtcatgact atgcatccct  38220
gccattgtag cactaaacaa tatgtagaca atacataaac aaatgggcat ggctgtattc  38280
caataaaact ttatttacaa aatcaagcag tgggccagac ttggctcctg ggtcatagtt  38340
tgccaaccct tgtcttaaac caggaggaca tttattcacc atataacaag aagtctagaa  38400
atagggtgga tccaggtgag ctactcaggc agctcagcag catcttcaga tcctaggttc  38460
cttcctgtta tttgcagatg acaacatcca gaaacagaaa agttcatgcc tccttggtca  38520
gaatagttca caggctaatc cctggctaat gggaaaggag ttatccagat tgccttagac  38580
aaatggtctc atccctggct gcaacattag aatcacctga gagcttttaa gaaacacctg  38640
ggcccagctg ggcacagtgg ctcacacctg taatcccagc actttgggag gcggaggtgg  38700
gaggataatg aggtcaggag attgagacca tcctggctaa caaggtgaaa ctccatctct  38760
actaaaaata cagaaaatta gccgggcgtg gtggtacgca cctgtagtcc cagctacttg  38820
ggaggctgaa gcaggagaat ctcttgaacc tgggaggtgg aggttgcagt gagctgagat  38880
tgtgccactg cactccaccc tggcgacaga gagagactcc gtctcaaaaa aaaaaaaaaa  38940
gaaaagaaaa gaaaagaaaa gaaacacctg ggcccctacc agagttttgc atttaatggt  39000
tatgaggtgg ggccttgtca ttgatatttt ttaaaaccat tcatagctgg aaaggaaagg  39060
cattggcaga ccagtcaaaa ctcactgcac gcaaaggcca attcatgatc accatcaaaa  39120
aagtatttta gcaaggagga agaagggtct attagtccat tttcacactg ctaataaaga  39180
catacctgac attgggcaat ttacaaaaga aagaggttta attggactta cagttccatg  39240
tgattaggga agcctcataa tcatggcaga aagcaaggag gagcaagtcc cgtcttacat  39300
ggatggcagc aggcaaagtg agaatgagga agacgctaaa gtggaaaccc ctgataaaac  39360
cataagatct cgtgagactt attcactatc acgagaacag tatgggggaa actgccccca  39420
cgattcaatt atctcccacc aggtcctccc acaacacatg ggaattatgg cagcacaatt  39480
caaaatgaga tttgggtgca gacacagagc caaaccatat caaagggcta aggctgaagg  39540
gccacatctc aatgtgatgc ttttcacttg caaaatggaa atcaaggtag gacctacttc  39600
aaaagtccct gcaaaattta aatgaagcag catgcctggt acagtgcctg gaaaaaataa  39660
gcactcactg cattaacagt tgattgctct taatcattat gaagtcctcc tagatgtctt  39720
atgtacattt tagagaatgt accaattgaa tgatgttggt tttttatggg atttgaaccc  39780
cagcctttcc tcagctatct ggaaaactgg gagtggcagg tatttaaaaa aaaatacaag  39840
tgactcacca caacacttcc ctcccaaata tttcatgtaa gaacacagca cagagatcaa  39900
ttgatctcta ctctctcctg aaaagcatca tggcacaaac actttcctga gggccgttta  39960
gaagcctcac tcttccttag tcatagaaga agactttctc ccccgttccg ctctgggcca  40020
tcttctcccc gtttccccat ctatttctag ccacttttca aagcaaagtg ggaaatctct  40080
```

-continued

```
cttaatgctc cttttcttcc ttctactagt tttctatggc tgctgcaaca aattaccaca  40140
aacttagagc cttaaagcaa cacaaattta tgaccttaca gctctaaagg tcacaagtgt  40200
aagatgggtc tcatggggct aaaatccagg ttccagcagg gctgtgctcc tatctggaga  40260
gaccacatat cctcgccttt tgcggatccg agaagtggcc tgcattcctc ggcttgtgac  40320
cccttccacc ttctctcatg gcactccctt gactcaccct tctaccccta tcttccacat  40380
ctaaggaccc ttaaatgtga tgacactggg ttcccccaat ccacctggat taatctggat  40440
aatccagaat gatcttcaca tgtcaggatt cttaacgtaa tcatacctgc aaagtccctt  40500
ttgccacata aggtaagata aggtaacgtt caaaagttcc agggatgtgg atgcgaacat  40560
ctggggacca ttattctgtc taccacattt tgtgatctct aatgctcccc attcctctcc  40620
agcctctcgt tcctcctttt cacctatggg gctctgtttg tcctctccca tttgccgtcc  40680
tgcaagatcc agatggcctt tcctgaaata gaggcacggg tgtcctggca tgtggggctg  40740
ttgggaggtt tagattaatg tttatgagtg cttagaacag tgtctggggc acagtagggc  40800
tacaaaagtg gttgttagct gccactgttg ccattaacgt gctcacaggc ctgccctcct  40860
tgggaatggg acttctactg gccttcctaa agggtgccta ctttttttta agcttgaaca  40920
attcaaaaac agccagtaac ttggaacagc tttctagaaa ctatcaacca tggctgggcg  40980
tggtggctca cacctgtaat cccagcactt tgggaggccg agacaggcgg atcacctgag  41040
gtcaggagtt cgagaccagc ctggccacca tggcgaaacc ccatctctac taaaaataca  41100
aaaattagct ggtcatggtg gcgcacgcct gtaatcccag ctactcagga ggctgaggca  41160
ggagaattgc ttgaacccgg gaggtggagg ttgtggtgag gtgagatggc cccactgtac  41220
tccagcctgg gccgcagagc gagactccat ctcaaaaaaa aaagaaagag agaaacttta  41280
tcaaccagtg tttcttcaag tgtccaccca catcagcatc tcctggggtg cttttaaaag  41340
cacatttgac tttagttctg ccctctaaag tttgtgaacc tcagtctgga actccagcat  41400
ttgggggttt ataatttgca accagaacaa aaaagaaaag ccccatccca ctgcctcact  41460
cagcccctct gctgctaaca acacactcac tgcagggcca ggggctgaag tctcccttga  41520
aggatgttcg gcaaggctgg ggccttcctc agggacccgc cattgaatgc cagcgaaggc  41580
cttgtcccaa gaacaggggt tgaaggcagg aaatggatgg gagggaggta gacagtgact  41640
atctgaccaa tggcatttat ccttttggag gtccctgacc ctctcaagaa cctggtgaaa  41700
gccaaaggtc tcttctcata cctgggcacc aggtatgggc agctggcccg atgactactg  41760
agaggaaaag aggaagctgg agctcccggc cagaccatgg tccaacctgt agctctgctg  41820
gccttagtat gagcagagga tgcaaaagcc agaaagaggc ccaactgtca aagcttcagg  41880
acacgcgaag tagagcttcg tgtgagctca gctcccaccc tgggactcct cagttggtgt  41940
taaggaaact tctaagccct agaacctgca aagaccccag gccctgctgt ttaatgaatg  42000
gaaagaatct tcttccctcc ttttgaggca ttccaggcct ttccagagcc cacccgatac  42060
ttaaataagc accccacggg gatggtgtgt atccagaact aaaataaact taaataatat  42120
cccagaaaat tataaattat gtatttagga atcggaatgt gcgaggcagg gttttctctt  42180
cctctattat agctttcatg aaagggagac aaataataaa gctcccccgg gctaaagtta  42240
gagtcgacat atagtttaca ccagaaaata tacacttagg tatccatttt gaatgcatgt  42300
acttccagtg caaaatcctc tcagtgacca caagctcctt aaagccaaag ccaagagcag  42360
ggaggtctct gtgtggtcca aatgctcagg aaggaaggaa agtagcatct attgaacgtt  42420
taccacccac ctggcacata actcacgccc tcttacaacg tcctcaaaac tacactgtga  42480
```

-continued

```
aattttttttt ttttttttt taggcagagt ctcactcact ctgcactcac ccaggctgag  42540
tgcagtgatg cgatctcggc tcactgcaac ctccgcctcc caagttcaag caattctctg  42600
cctcagcctc ccgagtaact gggactacag acatgccaca ccatgcccgg ctaatttttt  42660
gtattttttt tagtagaaat gaggtttcac cacatgggcc aggctggtct cgaactcctg  42720
acctcaggtg atccatcccc actttggcct cccaaatgct aggattacag gcatgaccca  42780
ccacgcccgg tgaaatcaat tttattagct ccattgttca ggtaggggaa aatgaaactt  42840
ggaatggaca agtaacttgc ccagcattgt ggggaacaat accatgagcc tgaaaccaat  42900
ttccctaatg atttatttgc ctagtcacct atttcatctt ttagcatcct agttttccct  42960
aatcttttgg gtatttgaag aactctatta aaagctaatc taaagatata tatttttggc  43020
agagtacggt ggctcatgcc tgtaatccta gcactttggg aggccgaggc aggcggatcg  43080
cttgagtgct ggagttccag accagcctgg ccaacatggt gaaaccccgt ctctactcaa  43140
aatacaaaaa ttagccaggt gtgtgagcag gtgcctgtaa tcccagctac tcaggaggct  43200
gaggcaggag aatcgcttga acccaggagg cagaagttgc agtgagctca gatcatgcca  43260
atgcactcca gcctgggcaa caaagcaaga ctgtctcaaa aaaaaaaaaa aaaaaaaacc  43320
cacagatgcc cgggcttcgc cccagaccaa atgaacccaa atccctcagg gtggggccaa  43380
gcatcagcgt tttcacctat tctccaggtg cttccacacc ccaaggtctg aagcccactt  43440
ctctatgaca tctcttggag gcgggttgtc tgcatgtctt gtctcacctc ccaatgcccc  43500
tccactggcc cctggggact cagaatcaag gaggggttta ggagtcccag tcactgcctc  43560
tggatggtta ccatacctct tgccctctat ttctgccctc attatagaga tggtgagtgt  43620
ggctgcccag ggactgctag atgattagag ctcaatcatt ccttcccaac agagggccat  43680
tttttcttga gaagtgcagg tttgctggat taacaagcta ccctggcttc ccaggggtta  43740
atgctgctcc ctcagaggtt gcctgtctga gggtgctgac cccaccgtgc tcctgttggc  43800
ccaaggagtc tcatgctcag ctggacattt atgcctctgc tttcctggcc tcactaggtg  43860
ggtgggggct gcttctttgc aatctggtgt ctcccctgct gggtgacctt gggaaggtct  43920
cttaacccct ctgagcctta gtattcccct gcaaaataga aaggatggtg cctacctcag  43980
aaggatatta tgaggattaa ataggtctcc acgcactctc agaacaccct aagtttttca  44040
ttcaaagtat gtatattaat catcgtttaa tgtttgtctc tagctggact aggagaacca  44100
ctagggccag gcctgtgtcc atgtcccaga atcttaacac agggcctggc acctcgtagt  44160
tgctcataga ccccttgttg aataaatgaa taaggatggg cagggcaagg aatggagtct  44220
gttgtcgatg agtcttaatt cctttccttt acttccctaa gatacttcca gaacaacctc  44280
cgcagatgta tattcttttg ttagcagtca tgcatgtcag caacttcctt cacccaactt  44340
ccttcaaaca agggtcccca ccacacactc actggccttc tcagtggtct tctggtggga  44400
acagatgtgg cttcattagt ggccgggcag aagcatggat atcagagact taaggggtac  44460
caatccagca ggttaagatg gcacagctat ctgtggctgt gtaacaagcc accccaaagt  44520
tggtgacata aaacaacaac cattttatta ggctcacaga ttcagaggtt taagaatttg  44580
gccagggccc aacagggtgg cctgtctctg ctctccaatg tctagggcca gggttgtgaa  44640
gactcaaatg gctagaggtg gctggaaagg ctgagggctg aaatcacctg ggggcttctt  44700
ccctcacatg cctggtgcct ggactgagac atctcagtgg ggactgtcaa ccagagtgcc  44760
ttcacatggc ccctctgtgt agtttgggct tcctcacagc atggtagcct tgggatagtt  44820
```

-continued

```
gaacttttta cctggaggct caggactcca aaggcaagtg ttccattaac aaaggcagaa  44880
gctgatggcc tgagatgact taggcttgga agtcatacag catcacctct ctgtactcaa  44940
ttaattgaag cagtcataac cctgccaata ttcaaagaaa agagagaaat agaccccaca  45000
gctcaatggg aagaccatca aagaatttgt ggccatattt taagactatg acacataccc  45060
tgctggttgc agttgcatgt gctagaacct gagacagggc ctggctcagg aggagggctc  45120
aggaggggct taccaagtcc caggctcttg gcccaatgct gtgtggcctt aggcacactc  45180
actcatgctg tgtggcctta ggcaagtctt ttccaccttc ttgacctccg tttccccatg  45240
tgacattcag agaataaaat gctgcaagat caacctctga tatggtcagg ctttgtgtcc  45300
ccacccaagt ctcatcttga attgtaattt ccaggtgttg agggagagag ctgctgggag  45360
gtgactggat catgagggtg gttcccccat gctgttctgg tgatagtgag tgagttctca  45420
ggagatctga cggttttata agatgctctt ccccccttcac ttcctacaca ctctctctca  45480
cctgccacca tgtaagacat gccttttccc ttccgccatg attgtaagtt tcctgaggct  45540
tccccagcca tgtggaacta tgagtcaatt gaacctcttt tctttataaa ttacccagtc  45600
tcaggtattt ctttatagca gtgtgaatat ggacaaatgt aactcctttc cttgttgctg  45660
gagaccctca ccatcatgca catacacagc tcaccaggga gacagagatc ccaatagggt  45720
ggggagcagg caccaacaga atcctcccaa ccagttggga aaataggagt gcaaaggaga  45780
ctgtgtccac tgtttatctg gaatgctgag tgggtggagt cctgttctat catggcaccc  45840
agggtcaatc agaacttccc tgggtcccta tagtatgagg ggccagctag ttttccaaca  45900
cttccaagga aggcatggaa ggtgctgggc agggcctggt gggctgggag ggcctcagct  45960
gcagagtcag gaggacacag agtgtgtggg ctaattacta cagaaaaaaa agatgtggat  46020
ttagcagaca ccaacaaaat ggggtgacca tgcccaagag gttagtgaag acagatactg  46080
atgaccatgg ctcggctctc cccctcctcc agctccccct cctatggcac agaagccact  46140
agaactaagt agatgacctg acaagggaag ttgaggcaac tgggaataga ttgaatttaa  46200
gtctgatatg accaacttca gctgacattg attattaaat aaacttaaat gtttttggca  46260
gttggacaga atggggagtc tataggagaa acagaaaaat gaagctgtgt ttttagaggc  46320
cccaagattt gtagctaatt catttcttct ttctgcttag caagggactg gctgagatct  46380
caggcctttc cagctgtgat atccagtgtg gctctgatcc ccaggcttta tgactctgct  46440
gctgctacca ctgcatccca ggggactgcc aaagtgtgtg caggtcacgt cccagtgggg  46500
ctctgcctga cccagcactg aaaaatggtt taccccctgag tcattcagac aattgatatc  46560
gttgagaaac cacggtgtgt aggccctagg ctgggcactg tgcctgcttc tggggacagt  46620
caattgaata agacactggc ctcatcttca acatgtttac aatcctgtgg cagcaaacaa  46680
ttagaagcca ctggttctag gaccttaatt aggaatttct cctgattact gctttcgtta  46740
aaaagacatg agcacatctc cagctaatca gtcaacaaat atttattgag cacctactat  46800
gtgccaggct ctgttttagg tacttggggt acatcagtgg aacaaataaa cagtagaaat  46860
ataaataaat gagccttgaa ggcctgcttt tatctctctg cccatctcgg tcctggggaa  46920
ataaatgtgg gtgtttcagg ccgaacatcc aaatgatcaa cttttttttg agacagggtc  46980
tccttctgtc tcagggtctc ctccttcacc aggctgaagt gcagtggtgc aaacacagct  47040
cactgcatcc tcaacctcct ggactcaagc aatcctagca cctcagcctc ctcgtgtaga  47100
tgggaccaca ggcatgtgcc accacaccag gctaattttt aaattttttg ttaagaaaag  47160
gtctcaccat gttgtccatg ctggtctcaa actcctgggc tcaagtgatt ttcccgcctc  47220
```

-continued

```
agcctcccaa agcactgaga ttagaggcat aagccaccgc aacaggccat catcaactta  47280
attctaaggc atttcccacc cccaccctca ttccctgaac tcccatcctc ctttgatcct  47340
cagtcaaggc caacttcgaa aactccttgg taatcagctg ggagcttgca ggtcccagac  47400
cttcagcagc ttgtgggaat gtcccatgag gaactttttt tttgtcaaaa gaatgccagg  47460
agtttaatta ctgtgtggcc catggaggtg atttccattt atcagccaga acccagacag  47520
atcctaggaa ggcccatcat gtgaggctgt ggccgccgtg gcctgctctc tccagcaaag  47580
gataaccctg gggcctgtgc cctgggcagg ggcagcagga atgctttgaa tgcttcccct  47640
gcatgtggcc ttgggtttta ccaatggcta cagcgggtgg tttaattaat aaatgtccac  47700
tgcttgtcat ttatcattag caaaacagga ggggttggag gtgggggcag ccaagagggc  47760
agggaagctt tctccaaaca aggtgcaccg ataaattaaa gctttatcca tcagtctcac  47820
aggctggctg ctgttgtaca gccccacgtt actttcctct ggttcagagg ccaatctcat  47880
gtttctgaag ggctttgcag cagctgtagg gggtttcatc tatgactgtg tttcccttgt  47940
caaatctcag caaaggactg tgttgcatgg tatggaggag agagagcagc atgtgcccag  48000
gggactggtt cccatcgggg tctcaaactg aaactctatg gtggatccag cctgaggcta  48060
gatttttgtt tggctacaat ggcatttgac aaattggaaa tttttacata aaaattcaag  48120
tttctggctt ctattgaaaa agcaaggcga ggcaaaacca aaccctcttt ttcagtatgg  48180
caacaagcag ctgatggcca gcttaggcag gcagggcagc catgtgaggt tgtgtgagtt  48240
gtgcactgca caaaagcacc tagcagaagg tgcaaatgga ggctgaatcc aggccaggct  48300
gtctttccag cagaagccct gtaggcagga tgcaggcctt ccacttcccc accaccgctg  48360
acaatccctg ctactttact cacctactcc attcatttac gttacctatc tgagcttggt  48420
aagcacttgg tgttttcatt cctagtatac aatcagggta ctatttcgtc ttctctatgt  48480
gagaaatgcc tcttcaacct tcaaggctca gctcaactca tagaagctcc ctggtggtac  48540
cctcctctgt attttctcaa cagcaaccca cactgctatt atagcactcg gcacaccctt  48600
gtgctctaat ttgttagcgg atcctgtttc ctgcagactt tgagcccctt gaagatagat  48660
cctaccattt ctacttttcc tctgcctggc acataatggg cactaaatca gtagggctga  48720
atgaatgggt ttatggccaa gtgtgcccca ggcaagggag gcctccaaga ggctgcctaa  48780
aatcctaagc caggaaggtc aggaaagggt gataaaaggt tttaactttg gggttttgaa  48840
agaccctaga ctcctaggtt tcttctcttg gacactctat ggggcactta aaatcctgag  48900
tcatgctgat tttgggattt cctctgacca gaaagctgag tgtttaagac ttttcacatt  48960
cgcttgtttt gttgcaagga gctagtaaga gctcagcctg gcctctccca aaaccactca  49020
taaaggagca gcagacatgg tgcagccaac agagacttca gggaacaagg atggctgtga  49080
cttgtgcaga gcaattctgg gatcctggaa cctgaaatac atctcctccc cagaaattta  49140
gcctgaaatt tctttaacca agatcaaaag gtgaaccttg cttctaataa tcagagagga  49200
ctgaatgtgt tctgcgaagg agagacacac tggtctaaat tatttccaac taacgtgtaa  49260
atgactgata gaggtttttg gttttttttgt tttgtttttg ttgatttttt tttttttcct  49320
aaatgctagt ttggtgagaa ggtaaaaaga gttataaaag tgcaacacca aggcgggtgg  49380
atcgcgaggt caggagttcg ataccagcct ggccaacatg gtgaaacctc atctctacta  49440
aaagtacaaa gaattagctg ggcgtggagg cgcgcccccg taatcccagc tcctcggagg  49500
ctgaggcagg agaatcgctt gaacccggga ggcggaggtt gcagcgagcc gagatcgcgc  49560
```

-continued

```
cattgcactc cagcctgggt gacagagcga gactccgtct caaaaaaaaa aaaaaaaaaa  49620
aaaaaaaaaa aagcaacaag ccctctcgct agtctctcct ttgtcgtcca gacccttcgc  49680
ggccgcgggc gttcgtggtt cgtccccttc cgccccctcc gtcccctccg ccctctccgc  49740
cgcgctgact cgccgcttcc tcctgggctc catcgcccca aacccgggac tgcacttccc  49800
ggcagacgcc gcggccaatg agggaggggc tgaggatttg gcggcggcgg cgctccgaga  49860
gtcggggtga cggggctttg tgcgctgagg cggaggctgc cagcacggag gcggaggccc  49920
aggggctgtg cacaggtcac cgcggagaga cgtgcgattt cccagccgag cgccgaggac  49980
cctgctgccc aggccaggct gccagccgta ggctcctctc tggcggcagc gggggcgcgg  50040
cgacacccgt ctctcggcct cccctcccca ccccacctcc ggagccttcc tcctgccgca  50100
gcacgcctgg cctggtccgg ctgtggccct cctcgatctc cgtgtccctc ctgtgatcgc  50160
attgagacgg ccgggcggtt agaacgggac aaactgaagg cccgatgaga gaaagggaaa  50220
gttaagaatg ctggagcaga acaatggatt tctctttctc tttcatgcaa gggatcacgg  50280
gaaacacagt tcaacaacca cctcaactca ctgactccgc cagcatccgt caggaggatg  50340
cctttgataa caaaagtgac attgctgaag atggtggcca gacaccatac gaagctacct  50400
tgcagcaaag ctttcaatac tcacctacaa cagatcttcc tccactcaca aatggctacc  50460
tgccatcaat cagcatgtat gaaattcaaa ccaaatacca gtcgcataat caatatccta  50520
atgggtcagc caatgacttt ggcgcagcta gaaactttag ccccactgac tattaccatt  50580
cagaaattct aaacagaaga ccacattaaa ttctagaaaa cccttcccct ccacagccac  50640
cacttcggta ccacaaactg tgattccaaa gaagagtggc tcacctgaag ttaaactaaa  50700
aataaccaaa actatccaga atggcaggga attgttcaag tcttcccttt gtggagacct  50760
tttaaatgaa gtacaggcaa gtgagcacac gaactcaaag catgaaagca gaaaagaaaa  50820
gaggaaaaaa cccaaaaagc atgactcatc aagatctgaa gagcgcaagt cacacaaaat  50880
ccccaaatta gaaccagagg aacaaaatag accaaatgag agggttcaca ccatatcaga  50940
aaaaccaagg gaagatccag tactaaaaga ggaagcccca gttcagccaa tactatcttc  51000
tgttccaaca acagaagtgt ccactggtgt taagtttcaa gttggtgatc ttgtgtggtc  51060
caaggtggga acctatccgt gctggccttg tatggattga agtgatcccc agctggaggt  51120
tcataccaaa attaacacag gaggtgcccg aaaatatcat gtccagtgtt ttagcaaaca  51180
gccagagagg gtgtgggttc atgaaaaatg ggtacaggag tataaaggtc ataagcggta  51240
tgaagaatta ctggctgagg caaccaaaca agccagcaat cactctgaga aacaaaagat  51300
ttggaaaccc tgacctcaga gagaacatgc tcaatgggat tttggcattg cccatgcaga  51360
gaaagcattg aaaatgactt gagaagaaag aatagaacag tatactttta tctatattga  51420
ttaacagcct gaagagggtt tatcccaagc aaaaaagaat gttggggccg ggcgcggtgg  51480
ctcacgtctg taatcccagc actttgggag gcccaggcgg gcggatcaca aggtcaggag  51540
attgagacca tcctggctaa cacggtgaaa ccccgtctct actaaaaaaa tacaaaaaaa  51600
ttagccgggc atggtggtgg gcgcctgtaa tcccaggtac tcgggaggct gaggcaggag  51660
aatggcatga accggagatc gcaccactgc attccagcct gggcgacaga gcgagactcc  51720
atctaaaaaa aaaaaaaaaa agaatgttgt ctccaaagcc gaagttaaaa aaacctgatg  51780
accaagatct gtgctttaaa ctcagccaga acagatcaat gcaggggagg tggcctcctc  51840
actctcaagt actgacattt ggagacacag cccgaggcag cacacaagcg cggacgagga  51900
agagccacct cctgttaaaa tagcctggaa aactgtggca gcaaggaaat cctaccagct  51960
```

-continued

```
tccattacaa tgcacaaagg gagcctggat ttgcagaagt gtaacatgtc tccagctgtg  52020
aaaattgaag aagtgtttgc tcttcagaat gctacagagg atgggaaatt aatttgttta  52080
ttcaacaaag ggaattggta acaaaacaga aataagtgtc agggggcaag acaggcttat  52140
aatttctaaa ccaaaccaga gaaatgaaaa gccaatgcag aatatatcat ctcttgaagc  52200
aacatctggt tctacaggct cagtagaaaa gaagcaacag agaagatcaa ttagaacttg  52260
ttctgaatca gagaagtcca ctgaggttgt gccaaagaag aagataaaaa aggagcaggt  52320
tgaaatagtt cctcaggcta cagtgaagac tggattacag aaagggtcgg cggactgggg  52380
agtgcagggc tctgtcagat tcagtgacag ctccatctcc acagcgattg aggaaactgt  52440
agactgagat tcctgtacaa tttcatccca gaaaatccag acttgtagtc tccatgcaag  52500
atttcttttt ctgtcggcag cttgataaac agtttatttg ttttagattt tgattttgcc  52560
agtcatcatt attggcattt tcctgcctgg tttcttcttg aagactctga acgattgctt  52620
taacattcaa atgatttttt tttttttcag tttgagctgg atgggtacag cttaaatcat  52680
gggtccagcc taaaaaccac catttaactt acactgatca gtttcaacac gacatggaat  52740
ggactgtttt tggttttttg tttttatttt ttatttattt gtggtgtttt tttgtttgag  52800
atggagtctc gctctgtcac ccaggctgga gtgcagtggc ccaatctcgg ctcactgcaa  52860
cctctgcctc ccgggttcaa gtgattctcc tgcctcagcc tcctgagtag ctggaattac  52920
aggcatgtgc cacgcccggc tgattttttt tttttttttt ttttgtattt ttagtacaga  52980
ctgggtttca ccatgttggt ctggatggtc ttgatctcct gaccttgtga tccgcccacc  53040
tcagcctccc aaagtgctgg gattacaggc ataagccacc gcgcctggcc aagtttttttg  53100
tttttaaata aagcatcatt aatgcacctc tgacaaaaat aaataaataa ataaagcagc  53160
aaattctgaa agggagcccc gcaatgggga aagaggtgcc caaagggaag tgtggagttt  53220
aggaaagacc aaagttagct caggatttcc cctggagcct gggagcgggg gaattgtatt  53280
gagataaagg agcaccaggc ccatctgtct ggagctgaca cggagacctc tgagtaatga  53340
tttcaaggag gaagagcagg caagacccac tgagggtacc agaaacagca aaattgggtg  53400
ggtagataca ccgtctacct ggactggagt agaaaaaggg aggataaaga agacagtatt  53460
caccccacac acatttgctg tggacttact atgtgcaggg ggccatgccc agtactgagt  53520
tcagtctcct gttggaaaag tttcatcaga gcctgacgga gagcagattt ccacaagccc  53580
atcaataaca cttaatgtgc agtgcatttt gggctcaaac cctgaaggtg cctcgaaaag  53640
gcttgtaagc tgggggtaca gtcccctgcc tgaggaagga taccacaggc tgggcatagc  53700
tccattggcc cttctcaggg tggctttcca gaccccatta ttttaaattg caacgcctag  53760
cacttctgat cccttgtcct atttttctga gcatcactta cccctttctg acatatgttt  53820
tatttatcta tgtgtttatt gtctgttttc cccagtagaa tgcttctcca taagagcaag  53880
ggttcttttt tttttttttt tttcaaggca gagtcttgct ctgttgccca ggctggagtg  53940
aagtggtgcg atctcagctc actgccagct ccgcctccca ggttcagtgt cccgagtagc  54000
tgggactaca ggcgcccacc accacacccg gctaattttt tgttttcgtg tttttagtag  54060
agatgggttt tcaccatgtt agctaggatg gtctctatct cctgacctca tgatccgccc  54120
acctcggcct cccaaagtgc tgagaatact aggtgtgagc caccacgccc ggccaggttc  54180
ctctaaatca acttaattga gggatcattt acatataata aactgtatcc atttaccatt  54240
taaagtgtat aattctgaac tgtgggatgt atgcggatat atatacctgt acagccacca  54300
```

-continued

```
ccactaccac gatactgaac attttccact acccccaaag ttgcagtcat ccccatttct  54360
cccatttcct accccacact caccccaggc agccacggat ctgcttcttg tcaccatagg  54420
ctagaattaa cagcagggat ttttatctgt tttatttctc tgtccccaac acatcagatg  54480
atgcctggca tataattggc actcaataca tccttggtga aagactgaat taatggatgg  54540
gaaatcagat gattaagatc tgtcttcggg gccgggcgtg gtggctcacg cctataatcc  54600
cagcactttg ggaggccgag acagacagat cacctaaggt cgggagttca agaccagcct  54660
gaccaacaca gagaaacccc gtctctacta aaaatacaaa agtagccagg catggtggcg  54720
catgcctgta atcccagtta ctcgggaggc tgaggcagga gaatcgcttg aacccaagag  54780
gcagaggctg tggtgagcca agatcgtgcc attgcactcc agcctgggca acaagagcaa  54840
aattctgtct caaaaaaaaa aaaaagatct gtcttcgggc agctcagagc ccagtggaag  54900
agacaggtga aaacaatagt tacaacctcc acagatcctc tgcaggaagt gagagagtga  54960
ggatgcacat gatggaactg cagagtttga gttctttggc atcagaggga tttgagctga  55020
aggaccagct ccacttctca ctactttaca atctcacgtg agcccctaca ttcctctgag  55080
tctcttttct cttttgtaaa tcttgtataa gagcagtacc caccagagag tgctgttaaa  55140
ggatgtaatg ggataacgct tgccaaaggc atagcacagc acctggcaca caatccatgc  55200
tcaacaaacc ttacctactg atattcttgg ccattcgaag aacatggggc tgggcatggt  55260
ggctcatgcc tgtaatgcca gcactttggg aggccgaagc gggcagatct cctgaggtca  55320
ggagtttgag atagcctggc caacatggtg aaatcctatc tcttctaaaa atacaaaaat  55380
tagctaggcg tggtggcaag cacctgtaat cccagccatt tgggaggctg aggcaggaga  55440
atcgcttgaa ccagggaggc agagattgca gtgagcccag atcgcaccat tgcactccat  55500
cctggactac atgagcgaaa ctccatctca aaaaaaaaaa aaggaaaaaa aaaaaaagaa  55560
catggttgaa gaccagctct ataatatgag taagatcaga ctcttgattt tgtgaaggca  55620
aagccaggga agagaggcag aagctgaagt caagaccagc tagtttatgc tgcagtaaca  55680
aatgagtcca tggtcccagg ggcctcgagc actgaggtga agttcatttc tctcacactt  55740
atgtgtgccc tgctccactc ctatgccagg ctggcagtgt ggtttctggc tggggcactg  55800
ccatccttgt aacagaggga agagagaaca aggtgagcca tgcttggctt tgaaagtttc  55860
tgctccccag taactcacat gtcccacttc actggccagc accagtcatg tggcgaagcc  55920
tgagtgaggc caatggatca aggaagtgta atccttctcc agagaggaag aggaaatatt  55980
tgtgagcaat ggtacggtgt accacaggca tgcaagcaat taattacagg atgtgagaag  56040
taccatctac ctctgcacgg tgctaggaag gaaaaggggc tgactctgct tggaaggcag  56100
atgtcaagca gggaaagggg aagtctggga aggcttcatg gaagaggtga tgtgtatctg  56160
ggtcttaaag aaggaataag agctcactag gcagaaagaa acaagggaac atttaggcag  56220
gatgaaaagg caattgtcaa ggataaaatt gtgaaagtct gatgtgctct ccgtggttgg  56280
agcatctggg tacaggggct ggccctggac aggtggactg gactaagagc ggtctttgac  56340
catcacacta aggattccga cttttccgga agagtggtgg acaggcactg aggtttctga  56400
acgaggagat atgactttga gccctggagt ggctggatgg agggatgttt tcatcccaag  56460
tgctgaaaag aaaccaaata aaaggggacc ctaaatcagg ggaaaatccc tgggaagaga  56520
tgaagttttt ctgcacgaaa acccagatag gaacgagaac tcagatagga acggtcgccc  56580
gggggagctg ggccccttcc tgttgcagag agcaggcaca gctcggtggc aaacgccgat  56640
cagggcacgg cgaggccgag ccgagccccg cggacctgcc tgaccccgcg cccgcccccc  56700
```

-continued gcgccgggag agaggcccct cctggcccct ggagacctgg cgtggcggat atttgtctgt 56760
gatacgattg taatttgggt cccttttggc cgcagtaaat tgtcctgttt gcacagcgcc 56820
aggctgaaat agcccggcgc gcgcgcccca ggaaatgagc tcagggccga cggccgcgga 56880
gagcgcgctg cagccgccct ggcgctccag gcgccccggc cagcccgcgt gggggcggag 56940
ctggtatttt ttcatttgac cgacttaaac aggtaattcg aattatgagc atgaaaaagt 57000
gcccaaggcg ctgtctgcca ccgaaagctc agagaaaagt gggagcgctg gcatggggac 57060
tggggaggct gcagcatctt tcttcaagcg cagcggtggg aggtaggggg aggaaccgag 57120
gctcggtctg agatgtgctg cctctgccac ctcccacgag gcaataagga aagtcaaaac 57180
ccctggtgac aaattgcgat tttacaaaaa tgatttcata ctagaaggac tccacagcta 57240
tggaaaagaa catttgaagc acagttacat ccgccttatc gtgccttaca ggtaacacta 57300
caactatcta cacatacatg gatttgtcag cattgccatt gatcacagca tatagacaat 57360
cctgtgctcc tttttcact tgcttttatt ttctgaacac tctttcttgt tgctacacaa 57420
ttttcaattt accattttta ctggcagggt aacatttcat tggatggatg tatcataatt 57480
tataggacca tccctctatg ttggctgggg agggtgtctc cagtttttcc ctatcataaa 57540
taacacccca ataaatgtct ttgtagatac aaaatggttc tttcttcctt gtgaattatt 57600
ttcttaggat taattcccag gaggaagatt attgggccaa aggctatgaa catctttatg 57660
tcacttgata ttattgccaa attgctttcc aaaagggttg tctctgataa tttatggtgt 57720
aaaagaagga actaaccaaa tgtgtacacc gtcctttcct atacacacac aaagggcgtc 57780
accttggggc ccagaggaac aggtgcttgg ggtagctccg agtgggggcg ggataggggt 57840
gcaggggaaa ggccattcag aggtgcgggt gctgggatcc acctcaccct ggtgtcggta 57900
ctttctggaa ggacaggctt cccggatttt ttgactccct cccttgtcct cccttttgct 57960
tccatcagat gtttagacct atcactccca agcccctacc ttactgtccg cctctcagag 58020
tccttcctgc cagggctgcc tgggaactgg cccaccctag gccctgaaat agcatgattt 58080
gctgagccag cttttatact aaatgggaac tattggcacc tttggcttct tgtcatcttt 58140
atgttttccc gagaggtagc actaacccct cgatgaggct caggagggga agctggggtg 58200
tgcccccagg tgataccctg ggagaggctg tcttccttgc agctgctcct caagtcattg 58260
ccaggttcgg ctctggtgga aacttctgta tttacaaaga tcaagtctgg gagatgaggc 58320
caaagacaaa acatcttctg tccacactcc tcacactatt caatttgcgg atgttgttcc 58380
tcccacaatt gttttggtat caccccagct gacatcgtgg acttttttt tttttttttt 58440
ttttttttta ctttcctggc aacactgtag gaagaaagca cgttcagggg acaattcacc 58500
agagggaaaa cagacttgat ttctcctccg ctgtagcaac ccatgtgttc ttgggacaaa 58560
tctcttaggg aatatgggtc ccaactttac tgacaaaatg aggttctggc tggaccagcc 58620
acatcattgc tgtccctagg acccaaaagc ccttggtgga gtttcttttt ttttctttct 58680
ttcttttttt ttttttttga gaccaagtct ttcactgcca cccaggctgg agtgcaatgg 58740
cgcgatcttg gctcactgca tcctctgcct cccggttcaa gtgattctcc tgcctcagcc 58800
tcgtgagtag ctgggattac aggcacctgc caccatgccc ggctaatttt ttgcattttt 58860
aatagagacg ggatttcatt atgttggtca ggctggtctc aaactcctga ccttgtgatt 58920
caccagcctc ggcctcccaa agtgctggga ttacaggcgt gagccaccat gcctggcccc 58980
aacttggtgg agtttcttat gctcccaagt tctcctccca tgactgcacc atggagatgt 59040

-continued

```
gggacagaag gtgcccttgg tgggagggac tctgaggggt agacagtaag gtgggggctg  59100
agctgggagt gacaggtctg agcatcagac aggagaagga cagggcagga tggggagtct  59160
gaaaactact gggacaaacc attacctgcc aaggagagac ctgacccaga cacacagggc  59220
tttccactgc ccctcaggcc tccacatatc tcctgtctcc agagatgcag cctgtttccc  59280
caggggctgc tgggaagccc cccactttat cactggaggg tgtcacactc agaatcacct  59340
ctccacccaa accgccaacc tcagtcccag gatcaggcct gtgcctctgg ctgtctcccc  59400
tcaggtgacg gtcacaccct gttgggtgcc ccgcctgcga ggacggagga gccatcactg  59460
ttccagctgc ctggagatct tggtgctggt gccagccctc agcctcaaga ggtctttcat  59520
ggtttcttcc ttgaagttcc tcacctccac gggcaaacag aagcccacat tcaagggaac  59580
tgcccagatg ggtaatgggt acatgccctt gggccccatt ggatgaaaat gaatgtagaa  59640
tgaggagcca agtcactcac tcttaggttg gtcttttctt gctttggcgc gtgtttccca  59700
caaacgctgc tgccatggtt tgaatgtttg tcctctccaa aaatcatgtt gaggtttagt  59760
tgccattgtg atggtattgg gaggtggacc ctgccctcac gatggatgaa tgactcatga  59820
tatgagtgag cttattatca tgggagtggg tttgcccttt cctgctccct ctctttccct  59880
ttctccctct ctttgccctt ccaccatgtg acaccctctg gcatgttatg atgcaacaag  59940
aaggccctca ccagatgccg gctccttgat tttggatttc ccatccttca gaaccatgag  60000
ccaaataaat ttctgtttgt tataaattac ccagtctgtg gtaatccatt acagcagcac  60060
aaaacagact aagacaattg cctactagca ggcatccctt tccaccaccc tactcagcca  60120
tttccaaccc cttcagctca atccctaatc tggaatattg tcccagtgcc tccagttcct  60180
acaacccaat tcgttttgta ctttgcgatg gcaccatcca atgagggctc aaagtcgtct  60240
tctctgggtg tctgcaaggt ccaactaaac cccactttat aatgtggtct tgtttatgat  60300
gtcatgcatg gtctgtctcc ccatagaccc cccggggcac tgcccacatc ttacacatca  60360
tttgaacacc gtggtactcc gcccagggcc tgcctgtcag cacatgctca gaaacatgtg  60420
ttgatccatt tccattgttc attcaaccct tcctgcacct gaataggctc ttggttgcaa  60480
gtgacagaaa caacactagc taagaagcag caaagcaatt aattggaggg atatttatga  60540
gcaaaaggag tccataggga gggagcacca ggatgggaat gggcaaggga ggccagggga  60600
caggaaacca gccagcttca agtctcatga acgtgggtta gggaggctgc ccagccctgc  60660
tcctactggc caccactacc accccctcgtg aagaccactg ctgagtgtga attctgggca  60720
agatggagga acatccgatt ggccaagcct gggtcacatg tctaacccca gatggaggtg  60780
ggaggatgtg gcctctccaa cttttgtggt ggggtccctg acttccccca ccaggcctag  60840
tcggtaaaag accccacacc cctaggccgg gcgtggtggc tcacgcctat aatctcagca  60900
ctttgggagg ccaaggcggg tggatcacct gaggtcagga gttcaagacc agcctgacca  60960
acatggtgaa atcctgtctc tactaaaaat acaaaacatt agccaggcat ggtggcacgt  61020
gcctgtaatc ccagctacta ctcgggaggc tgaggtagga gaatcacttg aacccaggca  61080
gcggaggctg cagtgagcca agatcgcacc attgcactcc agcctgggca acaagaatga  61140
aactccgtct caaaaaacaa aacaaaacaa aacaaaaaac ccacacccca atgtgggagg  61200
ctgagcagct ccccaaaaga caaatgtcta acagttactg agattgtgtt cactgtgtgc  61260
caggtgttac tctaggcact gacgtgtgaa gatgaggaag ccaggcccct gccaggcagc  61320
tggctgagaa agcaacccca gctccattca tcatttatgg ggcaccactc catgccaggt  61380
tcttgcccat gggctttctc agacatcatc ccatttaatc ctcactgtgg ctggggctga  61440
```

-continued

```
attaaagggg ctagtgaatg gtcaagggag cagcatggct gccaaggagt tagggcagca  61500
tcacagagaa gtgaccatct ggcagggact aaaatggact caaggaggtt gaaaaaagag  61560
aaaggccttc taggcagaag gaacagcatg tataaaggca cggaggcctg acaaagtcag  61620
agaggattca ggccatcatg gtttcttggt gtggctggac tatagggagc aaaagaggcc  61680
tagaggtggc tgttgcaggt agctcatgct agcaatgagc aggccttgaa taaaaacagc  61740
caatatttct caaacacttg gtaaatgcca agccctctat gaggcccttt acatccatca  61800
tctcccccat caggcaagca ctatttttat tctgaagatg aggaaactaa ggataagagg  61860
ggttaagtaa ctttttcaag gtcacacagc tagcaaattg gaagaggcag gatttgaacc  61920
aaagtttgtg tgttcaacca ctgatggtgc cagaaggaat aggaggagtc catgtaccta  61980
ccctgatcct ttaaaaaaaa aaattttttt tttttgagac aagatctcac tctgtcaccc  62040
aggctggagt gcagtggggt gatcacagct tactatagcc tcgaacacct ggatcaagtg  62100
atcccttcac ctcagcctcc tgagtagctg ggactacagc tgtgcaccac cacacccatc  62160
taatttgtta attgtttttt tttttttttg agacggagtc tcactctgtc tcccaggctg  62220
gagtgcagtg gcatgatctg ggctcactgc aacctctgcc tcctggattc aagtgattct  62280
cctgcctcag cctcccgagt agctggtatt acagccacca cacctggcta atttttgtat  62340
ttttagtaga gacggagttt caccacgttg gccaggctgg tctcaaactc ccgacctcag  62400
gtgatccgcc cacctcggcc tctcaaagta ctggggttac aggtgtgagc catcacgcct  62460
ggcctttttg ttaatttttt gtaaagacag ggtcttgata tgttgctcag gctggtctca  62520
aactgctggt ctcaaactcc tgggctcaag cgatcctccc acctcagcct cccgaaatgc  62580
tgagattaca ggcatgagct actgcacctg gccccttccc tgatccttcc catccccaga  62640
gactgtattt tgcaggattc cctattcccc tatctccatg gagagtggcc tccatagcct  62700
agggagtgtg gcttgtctta ccctcactct accaggtcac ttcaaggagg tcatggcaga  62760
gctagctcct ttgcaccatg acattaaaaa gtcagttccc tgttaccatt ctcagttttg  62820
tattcaggaa aaaggaactg gccaagctgc atagaacttt ttatggacag agagaattgt  62880
tgaaatgata aaatacagtc tgctgctttt ggctgggtca tttctaggca cttccactta  62940
gagggacagg tacagaaggc acccagcagg gcagcttcat gcttagggtt tggccctagg  63000
tcacctgggt ttggatccca gctgccccat ttcatagtca tgggactttc ggcatgttat  63060
ttaacctctc tgggactcag ttttcccatc cataaaacag agaataacca cagtgcctgc  63120
cctatagggc ttaggaggtt tagagatgtt tgtaaagtat ctggcatgta gtgagtacta  63180
aaaaaagaga aaaaaatgca atttgggcca ggcaccatta ttattctcca tccatcttca  63240
caataacccg tgtgtgaggc aggaggtgta cccatttgac aggtggggaa acagaggctc  63300
aaagatatta agtggccctc tcaagttcac tccctaagtg gaagagtggg aattcaatcc  63360
cagatgtgtc caattacaat gtccgtgagt tttacatggt ccctcgctgt ctcagggctt  63420
ctatgctggt gcacctcgcc aaaatgtcac ttgcggctga aaccacattg tcttccagat  63480
gatcagctat tgcaccagca acgcagggca ggagccaaga gcactgtgct gggggagcat  63540
ccaagccccc ccacgtgagc acgcccagcc caggcacttg tccctgctgt ctcaggtaaa  63600
actttggaaa cctcaacccc taattaccgc ctggcacagg gcacccggtg gtttccggat  63660
ggcttgtatt gactcgcgca gtcttcatag gacataggtc tgagctaaat ttaagccccg  63720
tcacagacaa tttaacagtt ttctgtgggg gggtaattga atggtaaacc ataattaccg  63780
```

-continued

```
atacaactga taccttaatt cccaaaacaa tctgtggagg tgtgtggaat tcaaatcagt  63840
ccaattagaa ttctatcttc tcataataaa atacagcata attgctaatt gccccctggc  63900
tcacaatatt ttaaggcaga aagttggttt tgttttttaa tatggctttt gtttttaatt  63960
ttgggctgtt gcacatgagt gggaaaggat ccaggtctct gtacttggga caagacgccc  64020
aggagaggcc agctatgcac agggctccac cgatgtcgga ggtctggctc ttggaaaggc  64080
caggatgagc tcttttgata gaagccacct gagctggaaa tgacctttgg gttgacaatg  64140
cattctgatg agcactgcag tcagaagttc taagtgagac tgtaggattt agggcaagtt  64200
tcttaacctg actcagtttc ctgatctgta caatgggtgt aataattgat cttcgtctgt  64260
gggttgttgg gaagactgac acagtgccca atatatggta aacactctag aaatggtagc  64320
tgctgttatt agtataaatt cactcactca ttgacccagc aaatacatac tgagtactat  64380
atgtgccagg cacaatttta ggtgctaagg acataacggc aaacaaaaca gatgaagccc  64440
ctgccgtttg tgcaacttct actggggaaa catgataata gacaaatgaa tacattaaag  64500
aatctggcct ctgcgagagg tcatgtgatg tggtcaagga ggatgtctct gaggaggtag  64560
cacctaggag cctgaattta ccaagaagga aactgagtct caaaagttca actttggagg  64620
accgggcatg gtgattcatg cctgtaatcc cagcgagctg ggagaccaag gcagacagat  64680
tgcttgagcc caggagttca agaccagggt gggcaacata gctagaccct gtctctgcaa  64740
aaaatttaaa aattagccag gcgtggtggt gcatgcctgt agtcccagct actcaggaag  64800
ctgaggtgag agggtcactt gagcccagga gttggaggct gcagtgagct atgatcacgc  64860
cactgcactc cagcctggat gacacagtga ggccctgtct ctaacaaaaa aaagttcaac  64920
tttgggcagc aggtgcacac cgcagatgtt tgggagagag gggcaggagg ataatcttca  64980
ggagagggaa ggaacaatct tagtggaaag gcactaggtg gtcaggcagc agctgccatg  65040
gagaagtcat gggttgctga actgttggaa tcccagctct ctagctttag tccgaaaggc  65100
tcctcatgat gacctgaagg tcgctgtgga ggagaaagtg cccaggcagt ggagctggag  65160
agacccagct tcagatcctg gccctgggtg acttgctgtg tggcctcaga cacctgctgc  65220
atctctccca ggctgcatct tctctcctgt aaactgggaa caagaagaca caggtcacag  65280
ggtcattggc aaggttgtgt gggaccatac ttgtcaagaa catggcacac attggcactc  65340
agcaagtgcc aagtctcctg aaactgaggc tgaaagaaag gaagtgactt gtccaagatc  65400
acacagtgag ttgtggcaga gaataggcaa gcttgggtcc agtgttctca ctcctgatag  65460
ccaagaacac agcttctccc gcggccagct agagggtctt tgcagggcaa ttgctgatag  65520
gcagcaggtc agaaaggatt tcagaggagg aaggattagg atcaagcaaa gagacacccc  65580
tatttggcat gcacctgagt tagtgcaaaa caagccattc agatttcaac ttccggcatt  65640
catttacttt caacagctaa gcatgttgga gatacctcct aggagctaca gagctgactt  65700
gcggggtaga gggaggctgg aggtatggga agggggctgt atggaaagga gacatatttc  65760
cccagcacaa ccccgtctgg cattcccaga cagccccgcc tctccccatt tgacaaatcc  65820
cacttcccgc ctgggatcca aggggtctcc aagattaaaa atctggtcac ccactggtta  65880
cagcgcaaat ggctcctatt acgagagggc tctaggggcc tgggaaccca gcaaggggtg  65940
ggcaggcgcc tgctgacaca gccttaccca ggggcaggcc cattcactgc ccacacagag  66000
gtgggaggtg ggggccctac ctggggtccc tgcacctcga cagtaattac tgctttctgg  66060
ctggccactg cccagaccac cttgttgatg ggaacttggt cccaggctga acagggcttg  66120
gccctactgc tcaagggccc cccctccca cgactgaggc atgggggagg ggtgttggcg  66180
```

-continued

```
ggggagggtt cagactccca gcagcctaag gaagaagcag cgagattcag ggacagtgga  66240
cgtagaaact gggactgata gtctgggcag gctcttaggg tttaaatcac acttttagcc  66300
aagggacccc ccggtgcacc ctcagaagtc ttctggatat aacttcagac acctgggtcc  66360
cctaatgcat aactaccgtg acagcaggta taactggtat gtcaaacaag cataactcct  66420
aggatcatca atacacaact ttatttttgt ctcctacctt cctttagact ttctttagtg  66480
caagtaatct cccctgtttc tgaattggaa ctcccgcagg cccataactt ttctgcccaa  66540
tcctaggtag aatagagtcc tgaagttact ttaagtcaca agaaacatct cagttctgat  66600
gctagaatat ccagtccaag acagtgacca aaactgaacc tgatttagtg acaagctttc  66660
cccctcccgg gtgggcagcc tgcagtgaga gaggaggcca gtggcctttt cctcagtttc  66720
tcagcagtgc cgtacccagc ctggtcttca gctctctggg gtggagcctg gggagaaaga  66780
gggggaggcc agggcagtcc taccctggga aacaggcttt gggcctctgg ctggccttgg  66840
cctatgtcta acaccagctc tttaggcctt ggttaggaga aagtcaataa atttctgggt  66900
tttgtgcaat attcctgtag taagaatggt cccctagagt aacaatgact aaaacaagat  66960
aatatctaca ttcatactct aacacaattc tcacttattc tgcaaactct gattaaaggt  67020
ccatatgtga ttaacgctgg gatagccctg gagatgcaga aaacagcctc gttgggatgt  67080
ttgatgccct tggcttcatc acccatctca caatgaccag aaactcaatg acacccaggt  67140
gaggagaaac tcatttttat ccctgtttag tcaataacca ggaagcacgg ggcttacaat  67200
ctagagaaca cttctaaaga ctacatcttc agcagtaccc actttactga tggggaaata  67260
agcctcagag agattaacta atgtgcctaa tgatatttgg taactgacaa ggtttagact  67320
ctaaccaagg tcttctggtc ctaacttcag agtcctgtgc acttaagacc acaatctgac  67380
tctcttttgt tgtctgtgtg agagaagagt gaggcaggga tctgagtaca tgagaacgaa  67440
ccagggagga agggcaggca ggctaaactc tccccgggat cagcagaaag cggccaggac  67500
tcagacactc actgtggcca tggaagctgc aaggcagatt taaactccag acatttgaga  67560
caccatgtaa gccctccagt actgtaatat ttttggcgag aggaagatgc aaggaacact  67620
taagatttgg aattgttaac agcagtgaaa acactacttg aaagctgaag ggaatagcat  67680
gatgcctgct tgcagctccc agctcacatt catcccctca gccacccaac ataaggagtt  67740
tattttccca agagttcaaa caggagtccc agaacagatc ctcattggct caggcgggtc  67800
acatgtccct ccctaaacca atcactatag ctagaggatt tggagccctg attggtcagg  67860
cctgggtcat gtggttgatt tggagtacgc aaggtggagt tagctccccg gccctactta  67920
caatgtgggt agggaagagc tcttagcaga agggggaagg gggaacggga aatgggaaat  67980
tagataagaa agagggcttt gtaccacaga aggatttcta ctttatagat tggcagtagg  68040
agcccacaaa tgctttcaca tgggaaaaga cattttcaat gttgggggtc atgaaggtga  68100
ataaggcagc caagaaattg ttgctaccta atcattaggt gtcagttaaa catgcatagt  68160
atcggctggg cgtggtgcta taatcccagc acttttggag gccgaggcaa gtggattgtc  68220
tgagctcagg agttcgagac cagcctgggc aacatggcaa aagccggtct ctacaaaaaa  68280
tgcaaaaatt agttgggtgt ggtggcactg cctgtggtcc cagctactcg ggaggctgag  68340
gtggcaggat tgcttgagcc ccgagttgag gctgcagtga gctgagattg cacgacggca  68400
ctccagtctg agtgaaagaa tgaggaccgg gcgcggtggc tcacgcctgt aatcccagca  68460
ctttgggagg ccgaggtggg cggatcacga gttcgggaga tcgagaccat actggtaacg  68520
```

-continued

```
cggtgaaacc ccgactctac taaatataca aaaaattagc cgggcgtggt ggcaggtgcc  68580
tgtagtccca gctactcggg aggctgaggc aggagaatgg agtgaaccag ggaggcggag  68640
cttgcagtga gccaagatca cgccccactg gactccagcc tgggcgacag agcgagactc  68700
cgtctcaaaa aaaaaaaaaa aaaagaatga gaccccatct ctaaaaaaaa ataaaaaata  68760
aaataaacat gcatagtatc tattaatgta agttactcgg caatatggac aatgagtaag  68820
agggtaaaat ctggttctgt cacttaccag actttgaagg agttacttaa tttctctttg  68880
cctcagtttc ctcatctgca aaatgaggac agtaacaata actgctccta ggtttgttgt  68940
gcagattaaa caaatgtata caccgtaagg cacttcaaga aggggtagtc agagtgtttg  69000
cttcagttcc caggagctgg gagacctcac atcctggcgg agcctctagt tctggctgca  69060
cagacctgac tagcctggcc tggccgcagt agctggccct gagtagtgac ccgctcgccc  69120
gctgccctcg gaagcctcac ttggctgaca aacaggaagg tggcagggct gcctgcgtgc  69180
ccttgccgcc cccacagccc tgtgtctggc cccaaccctc atctctactc gcggctgcgg  69240
tgaacttgga tggtgctact ctcaccacaa accacagtcc gtcacaaatt gccgtgtggt  69300
gagtagcgag cacatttata attgatgaaa tcagggggtg agagctcatc gctgagatgc  69360
tcagtaaaca aagacctggt ccttgggtgg gggagggggt gcttgagagt aaacaagggg  69420
acaggaatgt tggggggctt aactctcctg gagagtacat gaaaggtctc acccaccagc  69480
ttttgttttt attattaagc ttattttaaa gagtttcaat cctatagaaa agttgcacga  69540
atatatagac tcacatagat tccttttttt ttagagaccg ggcctcagtc tgtctccctg  69600
gctggagtgc agtgctgcaa tcatagctca ctgcagcctc aaactcctga ggtcctctga  69660
tcatcccact tcagcctccc aagaagctgg aagtacaggc gtataccacc gtgcccacgt  69720
aatttttact tttttttttt tttgtagaga tggggtctca ctatgttgcc caggctggtc  69780
tcaaactcct ggcctcaagt gatcctccta tctcagcttc ccaaaatgtt gggatttaca  69840
ggtgtgagtc actgcacctg gcctaataat tatattcttc agtcttttct tactagtctg  69900
ttcttagtct cattctgttt aaccatttgt gagtaagctg cagagatcat gaacttccct  69960
gctaaatacc tcaaggacat tttcttacat acctataaga atgactaacg gccgggagcg  70020
gtgactcatg cctgtaatcc cagcactttg ggaggctgag gcgggcagat cacgaggtca  70080
agagatcgag accatcctgg ccaacatgtt gaaaccctgt ctctactaaa agtacaaaaa  70140
caagctgggt gtggtggcac ccgcctgtag tcccagctac tcaggaggcc gaagcagggg  70200
aatcgcttga acccgggtgg cagaggttgc agtgagccga gatcacacta ttgcactcca  70260
gcctggtgac agagcaaact ccgtcaaaaa aaaaaaaaaa aaagaatgac taatatcaga  70320
aaatgtaata acacaatact aatataaaat ccatgttcaa atctcaccaa ttatccaata  70380
caatcctttt tagcaactct tttttcccaa tcaaacctga ttagcctttc aatagtcaag  70440
gtcccaggta attgtcaccc ttggtccccc accccactgg gggctagaat cccacagtca  70500
ggtaggagtg atgaagctgt ggtcagatca gaaaacaagg ccaagcttag gataacagct  70560
ggagccagat gtagaatctg gctaagtaag ctctgggagc cctggaagct gtttccagaa  70620
ggtccccagg gatgggagcc caggtgagca gggagagagg catggaagct cttactggga  70680
tcccaaggga gacaggaggc tctcacactt ctgtcacagc agccaaaccc tgggcatgga  70740
caggtgggga caggagagat gttaggaaga tagggaggag atcatcaaca tttcaggcac  70800
agaagctggc agaagagaga cacctttgtc atctgtatta tgctaattgg ttagtctgta  70860
tatttattta acaaatgtct attgcaccct tactgtatgc caaaaactat tttaagtgct  70920
```

-continued

```
ggggatacag acccagttcc aaccttaagg tgtttatgtt ctattgggag atgggatagt  70980
ttgcactgtt gttgtgaaaa cggtcacccc cccatcccct cccactcccc ttcacaacag  71040
gtgtaagaga gtaaacttgc ccaatccact gctattacac ttggccatga gacttctttg  71100
gccactagaa tgttagcggt gtgtcatgat cacccttaac cgtgctgtga ggtttggctt  71160
ggcttttaag ttcctgccat tctccaagac aagcatgtgc cccagggagc tgctggtcca  71220
aggagaatgg agagagacat ggagtccacc caaacccaag ccatagcctg gagctgccct  71280
gctcgggctg acacacagac tcacaaatga gaaagatcag cacttgtttg gagcctctga  71340
gtatcggggt ggtttgttac acagcatcat ttcagcagta gctgactaag atgggtggag  71400
acagaatata aacaagccaa ctaagacatg tgtgatgtct tagtgataag aacaggaaga  71460
caaagaaagc aggagaagag gaaaagagtg gtcagggctg ttatagatag ggcagccagg  71520
ggaagccccc tgataaggga gcagagatct gaaggaagtg ggggaaggag ttatccaggg  71580
caggaatttc tcaaggagga aacagcaagc gcgaggctcc ccaggcaggc acaagctgag  71640
cccaggagca agcctgtatg gctggagcag aaggagccag cagggatagg gtggagtgat  71700
aggagatggt tcagagagga ggctggggcc agatccagtg gaaaggactt agacatttat  71760
tggacttgga catcatctcg tataacttgt tcctagctgt ctgatgaaag agcggacatg  71820
cagaaagggc gctggctgag ctccctggtt tgggatgagt actggcagtg ccaatgtcag  71880
ccacattcaa gccagtgttc caggggcctt ctctcagtct catgctcctg cttttccttg  71940
agattctccc ctctcttgtc ccctccctat cttggctctc tacccaccac cccaacacct  72000
ccagctcccc ctctgctccc ccttttgctc ccctggacct tcctggctct cggccttcaa  72060
ccctcagccc tcagcccctt tggctctcaa ggtggggacc actcccacct ctccagccct  72120
gtcttggagc cctgggcatt ctgtcactag ctctctgctt ggtcctgtcc ctcaggtggc  72180
ctgtggtcct ttcacactgg acatgcctca aacggagccc atcgcgaggg gaagggctct  72240
cagggactat ctgaaacctc gggagcttcg tagacccctc tacaaagggg agccagtggc  72300
ccagccagtg gctttatttt cctaagatac tgatttcaac atgtcactcc ccagccttct  72360
gtcttggatg gcagctcttc tctatgggat gaaggaaccc tcctcggccc agcactgaag  72420
gtcttctacc gtctggtctc agctcacctt tgcatcggct cccaccgcca gccaagctgg  72480
atgccctccc accccatgcc tcaagcacac cctgcttcta ggtccttact cacagggccc  72540
tttgctcagt gggagtttgc tgagggccca ctgtgtgcgg gcgctttcca gggtgctagg  72600
cacagaggag cagctggcag acttacattc gtagagcaca ctcgggtgcc tctgctgcgc  72660
ctccctgcac ctccccttcc ttcccttccc tcaaggctgg tcacctatgg cctccacgac  72720
caatgtctcc ctgctccttg gtcattggga aggtaagcat accttgcctt gtgtctgatt  72780
gttcttttaa atgaagattt ccatttttaa ctatagaagt gacacatcct cattgtgaaa  72840
aatatgtaga atgtggaaaa gaaagaagca aaagaagtta tataacctgg ctaagaacat  72900
ggagaagctt ctcttaaaaa gaggtgtcct cagctgctcg ccttccacac gccttcctca  72960
cagaggaggc agccttgatt cctgggtggg aaatgccaaa aatgacggaa tcaaagcctt  73020
ttctggaagc gggcagagat ttctaggggt ggggaagaga gaatatagaa cttaagagaa  73080
ctgagctctt gatggaaagt gggggtgggg aacacagagg ggaggcccag agactgagag  73140
gtctaggaga acgggttaaa accgaggcca gagccccgga aaaggagccc agaggcccca  73200
gctctttccc tacttactta ctgtatctgt gtgaccttaa gcgagtccct tggtctctct  73260
```

-continued

```
gagatgcagt attttcccaa gtgaacgggc attgccacac ttcacctcct cagggcgttg  73320
tggggacctt caaagccgta aagccctttg taaatggtaa cgcctaacac aaataggaga  73380
gcacgctgcc ctctctgggt aggcccctca tctgggtcct ggttccagtc tggtactgag  73440
cctctggagg acaagggtca catttattcc aatttctctt ctgcatgccc cagtgcccac  73500
tgagcacagt gggaatacaa acacatttat tatgcactct gcatatgact agaaggaact  73560
ttggagctca gatccaccct ttacacagat ggggaaaatc aaggctcaca ccacaaggtg  73620
agcttggtgg tatctttaca actccaggta gtgacaaaac caggatgcag attctgagga  73680
atgaacgagt gagagaatga agggaaatgg ggcaacagtc agcatgagca agggctgacc  73740
tatggtgggt cttagccttt actgtgctca gtggccccac agcaccatcg tctctccaag  73800
gagcacggaa gcagcccccc gtgtggggta tgggcacaga ccccagggcc caggcaggca  73860
ggggatgtgc cagtggtcct tgccacgggc caccagcttt gccaccctgc tccagggccc  73920
tggcctctcc ccagggtgca ggacgccact cccaggcact ctggctccgt ttcttaccag  73980
gctgctctgg gatggcagca tcccagcatc gctataaata gcatctctcc tgggccccag  74040
acggccagtt ggcaaacact ataatttgct gaaaagtttg gaatgtgtct aaaaatgaag  74100
aaggcaaatg agaccagcca tgagggggag caaccggcgt atccatttca gagaggggct  74160
gagcctcact cctgcttctt gccaacttct ttacaagggc actgcaggca aagcttcagg  74220
gagaggggac aaatatgagt ctaggaaaga actattgtca tttccagcat cagctgtggc  74280
ggctacctct tgtattggcc tcacccctga ccttcctgtc ctaaccaaag aacgagagga  74340
actgccactg cttaaccctt tgttgggctg tgctaatgaa attgaaggga acatggtgag  74400
catgcgagga ctgtgagagc cagaaagaaa cccccaaaat aatttcattc aatagtttca  74460
tccaaactct cccagtttgc aaatgaggaa gtgacttgac aaaggccggg caccaagttg  74520
aagcagaacc agattttggc caaggtccct gggctcccag ctgggtgctg ggcattggat  74580
cccaggcctg ctgtgagggc tggctctctt agggaaaggg gaagggtccc atggctctcc  74640
catcatgctg aaggttgaca cctgacaagt cactgcagct ttcccttgtt ctgctctgat  74700
tctcattcta ctctaaggag gcacagccac cattatcctg attttatggc tgaacaggcc  74760
gagcttcagg gtagaaactc atcctcatcc acaaagccat gggaaggctt gattagaatt  74820
taccactctg tccccagaca ctctgggctg ttcccacctt caggtagaac tcactgcctc  74880
aaaagccacc ttttactgtt ctttgtctta tcttctggga ttgtgatttt ccctgtagga  74940
aaaatcatgg acaatggcag tagactggcg tggtggctca cacctgtaat ctcagcactc  75000
tgggaggcca ggcaggttga gaccagcctg gccaacatgg tgaaaccctg tctctactca  75060
aaatataaaa attagctggg cgtggtggtg ggagcctgta gtcccagcta tcagggatgc  75120
tgaggcagga gaatcgcttg aacccgggag gtggaggttg cagtgagccg agattgtgcc  75180
actgcactcc agcctgggca acagagtgaa actccatctc aaaaaaaaat tctgaagtag  75240
agccccagat ccagcagtct cactgtatga tcttgggcaa gtcacttccc ttcactaagg  75300
ctgaatttat ccttatgtaa aactataata aaaataaaag cttcctttgg gaggccaaag  75360
cgggcagatc acgaggtcag gagtttgaga ccaccctggc caacatggtg aaacccagtc  75420
tctactaaaa atacaaaaac tagctggcca tggtgacagg cacctgtaat cccagctact  75480
cagaaggctg aggcaggaga attgtttgaa tccgggagat ggaggttgca gtgagccgag  75540
gtcgcaccat tgcactccag cctgggcaac agagcgagac tatgtctcaa aaataaataa  75600
ataaataaaa ataaataata aaataaatga atgaataaat taaagcttcc attcacaaag  75660
```

-continued

```
cacatggtca cgggctttat gtgcatttgt tctctttgtc ttcataacaa tcagacgggc  75720
aagatatatt cctatcctat tttacagatg aagaaattga ggcagggggt taagtgactt  75780
gtccgagatc acatcagatt ttcacaagtt ggaaactcac tgcaccagat gctctgaggt  75840
cctttacagc cttaataatt ctgccttttg tggttccaaa cacaatagaa attagcaatg  75900
gctcgcttgg tagttctcag ctcttgccag ctgagaggct tcatttgggg gcagaagaca  75960
gggagtaggg agagttcaca tctgtgaaaa gtctgtacag aggaggagcc aggatgcccg  76020
gtcttggcct gtcagccaag gccctctctc tctctctgca gaaggcacct gccgccctgt  76080
ggggccgctt agtgagaact gtggctgaaa agcgacatcg tgtgtccagt tgtagaactg  76140
cactgttaga gaactccagg acaatgagga gtggagggaa atattctgtt gttgtggact  76200
tgaaggcgct tttaaattat ttgtaaagtt ttaaaaacac acaggtgcca gaacctcaga  76260
cctagagaac cagcatctca agcagtagga cagagacctg tttttttaag acttgggcga  76320
ttctgtggca gcctagctga gaaccgcaag tatagacagc ttttaagggg gtgctggtat  76380
gctggtcaga acttctcagc tgcaacacct ccacctggtg ttgcacttct gtctgggata  76440
ccagaatgtt ctaggcagct gacagaaaca aatccattag acattattta taaaggaaaa  76500
tctagctgca ttgtacattt gatttgtgct ttgttaagaa ataaaatggc cgggtgcagt  76560
ggctcacgcc tgcaatccta acactctggg aaatgaaggc agaagaattg cttaaaccca  76620
ggagtttgag accagcctga acaacattgg gagaccctgt ctccacaaaa aaaataaaat  76680
aaaataaaat aaatagccgg gcacagtggc gtgccagcta ctggggacgc taaggtggga  76740
ggattgcttg agcccaggag gtcgaggctg cagtgagcca taattgcgcc actgcactcc  76800
agcctgggtg acagagtgag accctgtttc ttaaaaaaag aaagaaaaga aaaataaata  76860
aaatggcagc tggtaaaaaa aaatgagtat agaaatagat tcagttattt tagagaaatg  76920
tcagtgaaat tcagtccatg tatagaggat acagaaatct tttttatttt tttttcttta  76980
atgaagtggc tctcaactgg gagcaatgtc tggagacatt ttacggcttt cacaactgga  77040
gggtgctact ggcttctaga gggcaggggc aagggatgcg gcggagcatc ctgcaatcta  77100
caggacagcc ccccacaaca aagaattacc cggccccaaa tgtccatagt gctgaggccc  77160
caaggccctg cttccatgag cacaaaggac tcccattttt caggtcccct gagggtgggg  77220
gctctgccct cttcatcctc tctcccggga cctagcaaga ggcaggtgct cagtacatac  77280
tgcatgacag aagttcagtg aggggcattt tgagaaaaat tatctaatgt ggacacattt  77340
gcaaacctcc ctaatatgca cagtcctggg tgcatttcta catggcatag actgtctgaa  77400
gctaaaacat ctcatttgtc agctggacac tacccaagta caccaaacac aacctgggag  77460
tcaggggaga taggggtggt aaggaggatt cagaccccgt agaaacgggt taaacctcag  77520
ctccttcaag ctgtgtgtcc ttgggcaagt tgcataactt ctctgggcct tagtttcttc  77580
ctctgtaaaa tgaggctaac acaccttctc acaggctgtt gtgaaggtta aatggcattg  77640
tgcgcaaaaa atgatgagca tggccctgta tgtgctgatt aaatgttagc tatgtgggcc  77700
aggtgcggtg gctcacacct gtaatcccag cactttggga agctgaggca ggtggctcac  77760
aaggtcagga gttcaaggcc agcctggcca acatagtgaa acccccatct ctactaaaaa  77820
tacaattagc cgggcatggt ggcaggtgcc tgtaatccca gctacttagg aggctgaggc  77880
aggagaatcg cttgaaccca ggaggcagag gctgcagtga accaagatcg tgccactgca  77940
ctccagcctg ggcgacagag caagactccg tctcaaaaaa aaaaatgtta gctgtgattg  78000
```

-continued

```
gcaccctcat gactgaggtc tggattggtt gggtgtggct gctgtgctgc cagagacaag  78060
ctatcactca cattgtatct gaacaagagt aatgatggtg cataatgaat acattgggaa  78120
gaggcagaag gccttggact cactaactca aaacctccgt aggaggtgcc tgggaatatg  78180
catctgtaat aaactcccgg gcttttattt ttttgagatg gcgtttctct cttgttgccc  78240
aggctggagt gcgatggcgc aatctcagct cactgcaacc tccacctttg ggttcaagc  78300
aattctcctg cctcagcctc ccaagtagct gggattacag gattacaggc acctgccacc  78360
acgcccggct aattgtttgt atttttagta gagacagggt ttcaccatgt tggccaggct  78420
ggtctcaaac tcctgacctc aggtgatcca cccacctcag cctcccaaaa tgctaggatt  78480
acaggcccag gtgattctta cagttgggca aatttggaaa atctggcttt agtacaaaga  78540
ctttggagtt aagctgccag gctctgctac ttactaactg ggtgatctta ggcaagctac  78600
ttaacctctc tgtgcctcga tttccccacc tgttaagccc ttgcccagca ctactgctgg  78660
catccagtag actcaagaaa tggcagctcc tcccgcctct ttctcaagtt taatggtgta  78720
tgatcttcac cttcatcctc catacaaggc ctgccttctg ctcctgtcat ttctctctga  78780
ctcatccttt ctctaagtcc ccactggtcc ttggtgggtc tatttggtgc cccttggcct  78840
cctcatgggc ttctctaatt cttgtcccca ccatctcact gagtccatca agcagaagca  78900
aaaacagaac atgtgctgtg gtttgtagtt ttcaaggcat atttcacata ttttacctca  78960
ttgactcttc ccagatcatc ctgaagcatc gccgtcagga tctctgcaaa atgagtgagc  79020
tgagtctgaa gctcagggtg actgactgtc ctgagcccca gagcaagaaa acaggagcat  79080
ctctgcctcc cggccctgtg cattttctcc ggtgacctga ggcctctcag ttcctcccac  79140
tgcccctagt ctgattcgca tcctgccctt ctgctgctca ggaagcagct ctggctcccc  79200
agcgatcaga tccaagtgcc tacacctggt ttcaaggccc atcacaggcc acagcttgga  79260
atcattctcc ccctcctgga tttcctgcat ttcccagact ttccatcaac ccagctgggc  79320
tcctctctgc ctctcatcct ccctgcctcc ctgcttggat gcaagctgtc tccctgcaca  79380
gcacccctta tatagagtgg atagcacagg gaggaatgga ggcatgccat gcctggggtc  79440
cctccaaacc cccatgcctg gcatcactcc ctcagcccct gccaggtctc cttctccagg  79500
aagcctccct gcccttcagt gagtatccag tgctcagcca ggcggtcaca gccttttgct  79560
gctcctctcc tgccctgccc ccacccctca cacacacact ggcctttggt ccctttctgc  79620
ccagcaactc aatcttttgg tgttatttgt atttgtatta ccctatctgt cgaaaggggt  79680
cgggtggggt gggggagagg gctgccaccc cccatgtgga gcccaccgtg agaccatgaa  79740
cagaatgggg gtgactgaca gggctcctct gccaccttgg ctgctggggg cagtggtaga  79800
aatcaccact ggctattgtg acctccaaag gcacttgtca ctacacagtg acacaaaggt  79860
tggtttccgg ctcctccccg tggccagcat atccctggga tccaagacag gtccgcatca  79920
tactgccagg ggatcctcgg ggttaggcac ccaggaatgg atgggatgca ggcagggctg  79980
ggactggtgg ctggctctat tgtgctctga tgctgcagga acagaccaga tgtcatccag  80040
gggcccggaa tttggggggc gccgctgggt gtggcagcat cagaagcctc agatccgcat  80100
ctccatctgc cacaggtgag ctctatacct ctgagccagt ggcctgtggg agtgaaataa  80160
tcagagccac tttgaggtca gaaggtacaa caggggtgaa ggattggggt gggggagggg  80220
ttgggggtcc tggagggctg gtgctgtgtt tctgccttca ctcctgacat cctcttgcag  80280
tacagggtga atatttttac ccacatcttg caggtgagaa aatagaggcc tgagaggctg  80340
tgctgggagt tcacacaaga ttcttagtcc tggcaccaca agagtcacat gccaagtccc  80400
```

-continued

```
aggctgcatc caaaccaatt gaatcaaagc ctcaggggag cgggacccag gcaacagtat  80460
ttttatggtc cccatgtgat tgtggtaggg cagtcagtgg ggagaaggga gactaatggc  80520
tcagacggca ctttgcaaac tttcaagttg tgcaaagttc cctttgtgtc tttgtgtagc  80580
tcctaatcca cgctgagcct ccgtcctcat ctgtaaaatg gggataatac ggttccttga  80640
gttgatgagt tgaagtgctt tcttaattaa cattgcaact tgaccacccg gcactcttgg  80700
ttccctttc cctgtgtgga gggtttgttt ctgttttgcc atagccctta ccacgtgtga  80760
acatatgata tattttacct attcaggatt ttcattcatc agtgcttgac actcccctac  80820
ctctgctaga acaccatatg catgaaggcc aagatcttca tcactgcttc acttttattc  80880
tttcctgtat cccaagcacc aagcagcaca gtgtttggca cacagtaaag tgcttaacaa  80940
atagctgttg aatgaatgaa tgtgcctgcc accatctcat acatgttaca ggcatcactg  81000
ctgctgctgg gcttgtggtc tggtctgcag ccttctcgcc tgaaccgctc acctcccaag  81060
ctgcttgcaa actgaataaa gctctcccaa agtcaagctg atcgctcctt tccctgagaa  81120
acatgcctct gtccctgctt cttggggtct ccccagccca ccatctcccc ttggacacag  81180
agtgccagag cactagcagg gagaagtggc aaagtttcaa gatttcattt gtaattcttt  81240
tcagatgaaa tgtcagaaat attagaaagg cagagtcata aatctgatcc taatatagca  81300
tagagcttat taatgaagaa taaatcacca agggaaacct ccccggggtg cttctccagg  81360
gcctgtgggg aagatggcat atttatgtgc aagcgtagcg ggtcttttac cttctcagat  81420
atatggccaa ggcagatttg tcagggcagt agccttaaca tcagccaatt atattttttt  81480
ctagtaaaaa ttaatctatt ctatagaagt ctcctaagca tttattggat taggatcaca  81540
tccaaatgta gaaaattaaa cacacacaca gtgcacacca cggcaggact ctgagaggcc  81600
ctgaaatgga atgacaacca cccccgccga cctctgctcc ctgccaagat attctcccaa  81660
ctgaaaaact cagagtgaag gagccagagg gaacagcctc attgcacagg tggagaaaca  81720
aaggcccaga gaggggatag gccttgccca gggtcaccca gattgctaag gctgacatga  81780
gacaggaacc ccaggtccgg gctgggtctg gtggcacaca cctgtaatcc cagcactttg  81840
ggaggctaag acgggaggat tgcttgagcc caggagtttg agtccagcct gggcagcatt  81900
aaaagacctc catgtgtaca aaatattaaa ataatacaaa aatcatctgg gcatggtggt  81960
gcacacctgt agtcccagct actcaggaag ctgaggtggg aggatcactt gagcccagga  82020
ggttgaggct gctgcagtga gtctcaatca caccactgca ctccagccta ggtgacagag  82080
accctgtctc aaaaaaatgt taaaaagaac cccagctcct tcttcccacc tcaaaagatg  82140
tccacatccc aatcccctaa ctgtcccaat gtgaatatgt taccttatgt ggcaaaggga  82200
accttccagg tgtgattaaa ttaaggatat gaggatggag ggatttatcc tggactatcc  82260
agatgggtcc aatatactca aaagcgttct tataaaggac agagggaggc aggagaggca  82320
gaggaggaga tgtgatggca gaagcagagg ctacaatgac acggggccat gagccaagga  82380
gtgcggcagg ctctagaggc tggaagaggc aaggaccaga ttctccctgg agcctgcaga  82440
agcactgcag cctgcgggca ccccgctttt caaacttctt ccctccacaa ctgtcatagt  82500
ccgtctgtgt tctctgaagc cacttggttt atggcagttt gttacagcag cactaggaaa  82560
ctcacatagt gttagaagga gaagcattgc cagggaaact gcacctggca gtgtaggctt  82620
ccctctgtac tcagtgctag ggaggtaccc ttaccctgag ggtcacccca gatcacccca  82680
gagtcatgtg gctcctcctc tccagaggcc acaaggccac cacccctgc ctgctcttcc  82740
```

-continued

```
ctcattcatg acgttctcac cctcacgtgc tgggctgcag cggggtctcc cactgttttc  82800
ttagtccccc agactcctgc agcttttctg cagcctgacc tccttccaga tggttttccc  82860
tagtacctca cctttcccca tccctcctct caaagacgct aaggaaagag cgacttgcac  82920
ccagggcttt ttcccgcagc cctccctgg ttctcagcca ctgtcttcgg tcacctctca  82980
ctgcctccgg tcacctctca ctgcctcggg agcctcagaa caccagcctc cccttcccat  83040
ctccgctctg gggcctgct ccagtctggt gattcctctc tccatctccc agcacttggg  83100
gacagttatg tcactcagag agctcccagg gaagaacctg aagaacagac ccagatagag  83160
gggagagagg gcagtggaac cttatggaaa aaggggcagg tagccagtgg ctgtggtgca  83220
aatgttctcg agtgtggccc ccggcctgcc tagcctggct gatgcttatt aaaagtgcat  83280
attcggccag gcacaatggc tcatgcctgt aatcctaaca ctttgggagg ccgaggtaag  83340
cggatcactt gcagtcggga gtttgtgatc agcctgacca acatggtgaa accccatctt  83400
tactaaaaat gcaaaaatta gccgggtgtt gtggcagaca cctgtaatcc tagctgcttg  83460
ggaggctgag gcaggagaat cgcttgaact cagaaggcag aggttgcagt gagctgagat  83520
cacaccactg cactccagcc tgggcaacag agtgagaccc cgtctgaaaa aaagaaaatg  83580
catattctgg ctggtgacga tggcacatac ctgtaatccc agcactttgg gaagctgagg  83640
caggaggatc acttgagccc aggaatttta gtccggcctg ggcaacatgt cgaaaccctg  83700
tctctacaaa aagcacaaaa attatctggg tgtggtagca cacacctgtg gtcccagcta  83760
ctcaagaggc tgaggtgaga ggattgcttg agtccaggag attgaggctg cagtgagctg  83820
taatcaggcc actgcactcc agcctgggca accaagcaag atcctgtctc aaaaaaaaaa  83880
aaaaaaaaaa aaaaggccgg gcacggtggc tcacgcctat aatcccagca ctttgggagg  83940
ccaaggcagg tggatcacga ggtcaggaaa tcaagaccat cctggctaac acggtgaaac  84000
cccatctcta ctaaaaatac aaaaaattag ccgggcgtgg tggcaagtgc ctgtagtccc  84060
agctacttgg gagcctgagg caggagaatg gcatgaacct gggaggcaga gcttgcagtg  84120
agccgagatc gtgccactgc actccagcct gggtgacaaa gcaagactct gtctcaaaaa  84180
aaaaaaaaaa ggtcaggctt ggtggctcat gcctgtaatc ctagcacttt gggaggccaa  84240
agcaggcggg gctgatcacc tgaggtcagg agttcaagac cagcctgacc aacacgaaga  84300
aaccccatct ctactaaaaa tacaaaatta gcctggtatg gtggcacatg cctgtaatcc  84360
cagctcctca ggaggctgag gcagaagaat cgcttggacc tgggaggggg aggttgcggt  84420
gagccgagat cgcaccatta tactccagcc tgggcaacaa gagcaaaact cggtctcaaa  84480
aaaaaaaaag tgcatattct agttgggcat agtggctcat ggctgtaatc ccaaaaattt  84540
gggaggccaa ggtgggagga tctcttgaga cctgaagtta aagatcagcc tgggcaacat  84600
cacaagaccc caactccaga aaaaatttaa aaattagcca gacatggtgg cgtgcacctg  84660
tagtcccagc tacttaggag gctgagatag gaggatcgct cgaacccaga agtttgagat  84720
tgcagtaagc tatgattgca ccactgcact ccagcctgga caacgagacc ctgtctctag  84780
aaaaaaaaaa aaaggcacgt attcctggac accctctca ccaataaaca catccttgcc  84840
agagcagaat ctctgagagt gggcccagga gtcttcagtc taccatgctg ctgggatgtg  84900
tcttatacaa aaatcaggaa gtaggccgag cacagtggct cgtgcttgta atcccagcac  84960
tttgggaggc caaggcaagc ggatcacctg aggtcaggag ttcgagacca gcctggccaa  85020
cacggtgaaa ccctgtctct attaaaaaca caaaaaatta gccaggcatg gtagcgggcg  85080
cctgtagtcc cagctactcg agaggctgag gcaggagaat tgcttgaacc caggaggcag  85140
```

-continued

```
agactgcagt gagccaagtt tgtgccactg caccccagcc tagacaacag agtgaaactc  85200
cgtctcaaaa aaaaaaaaaa aaaaaaaaaa tcaggaagta gaaagagaat ggactttgaa  85260
gtcagggagc tctgggctga actcctagct ttccccacct cctagttgtg ggaatgctct  85320
ttatcttctc caaacctgtg ttctcttcca taaagctggg ggctctgatc tgcatgtggc  85380
gggaattatg aggattcaga taaacaggga aagcacagag gcagatgctg cggacgccct  85440
cccgcatctt ctgggggtcc cctcatcctg gagcccaacg gacctaactt ctgacagcct  85500
gagggcccct gggagtgctg aagaatgagt gtcccaccca ctccatccag cagccttaac  85560
aaaggacggg gatggagttg gtgtataagt acccgctccc tcatccttcc agtgggataa  85620
ctctgaggtg caggttccat gctggctcct gagtttccca gcaaaattaa gcttccgtca  85680
cccgccgggg tgcccttcct gacaacacgc ccctgtaagc tgccttcctt ccctgggtca  85740
cctccctacc ctcctactgg agcttcctgt gagcatccct caaacaaaca acttgccctc  85800
aagtacttgt ctcaggtcag ctcctgcggg accccaggct aacataagcc tggcagcctg  85860
gaaatgagcc tttttttga gacagtgtct tgctctgtcg cccatgctgg agtgcggtgg  85920
cacaatcaca gctcactgta gcctcaacct cccgagctca agccatcttc ccacctcaac  85980
ctccagagta ccaccattcc tgggtaattg ttctctattt tttgtagaga cggggatttc  86040
gccatgttgc ccaggctggt ctcaaactcc tgggctcaag ggatccaccc gcctcggcct  86100
ctcaaagtgc tggaattaca ggcaggagcc accacgccta gccgtgagtt ctttttcctc  86160
tcctcgtctt tgactgtcag tgtggagacc aggttggccc agaccaagca aagccaccag  86220
agggcctgga tagtgctgtg gcttgcaggg atacatagac actgatgtcc gggacccagc  86280
aaggacagtg tcccctgact gtaaggatgc catcgaagtc ccaggaaagg cagctcaccc  86340
ttcccttccc cagatcccca gtatctgcta gtcaggaagc agagctatag gcccatccac  86400
aagaatcccc taatcccaca tccctcagtc tgaaattggc cctaaccaca actttcccta  86460
tcttcatctt tctttcctag ttcctcagac acaaagcaaa cagccacttc cccgctcctc  86520
agagacacct tgcctctaaa tcttgaaact gccaagcccc agctggctag gccactggcc  86580
acatgaattc tagtccccag gggcactgaa gtcacctccc agagaaatcc ctatgatttc  86640
atcttctatt taatctttat ttctcctcat acttttcaga acttcaaata atttctcgtt  86700
tgtagtaact aggaagccat aaatcgcccc tttatgtcta aggaaaatca attgttattt  86760
gacattttac cttaatattc ccgacttcct tcaactgtaa taaagcttcc atctgccttt  86820
tattttacag gcaattagta agtcaccttt ttaaaatttc tccacatttt ctatcaaatg  86880
aatgctagga ttgaaagggg agagctgttt tatgggattg aactcactga gtagaaggga  86940
tttatctgta gccttcgagg taccaacact cattaatggg ttttattgat ttgggggctt  87000
tttaaccctt agcaataata caggtgtcac ctgcccaagg cagttgggag ggggcaggga  87060
tgctgggagg ggctgtgagg gagtccacac atttctgagc cctgggccca agctagaaag  87120
gcagagaaat gagatctaac cctttgaagt gtgatcacgc tcagtgcaac cacaccctca  87180
gaggtaaatc atagcccaga caccctcttt ttcctggaga caaagttgga gtttttgggg  87240
ttttttcttc aaattaccca ggggaatgca atgcttttgc acccctatca tgggatcaaa  87300
agaaagaggc ccattgttgg ggttcaaggc cctgggcttg gtctgcctct tttagccctg  87360
gggttgtggg caggccaggg aaggaacctc tgagactcag tttcctacga tgtgaagtgg  87420
agagaagaat ctcctcttta gccacctctc agggctgctg gtgttcgccc ccagaccacg  87480
```

-continued tctgtgagaa atgcttagaa gactatgcag ggcgtaagaa actacataag gaaccaatga 87540
gaatcctagt cacaaatgga aacctcagtc cacaaactcc agaacgaaac cttccttgct 87600
tttctagaac tcatcttatg ggttctgtac cccccattgc ctgggctggt ggaactctgg 87660
tgccagtctt tccctagcaa tttctccaaa accccccacg gccttttcca ccattcccct 87720
tccttgaagg ccgccatttg acactcagag cccaggaagc ctttcttggt ccagacagca 87780
ggactggaag ccttagagct gtcggcaaga gatgtgagtc ctgtagctga ggacagtcca 87840
ggcagagtat gaataagacg gcaaaagtaa gtccagaaga cattaatggt agactttggg 87900
tggcaggtgt atgggtgctc actataaaat cttttcaaca ttgctataca cttgaaattt 87960
ttcattaaaa tgttagaagg gaaaaaaaag gcttattctg gggcaaatcc cccaaggtag 88020
ggtacccgcc tgtgatggga gaaaggaacg aatgtgagca gaggaggaag gcaaggggcc 88080
ctctgaatct agacgaattt gtttgtggga cctgctacgt tatttgtggg cccagtgcaa 88140
aatgaaaatt tggggccctt ccttcataaa ttaagaatat cagctaggca cggtggttca 88200
tgcctgtaat cccagcactt tgtggggccg aggtgggtgg atcacctgcg atcaggagtt 88260
cgagaccagc cagcctggcc aacatggtga aaccccgtct ctactaaaaa tacaaaaatt 88320
agctgagtgt ggtggtacat gcctgtaatc ccagctactc aaggagctga agcaggagaa 88380
ttgcttgaac ccaggaggca gagattgcag tgagctgaga tcacgccatt gtactttatc 88440
ttgggtgaca atagtgaaac tccatttcca aaaaaaaaag aaaaaaaaaa cagtatcaag 88500
atgggacagc aaagcattaa actacgtgcc tttcttatct tagagccctg ggtcctgcat 88560
ggttgcccgg ccatgaagcc agccctgtct gcttgggttg agaggtctat tttgaccaac 88620
cccttctgac ccatctctcc atttctaatc ttacaagaac aatacactga acctagcatt 88680
tgatgcaagt gaacaataag tgagtaggtt gggacctttt ctttttttct ttctttcttt 88740
cttttttttt ttttttttga gatggagtct cactctgttg cccaggctgg agtgcagtgg 88800
cgtgatctca gctcactgaa acctctgcct cccgggttca agcgatcctt ctgccttagc 88860
ctcctgagta gctgggacta caagcacgca ccactatacc ggctaatgtc ttttgtattt 88920
ttagtagaga tggggtttca ccatgttggc caggctggtc tctaactctt gacctcgtaa 88980
tctgcccacc tcagcctccc aaagtgctgg gattacaggt gtgagccacc acgcccagcc 89040
aacctttcta ataataataa tatttactgc tcacatggcc ttcaccgtat gccaggcact 89100
gattcagcac cccatggaca ttaactcatt caagcctccc agcaaccctg tgagacagga 89160
ctattgttac tcccatttca cagatgaaaa ctcagaggca cagagagaat aggtcacttg 89220
cctaagctct cagagctggt aagcggtaga gacgagcttt gctcccaggt agctgggctc 89280
cagaatcatg cttttaacca ctccactctg ccgcctctcc aaaaagatag tcaggacaag 89340
cctgacagag atggccccct ggatggaatt tttgctggtc ccaggagggc aaccttcttg 89400
gcatggctat agcgctcagt gcttctcaac tgcaaggtca ccacacacca tcttgaactg 89460
agtcacaggt gtcacattac tagtcagaaa gaagcaaagt ctgtgaataa ttaaactttt 89520
taaaaaatga aatcagattc aagcagtgtc ctctcacata tttgtatctt aactggcttt 89580
tcagactgca ggaacagcca gcaccagaga tatctcctgc aaggcctcct aggtgggttc 89640
ttggaagaaa ggaatgccaa tgaatatgat tgcaaggtga ggcagggcag gagacgcaag 89700
aactgcaccg ctaaccttat taatagggat tgaagagtgc tgaatttata aaaacaatgc 89760
ttttggtttc acaggctccc gctctcatta cacccgcccc aggacaccac ggacacctgg 89820
tagccaccag tggaattgca ggcttagtgt ccagaagggt ctttctcaca ttagctagag 89880

-continued

```
acgagagaag cggcgtcctc aactccaaga atcccgtatt ccccaaccca catccttcag  89940
tctgaaagtg cccctaacca ctactttccc taccacgtct ccctttccaa gttcctcaaa  90000
cgcaaagcaa acagccattt cctgcacctg tgtgcagtcg tagcagtacg taggagatcc  90060
aatatgcctg ggtgagtcag gagaactccc tgagatcatg gcccttgaga atgggtagga  90120
aatggccagg gagacaatag gggaagggca tcctcagaaa gaggggacag atttgggggc  90180
acgccttgta agaaagagct ccaggatgca cccgtgatta ttgtttcatt ttaccctcac  90240
aaacaacctt gccagggaga tagtattgct cacattttaa ggtgtggaag taaagattca  90300
ggaaaatgag cttacctgcc caaagtgatc tgacaggtaa gtggcagggc cgtcttgtct  90360
gatgtgagtt gaggaggatt tcagctggta gagttcggga gtaattctgg atcacctggg  90420
gaaaacaata aacatacagg gcggctttca agtgctcgca ctacccttgg caccgaagcc  90480
tgcccagtcc ttggggcaca gccaggagga tgagggccct tcctaccaag gtggctgcca  90540
ccgactggct gggctgcact gcatgcaggc cagagggccg gaaagatgag atttacgatg  90600
gccatggcct tcacgactta atggtcagga gttgagctat tttatcttat cagacagttt  90660
tgcctagaaa tagccacaga ccttcattcc aggatggctt ttagtcatga gggggtgacc  90720
tgcaggtctc ctaaatcatg ttaattccca gggcagcagg ctgtgctttc ttttctctgc  90780
agtgtctttc accattcccc agccatttgc ttctctgaag gaaagtctct ccggggccag  90840
caatgttgag gaatgcaggg tgtaggggag cagaaaggcc actctggtgt ggcctgactt  90900
gggaccatct gtccactcag acagagctca gcaaacggtc aaggagctga gaatcggctc  90960
agtccctccc tctccctctc actctcttct tccctctttc ccctccccac tctctcagcc  91020
cctcacctag ctagctgccc ctcccttacc tcgcaggacc ccctgggatg gaactgcttg  91080
ctgagcagtt ctgatgaagg caggaccctt tcctctctgt ggactcagtc cacagtgtct  91140
gtagacactg gccctccaga ggaccagtgt gtgagggggt gttgccagcc tctgtttctc  91200
ctgagccctc ctcccaagtg caagtatgag aactcctctc cacaccttcc tgcgtgtcca  91260
ggggcttcct ttagggttct aggagtccca agacatcatg ggtaggcagc agatggagaa  91320
agagcagaat gttccatcca ggccaggcac agtgactcac gtctgtaatc ccagcacttt  91380
gggaggccga ggcagcagat cacttgaggc cagaagttgg agaccagcct gatggagtag  91440
aaactccatc tctactaaaa atacaaaaat tagccagatg tggtggccca cgcctgtaat  91500
cccagctact tgggaggctg aggcaggaga attgcttgaa cccgggaggt ggaggctgca  91560
gcgactttga tattgcgcca ctgcactcca gctctggatg acagagcgag actccgtctc  91620
aaaaaaaaaa aaaaaaaaaa gaatgtccca tcatccaatg gcaggaccct gggcacacgc  91680
catgggacag tctcagtcat agccactggc tgggacaact ccagcaaaca gtgtcttcac  91740
tggtccttct caccatccac ccaccggctt ttcttgactc atggaggggt cttgcagacc  91800
ccttccccag atctgattcc taggtctggg atccccccag caccctcgct cactcttcat  91860
tcccctggag gtcccacccc acaccctctt gactctccaa ggagtgaaaa gctcctttca  91920
ctttcacctt gatattctgt taaaagccaa atccaaatcg ttagcaacag aagccagctg  91980
cccttctcta aaagccggag ggccggtcct caaacccctc ctgggggtg agatactttt  92040
gtatcctacc tggctggagt catgccttcc cctcaccctc aacccccaga ataggcaata  92100
aataaaatga aagttttcta atgcagtaaa taaaaggaag aaaactggag cagaccagat  92160
tctgttttat ttcctaataa aacagaggct gtctcctgac agtccccaga gggcccacca  92220
```

-continued cctcatgatg tattagtaac acaccagctg ccttgcaaca agacttggtt atcatttacc 92280
tttataagga ggcttctcag atctcatctc accatgtgag ttgggcatta ttaataatcg 92340
ctaccattaa acatacctac aatgtgctgg gtgctttcta tacggtattc tatgcaatcc 92400
ttacaccgac cctgaagtgt aggcgctatt atttccactt cacaggtagt gctctgaggt 92460
tcattagctt tcttaaggtc atgcagctaa aaaaaaatga caaagtgaat ccaggtgggt 92520
cctcactcct gtggggcccc agggaacttc cggctgattt ctggggcgtt tgcgcgcaga 92580
gcgagacttg gccagcagag ggcgccagcg ccccgccaag gcagtgggag accggcggga 92640
aggcggctgt gaggcctggg ctagtttcgg cttagagact gcagcctcta gactcagcac 92700
gcagagctcg gaccagtggg acccaaggct tctctctcgg agactgccct ggagccaaag 92760
tctgtgggca gaggagggcc aaacactgcc tgggccttta ttttgcatcc agaaacaggg 92820
tgctctggat agcggcagcc cccacccgct gagcgagctc aggctggttg caaggagaga 92880
aaaaggaggt ggctgtcccc gtcctgcgac ctgggttctg gtcccagtgg gccgtgggaa 92940
agctgagact ttctccgtgc ctctgtttcc ccatctgtaa aatcgcagga tttgtgcgcc 93000
gcagactcca gagtccatgg tggggggcgg ggcgtggtcc tctcccattt cagaaaacct 93060
atcttaagag gcacatctag gaggctgcct agagtgacca aggtaccagg ggctgagcac 93120
cctgcagaca ttggtgatct ctggttgatc caaaacgaag aagcctccct gcgtgtcgat 93180
atgggaaaga gaattgatat gcaaatacat gcagcttctt tggtaaataa gaatatcaaa 93240
tcagagtcta tgagagttgg gggctggggt cggtggtcag agatgggatc cccaggcctg 93300
tagggccttt cttcctttcc agctctccaa gccctgccag tctttcctcc tcaaccttct 93360
ctcttgccta aagagaaatt gtcatgagcc tgctaatcgt gaaaggttct gtgccttccc 93420
tgctgccaaa cccatcaaac ctatttacca gaaatggctt tgttctaaga ggaacaaaat 93480
gaggctcaag ggtgagggtc cacaggtctg gcccccagat gcaccctgga gcaatgaggg 93540
cccccggggc agggactttt accagccttc cctggtggag gcaagattca cagtgcaaac 93600
tcttctccaa tgcagggaca gatgaccaaa ccttgcagac agcagcggga gctggaggga 93660
ctttgttgag gactgggacc caggtgtggt tgctgcaatg ccctctgctt tggcagagaa 93720
aagatgcaga ttcccaggtc acaccaagtg acctctccag aacctggaac agcctctgtg 93780
tggactgcca tgggagagct ggagccacca cagaatcttg ctcaccccag ggaggtggca 93840
gcaataggat catcatgact tttcaccttg acctttcacc acagcctgac ccctccaagg 93900
tgggagtgag cacaatggca caggggttgg gggtctgtgt ccgagtagga ggggtgttta 93960
aacgggaagt aagagagcat tgcagagaat gttaactgcc cctctcttct gtttgccaag 94020
cccatttggc ttcatgctgt ctccagcctc aggagtcagg aggctctgaa atgtctaaat 94080
gtcacatggc ttgaccacag ccagggaggg gcaaagccag gcattgaggt ttcttttctg 94140
attcccaaga agaaggaagg agggcgggag acaataattt aaaaaaaaaa aaaaaagaga 94200
gagagagcaa gacttgttag aggccacgag gagtctcagg ccagaggtgt ctctccccaa 94260
acccgggatg ggagggagct gggggccacc ctgccctcct gctctttctt ctgccctggg 94320
atttaattgc tctgcaagtt cagtgagctg ttcactgaca acactggggg ctctgggctg 94380
ctcagactca gacacaggtg tgccctcccc gctgaattta tgagacccca gacttagggg 94440
gcctcagggc agtaattcaa ggcaaatcct agagacctgt tgaacccatg gctactcagc 94500
agcagaattc cctaggaagc attagaaagc tacagactgc tccgggcttc tgcaggctca 94560
accctctgcc tcctgctacc tgcccctccc tgcctacagc agcccccctc agagcatttc 94620

-continued

```
tctcccccca tcactaactg cctgtctccc accaccccct ttaggaccgt ccctcctcca  94680
gcccatcctt ggagctgccc agttccctgt gaaatgctcc tccccacctc gccaccaaca  94740
tcagcccctc tgttgccctc tgtaccccat actgggcatt ctggctctca gcccttctaa  94800
cattctcttt ccttgctttc catcagaact ttccccttga gccaaactgc tttgttcctg  94860
ttctgcattg ccctggcttc tggatgcctt gtgcaccctt ttgctttgtt ctttcccagc  94920
cctacacagg cctgcatgcg cgcgcgtgca cacacacaca cacacacaca cacacacaca  94980
cacaccctgc ctactgctca cacactttcc tcctcctctg agtctcctga gccctctccc  95040
tttttcaagt ccctgctcca gccccaccct ccctgggcct gcccaggcca gccctgtccg  95100
ggagacctct cctctttgaa tggcagtgcc tgcgtcctca tctgttccac gccctcccca  95160
agttcattct cttcctccag agctagccag acctcccaaa gagccctggc aggagctccc  95220
aaagtaagag tttctttgat ctcctaggta gctgctcaat gccagtttgt ggatcgacat  95280
gtgattctta catttgcaac aacatcttct gtgagtagcc tgctccccca gcacgaggaa  95340
aatgagactg atcctgagag gatttgattc gtgcattctg gagggacaag cctgcctgga  95400
aaagtctcct gcaggagagg cagaccaggc tgccccaacc tgagtgtgga ctccagccct  95460
gggctgccgg gctatatgtc ctcccatgta cccactaccc tcacccagtc tcagcagcga  95520
ctcagaatct ctgtctgggt ctggtccacc accttcccct atctggactt gaactccttc  95580
agggctggca cagtgaccca tcatcctatc atgcccacag tgacctgctg ggtgctgtga  95640
gatgtcagtt tgggccctgc tgtgtgcacc aacttcactg gtgatactgt taccacctta  95700
agggtcagag aggtttaaga actcacccaa agtcacccag ccagtaaatg gctcagttgg  95760
ggttcaaacc caagtctata agatgccaga tcccctggtc catccagaca cctgactgca  95820
tctcgtacat tgcacacagt agatgtaaac aatacaaacg tctacagaag tcagggactg  95880
ggcgcggtgc ttcacacctg gaatcccagc atttcagagg ccaaggttgg tggatcgctt  95940
gagcctagga gtttgagacc agctgggcaa catggtgaga ccccgtctct acaaaaagta  96000
caaaaattag ccaggtgtga tggtgcacac ctgtggtccc tcatactggg aggctgaggt  96060
tggaggatca cttgaagttg aggtcaaggc tacagtgagc cgagattgca tcactgtact  96120
ccagcctgcg ggacagagcc agaccctgtc tcaaaaataa ataaataaat ctacagaagt  96180
gaatctgcct ggaaacggag aacctaaaag aatcatcagg aggtttggtt ggtgatgtag  96240
cattaaggtg cctgagagcc tcttacacac acaggccaag tggggatcta agccaaagca  96300
ccccctccat ggttttaggc ctatgctggt gaacaaggca gatgcagccc cgacagcacc  96360
tgccttccag ctctgccact ggacggagac atcacagact tgtagcaggg acagccatcc  96420
agcccactgg gtgttcacat atcttccact taaaacctag aaaatggaag cgcagagtag  96480
acataagcct ggtgctgttt taaaagggaa tggtttagta acctgtaggt agctctcttc  96540
ctatcccctg tgcctgcatg cagctgtggg accacagtgg cttgacacct ccatcagttc  96600
ccccattcta gggtcagaag tgggtcctat cagaaggtag agctttctgg cctgggcaca  96660
ttgcagaaag tgctgcggtt ctaattctca ccaccagaag gcgctcccag accctccgct  96720
gggttcatac tacaatgttt ccatctaaat ccatgaatca gttttttctc actcctctgt  96780
atgtgaaagc tacacctaaa atgtttctac ttaaatccat gaactagttt cccttacacc  96840
ttcctctgta ggtgaaagtt cctccagaga ctagagcagg actttgaagg cccatgaact  96900
gggaaattaa ctgtttaggt gccaaaagtg ggagttgtga tgggggttaa actgacagag  96960
```

-continued

```
gaggcgaatg ctattgctgt ttgaaaacgt aggccgggca ctgtggctca cgcctgtaat  97020
cccagcactt cgggaggcca aggcgggcgg atgacgattt gaggagatgg agaccatcct  97080
ggccaacatg gtgaaaccct ggctctacta aaaatacaaa aattagctgg acgtggtggt  97140
gcatgcctgt aatcctagct actcaggagg ctgagacagg agaatcactt gaaccgggga  97200
gtcagaggtt gcagtgagcc aggatcgcgc cactgcactc cagcctggtg acagagagag  97260
actccgtctc aaaaaaaaaa gaagaaaaag aaaagaaaat gtaaccacac attcagcttt  97320
caaaataccc gaaggctcgg ccgggtgcgg tggctcaagc ttgtaatccc agcactttgg  97380
gaggccaagg cggaaggatc atctgaggtc aggagttcaa ggccagcctg gccaacatgg  97440
tgaaaccctg tttccactaa aaatacaaaa attagtaggg tgtggtggcg ggcgcctgta  97500
gtcccaacca cttgggaggc tgaggcagga gaatcacttg aacccgggag gtggaggttg  97560
cagtgagctg agatcacgcc actgcactct agcctaggca acaagagtga aactccagct  97620
cagaagaaac caaaaataac caaaggctga ggacatcatt tcaatgtgtg tgtgtgtgtg  97680
tgtaacaaag accacagtgt gtagacattg ggtttcagag atcacctctg tgtccagctg  97740
tctgcgagtc tggactgatg agactctacc ctaccccact ggtgaatgtg gacctgcata  97800
tgtgtatggc agcgggagtg gaaacattgt cctgatgtgt ctcctagcgt gtctagctgt  97860
gtgtgtgttg ttaggaatgc tggatgtgga ttgagctttt gtggctgtgc tagtgtgtgt  97920
gtgtgtgtgt gtgtgtgtgt gtgcgcgcac acgcgcctgc ccctgctttg gcatttctgc  97980
ccagatccag gggctctgcc atatgggtga gcaggtacac acacgtgctt agtagtatct  98040
ctaagggtgt caaggacata cgtgtgtgct ggtgctctga gcctgcctgt attcaatttt  98100
gtgtgatgtg tggcccacat gcacctgctg tatataggga ctctcaggct ccagggagga  98160
gacatacatg tgtatgtgtg tgtttatggg tgtgcacccc tggtgtcctg cctctcctgg  98220
ggctcagtca aggccttctg ctctctgttt ctgggatgtt ttacttcccc atgacacaga  98280
gcccttctag gctgctgctc tcctctgtga gccttgcacc tgcctttctc cttcgccaag  98340
catgccttag gggagatggt ttatttcttc aattaaaaga agaaagaccc tgggaggctg  98400
cacacttaaa attaccacat tttaaaaagc tctgacagtc atgaaactat aaacctcaca  98460
gcagtgtctc tgctgccccc aggctactcc cagccctgaa ctaaggggtt cacctcctcc  98520
aggacttgga tggcccctct cctgaggctg gaagatcaca ccttctctga tcagagagac  98580
cccagtattg tttgcatgtg taatcatgtg ttcatctttc cgttcctcca gatctttttc  98640
ttccatagtg ttatattcag gaaagaggtt aggaagcaga aaacccaggt tctagcaccc  98700
tctccctggc tgggtgacct tggacgaggc tcctaacctc tctgggcctc agatttttcc  98760
atggcagaat gaagctggtg catatcatga tctaaagttt cttcctgctc tgacactgac  98820
atctgagccc cacaaaacct tgacagtgag tataggagtc tgcattaccc cattttaata  98880
aagaaacaga agctcattaa ggttaagtga cctccccctt ccagggacac tgcattttcc  98940
acaacagcac cctgaaattg acaaaggcgg agagagcagc aagaaacaga caggcacacg  99000
ttcacactcc ctgcatgatc ctctctgaaa acaccccgac agccaggagg ggattgatga  99060
gaatttgcgt cacagcccta cacagtaatt attggtgttc ataatgatgc cctaaggcat  99120
tacattcccc tgaaatgcct tcagaatcat caaagaaaga ttaagccatg cctactataa  99180
ttgctctttg aaataccttc tattttattc tcctgcttgg aaaattgata acctatggat  99240
tttcaattaa ctttaagtta caaagaatat tcagtttacc caagtatctc atccatttat  99300
ggttcccttt taggaggagt tgattatcca tctcaagctg tattccccaa ggagcctgac  99360
```

-continued

```
gtttttacga gatgactgag tttgggggtg gaaaaaccct tgatctgtaa ttggaggccc  99420
tggctgcagc cctttctagg actgtgactt tggcaggtca ccagcctctc caaacctcag  99480
tgttctcacc attaaaaaaa atggattaat gccagttctg ctccctcggt gtcattgcca  99540
gaatcaagta gatgatggat gtgtttgtaa atgtcatgtc tatgcaaatg agagatgctc  99600
aggaagcact tgagaactgc atggtgagac ctctggcata gccaagccag ccaaactgct  99660
aggctgggca aagaacacat aacaggcatc ctggcctcat ggcattccca ataacaactg  99720
ctgcagccat ggctaagtcc ctaggcctct ctgggcctca gcttcctgat ctgtaaaatg  99780
gggagcagag agagttggac aagatcagag attgcagatt ggtattccaa gaaccagtcg  99840
tgccatgttc tgggctgctt ttaattgaat ggcagtgttt tgaattcatt gccaacattt  99900
aaaagttgac aggttgccta taaaaaatct ggaaatatgg ctttttttttg acaaatggaa  99960
agatatggtt ggttacactg ggcccatgtt catgcaaggg aaaattggcc agtgccaagt 100020
agctgttggc cccctctttc tcccatcaaa ggcacccagg tgtctccctc ccagctggct 100080
tggggaacct gtgtttactt gcctggctcc atgggttctg accccctaaac tgactgatct 100140
ctaaagcttt agaccttgaa ccatcatcac acctccccca ggtgtgctgg ccttcgtcgg 100200
gaggggaagg gtgaggtggg cagtgatctg ggaacttccg cagggccacc ttctccacct 100260
ggcctgggat ggggagaggc acattccttc agtagctccc aggccagtgg acagagggct 100320
ctgaagagac tccccccacc ccagccctca cagccagagc tagtaactca cagctgcggt 100380
tacccacacg ctgatttctg ttttaaaaaa tactgctggg taaacaggga gggaaacctg 100440
agctgttccc acaccacata aatccccggt ttgctgtcct atctggttag ctggtttccc 100500
caaataatgg cactgctgcc tcgaaagcaa ggggctggaa aagggaggcc ccgagaagtg 100560
ggcggctggg agtctcccag gctggctcca ggcccaggcc tggtggcctc cctccttctc 100620
tctttcagca cttcctgccc aggggcactc acctttgtcc tcactccttc cacctgagcc 100680
gcccttcctc cacccctctg ctttgtctct ctcaaaagac cntccacaga aggctttcct 100740
gggggaccct gggnccctcc ggcagccaga aagcccatag ccaaaggcag acctacccca 100800
acaccgcatt tccctctgga aggctccctt taaagtttcc ttccagagcc ttctgtcaaa 100860
gtgcaacgtc ctgactcaaa aggtaaggcc agagcctttt gcgtcctgaa aatgagttta 100920
gccttggatt aggattgcca gatttagggg gaaaagaaga cactcagtta aatttgagtt 100980
tcagataaac aaacaacaat tttttagtct atgtcccaat attttctgga acagacttac 101040
ctcagcattt tatctggcag cctaccttag ctcttttcct tgagaacagg ttctgatggg 101100
gaagaagaag aagataaaag agttattagg gccaccaagg tgcctatagg ctgaatctcc 101160
cagcctcccc agcagttcct cactgccaag tatatagttg cgggcaattg gtctgtagag 101220
taattgttga acaggaccct ccttaaaaca gggcagggag ggttgggcac aatggctcat 101280
gcctgtaatc ccaggacttt gggaggccaa ggcgggtgga tgatttgagg tcaggagttt 101340
gagatcagcc tggccaacat gacaaaaccc tgtctctact aaaaatacaa aaattagcca 101400
ggcgtgtagt cccagctact tgggaggctg aggcaggaga atcaattgaa cctgggaggt 101460
ggagattgca gtgagctgag atcacaccac tgcactccag cctgagggac tgagtgagag 101520
tctgtcttaa aaaaaaaaaa aaaaaatgta gagaggctgg gcactgtgtc tcactcctgt 101580
aaatcccagc actttgggaa gccaaggtgg gagaatcact caaggaagga gtttaagacc 101640
agcctgggca acatagcaag accctatgtc tatttttttt ttttttttga gacggagtct 101700
```

-continued cgcctctgtc gcccaggctg gagtgtggtg gcacgatctc ggctcgctgc aagctccgcc 101760
tcccgggttc aagagattct cctgcctcag cctcctgagt ggttgggact acagccatgc 101820
gccaccacgc ccagctgatt tttatatttt tagtagagat ggattttcac cacgctgacc 101880
aggctggtct cgaacccctg acctcgtgat ccgcccacct cggactccca aagtgctagg 101940
attacgggcg tgagccaccg cgccaggccc ccatgtctat tttttttttt tttttttttt 102000
tgagatggag tctcgctctg tcgcctaggc ttggagtgca gtggcgcaat ctcgccttgc 102060
tgcaagctac gcctcccggn tcacgctatt ctcctgcctc agcctccaga gtagctgaga 102120
ctacaggcgc ctgccaccac catgcctgga gaatttttttg tatttttagt ggagacgggg 102180
tttcaccgtg ttagccagga tggtctcgat ctcctgacct cgtgatccac ccgcctcggc 102240
ctcccaaagt gctggggtta caggcacgag ccaccgcacc cggcccccca tatctatttt 102300
ttaaacgggt tgtggggagg ggggcagtgg gcagagagat ggggagagtc catttgtcct 102360
tcctccttcg tgctgtgtgg aatgctgaca tgccagctga acaaggtgcc gcaggggggc 102420
aaagtagaga gacagtgcct gggggagagg ccatctcagc ttggactgtc acctccggcc 102480 tttttatgg gggagaataa taaactctgt gtgtttcccc ttttgtcatt tgttttcatt 102540
ctatacagct gactccaata cagaacccct ggaaggtgtt catttgctgg gtgcttactg 102600
agtgtctgta cagtgagcca ccactttaca gttgaggaaa ctgactcata tgacttccaa 102660
gagccaggtt tctatgcagg ccattctgtg tgttacattt ttcagtcatc tgcctacaat 102720
tttggtagca gacaagtaga gcaccaaagg tttaaatgta tatatatgtg tgtatatata 102780
tatatgtgtg tgtgtatata tatatgtata cacacacaca cacacacaca cagagaaaac 102840
ccatctgcag aacttacctc ccttagctta gtgttttctg agatttagag aaagacctcg 102900
ttattgggcc cctggggtgg aatgcaagga ctatgttcta tagtttactc aactctgacc 102960
cttggatcat attatttgag cattacaaag ccctgtcagg gccaggcgcg gtggctcatg 103020
cctgtaattc cagcactttt ggaggctgag gcgggcagat cacctgaggt caggagttca 103080
agaccaccct agccaatata gtgaaacctc gtctctatta aaagtacaaa aaattggctg 103140
ggtgtggtgg cgcgtgccta tagtcccagc tacttgggag gctgaggcaa gagaatcact 103200
taaacttggg aggcagaggt tgcagtgagc cgagattgca ccactgcact ccagcctggt 103260
gacagagcga gactccatct caaaaataaa taaataaata aaaataaaaa taaaaaatat 103320
tagccgggca tggtagcatg cacctgtaat cccagctact caggtggctg aggcaggaga 103380
atcgcttgaa cccagtaggt ggaggttgca gtgagccaag atcacaccat tgcactccag 103440
cctgggcaac aagagtgaaa ctcatctcaa aaaaaaagaa aacaaaacaa aacaaaaaac 103500
cctgtgaggc aggctggcag gcagtagtaa ctctgctgcc tcaaagtgtt ctgagaagca 103560
aaggacacat gtgtacattc caaatacatc ccaggcccag tagtaaacac gctagcccac 103620
agccacgtat accatatcca aaatctgcct gtcttctgtc catcccttaa ggtcttacta 103680
gagaccaagc atctcatctg attcacacat tctactatgt aagcgcaggc taatggcttc 103740
atcttgtgcc ctgttcagtg gcatataaat atttcacagg gctctctgga gttgtctgta 103800
aggcaaaaat ctcaggtatc atcatcttca tcatccagat gttacccctg catgccaggc 103860
tatgacaaga gctttcatag accacctcac tcacgtctct cagcatcctc atgcggacgg 103920
aagaagttta tccccatttt acagatgagg aaactgaggc tcaagtgata aggcaagtcg 103980
ctcaaagcca tttagcttat taataacaga gctgaggtca ggcacagtgg ctcatgcccg 104040
taatcccagc actttgggag gccagggcgg gcagatcacc tgaggtgggg agttggaaac 104100

-continued cagtctggcc aacatggcaa gaccccatct ctactaaaaa tacaaaaatt agctaggtat 104160
ggtgccagac acctgtaatc ccagctactc gggaggctga ggcaggagaa tcgcttgaac 104220
ctgggaggca gaggttgcgg tgagccgaga tcccaccact gcactccagc ctgggcaaca 104280
gagctaagac tccgtctcaa aacaaaaaac aaaaaaacag agctgaggtt tgaacccaca 104340
ggcccccaat tcccaaggcc atgatttgga cccttgtgtt atgttgccat agaaggtatc 104400
tgggggctgg gatgagccgt cttcacctac attgtgctgt gtcctgccca gtggttcagc 104460
atagttaagg acaagctatt cctcacatgc atcacccttt atagtcagcc agctctgttc 104520
tcagatgcag ttcatttatc ctcctaaccg ccaggtgagg ccggaactgt caactccatt 104580
ttgccagtga gaaaaatgaa gctcagagaa gggtgtgatt tgcctgagac cacacagccg 104640
gtaacaggca aggtcacacc ttgaacccgt gtcttctgcc tccaggtcca gggccttgcc 104700
ctgacaccct gcctctccaa gcacaagggg gtggggtggc cacaaacaga agcagccctg 104760
tcctgccaag tacacgcctg cctgccacgc acaatgggag acattccgca agttccacgt 104820
gatggctcag gtgtggccag gctgaaagcc tcctgggccc ccccacgccc ctgggggacc 104880
tcctcgtgac tcacactttt cctcttcctc cccttattct ccccaacaat cagaaaccgg 104940
ggtcccctcc cttcctgaaa acagagctct cctcatgagg ccacagggct ttttcgacac 105000
acagctcctt ccatccatct ctgtctctgg ccctgtgggg ccttgacagg gaaacgctga 105060
ctttgaggag gttaaaggtg ctggtgcccg gccttcatct aacaaatggg ttgccgtgag 105120
gggaggaact gttgttgttt tttcctggcc tcagaagagg ggcctgtcag gaagatgtag 105180
gggccagcag gcccccggcc gcgccccgca aggtggctga cagacgccag cagctgccgg 105240
gggctccggg gtgccagagg cctgtgttct cagggcaaag caccccaccg cgccccctcc 105300
ccatggccct cctgacctcc ccacccaccc caccatgacc cagggcccac cccgtccagg 105360
ggcaaagggc caggcgctgg gcctccctgc catgaggtcc ctgggccaga tgcagaggtg 105420
gagcaggaat ccggttacag cctgcggcca gcccagggga aggttttcct agggaagctg 105480
acaagccaga tcttcctccc agcctcccac ggattccttc cagaaccccc acagcacagc 105540
gtgcccccca caaaggacct cacaaggctg tttctgtaga atttcctcag aactccccat 105600
tcccaggttc accctttggg atcatcgagg ttaaccagaa atagatgtgc taggaaggga 105660
gccacatttg tccattactt actctgcctt ttgcataaag gatttctttc tttatttctt 105720
tttctttttc tttttttttt tttttgagac agtgtctcac tctgtcgccc aggccggagt 105780
gcagttgtac aatcttggct taccgcaacc tctctgcttc ccaggctcaa gcgattctcc 105840
tgccctcagc ctcccgagta gctgggatta caggcatgtg ccaccacacc cagctaattt 105900
ttgtatttct tttttttttt ttttttgaga tggagtctcg ctctgtcacc caggctggag 105960
tgcagtgacg tgatctcggt gcactgcaag ctctgcttcc cgggttcaca ccattctcct 106020
gcttcagcct cccaagtagc tgggactaca ggcgcccgcc accacgcccg ccttttttttt 106080
tttttttttg tatttctagt agagacgggg tttcactgtg ttagccagga tggtctcgat 106140
ctcctgaccg catgatccac ccgcctcggc ctcccaaagt ggtgggatta caggcatgag 106200
ccaccgcgcc cggcctaatt tttgtatttc tattagagac ggggttttac catgttggcc 106260
gggctggtct tgaactcctg gcctcaaatg atctgcctgc ctcagccttc caaagtgctg 106320
ggattatagg tctgagccac cgtgcctggc ctacataaag gatttcattg aagatttgca 106380
aatgtctgtg ggctgggctg cctcaatttg aatcctgggt ccgctgcttc cctgctgtgt 106440

-continued

```
ggccttgtgc aggttacaca gtctatctgt gcatcagagt cttctgctga aaaacggagc 106500
tgataaaaag aaaagagaga gagagaaacg gagctgatga gaatgactgt tgcctcagaa 106560
ggcttttgtg ggaatccgtg ggggtaaaaa tgtgtaaggt gcaaagtgcc ttacacagat 106620
cccactctga ctgtcatctc agatgaggaa acagaagttc agagagatgg ccaggcatgg 106680
tggctcatgc ctgtaatccc agcactttgg gaggccgagg cgggcggatc acgaggtcag 106740
gagattgaga ccatcctggc taacacggtg aaaccccgtc tctactaaaa aatacaaaaa 106800
attagccggg cgtggtggcg ggtgcttgta gtcccagcta ctcgggaggc tgaggcaaga 106860
gaatggcgtg agcccgggag gcggagcttg cagtgagctg agatcatgcc actgcactcc 106920
agcctgggcg acagaacgag actccatctc aaaaagaaaa aaaaaaaaaa gaagttcaga 106980
gagataaggt gacttgttcc agggcacaca gccaggaagt ggcagacctg gggcttgaac 107040
tcagacccgt ctaacctcaa accccatgcc tcctcctctg catctggcct gctccaaact 107100
gaacagcagg acacctgagg ccaagtgctg attccaccat ttcttagctg tgtgagtctg 107160
ggcagcccag tcatccatct gagcctcggt tttgtcatct gcaaaatgga gacataattc 107220
ttacttaccc atcctaggaa agttgtgagg ctcagagaat tgtgtgtgcc acagctaagc 107280
cctgggcaaa gcagaaagat gagtctggtt gacagctatg accccatcca ctctactggt 107340
ctacaacact ctgaccgctt gttccagaag agggcacatc ttttcatatg tacacccctc 107400
cccatctttt acagctgctc ctgctcccag gatgtgtatc tgactggagt ttctggatta 107460
aaggccagtc gtggcttcat tccacatccc tgggtgccct tcggctcctc ctaggagcat 107520
ctcctgcacc caccccccag ggccccacct ccaggctgca gagctaagac ctaggggccc 107580
ctcctcaggg aaccctcgcc gtctttggaa gcagccagca gagacgctgc tgttaaggtc 107640
catgcctgtt tctgccccca tcctgctgct ctgggccatg ggaataacca gtggggaagg 107700
agttctggcc cctgggtgtt aggaatgtcg tcctccaaga aattgcatta accctctgag 107760
agaccagcag ggcgcagcca tgaggaagac tgattgggca tcaagatggc acttgggctg 107820
gctgccctgt gatgtgcacc agcccggaga cccacgtgcc tgcttgccaa agaggctcct 107880
ttggggaatg aggagcccct gattcctatt tccctacccc aaattcctcg gaagcctccg 107940
cctctggggg atgagaaagg gaagcaggtg ggtggaggtg aagggggcag ggagcaggtg 108000
ggaggagacc cgaagaaact tcaaggacct tatttaagag ccttgccatt gctgtgaaga 108060
aaaatgactt gaaacctctc tagagaagag tgtggctaat tggcatgtat gttggaggtt 108120
aaagagcgga aggaagaatc tgattgtttt tttaagttac tgagaaagtg agaatgtcac 108180
tctgggcaga gagaaattct ttttttctag agtgtgcctt tctttgtact gcagaccaca 108240
gtgggccgct gagacttgca aaaaagattt cttttaatcc accttccttt ttcgcaggca 108300
gcagtagaag ggcctttaaa tcaaatgcaa tcaccaagct tgtctcttgc tcttattcct 108360
cacttcactc cctggaattt ggcatttgat ggattctgga tctgacttaa ggctttttct 108420
aaatccaaga cttggggaat tttgttaaca gtgcaataaa aataacttca tagtgttaca 108480
ggaggcacat taaagacggt gtgtgtgtat gtgtgtgtgt gctgctctct ttccttaaaa 108540
aaaaaataca gacaatgttt ctttaaaagt ctccatctgc aaatcccatt agatgtgcat 108600
ataaggtttc tgatgattaa tagttgcctg ctagggtttt ggttggaggg gatcttgtgt 108660
gtgtgggtta acccctccct ctcctctctc acatttcact tcagaaattt gtcactctct 108720
ccccaccgca ggatttaaaa gtgtgtccca gcagccctgg tccagccctc tgcaggcatt 108780
tgctctgggc tccaggacga actcctcgtc agctggtgcg tctgggttgg gacagtgaaa 108840
```

-continued atgtttagtg tcattggcga caaatacaca tacaggggat cccagtaggt aggctggtgc 108900
attggagggg caggagcaag cccgacatag gtgtgtgcac acacatagga gtagctggcc 108960
acatgtgtgt gtactttaag gagagacttt agttttgggt ttttttttt ttttggttcc 109020 tggggtaaat tttctgttga acatttttcc ctcctattta gttttttttc ttttgcattt 109080
ttaaaaattt gaacataaaa agtataaaga atcaaatctt tgaaaggacc gaggcgtgca 109140
gcggacagca gatggatccc gcggccagca gctgcatgag gagcctccag cccccagccc 109200
ctgtctgggg ctgccttcga aaccccccact cggaaggcaa tggggcctca gggctacccc 109260
actacccgcc caccccgttc tccttccacc agaaaccaga cttcctggcg acagcgacgg 109320
cagcgtaccc tgacttctca gcctcctgcc tggcagccac cccacacagc ctgccccagg 109380
aggagcacat cttcactgag cagcaccccg ctttcccaca gtcccccaac tggcacttcc 109440
ctgtctcaga cgcccggcgc aggcccaact caggcccggc agggggttcc aaggaaatgg 109500
ggaccagcag cctgggcctg gtggacacca caggaggccc aggcgatgac tacggggtgc 109560
ttgggagcac tgccaatgag acagagaaga aatcatccag gcggagaaag gagagttcag 109620
gtaggtggct caggagcagc tgatcattcc tttactgtgt gaccctgggg aagttactca 109680
ccctctctgt gcctaggtgc tctgagcatg aatttctgtc tagtccatcc aaatgcagga 109740
gactggacca gttacctttg gggtttcttc cactgagagt tctaggattc tctggtgatg 109800
gggaccatgt ctgtgtccca gcactcctgg gccccaggaa gggtgtccag caagagaatg 109860
aaacaggatc agccaggatt tggaggacac gtgaaatgga tcctctgggt gcagactggc 109920
gagggctggt gaggggcttt cctgaatcag gctgccattg agtcatgctc ctccccacca 109980
tgctttggcc agccccaagt ggtcctagag ccacagggct cgcttaccag ggaagttcag 110040
ctgaggttaa ggctctgaga gctaagactg aagctgggac cctgggtggc cacccaaagc 110100
caagacccta tgtgtccagg agcctagagg cagagaagca ggcctgcggc tgggatggga 110160
gaatcaaggg gtgaggggga gatggagggc tgaggtttgg ggcagactgc ccaccagata 110220
tcaccctgcg gagctgggcc atgtccaggc caaggggaca gacaactcag catgctgaga 110280
tctggctgac cccccaggaa ggcagccccg caaggagctg caagggatgg gcagcctctg 110340
agagagtcag ggaggcaggc agccaaggga gtccgtgctg gagtcccaga ggctggagga 110400
tgagattggc ctatttgtta agattccagc taaagccctt ctcttcccca gggtggggac 110460
ctgctgcttc ctcacctccc caccaggccc tccctggttg ctcactatac ctgtccacct 110520
tttgtctggt tccttgtccc ggcctcgttc agaacaaagc agtgaccaag cctcctgccc 110580
gtgctgccct gttttcctcc tgacagccgc cctcaggggc acgcctgtct gtcggagcct 110640
gtagaggacc ttcccatggg gctaaccagg gcaggacaga aaagaaggac accaaccaac 110700
aggtgggaat gctttgtgct ttgctttata agcacagctt tcccgagttt ctgctcttag 110760
ccaagcccag gaatgctctg agatgaataa aggggtctca cccaagaaag ctcaaactga 110820
gaggaagaag aggcctgcag aggtgtgtca gcagtgggat gtgccctgat ggggaggctt 110880
aaggtgccat gggatactga cgtcagctct tttgagtccc acgggtttgg gagatgggga 110940
cagcaggttt tattagtacc ttgattctct caatctgcaa aatgaaagac tgaaagttgg 111000
tgagaacaca gaaagaatgg ggtcaaacta gagtgagcag ctcatctcca tttgcccagg 111060
acttttccag ttttagcact gaaaatcctg tcgtaggaaa ccccacagtc ccaggcaaac 111120
agaagaattg gtcaccctag aagtgagctc aaaccccagg cttcaggccc ccggtatcac 111180

-continued

```
ccccttcagt agatttcaaa tgcagtcctc attttgaaat gatgtttggt ctgtctgctt 111240
gaagaagccc cttcttcaat gggagatagg aactctagca gccctcatgg ctgctaaata 111300
gaagggccct ttaaaccgcc agccagttag atccccatcc cgaaaattaa ctcatcctgc 111360
ccctggtagg aaatgtgcta aggatgagaa gcaactctca gcgacttggc tctgaacctg 111420
gttgaagagc tttccccttg gtggcggcac gcagcactgt ggctccttcc tctctgccac 111480
tttccagaga actgacagcc aagggcattg ggaagggata gcaaagccaa gagcctgctg 111540
ggctcaggca gaatcttcca gcattccgag tctcagcaaa acccaaatgc accagctctc 111600
tttttggcga gtggccgatg gccctgcaat gcagagagac cattcacact aagcagctgg 111660
ccacccagga gtacagggac accctcggct gaacggcctg catgcttcag ggtcagactt 111720
tggtggaggg aggttcccat ccgcaggggc cctgggcttc cctaagggtc ccctcaggag 111780
caccagcagc agatgaggca gggcccagtg agctgactct cactcatccc cctgtgattc 111840
cagacaaact cactgttcag catggaaatc tttattgccg caatgcttgc atcctccttt 111900
ggaatttaac tgaaggggag gaaggaggca agaaagatca gctttgtaag agcccaaaga 111960
aggggggaaag tgacgcaagg ctcatgacct actccaggaa tctggaattc agctcagaaa 112020
aggcaaaccc acagagagcc ccccacccaa ccctgccaat cctgagtcta taattggatc 112080
ccctctccaa aattgtgata ttttgttcat tatcaatttt ttgcattact tttgattttt 112140
acaaatattg ccttaaaata ttcttttttt tttttttttt gagatggagt ctcactctaa 112200
cgcccatgct ggagtgcagt ggcatagttt caattcactg caacctctgc cccttgggtt 112260
caagcaattc tcctgtctca gcctcctgag tagctgggat tataggcgca cgcccccctct 112320
cccggctaat ttttgtattt ttagtagagt cggggtttta ctatgttggt caggatggtc 112380
tcaaactcct gacctcgtga tcagcccacc tcggcctccc aaagtgctgg catgcgccac 112440
cgtgcccggc cttccttaaa atattattga tcttgactac agaggggttg ggcatgccct 112500
tgcatttggg cctccccaag tccaggctga gtggtccctg gaaggttaac cagcattgat 112560
cagaaacgcg ttttccatag ttcttcccag ccagacagac aggctgcagt gtcagcacgg 112620
caacttttgg ctgcatgact ttggaaaagt tcataacttc ttccagcctt tgtttccctg 112680
gctgtaaaat gggcatatag cagtagcacc ttccatagag agtctctctg tgaaggttag 112740
atgcagtgat ccatgagatt aactctgtgc ctggcacata gtaagagttc aataaatagc 112800
agctgtaaat ggtattaggc ccatatttcc tgaaccagcc ttcagaatat aaggtctgac 112860
aaatatttct atatttatgg ggatggtgga attgaatatt tcaattatgc tgtctcagaa 112920
attcctgagt ctagggaact tctggcaatc attttgttcc agttgtcatc aggagcatgg 112980
agctcagaga cctgccggag aggttatggg gtgagttggg cctggcaaat gcaccccata 113040
ttgagtggct gagaagcctc cagaaatgga aagtttattg taagaggaat gttctctgcg 113100
cttccttcct cctttgccat ctccttcaac tgctccccgc tcactcccag tagaatctgg 113160
agctgatcta ctcaaagaaa ttatcaagaa agcaagggtt ggccgggcgc ggtggctcat 113220
gcctataatc ccagcacttt gggaggctga gccaggcgga tcacctgagg ccaggagttc 113280
aagactgacc tggccaacat ggtgaaaccc tatctctact aaaaatacaa aaaaaaaaaa 113340
aaaaattagc caggtgtggt ggcaggcacc tgtaaatccc agctacttgg gaagctgagg 113400
caggagaata gcttgaactt gggaggtgga gattgcagtg agcagagatc acgccactgc 113460
acttcattca gcctgggtga cagagcggga ctacatcaaa aaaaaaaaaa aaaaaagaaa 113520
gaaagaaaga aagagagaga gaaaggaaga aaggaaggaa ggaaggagac agagagaaaa 113580
```

-continued agagagaaag aaaaagaaag aaagaaaaga aagaaagaag gaaggaagga aagaaagaaa 113640
gaaagaaaga aagaaagaaa gaaagaaaga aagaaagaaa gagaaagaaa gaaagaaaaa 113700
gaaagaaaga aaatgaacaa acggggagaa agaaagaaag cagggttcct ggcctttggc 113760
acttccccac cctggagacc agcatggtgt tatcttaccc aaaccactcc cagccccagg 113820
ccaatgggga ttaaagaccc ctgctggcag ggacagctgt gaggccactg ttgttttccc 113880
ccaaactgtc cttgctactg tggttgtctt taatttatgg gaatgaggga ttttgcggtg 113940
gtttcctcat ggggttcaag ggaaggttgc gtgtgattag agtggctaca ggtgaatccg 114000
atcgcccgcc tgggaaagcc atggtgctag aactcagcac tgctccctcc tgctctcacg 114060
tcctcactct gctgagacat gcctttaatc agacgtgatt tgtctcatcc ttcttcagct 114120
ccaacacgtg tgttcccaga gctgtcctgc cccaatttct ctttgcaaga cctgctctat 114180
gcctgcctcc gcccaaccac aaatttgcct aaggtataaa actccacaaa taggcctctc 114240
tcctcttttc cctcctgatg cccctttaca ggccacctcc ccgccccagg tcccctccac 114300
taccccctgcc acgaagccac acccagggac tgaccttgca aacacatcct gcattttctt 114360
ccccctctct gactgtgctc tggtggtttc tccttgccta gagcactctc cccttccccg 114420
tacttctgcc tgttgaagtc ctacttaaaa accacccagc tcaaaaacaa cccctttccaa 114480
gaatattttt gttcttcttt ttcaaaaatt tatagctaca tttgcatata acatagtatc 114540
aaagaaagct acagttaaga aatgtcgaag tctagtatct gctagaatct gtgttgattt 114600
tctcacttta gcttgcagtt gtttcataaa ggaactcttc tgaggtttct tacctgggac 114660
atcttatatt tgaaatctcc ttttttaaaa attggggtca aatacacata acataaaagt 114720
taccgtctta acagttttta agtgatacag tacagtagtt gtgcaatcga tttctagaac 114780
ttttaatctt gcaaaaccga aactctatct ccattaaaca acgacctttt ttcccttccc 114840
ccaccccccta gcaatcacca ttctttctct tgctaaacat ttgactattt tagatacctt 114900
acataagtga aatcatgcaa tgtttgtcat ttttgtgact ggcttatgtc acttggcata 114960
atgtcctcaa gtttcaacca ggttgtagca agtgacagga ttttcttctt tttttttttt 115020
tttttttttt ttagaaagac agggtcttgc tatgctgccg aggcgggtgt tgaactcagg 115080
gcttctagca gtcctcccac cttggcctcc caaagtgctg gaattatagg tgtgagccac 115140
catgcctggc ctccttcttt ctgaagacaa taacattcca ttgtatggat ataccaaatt 115200
tctttcttct tttttttttt tttgagacgg agtctcactc tgttgccagg ctggagtgca 115260
gtggcgcgat ctcggctcac tgcaacctcc gcctcccgta ttcaagtgat tctcctgcct 115320
cagcctccca agtagctggg actacaggca cacgccacca cgcccggcta atttttgtat 115380
ttttaataga gacggggttt caccatgttg gccaggatag tctcaatttc ttgaccttgt 115440
gatctgcctg cctcagcctc ccaaagtgct gggactacag gcgtgagcca ctgtgcccgg 115500
ccaccaaatt tctttatcca ttcatctgtt gatgaacatg taggttgctt ccacctcttg 115560
gcagttgtga ataatgctgc aatgaacatg agtgtgcaaa tacctcctgg agagtgtatt 115620
ttctttttct ttttcttttt tgagacggag tctcactctg tcacccaggc tagagtgcag 115680
tggcgcgatc tcagctcact gcaagctccg cctcccgggt tcatgccatt ctcctacctc 115740
agcctcccga gtagctggga ctacaggcgc ccaccaccac gtctggctaa ttttttgtat 115800
ttttagtaga gacggggttt cactgtgtta gccaggatgg tctcaatctc ctgacctcgt 115860
gatccactgg cctcagcctc ccaaagcact gggattacag gtgtgagtca ctgcacccgg 115920

-continued ctggagagtg tattttcaat tcttttgagt gtatacctag aagggaaatt gctatattat 115980
gtagtaatta tatttttaat tttccaaaaa aattatttat tattagaata aaatatagag 116040
acaggggtct cgctatgttg gccagattgg tcttgaactc ttggcctcaa acaatcctcc 116100
tgcctcggcc ttccaaagtg ctaggattac aggtgtgaac cactacacct gaccatattt 116160
ttaatttttc ctttttcttt ttttttgaga caagagtctt gctgttgctc tggctagagc 116220
acaatggcgt gatcacggct cactgcaatc tctgcctccc aggttcaagt gattctcttg 116280
cctcagtctc ccaagtagct gggattacag gcgtgtgcca ccacacctgg ctaatttttg 116340
catttttagt agacaggggt tttaccatgt tggccaggct ggtctcgaac tcctgacctc 116400
aggtgatccg cccgccttgg cctcccaaag tgctgggatt acaggcatga gcccctaatc 116460
tccccttctt ataagcatat caggcagatt ggattgggac ccaccctaac agcctcattt 116520
taacttaatc ccttctttaa aggccctatg tccaaataca gacacactct aaggtactgg 116580
ggttagggct tcaacatagg aattggggag ggaagcacaa ttctgccctt atagggactg 116640
tacaggactg tacggggaca ggaacaaggg acaaggttca aactgtggca cagacccttc 116700
agttgaaaac ccctttagtg aaagcagcac ccagatgtgt gcctgacccc agagctttcc 116760
tagctcaggg tcctgtcggc tggtagagct tttccactga gacaggaagt tgtttctagc 116820
cacaagcaga tccctgattt cctatcttac accaacaagt acagacataa aaagtggagg 116880
cagttggccg ggtgtggtgg ctcacgcctg taatcccagc actttgggag gccgaggtgg 116940
gcggatcatg agctcaagaa atcaaaacca tcctggccaa aatggtgaaa tcccatttct 117000
actaaaaata caaaaattag ctgggcgtgg tggcatgcgc ctacagtccc agctactcag 117060
gaggctgagg caggagaatc gcttgaacct gggaagtgga ggttgcagtg agctggatca 117120
caccattgca ctccagcctg ggtgacagag ccagactctg tctcaaaaaa aaaaaaaaaa 117180
agtggaggca gttttaggag tgaatctcta aagaagggag ctgtttgaca gaggaaagga 117240
gaaaagaggc atgggctgga tgcggtggct cacgcctgta atcccagcta tttgggaggc 117300
caaggtgggt ggatcacttg aggtcaggag tttgagacca gcctgaccaa catgatgaaa 117360
ccctgtctct actaaaaata caaaaattag ctgggcgtgt tggctcacac ctgtagtccc 117420
agctaatcag gaggctgagg caggaaaatc gcttgaacca gggaggtaga ggttgctgtg 117480
agccaagatc gtgccactgc actccagctg gggagacaga gtgagattcc gtctcaaaaa 117540
aaaaaaaaaa aggcaatggt aggctgggca cggtggctca cacctgtaat cccagcactt 117600
tgggaggctg aggctggtga atcacgatgt cagaagatcg agaccatcct ggctaacacg 117660
gtgaaatgcc atctctacta aaaatataaa aaaattagcc aagcgtggtg gcaggcgcca 117720
gtagtcccag nctacttggg aggctgaggc aggaaaatgg cgtgaacctg ggaggcacag 117780
cttgcagtga gccgagatca caccactgca ctccagcctg ggcgacagag tgagactccg 117840
tctcaaaaaa aaaaaaaaaa aaaaaaaagc aatagtagag atgagaatga aataaatgga 117900
caaccccaat aagtgtcacc tgggtcgcca gagtgatgcc aagtcccata caagtgacct 117960
catgcccatg ctcaccttct tgctgggcca cggtacagta ataggaggaa gggtggtcag 118020
agactaaggt caagcgaatt aacaaggtag ccctggttca ggtccctgat ccacaacttc 118080
ctggctgtgt ggacgtgggt gagtcctaac cctccctgag tctcttctga gaaatgaggg 118140
taacagtacc tacttcataa ggtgggtagc tgtgagacta aatgatatca gagatgtaga 118200
gtccacagcc aacacttggt aacccctggc tccagttttc ccaaacccac atatgagcac 118260
ccctctctct ttaaagtcct cccctgatgc tggctggctg catcaggttt cccacgttca 118320

-continued

```
aaaacaggcc aaagtgtcct gagctctgct gaagtctttg ccccctgctg tcagccgggc 118380
ctgcctgact ctgacgatgc tactggctta gggttgtggc agtgctgggt ggggtgtggt 118440
ttgaggggtg caccgctgca gcagctcctc ttgtcccgag tccatgtcca gaacccctag 118500
tgaggaagaa gttttatggt ccagagtggc cagcgtggga ggggagacag caactccaca 118560
ctcagccagt atccctctgg gcatccccgg cctcctgatt agagctcctg acctcctctt 118620
ctgacaagca aagaaagctc agagcccaaa gcaggaccca ggcctcggcc accatctgaa 118680
ctcagaggct ccagcacaaa tcccacgcct gggcctgctc aggcccctga tcaggtatag 118740
tcggaaactc tggagaaagt ccgtttctgc tgaggcagca ggatcctgac caacatcgaa 118800
gagggaaaga tccaatgagc ccgtgagctg taagaaggtc agcccagggg tcacctcagc 118860
tctgctccgc cactctccca tgctagggac tcaggattcc tgcccgctca cctatttctc 118920
tggcttgaat aaatcacggg cacttgggcc cagggagggg ggataactca gaggcagaga 118980
atcctttctg cctgagagac aggactcaca gcccctgcag acctccagag ctggcccttt 119040
tccccaactc cctctctgcc cataacttgg gcttctcacc caatttggct ccctggcctc 119100
tggccaggac ccaccccctt ccttttcttt tcttttttttt tccccccttgt ttttcttgca 119160
tgcagaggta caggaacagc gtgagcagtg ggcctgggtc tcaagcccac acttcctttg 119220
gtgacagctg agggtgacat atggaactta taaacaaaac ccagaactac ccatgcctct 119280
ccccatcccc tcttgaaagc tgctgcgctt ccccctcacc aacccacccc gcctgggact 119340
ctcagcaaag actatagcac cagacttttt tttctgagac ggagtctcac tctgtcgccc 119400
aggctggagt gcagtggcac gatctaggct tcctgcaagc tcggcctccc agtttcatgc 119460
cattctcctg cctcagcctc ccgagtagct gggactacag gcacccgcca ccacacccgg 119520
ctaatttttt tgtattttta gtggagatgg ggtttcacca tattagccag gatggtctcg 119580
atctcctgat ctcgtgatcc acccgcctcg gcctcccaaa gtgctgggat tacaggtgtg 119640
agccaccgcg cccagccagc attacgcatt ttcattccag aagaacctgc ctctctccca 119700
tgaaatatcc cttgaattcc ctggccccag agaggctggg agccctgccg atgtctcttt 119760
aggcacctac aggagaggaa aagggcctgg acactggggt ggggcagggc tcagtgagac 119820
agtcaggcca accccaggaa gccagggaga tcctggatgt gaacatccaa ccagtctcgg 119880
gctggctcca tcccagtctt gtctatttcg acgggctttg acccctcctt ctgaggctga 119940
aagtaggaga gcttacgggg acatcaaagt gtctatgctg tgacagtgca ggaagccaca 120000
gacaccgttt tccgaggatt tgccaaggtt tcacctactg atgtcatgct ccaaatattc 120060
ccttcttttt ccctctctgg ggagtcccag ggagagagat ctgaacccag actcagacaa 120120
tgtccctaag ataggcacag cctccatact catcctcccc cgagggcagc gtgacatgag 120180
gctatagccc tagactggtc ccaggggcct tgggcaagtc atttagtctc tggatcttaa 120240
ttgctcatat gttcaacggg ctaatgtgta ccttacctac ctaatggaat aattaagagg 120300
ataaaatagg agacagccca atagggtgga aagagcttcc taacaagaaa atctgggttc 120360
taggcccaat tctgccccta acttgccgtg tgtccttaca ggagttcctt accttctcta 120420
agctcaccta taaaatgaaa aggtgacatt gatcatctct aagtccctcc cacctctact 120480
ttctatgatt ctgtagtatc tgtgaaagcc taaaagaagt tctctttgga ggaaagaaat 120540
cccttgtcaa ctgcacagtg ctatttgaat gtgaggcatt tggcatcctg tctgatttgg 120600
atattaattt atgtaaactg gtgccctcag agttggactg tagagtacag aactccagaa 120660
```

-continued

```
atgttcagac agggatgggt ctgtctgaac ctccctgtag ctctgataaa gctgtctgct 120720
cactttacga aggcctgcca aatgtggcag ctacatatga aataatttgc cctggatggt 120780
gtggaagctc atggtggaaa ccgcaatcac atgcacaccg tttgcatttc tctgggcatt 120840
tgactgttcc ctcacagccc tgctccagca gagggtgagg gctatgcagg ggctggggtg 120900
gggcaactcc ttcctaatca cagaggcagc ccactgaggg ccagcatcct ccctccgcag 120960
ttctggaaga ggcatctgcg gcccccaaga gagaagcagc gcaggagtga tgtggattgc 121020
catgtgacac atctagttgt tgtgcctgga attgtggaac tctgaaggct acagcaatag 121080
tggcctaggc caggtgcagt ggctcatgcc tgtaatctca gcactttggg aggccgaggc 121140
aggtggatca cctgaggtca ggagttcgag acgagcctgg ccaacgtgga gaaaccccat 121200
ctctactaaa aatacaaaaa ttagcctagt gtggcggcag gcacccataa tcccagctac 121260
tccagaggct gaggcaggag aatcgcttga acccaggagg cagaggttgc ggtgagccga 121320
gatcccgcca ttgcagtgac caatctccag cctgggtgac caaagtgaga ctcagcctca 121380
aaaaaaaaaa aaaaaaaaaa aaaaaagctg aaaggccaga catttaaaag ataacccttt 121440
cacacaggtc tggagatgtg gtgccttaag gagcatagtg ctctaactct gcccgtgagt 121500
catctcagat ataatctcca atagaactct ttctgatggt tcttgtgaac agagcttcag 121560
tgacatgcca ggcactgtgc taggtgttaa cgcccgctat ccagctcctg ttacttctca 121620
gcctgataag cacagcgggt gtagctattc ctgctttgca aatgaggaaa ttgaagctcc 121680
aagaacctaa aggacttgcc caagatccaa aagctcttcc tcggtgcctc actcacctat 121740
gagtgctaag gcccaggttc accaacaggt cctccgacac gtctgcatat ataacttccc 121800
tccacacagc tcaaggcagg gagagagaaa cggcccagca gagccctgat cattgagctg 121860
tgggaaggct ggggagggct ttggaacaga gcacacagca agacctcaga tctgactgaa 121920
gggaggaact aggagctgag acaagaatac gtgaagttgg aagagcctca gacttcatca 121980
aggctaaggg ttctcaatgg aagagagagt agggagtgta gggcatcaag gcttatgttc 122040
caggaaggaa ttctgacacc agctccctgg cagaaacaga atccggtcca atcccatact 122100
tctacacatg gggaaactga ggcccacaga ggagaggaag cctccctaac aaagttgtac 122160
tatcctggga acagaccatc ttgggaagca tgagttagtt tctttttctt ttcttttttt 122220
ttttttttt gagacagagt ctttctctgt tgcccaggct ggagtgcagt ggtactcgtg 122280
gctcactgca agctccgcct cccaggttca tgccattctc ctgcctcagc cttcccagta 122340
gctgggacta caggcgcccg ccaccacgcc tggctaattt tttgtatttt tagtagagac 122400
ggggtttcac catgttagcc aggatggtct cgatctcctg accttatgat ccgcccgcct 122460
cggcctccca aagtgctggg attacaggcc tgagccacct gcgcccccacc cagcatgagt 122520
tactttcatg tggcagggtg cacaggaact gtgcccatga gcagggtgac tgaacagctc 122580
ccagaaacgg catgcaagtg ctcatagtgt ttccatcttg ctgaatatat tgcaatttgt 122640
aatactgttg cagaacaaag agagcgtaac ttccacttca actttcatag cttgcttccc 122700
atacttctgg tcccttcatc atttccaaca gtggtgaacg ttgatcccac tctgggaagt 122760
tgacaaggga caaccgccct cccagagcca atatccatcc cacccaccat tagtaggtat 122820
tgcccccagg ttcacacagg gagttagctg agaccgtcag ttcccaaccc agacttcttc 122880
ttcctgtttc ctctgctgga aatcggcact ggaaccccag aggctaaatc agggcaataa 122940
gagacaggag aggagaggtg gccagggatg gggcatagct tggctggcag tagtcagctg 123000
ccctatttgc agaactgggg tgggggaagt tatttggggg acatcatggg gcacctgtgc 123060
```

-continued acacctaagc aggtcttgga ggagggtaga tgtgggtagc aaacagggtg gtgaccccag 123120
gacctctgga aggggtgaca agcccagctg ccatggtcca gctccaggcc ccaacctgag 123180
ccagccagcc aggagatatg gagagccttg gctctaatca gatggatctg ggttcaaatc 123240
tcccttctgt cacctaaaag ctgtcaggca cactgggcaa tttcctgggc ctgtctgagg 123300
ctggctcttc tgtataacag gattatttag caaatactta gcaagtactt tttcctcttc 123360
tctctaggag aattatgtgc agaactggtt gggggcgcgg taggggtcag ttgtgccagg 123420
tacagaagca actatggcta gatgctaggg tgagaaaaag tgtttccctg gggagacagc 123480
tattaatcaa attatcacac aaacccatgt taagagtgct aaagggggta agaacagtat 123540
ccactcatag gccgctgtgt ggtgaggtta aagccgcaga tgcctctggg cacacacaga 123600
aaccttcaag aagtgcatct gtttctatcc cagcccttca atggcatctc gtggagctga 123660
taaattggag aatatatttg tccagcactt ttagattttt cttttttttg agacggagtt 123720
ttgctctcgt tgcccaggct ggagagcaat ggcgcaatct cggctcaccg caacctccgc 123780
ctcccaggtt caaacgattc tcctgcctca gcctcccgag tagctgggat tacaggcatg 123840
agccaccacg cccagctaat tttttgttgt tgtttgtatt tttagtagag acggtgtttc 123900
tccatgttgg tcaggctggt cgcgaactcc cgatctcagg tgatccgccc gcctcagctt 123960
cccaaagtgc tgggattaca ggcgtgagcc accttgcctg gccactttta gattttaata 124020
gcatgttgca cacacatatt aactcgttcg gtcttccaat aaccctagga ggtaggtgaa 124080
atttcctcaa tttcttgatg aggagactga cgcccagaga ggctaagtga cttcctcaaa 124140
gtctccagca tggagattca ggattcaagc ctctgcggtc ctctgggcta tccactcccc 124200
gcaaccgtgg aaaggaaggg ctgggaaaca ctaagcctcg ggacgggaga agattgggaa 124260
accagtcccc gaccgcgccc gtcgtctaag cccgggtttc ctgcctctct ccgggcccgt 124320
gggccgggct gtgctccggg aagcccgtca tccgctcgtg accgaccctc cccggcccgc 124380
tgccaggagg gggcgcggcg ctggcggngg ccaaggccgg agggctcctc ggggaacccg 124440
gcccggggct gcgcgtcttt ccctgctgcc cacgctcccg cttccggagg ggtctggacc 124500
tgccttctcc ggcctggagc cagaggccgc cnggcaggca gcccgcgcca ggaactcggc 124560
cccctgccct gctccccggg cgcgncccgc gggcggccaa cccggatcgg acgcggaccc 124620
ccgggccagg gtgccacgac accctgaac cgggcaccgg gactatcggg cccctccccc 124680
gccttctcga gttcccggaa cggtggcacc cactcccctt ccatcccccg gcggaggcca 124740
cggacgcgca gcgcgaggtg ggccaggcgc ccaaatcact ttaccgtgcg cctcctgcta 124800
gagagtcgcc cagcccaagg cagtggggcg cggaggcgga ggacggggaa actgaaatac 124860
aaagggattg agtggaaagc aatagagggg ggtgctggga ggggaaccag ctaggctcaa 124920
agctccaaag tggatcgccg ggttaatgtg gggtnntcct gcnnncntcg ccacccactc 124980
ccaatgcggc tgcttagccg actgcatagg cggcttctct gctttacact agggggtctg 125040
aattccccag cccagtcccc caggtagctt agacccggcc tctgaaaaca gaagatccct 125100
ccttccaaca ctcctcgccg gcaaggcaga gatgggtctt tcagggagca ggacgttggg 125160
ccgcaggttt cggtaaagca cctcactcgg agccacagcc tccatgtcta taaaatgagg 125220
aaaatggacc gggcgcagtg gctcacgcct gtaatcccag cactttggga ggccaaggcg 125280
ggcagatcac gaggtcagga gatcgagatc atcctggcta tcacagtgaa acgtcgtctc 125340
tactaaaaat acaaaaaaat ttgccgggcg tggtggcggg cgcctgtagt cccagctact 125400

-continued cgggaggcgg aggcaggaga atggtgtgaa cccgggaggc ggagcttgca gtgagccgag 125460
atcgcaccac tgcactctag ccttggcgac agagcgagac tccatctcaa aaaaaaaaaa 125520
aaaaaaaaaa agataattaa tgaagcaaac gtcttttaaa tgttagagcc ccgggctcct 125580
gcagccattc cctggccacg tggcatgcat tgcgagttaa ttgtgtaagt gtgtggtctt 125640
cttcccacct cctctccacc caccacctcc attcattaaa gtgaaggtag agctgcctcc 125700
cacccgtctg ctcaagagat aaccattcag ccccttttat ttgttcagga ctttaccgtt 125760
tgtaagccct tcctaaattt ttttttcaag acgtagtctt gctctgtcgc ccaggctgga 125820
gtgcaatggc gtgatctccg ctcactgtag cctccgcctc ctgggttcaa gcgattctcc 125880
tgcctcagcc tcccaagtag ttgggattac aggggcgtgc caccgcgccc agctaatttt 125940
ttgtattttt agtagagacg gggtttcgc catgttggcc aggctggtct cgagctcctg 126000
acctcgtgat ccgcccgcct tggcctccca aagtgctggg atgagccacc gcgcctggcc 126060
cctacatact tttcatttga acagtatgtg tgtgtcaaat cgcctgaatt taattcttgt 126120
ctcccacacc ccctggctga ataaacttgg gcaatttgct taacttctct gtgttcgttt 126180
tctggtccat aaagtgatac taatactaga accacttggt tgggctattg aggaataaga 126240
ggctaatata tgtcaggtac agcacctggc acagagtgtg tcccctgacc ctgttggcag 126300
ttatgactga gccccgctga atctaacatg cagcctgctt cagagggctc cagatggctt 126360
tccagacttg gccctctggg gcagattctg attccgtagg taggtctggg gcaggcctga 126420
gatccttcag gtctgaacag ctccctggtg ctactgatgc tgctggcacc caggcactcc 126480
tttgagtggt gaggtcttag agcagcggac ttgactgtgc accagacgca tctggagggt 126540
ttgtaaaaat agattgctga gtgccatccc cagagtttct gacttagtag gtctggaatg 126600
aggctaggat ttgcatttgt aacaagctct caggtaatgc tgatgctgct gatctgggga 126660
ccatagtttg aggctttgtt ttagagcatc tcacccctca agcttatggc caccagtaat 126720
gtcatgctgg ggggtgggct ggggagtaga ggtcattaaa cagccaagag tagcttctta 126780
tgctttggga ataaaagaaa gtttggggtg gggggagggt gggaggcagg tacctgagat 126840
tggaaaccaa aaataaaaaa tcttcccaat tctaatatgg gtaagacacc agaaggaata 126900
aaaaggacag tgtagctttt ttctcagcat cctgtaaaaa taagggagac tggtaaagac 126960
tgcctagttg ctcaagggca aaagaaaggg aatggagtct ccctcagccc atgtcttcct 127020
gtttggggtc ctctctcccc agacaaccag gagaacagag ggaagccgga gggcagcagc 127080
aaagcccgca aggagaggac ggccttcacc aaggagcagc tgcgagagct ggaggcagag 127140
tttgcccatc ataactacct gactcggctc cgcagatatg agattgcggt aaacctggac 127200
ctctctgagc gccaggtgcg cccccggtgg gcccctcctc ttctttgctc tctcatctcc 127260
ctcccttccc tcctttccca ccacccctcc ctggaccttc tccttttct tcctccagcc 127320
agtccagcgg ttttcaactg tggccacacc tgagaatagc ctggggagtt ttgggttttt 127380
ttgttttttg ttttttgaga cggagtctcg ttctgtcgcc caggctggag tgcagtggcg 127440
cgatcttact gtaacctcca cctcctgggt tcaagcaatt ctcctgcctt agcctcccaa 127500
gtagctgggc tactggcgtg cgccaccacg cccggctaat ttttgttttt ttttttagta 127560
gaggcggggt ttcaccatgt tggccaggat ggtctcaaac tcctgacctc aggtgatccg 127620
cccgcctcgg cctcccaaag tgctgggatt acaggcgtga gccactgcgc ccggcccctg 127680
gggagatttt aatagtgctg atgtctgggc tccacccta gggatgattt taattggcct 127740
aggatgggat acaggcctca gaatttttca aaggccccct aggtgattct cacatgcagc 127800

-continued taggttggga cctacggtct ggctattccc aaatttgagt atatgttgga atcccccaag 127860
gcacttgttc aaaatgtgga ttctggaggt ccggagagag attttaccat aatgagtggg 127920
cctgagaatc tgtatttcta gtacattctc caggtgatct ggatatgcag ctggttcctg 127980
ggcacacttt gagaaaaact tccctggccc ttcgttttgg actttccctt cagccacccc 128040
acaccccccac acccatgctc tgatacggaa taatagtaat aataaccgta atatttgata 128100
gcagatttca gttgacagag cactctgcca gagggctgga tattgaatca gaagacttag 128160
attcaaatcc tgcctctatc acttttccta gccctgggac ctctgggtct ccatctgtaa 128220
aatgggatca taatcctgca ggtaatactc aagctcagat gagaaaatgt gcttaccaga 128280
gctatctaaa ccaaaaagtg ctctataaat gtgcctaagg ataaggctga tgacctctgc 128340
tcccagaccc ttggggaatg gaggtagggg gcagggggac ctggcacagg cagggcaggg 128400
catgtgaagg gggtggggcc aatgcagagt gcttttagaa catgttcccc cgtctggggc 128460
tttatccgaa gccacaagac agacctctgg gcagattggt atgtcctctc ttcggtccta 128520
gttcctgggg cctttgaggg agtagggagt ggtaagtgat ggtttcaagc tggggtccct 128580
ggagttacac cctggctagc ctaagcattg acatggggag gaggtcacac cggccctgga 128640
gtgaccaggc tcctttgctt cctcccccag gtcaaagtgt ggttccagaa ccgaaggatg 128700
aagtggaagc gtgtgaaggg aggtcagccc atctccccca atgggcagga ccctgaggat 128760
ggggactcca cagcctctcc aagttcagag tgagattctg catggaggaa aaatgactaa 128820
ggactgagcc ccctacccaa ctacccccac cccaatccca ccttcaccct cttccttccc 128880
cagccagggc agcctctcca catctttccc tgactcttgg atatgaaact gcccagcatt 128940
cctgggagtc ttaggatttt ctaggaagtt ctgtccagcc tcttagcagc ctcttcccta 129000
gggcctttgc tcccacactc tcatggaatc agacagagat cctaccgggc cggatgaatc 129060
tggaaacagc ttcagagata ctgcttctca gcgtctcttg gctgccaccc atgcctcctc 129120
ctaccgctgt tctcctaggt cagccaggcc tcctcctggt ctggacacca cctggcctgg 129180
tgggagagga gctttggaac cagctggcga ctcggaaagt aaatgcttca aaaggaagga 129240
aatgacagag acacacgccc ttgcccacct tcctctgtag gctgcacatc tgaggctttg 129300
gggcccctta gttgtcccga aaccccaaga aaaatcagaa tgaggagagt caaggacagc 129360
aactcagctg ctgcaagcca gaaacacatc cctgtctcca aatttgttgg ctaagtggag 129420
acacttctga gaactgacta gagaagacag aaaaatagcc cgatgtaggt ttcggtgtcc 129480
ccatataggc ccgtccacac aggcttgact gggtggacaa gaatgaaccc atgacagcac 129540
ctgctgcttc aaaatcaaaa tcaatttagg gatacagcag gggctgttgg gctgtgctcc 129600
agagaaaagg agcagctact ccttttaaat ccacgatttc tggattgaaa acctgtccag 129660
atgctgagtt gttgggctga acaactagga gctgaaaaca acgtagaggc tggaaagtgt 129720
cccctgcatt ctggaggga ggggagataa taaggagggc tgctgggtga gggcctggag 129780
atgtggaacc ctggagtgga aggttctcca gtgacagtgt cctgtgactg caaaagggga 129840
caagaaaatc cctcttcctc catgggatgg atttaagctc ttgctgtgtg ttctacaaat 129900
gctgttattg tgggaggaaa tgctaggttt ttgtgtgtgg actgcccaga cctcagccag 129960
gtcttctgga gatgacattt gaggactgat ggccaaagag catgggggac tgaagccctg 130020
gctgcctcag cgctctgtct cccaacacca gctggtgttg cagagggagg tcaacgtgag 130080
tttggatctc ttgtacgcag atgtaatcat tcacatgtaa aaataacccc acctccccac 130140

-continued cccaaaaagg gcaagagctg tggaaaatga ttgccaaatg agatggctgg ttagagcatg 130200 atttttcta aagcatactt catatatttt cttaagatta catcaagcta attgtgcgag 130260
ctcaattcac tttgtaagaa aactctcgga gaaataaaat caataaaaag caaagttccc 130320

<210> SEQ ID NO 2
<211> LENGTH: 18
<212> TYPE: DNA
<213> ORGANISM: Artificial Sequence
<220> FEATURE:
<223> OTHER INFORMATION: Forward primer

<400> SEQUENCE: 2
ctttccacag gctcgtct 18

<210> SEQ ID NO 3
<211> LENGTH: 19
<212> TYPE: DNA
<213> ORGANISM: Artificial Sequence
<220> FEATURE:
<223> OTHER INFORMATION: Reverse primer

<400> SEQUENCE: 3
ctctcaaccg gaaatgtct 19

<210> SEQ ID NO 4
<211> LENGTH: 458
<212> TYPE: DNA
<213> ORGANISM: Homo sapiens
<220> FEATURE:
<221> NAME/KEY: misc_feature
<222> LOCATION: 184
<223> OTHER INFORMATION: n = C or G

<400> SEQUENCE: 4
ctttccacag gctcgtctgt gtccctgcca ctctgagtta tccagaaacc accacctaca 60
aatgagggga ctcatctaga agacctctaa ggtccccttt tggctctgag ggtctctaa 120 taatccccac ttggaattca gcaccgcaag gaaattatgg gtatgtgagc cataatatga 180
tggncagcag gtggcgctgc cttccaccca tggtgatgga tggtttggaa agggaatgtt 240
ggtgcctttt gtgccacaag ttaagatgct actgttttaa aggaaaaaaa aaaaaaaaag 300
tactgatctt caatatgaag acatgagctt ttctcgcagg aaattttctt tttcacagaa 360
ctggtgtcag gaatcactga agggctaacc gtgatagtcc ttgcaagtaa gtcaaggttt 420
tatcctgatt ggaaatagaa gacatttccg gttgagag 458

<210> SEQ ID NO 5
<211> LENGTH: 24
<212> TYPE: DNA
<213> ORGANISM: Artificial Sequence
<220> FEATURE:
<223> OTHER INFORMATION: Forward primer

<400> SEQUENCE: 5
gctcaaggaa cccaggcatc agaa 24

<210> SEQ ID NO 6
<211> LENGTH: 24
<212> TYPE: DNA
<213> ORGANISM: Artificial Sequence
<220> FEATURE:
<223> OTHER INFORMATION: Reverse primer

<400> SEQUENCE: 6

-continued

```
caagccagac agaagccccc tcag                                           24


<210> SEQ ID NO 7
<211> LENGTH: 297
<212> TYPE: DNA
<213> ORGANISM: Homo sapiens
<220> FEATURE:
<221> NAME/KEY: misc_feature
<222> LOCATION: 143
<223> OTHER INFORMATION: n = C or T

<400> SEQUENCE: 7

gctcaaggaa cccaggcatc agaactgctc tctcccaagt ccattgcaag aaggcagtcg     60

tctggtcatg agagggttaa cagtccacat tccagagcaa gggaaaagga ggctggaggg    120

tcatagacaa ggggaggtgg tgnggagggc cagcttctca caacactacc ggctctgctg    180

ggagagatag atcaccccca acaatggcca cagctgtttt catctgccct gaaggaaact    240

gacttaggaa gcaggtatca gagagggccc ttcctgaggg ggcttctgtc tggcttg       297


<210> SEQ ID NO 8
<211> LENGTH: 18
<212> TYPE: DNA
<213> ORGANISM: Artificial Sequence
<220> FEATURE:
<223> OTHER INFORMATION: Forward primer

<400> SEQUENCE: 8

agatcacccc caacaatg                                                   18


<210> SEQ ID NO 9
<211> LENGTH: 18
<212> TYPE: DNA
<213> ORGANISM: Artificial Sequence
<220> FEATURE:
<223> OTHER INFORMATION: Reverse primer

<400> SEQUENCE: 9

aaggaaggcc agaggaat                                                   18


<210> SEQ ID NO 10
<211> LENGTH: 356
<212> TYPE: DNA
<213> ORGANISM: Homo sapiens

<400> SEQUENCE: 10

agatcacccc caacaatggc cacagctgtt ttcatctgcc ctgaaggaaa ctgacttagg     60

aagcaggtat cagagagggc ccttcctgag ggggcttctg tctggcttgt aaaactgtca    120

gagcagctgc attcatgtgt cggatgatgg atgatggaaa ggaggacagt cggctgcaga    180

tggacacagc gacttgcaag ttgaggcagg tggcaaagga cttgcagagg ctctgcaggt    240

ggggcatgct gattcattgc ccagttaaaa taccagagga tctgggcagc ctcttcacag    300

gagctgcttg tcctcaaaca atctgtcttc aatgaaagat tcctctggcc ttcctt        356


<210> SEQ ID NO 11
<211> LENGTH: 24
<212> TYPE: DNA
<213> ORGANISM: Artificial Sequence
<220> FEATURE:
<223> OTHER INFORMATION: Forward primer

<400> SEQUENCE: 11
```

-continued

```
aggtggggct ataagcatcc atcc                                          24


<210> SEQ ID NO 12
<211> LENGTH: 24
<212> TYPE: DNA
<213> ORGANISM: Artificial Sequence
<220> FEATURE:
<223> OTHER INFORMATION: Reverse primer

<400> SEQUENCE: 12

gtcctttgcc acctgcctca actt                                          24


<210> SEQ ID NO 13
<211> LENGTH: 438
<212> TYPE: DNA
<213> ORGANISM: Homo sapiens
<220> FEATURE:
<221> NAME/KEY: misc_feature
<222> LOCATION: 172
<223> OTHER INFORMATION: n = C or T

<400> SEQUENCE: 13

aggtggggct ataagcatcc atcctacctg ctcaaggaac ccaggcatca gaactgctct     60

ctcccaagtc cattgcaaga aggcagtcgt ctggtcatga gagggttaac agtccacatt    120

ccagagcaag ggaaaaggag gctggagggt catagacaag gggaggtggt gnggagggcc    180

agcttctcac aacactaccg gctctgctgg gagagataga tcacccccaa caatggccac    240

agctgttttc atctgccctg aaggaaactg acttaggaag caggtatcag agagggccct    300

tcctgagggg gcttctgtct ggcttgtaaa actgtcagag cagctgcatt catgtgtcgg    360

atgatggatg atggaaagga ggacagtcgg ctgcagatgg acacagcgac ttgcaagttg    420

aggcaggtgg caaaggac                                                 438


<210> SEQ ID NO 14
<211> LENGTH: 17
<212> TYPE: DNA
<213> ORGANISM: Artificial Sequence
<220> FEATURE:
<223> OTHER INFORMATION: Forward primer

<400> SEQUENCE: 14

cctaaggtgg gatggtc                                                  17


<210> SEQ ID NO 15
<211> LENGTH: 18
<212> TYPE: DNA
<213> ORGANISM: Artificial Sequence
<220> FEATURE:
<223> OTHER INFORMATION: Reverse primer

<400> SEQUENCE: 15

ctcagggatg gaagatgt                                                 18


<210> SEQ ID NO 16
<211> LENGTH: 310
<212> TYPE: DNA
<213> ORGANISM: Homo sapiens
<220> FEATURE:
<221> NAME/KEY: misc_feature
<222> LOCATION: 98
<223> OTHER INFORMATION: n = C or G

<400> SEQUENCE: 16

cctaaggtgg gatggtcaac tggaaagctt taaattaagt ccagcctacc ttgggggaac     60
```

-continued

```
ccaccccac aaagaaagct gaggtccctc ctgatgantt gtcagtttaa ctaccaataa    120

cccacttgaa ttaatcatca tcatcaagtc tttgataggt gtgagtgggt atcagtggcc   180

ggtcccttcc tggggctcca gcccccgagg aggcctcagt gagcccctgc agaaaatcca   240

tgcatcatga gtgtctcagg gcccagaata tgagagcagg taggaaacag agacatcttc   300

catccctgag                                                          310


<210> SEQ ID NO 17
<211> LENGTH: 18
<212> TYPE: DNA
<213> ORGANISM: Artificial Sequence
<220> FEATURE:
<223> OTHER INFORMATION: Forward primer

<400> SEQUENCE: 17

cccctgcaga aaatccat                                                  18


<210> SEQ ID NO 18
<211> LENGTH: 21
<212> TYPE: DNA
<213> ORGANISM: Artificial Sequence
<220> FEATURE:
<223> OTHER INFORMATION: Reverse primer

<400> SEQUENCE: 18

gaaaccccgt ctctatcaaa a                                              21


<210> SEQ ID NO 19
<211> LENGTH: 336
<212> TYPE: DNA
<213> ORGANISM: Homo sapiens
<220> FEATURE:
<221> NAME/KEY: misc_feature
<222> LOCATION: 202
<223> OTHER INFORMATION: n = A or G

<400> SEQUENCE: 19

cccctgcaga aaatccatgc atcatgagtg tctcagggcc cagaatatga gagcaggtag    60

gaaacagaga catcttccat ccctgagagg cagtgcggtc cagtgggtgg ggacacgggc   120

tctgggtcag gtttgtgttg tttgtttgtt tgttttgaga cagagtctcg ctctattgcc   180

caggctggag tgcagtgtca cnatctcggc ttactgcaac ttctgccttc ccggattcaa   240

gtgattctcc tgcctcagcc tccagagtag ctgggattac aggtgcgtgc caccacgcct   300

ggctaatttt tgtatttttg atagagacgg ggtttc                             336


<210> SEQ ID NO 20
<211> LENGTH: 21
<212> TYPE: DNA
<213> ORGANISM: Artificial Sequence
<220> FEATURE:
<223> OTHER INFORMATION: Foward primer

<400> SEQUENCE: 20

taaggtggga tggtcaactg g                                              21


<210> SEQ ID NO 21
<211> LENGTH: 21
<212> TYPE: DNA
<213> ORGANISM: Artificial Sequence
<220> FEATURE:
<223> OTHER INFORMATION: Reverse primer
```

-continued

<400> SEQUENCE: 21
caggagaatc acttgaatcc g 21

<210> SEQ ID NO 22
<211> LENGTH: 473
<212> TYPE: DNA
<213> ORGANISM: Homo sapiens
<220> FEATURE:
<221> NAME/KEY: misc_feature
<222> LOCATION: 96
<223> OTHER INFORMATION: n = C or G
<220> FEATURE:
<221> NAME/KEY: misc_feature
<222> LOCATION: 423
<223> OTHER INFORMATION: n = A or G

<400> SEQUENCE: 22
taaggtggga tggtcaactg gaaagcttta aattaagtcc agcctacctt gggggaaccc 60
acccccacaa agaaagctga ggtccctcct gatganttgt cagtttaact accaataacc 120
cacttgaatt aatcatcatc atcaagtctt tgataggtgt gagtgggtat cagtggccgg 180
tcccttcctg ggctccagc ccccgaggag gcctcagtga gcccctgcag aaaatccatg 240
catcatgagt gtctcagggc ccagaatatg agagcaggta ggaaacagag acatcttcca 300
tccctgagag gcagtgcggt ccagtgggtg gggacacggg ctctgggtca ggtttgtgtt 360
gtttgtttgt ttgttttgag acagagtctc gctctattgc ccaggctgga gtgcagtgtc 420
acnatctcgg cttactgcaa cttctgcctt cccggattca agtgattctc ctg 473

<210> SEQ ID NO 23
<211> LENGTH: 24
<212> TYPE: DNA
<213> ORGANISM: Artificial Sequence
<220> FEATURE:
<223> OTHER INFORMATION: Forward primer

<400> SEQUENCE: 23
ccctacctta ctgtccgcct ctca 24

<210> SEQ ID NO 24
<211> LENGTH: 24
<212> TYPE: DNA
<213> ORGANISM: Artificial Sequence
<220> FEATURE:
<223> OTHER INFORMATION: Reverse primer

<400> SEQUENCE: 24
gtgctacctc tcgggaaaac ataa 24

<210> SEQ ID NO 25
<211> LENGTH: 169
<212> TYPE: DNA
<213> ORGANISM: Homo sapiens
<220> FEATURE:
<221> NAME/KEY: misc_feature
<222> LOCATION: 90
<223> OTHER INFORMATION: n = T or C

<400> SEQUENCE: 25
ccctacctta ctgtccgcct ctcagagtcc ttcctgccag ggctgcctgg gaactggccc 60
accctaggcc ctgaaatagc atgatttgcn gagccagctt ttatactaaa tgggaactat 120
tggcaccttt ggcttcttgt catctttatg ttttcccgag aggtagcac 169

-continued

<210> SEQ ID NO 26
<211> LENGTH: 17
<212> TYPE: DNA
<213> ORGANISM: Artificial Sequence
<220> FEATURE:
<223> OTHER INFORMATION: Forward primer

<400> SEQUENCE: 26
gagcaaccgg cgtatcc 17

<210> SEQ ID NO 27
<211> LENGTH: 21
<212> TYPE: DNA
<213> ORGANISM: Artificial Sequence
<220> FEATURE:
<223> OTHER INFORMATION: Reverse primer

<400> SEQUENCE: 27
ggggtttctt tctggctctc a 21

<210> SEQ ID NO 28
<211> LENGTH: 324
<212> TYPE: DNA
<213> ORGANISM: Homo sapiens
<220> FEATURE:
<221> NAME/KEY: misc_feature
<222> LOCATION: 108
<223> OTHER INFORMATION: n = A or G

<400> SEQUENCE: 28
gagcaaccgg cgtatccatt tcagagaggg gctgagcctc actcctgctt cttgccaact 60
tctttacaag ggcactgcag gcaaagcttc agggagaggg gacaaatntg agtctaggaa 120
agaactattg tcatttccag catcagctgt ggcggctacc tcttgtattg gcctcacccc 180
tgaccttcct gtcctaacca aagaacgaga ggaactgcca ctgcttaacc ctttgttggg 240
ctgtgctaat gaaattgaag ggaacatggt gagcatgcga ggactgtgag agccagaaag 300
aaaccccgag caaccggcgt atcc 324

<210> SEQ ID NO 29
<211> LENGTH: 18
<212> TYPE: DNA
<213> ORGANISM: Artificial Sequence
<220> FEATURE:
<223> OTHER INFORMATION: Forward primer

<400> SEQUENCE: 29
ccagcaatgt tgaggaat 18

<210> SEQ ID NO 30
<211> LENGTH: 18
<212> TYPE: DNA
<213> ORGANISM: Artificial Sequence
<220> FEATURE:
<223> OTHER INFORMATION: Reverse primer

<400> SEQUENCE: 30
cgcaggaagg tgtggaga 18

<210> SEQ ID NO 31
<211> LENGTH: 418
<212> TYPE: DNA
<213> ORGANISM: Homo sapiens
<220> FEATURE:
<221> NAME/KEY: misc_feature
<222> LOCATION: 232

-continued

<223> OTHER INFORMATION: n = A or G

<400> SEQUENCE: 31
ccagcaatgt tgaggaatgc agggtgtagg ggagcagaaa ggccactctg gtgtggcctg 60
acttgggacc atctgtccac tcagacagag ctcagcaaac ggtcaaggag ctgagaatcg 120
gctcagtccc tccctctccc tctcactctc ttcttccctc tttcccctcc ccactctctc 180
agcccctcac ctagctagct gcccctccct tacctcgcag gaccccctgg gntggaactg 240
cttgctgagc agttctgatg aaggcaggac cctttcctct ctgtggactc agtccacagt 300
gtctgtagac actggccctc cagaggacca gtgtgtgagg gggtgttgcc agcctctgtt 360
tctcctgagc cctcctccca agtgcaagta tgagaactcc tctccacacc ttcctgcg 418

<210> SEQ ID NO 32
<211> LENGTH: 353
<212> TYPE: DNA
<213> ORGANISM: Homo sapiens

<400> SEQUENCE: 32
agatcacccc caacaatggc cacagctgtt ttcatctgcc ctgaaggaaa ctgacttagg 60
aagcaggtat cagagagggc ccttcctgag ggggcttctg tctggcttgt aaaactgtca 120
gagcagctgc attcatgtgt cggatgatgg atgatggaaa ggacagtcgg ctgcagatgg 180
acacagcgac ttgcaagttg aggcaggtgg caaaggactt gcagaggctc tgcaggtggg 240
gcatgctgat tcattgccca gttaaaatac cagaggatct gggcagcctc ttcacaggag 300
ctgcttgtcc tcaaacaatc tgtcttcaat gaaagattcc tctggccttc ctt 353

<210> SEQ ID NO 33
<211> LENGTH: 435
<212> TYPE: DNA
<213> ORGANISM: Homo sapiens
<220> FEATURE:
<221> NAME/KEY: misc_feature
<222> LOCATION: 172
<223> OTHER INFORMATION: n = C or T

<400> SEQUENCE: 33
aggtggggct ataagcatcc atcctacctg ctcaaggaac ccaggcatca gaactgctct 60
ctcccaagtc cattgcaaga aggcagtcgt ctggtcatga gagggttaac agtccacatt 120
ccagagcaag ggaaaaggag gctggagggt catagacaag gggaggtggt gnggagggcc 180
agcttctcac aacactaccg gctctgctgg gagagataga tcacccccaa caatggccac 240
agctgttttc atctgccctg aaggaaactg acttaggaag caggtatcag agagggccct 300
tcctgagggg gcttctgtct ggcttgtaaa actgtcagag cagctgcatt catgtgtcgg 360
atgatggatg atggaaagga cagtcggctg cagatggaca cagcgacttg caagttgagg 420
caggtggcaa aggac 435

<210> SEQ ID NO 34
<211> LENGTH: 94752
<212> TYPE: DNA
<213> ORGANISM: Homo sapiens

<400> SEQUENCE: 34
ggatcagggg ttagagcctt ggcatggaga cgcctgaaag gcacccaagg caattagtgg 60
tgtcccttct ccacccccta cataccttca ggccctttgc acttgctgct ccccctccca 120
gtgcacacac ccccagatcc ttgtgtggct ccctctccca ccacattttg gtcttagctc 180

-continued

```
aaatgccacc tcctcagaaa tgcctggcct ggccgccttc agggctgtct atatgctcac    240
cagctttatt tttctttcga gaactttcca ttcccggaca ttgtactaaa tgtttatttg    300
ttatccgtcc attatccatc tccttgccag cactccctgt gagctccatg aggctccaag    360
attacaacca catgcccaga gctagggtgg tgcctggctc acagctggca tccagtcagt    420
agcaatggaa tgaatgaatg atcaccctct cttcctctcc atccccaccc tctccttttt    480
cacttcctct cccgccccat ctcccctgcc tccgccttaa atctgctggc atgaccagcc    540
ctcaggaagt tgtcaggcag gggaggtgtg tgctctgcac ccctctcctt ccatctctct    600
ttcccacctc ccttatgggt acctatctct cctacctgca gctgctcgct gccagctctg    660
gccctcttgg tgggcagaag cttaggcacc ccagacaatt gtagggaaat tgggcattgg    720
agggcagccg taagaaagga ttcagtacct gccaaggaat gatgaattta gtctctcacc    780
catgaacagg catgcacttt cagggctcag gttcggtctc taaagcagaa cgtcattcag    840
ggcacccttc agtacccatg acccagtgtc tcgcctttcc tgcaggagtc ggtgctgcca    900
ctatggtgac tcagcccctc tcttctcctc attcattacc tgggttcttc ctgcagtgat    960
tgacagtatc ctttttcttt tgagatgaag tcttgctctg ttgccagggc tggagggcag   1020
tggcacaatc ttggctcact gcaacctctg cctcctgggt tcaagccatt ctcctgtctc   1080
agcctcccga gtacctggga ttacaggtgc atgccaccat gccttgctaa tttttgtatt   1140
tttagtaaag atggggtttt gccatgctgg ccaggccagt ctctaactcg tgacctcagg   1200
tgatccaccc gccttgacgt cccaaagtac tgggattaca ggtgtgagcc accacgccca   1260
gcaagttgca gctcttaata gcatgggcac catataattt actgcccaga ttgggtcatt   1320
ttttagagta gaagtgggag ctgttaataa ttacgcttgg cctacaggtg taaacgagac   1380
caccctgggc aaaccaggca catggtcgca ttgactaaga ggaatattcc cctgcctcct   1440
gcatctccag ccacaaaagg agcctcagct gttggtcaaa gctgcccaat agctgagccc   1500
ttgcctgccc ttggacaagg gagaagacag agggcaggtt ccaagaatgg ggtggggatg   1560
tggcaggaag gacggtgcag gccccagagc tataatcaat gatctgggag ccgggttgtg   1620
gagcacaggg ctgtgtcaag gagcaggtgg gaggtgggcg ggtgtgggac atggcaccag   1680
cttttggtgt ctgtgactct gaacttggct tactcgcagg tggcttctgc aggctctcca   1740
ccctcccagc tgcgtaagtc ctgcctgatt caaggaaaac agggaatttt ggggtcctgt   1800
ggctcctcca acgttctttt cctttacctc cttgtgtaaa tgtggcctga tttgtacttg   1860
gagcataagt agacccctac agagcgtgtg tgtgtgtctg tgtgtgtgtg tgagagagag   1920
agagagtgag agagagagag agagagagag agaaagggac ctatttcctt ctatccctct   1980
gtctgtctta ctctcagact attaatacaa gccctgagtc tggctgtacc cccagaacat   2040
gtgccccgcc ccctacaaca aaatgctgcc cctcccagct aggtctgttg tttgttcctt   2100
ttctgattgg cgccaggctt atagacccca tgtaggtaga atataacttt ccataaataa   2160
cctctaaccc gacctacaat ttagccttca ggtttttttc cccctcgtgg taatgggatt   2220
gcagcctggg ctgatccatc ctgtatcttc aggtcccaga aagcagaccc taggtttgga   2280
cattgcttgg aattcctggt acccccatgt tgccttgcac atggcaagga ctcggtacat   2340
gttgaggaat ggtggattct cttctaccca tgagcagcca tgcacttgca gtctttgctt   2400
gggctatgcc ttctgcctag aagccccctt ctccacctgg aaaatctcta agcaacaccc   2460
actttgtgaa gctttcccta accactatcc ctcatcccct ccacagagca aattactcct   2520
```

-continued

```
atcttggatt cccataacac ttggtacaaa acagtgtgac ctggttattg cccatgtgcc   2580
caccaggttc taagcagctc aagtgagggg tagggcaagg aactgagccc aagtatggct   2640
gtgggcaaaa catttaaccc cttggtgctt cagtctcctc agattcaaac accaacctgg   2700
ggctgggtgt ggtggctcac gcctgtaatc ccagcacttt gggaggccga ggcaggcaga   2760
tcacttgagg tcaagagttc gagactagcc tggccaacat ggtgaaaccc cgtctctatc   2820
aaaaatacaa aaattagcca ggcgtggtgg cacgcacctg taatcccagc tactctggag   2880
gctgaggcag gagaatcact tgaatccggg aaggcagaag ttgcagtaag ccgagattgt   2940
gacactgcac tccagcctgg gcaatagagc gagactctgt ctcaaaacaa acaaacaaac   3000
aacacaaacc tgacccagag cccgtgtccc cacccactgg accgcactgc ctctcaggga   3060
tggaagatgt ctctgtttcc tacctgctct catattctgg gccctgagac actcatgatg   3120
catggatttt ctgcaggggc tcactgaggc ctcctcgggg gctggagccc caggaaggga   3180
ccggccactg atacccactc acacctatca aagacttgat gatgatgatt aattcaagtg   3240
ggttattggt agttaaactg acaagtcatc aggagggacc tcagctttct ttgtgggggt   3300
gggttccccc aaggtaggct ggacttaatt taaagctttc cagttgacca tcccacctta   3360
gggcaactga agagtaactt tagggttact cttcatctga agatgctaac tcagctagca   3420
tccagcacta ttaagacacc ttggggaggc gagactttga gagaagtgca ggaggctggc   3480
ccacttttga agatcctaca tttctaccca ggaggcatca aatccacact tcgaagaaga   3540
tgaagtttcc tgtgagctgg tcctgaattg tacttggctt tgtgttgtct atgccagtac   3600
taagcaggac ttggccaggc tggtcctcca tgaatgactg tcaaatggaa aacagaatta   3660
ggaaccaaag tagtggtgta gacaaaaggg gctggaacct cagaggagag agggatcatg   3720
ggagattgga acatctctgg aaggttaggg gaagagatga caagtaatgt gaatcctaaa   3780
gaaagaggat tagttattgg gggtgctaag tgtggatggc aaactaagga agcagggatc   3840
tgcatgacca tttggagtca gtaggaagct tggtggagtg ggaggtggga gtcaagcaga   3900
gaaggcctcc catgtcagat agggaaactg cacttgatcc tgggcaaggg ggagctatgg   3960
aaggcttttg agcaggggag tgatacaatg agaacagcat tttggaagcc agcatggagg   4020
ggaggctgct aaaaggatac aaggctgagg ttattaccat gccctgggtg aagaaatgcg   4080
gtctgggttt ggaaaggaag ggataaacat gacttttcaa aggaagacat aattgccaca   4140
agggccacca gagagcagtc aaaggtgtgt ccaaggttgg agctctagtg accaagagaa   4200
gggtgtcaac tttgacagaa atgacgtcat gtgtggttga caaaatgaga ccacatcctt   4260
tcggtcatga ttcattgtct ttattaacaa tgtctctgga ctctggaaga acagactgtt   4320
aattcataaa gcaatattaa cattgtcatt ctctacaaga aaaacttttg cataaataac   4380
ttaagtgaga aaataaatat gtaacttaac tctttaaaaa ccactacttt cattcttgtg   4440
gacaagtccc acgtggaaga attgccaaaa aaacgaccag tcctgcaggc tttcatatgt   4500
catgtgcttc tgtttaaaac ttttttttt taacaattaa aaactacaca gaaagtaaga   4560
ggttgtctgg aaatgatttt caaaaagatt tttgggtggc agctattatg ctctgcagtt   4620
tctcagcata tgtacagcac ttgtagtttt tcccccaata atattctttt agtgtaagat   4680
atgccatcac atgtaagagc agtaagaagc tgttttctag gcagaaatgt gtccgtgagt   4740
ggtgggcaga aggcggtgtc tcaaaaggga tgtgctggtc tgtgagtttg tgatggctgc   4800
tccctcgggc ctgcaaggcc agtgtccttg aacctttcac ttctcttcgg aaggtgactt   4860
taaaacatgg ctatgggtcg ggggagggat gctgctcttt gggaagttgg ggcggatgtg   4920
```

-continued

```
atttctatcc ctcccaccac cctcggaccc tctccttttc taccccaatg gatgatgtta   4980
tttctttgag atggaggggt ggaggtagcc aaacatccgg ggaagccagg ctgggaagca   5040
gcatagcttc ttccaggagt ttgtcagccg taaatatgtc agccataaat agactcttta   5100
cttttttttt tctgtttgtt tttcatcttt ggctgtcaga agagagcatc acaactctga   5160
attctggaag tgaccttggc actgaatcaa tgcaactgca ttcattctct ctctttctct   5220
ctctctctct cacctctgcc cattcaaaag gcactggagt ccttggaatc atatgccaat   5280
agtctcctcg agatcctatt cccacctcca ccctcatttt acaaagtgga aattgaggtc   5340
ccgaaggaga attgtgtagt tcaaggttac acagcaagtt agtggcagag ccaggactag   5400
aaaccacatc tacagttgcc cccagtcttg tgctctgggc acgcctcagg ctttctgatg   5460
ggcagcgagg tgcaaggggg aatcttatcc aactttctta accagtccct ggactttccc   5520
actcccacac cgctccctta aaaccccagg gcggtgaaaa tgcttccatt tctgcctcct   5580
ctgaagtggg accagcaaag gtaggcggcc ccagaggcgg ggctgcgtgg ctcagtgtct   5640
gtgactctca attccctccc ctgccccgtg ggacccctca gctggcgggc tgagggggc   5700
cttgccggcg cccgggattc ctcagggcct ggaaggtctc agccccctgc cctgggttgc   5760
aggcatttac aatgaaatat aaacaatcaa accacgcgca gaggacagaa atgtggggcg   5820
cgggttcagg gccggggcgc ccgccggtgg ggaggggcgc gggcgggctc tagtaggcgt   5880
tctccagctc ggcctggttg gctttggcgc tccgggcgcg gggccgcggc ttccggccct   5940
tctgcggccg agcggcctcg gtcccgaagt ccttgagctc cgactggttg tggaagcggg   6000
tgaggcgctt gcacttgcac gaggccacca ggcgcacctt gcgcgcgcgc ggcgcctcac   6060
caccgggaca cagcagctgc acgcgctgcg cgcggtagcg gtcggggatg cagcggaagt   6120
cgggcccact aggtcgccac cacttgccgc ggccgatggc gttgggcagc aggcgcgccg   6180
ggccgcactg gccggagcac accagctcgg tgaccggctt ggcgctgcgg cacggcccat   6240
cggtcacgta gcgggtgaag tgcagctcgc ggcagctgta ctcggacacg tctgtggaga   6300
gaggcgcgcg tgagggtggc cgcccgcctg gccacccctg ccctggaccg gcccgtctct   6360
ctccacccca gccctgcttt tgccaagcct gtctccagag gcttttgccc ctgaacatct   6420
attgcaggaa ggtcccagat gctctagagc tggtggaaag ctctcctgcg caccctgtcc   6480
cctcggagcc aaatgactgc tggggttcaa acaccagggc tccatcgctc actgcaggtg   6540
tcatcttggg caagttcctt aacctctctc ttcttcctgt ctgcaaaatg ggccgcccca   6600
agcattgcga gttaatccat tacacacgca atgcagaaaa taccatttgg cacatatagc   6660
tgaaagcgtc ggctgttatg tattattatt atcatttctc ttctggggtc ttcttatgat   6720
ttaagccaca cttgtgccgc agggtccctg gcctgggcag ggtaagtact cagcacacct   6780
tctgcctggc tctggcttct cccaaattcc ttttccagcc acttgggagg ggtggacagg   6840
ggatggagaa aggagtagag gttaattgaa ggtaataaat cagggcagct gctgtggagg   6900
cgagggactg aaggggaggt gatcaggaca ggaattcatt agacttgaaa ggaatcaaag   6960
gcagtgtgtc caaccccctc attatcaatg agaatactga ggcccagcca gagaaaagaa   7020
cttgcccaaa aggctgggct gcatctccgg actccacttc cctggggtcc cagcaccttt   7080
tggctccggc aagagtggag gctctgcgtt cgagcatcca tgggaggctg ggctggggga   7140
tggagctgag ggctgctttt tactgtcgtt actttcctac catagggggcc ctgagctctg   7200
acccaaaacc tacaggttca gctgccacaa acattgacct ggctctctgc tgggcacatt   7260
```

-continued

```
tcttgttctg tgttatctga atgggcgcct catggtgata ctccctgggc aggcagagat   7320

tgggctccga ggcctggcct gatcccctgc acacaccttg accatgtctc ctatggtgga   7380

cttagatggg tgggagcttt ttaaatagct ggtcgtcgtg tgagtaccag tccaccccca   7440

aaggtttcat ggggatagtt ccaatgtgac aagaaagaat gaaaaatagt cttaagacca   7500

aaccagagag gggacagaga aggccacccc ccaccccac tctgaagagc aagcacagca    7560

ggggagatgt ggccactgcc atcgtctggg gctgctttct ggtctgtggg ctggtttgca   7620

tcctcacctc tgcagggctg gaatgtgtgt gtggtcaggg gggcatttgc ccaggaaggg   7680

gggcattttg cggcttttcg agaatagcgc ccctaggcca ggcacttcct ctgcagatca   7740

tgactttgtt ttgagcatgt ggcttcctca ggggctgtgg cctctcgtgg gagtccagca   7800

aggtggacat tttgtgtttg ggttccttac agcccttcag gcagtcgctg gagcccagct   7860

gaccttgcct agaaggggag ctgtgggggg aggcgccctt gtcctccatt ttgaagacgg   7920

agggtcctgg ctggcctccc atgcagttgc cctttttagc accccatagt cccaacaggt   7980

tgtgaggcgg ggagggctgg ggtccaggag cctgggcagt ggacttctct gccacctgga   8040

taatggccag aggacaggga agctcttagt ctgaagtgtc atttcagacg cccccatggc   8100

ctcaggattc ctgccaatta tagagccaga tgcacactgt cacctgggct tctctgtgca   8160

ggcctgacca ggaacccagg gttcctcttc cttctccctc ccctggaatg aggcaaggtt   8220

gggactgggg tggctgctga ggacagatgt ccctactcct gcacagagga tgctgctctc   8280

ccctccaggg cctggactca gctgcaccca tgtcaggggc taaaactgtg ccgaaaactc   8340

ccattccttc aagtgccagc tccctgggca ggccatgggc aatgcacact gcaggggtgc   8400

ctctctggcc ttcctcccca ctgctttgtg gagatctgtc ccccacaccc ccccacacac   8460

cagggctatc ttgcagttgg atcaaaccag gttcacacct cagctcttct cactaccaag   8520

ttactgagtg cctggaacct gtttcttccc cttcgagctg ggggttcacc tcctggggat   8580

tccatgatgt gggtctgtgt ggtggggaca gccaccacca gcatagagtg tccggtgccc   8640

cacaggtgct gttctgtgga tgggaggctc ccttaccttg ttcccttccc agtggtacca   8700

gcagctggac gtggctccta tattcccagg aggagattct ttgaaacctt ttcttttctg   8760

agcccctgag cctgttctga tgccctgatg ccataccctc accaccccag cgtcctccct   8820

gccctgggct ctcaccagcg tctgttgcct catgcctctg cacctgaatt tgaaggctgc   8880

accagcgagc cattcttccc ccacctccag gcaagactgt tcctcgacca gtgctggcag   8940

aggccagcaa tcttcactgg gtctacccca gtcttccaag cctcccaaag agaagtttct   9000

aaaacctccc caggatcttt tactaagaat tctctcctcc accccatacc tttggtctca   9060

aaggggtggt ggggaggccg ccctccgttc tccgcccggt tcatggtctt gttgttctcc   9120

agctccggtg gaggctcggg gtactctccg agctcgggga tgatttccgt ggcatcattc   9180

ttgaacgcct gccacccctg gccctccact acacggaagg ctgtgtgtac cagcaggcag   9240

acgagacaca gggccagtgg gagctgcatg gtaccagcca gaggagggca cgccaccttc   9300

cagtagcaca ggctctggtc tccagccgag acacggtcgc ctttttaaag cccctctctg   9360

cttcatgcca gccaatgagg acaggctggg gcagggctgg tcccatgttt ccctcagccc   9420

cggagggagg gaaaggggtg tgctcagagc aaaccctccc caaagacttc tcctctagct   9480

cagcaaactt ccaaattgct gctggcactc ccaggtgacc cagagagagg gggcgtgtga   9540

ggcaaggccc aagcctgctc tccggcacct cccacgtgct ggcggctgtg gttttcagat   9600

atcaaaatga gctccggctt ttaattgtct gtctccctgg gccctcgggc attctcaaaa   9660
```

-continued caaactgtgg acccgctcaa caaagaaaat gtgcagttct gagtgcttcg cggggctgag 9720
cccggcctat tccatttctc aggccaagtt catttgtcac cccaccaaca aatggcccaa 9780
ggtgtttctg tttgaccccc atagacccag ccagaggcaa aaagatgctt ttaaagaaat 9840
cccattggtc ccaactccac aagtctcagc attcattgtc ctaaccaaga aagcctctct 9900
tggtattctc tggaaggcaa gagagagaac tagagggtca gagcaagggt gcccgcttgg 9960
gagagagggc aggattctgg ttacaaatcg aggatgcgct ggtcactcag gctcctgtga 10020
tggacagcac agaggaaatc ccagctcatg ctcctcaggg atcctgtgca ctgtgacagg 10080
cacttctgag ccagggcact cactgtggct cgcagggtga tgtgctgaag acagtcattt 10140
ccccaaccag tctgtgtgtg tgagaagaca acaccaaatt cctttcctta gcaaaagcca 10200
cagccagcgt ttttagtgct gacattttat tttcttgtct tccagctggt tacatttttc 10260
aaaaacagtt ttgagtcctg tatggaaagc ttcattggtg cacaccacag gatgtgttcc 10320
atgaagccat cccaggacca actggtcaca aagaagctaa gagaaaatgc tgccttggcc 10380
ctgcatataa tgagccacac agggccgggg cggggggcgg gggcgcaggt agaggcgtgg 10440
gggagaagga ttcacacctg aggtgcaaga agagaaagga aggccagagg aatctttcat 10500
tgaagacaga ttgtttgagg acaagcagct cctgtgaaga ggctgcccag atcctctggt 10560
attttaactg ggcaatgaat cagcatgccc cacctgcaga gcctctgcaa gtcctttgcc 10620
acctgcctca acttgcaagt cgctgtgtcc atctgcagcc gactgtcctt tccatcatcc 10680
atcatccgac acatgaatgc agctgctctg acagttttac aagccagaca gaagccccct 10740
caggaagggc cctctctgat acctgcttcc taagtcagtt tccttcaggg cagatgaaaa 10800
cagctgtggc cattgttggg ggtgatctat ctctcccagc agagccggta gtgttgtgag 10860
aagctggccc tccgcaccac ctccccttgt ctatgaccct ccagcctcct tttcccttgc 10920
tctggaatgt ggactgttaa ccctctcatg accagacgac tgccttcttg caatggactt 10980
gggagagagc agttctgatg cctgggttcc ttgagcaggt aggatggatg cttatagccc 11040
cacctgctgt tgggagcggc tggaccgtct gcattaaaca gaggcagtgg gattcatccc 11100
tggaacgcgt ctgccacctg ctggagacaa aaggaggggt gactgcagga tggcaagtct 11160
caggactgga cgtgatttcc tttcctttcc tttccttatt tggaagtgaa gtaatattaa 11220
aaggaaaaag aagaatccag tggacttgaa cctctaaatg atccacaccc ctctgaatgg 11280
ctcagcgaga acctgctgtg acatcttctg ctgtttcatt taatgttaag tcattgacag 11340
ctgtttattt ttactcagtc cacaaacttg tcattgttca cagtattccc tggaattaaa 11400
cccccagggt tttagctgat tcctattgtg agtagtttag gttatttcca attttttttc 11460
ctatttccag cagggttgct atgaacatcc ttgtacggct gaaatttttt tttttttctt 11520
tttttggcag attctctctg tggcccaggc tgcagtgcag tggcacaatc ttggctcact 11580
gcaacctcca cctcctgggt tcaagcaatt ctcctgcctc agcctcccga gtagctggga 11640
ttacaggaat gcaccaccac gcccggccaa ttttgtattt ttagtagaga cgggggtttc 11700
tccatgttac tcaggctggt ctcgaacttc tgacctcggg tgatctgcct aactcggcct 11760
cccaaggtgc tggggattag aggcatgagc cacaatgccc ggcctcagag taattttta 11820
aattaaaatt ttaaaatgtg gatataatta taaatttaaa tatacttata agaaataaaa 11880
gcctgggcaa catggtgagg cctagtctct acaaaaaatt taaaaattag ctgggcatgg 11940
ggtcgcacgc ctgtggtctt agctacttgg gaggctgagg tgggaggttc acttgaggtt 12000

-continued

```
gaggtcgagg ctgcagtgag ccatacttgg gccactgcac tccagcctgg ttgacagagt 12060
gagaccccgt ctcaaaaaat aaaaataaaa aaaagaaaat gcagactccg tgtatccttt 12120
atccagtttc ccacaacaat aacaccttgc gaaactatag gacaatatca caactaggat 12180
attgatattg acacaattta ccaatcttac ccacatctcc cgtggcttaa cctctactgt 12240
gtgcgtgcac acgcattcac gtgtgtgtat acttagttct atgcaatctt gtcacgggta 12300
aatttgggga tccaccacag tcaagataaa gcacagctct gtgaccacaa gtctttctcc 12360
tgttgcccac ctccttccct ccttttccct ccctcccaca actaacccct ggcaactact 12420
catctaatct ccatttctgt catttttttt ttcacttcaa aattgttaca taaatgcgac 12480
caggtgcggt ggctcactca tgtaatccca gcactttggg aagccaaggc aggcagatca 12540
cttgaggtca ggagttcgag accagcctgg ccaacatggc gaaaccctgt ctctactaaa 12600
aatacaaaaa ttagctgggc atggtggcac gcacctgtaa tcccagctac ttgggaagct 12660
aaggcaagag aatcgcttga actcaggagg cggaagttgc agtgagctga gatcgcgcca 12720
ctgtgctcca gcctgggtga cagagtgaga ctgtctcaaa aaaaaaaaaa aaaggttata 12780
taaatggaat caattagtat gtagcctttg gggatttttt tttcactcag cattatttcc 12840
attatccaag ttgtacatat cagtaacatg ttcctttttc ttttcttttt tttttttttt 12900
ggctgagtag tattccacaa agtttaaaaa aacaaaacaa aactttagag ttatttctgg 12960
aagtgaatgc tgtgtctgag ggagtgtgaa gagtttggtg gtctgatgag ggtattgcag 13020
ggctgttttc cagaaaactc agcccagtcc ccgccctcac ctgcaaaata gaggctccca 13080
taggtggtac tttgatgagg ctgccgtaac taagtaccac aaattgggtg gcataaacaa 13140
cagaagtcgt ctcacagagc tggaggttag gagtgcaagt tcaagacatt ggcagagttg 13200
gttccttcga ggacagtgag gaaggccttt tacctgcctt ctgctggctg ctgacaagct 13260
gtggcattca ctggcttgca gaagtgtcac ccccaatccc tgccttcatc ttcacatggt 13320
gttctctctg tgttcgaatt ttccctttttt tctaaggagg tcaggcatat tagattaggc 13380
ccagcctaat gacctcatct taacgagtta catctgtaat agccctattt ccaaataagg 13440
tcacattctc aggtactgtg acttaggact tcaatatatg catttgggag gaatgcagtt 13500
caacccataa ataagactgt caacactggg tttgggatgt tgattttttt tttttttttt 13560
gagacagagt ctcgctctgt cacccaggcg ggagtgcagt ggtgtgatct tggctcatat 13620
aacctccacc tcctgggttc aagcagttct cctgcctcag cctcccgagt agctaggact 13680
acagactccc gccaccacac ccagctaatt tttgcatttt tttttgtttg ttttgtagag 13740
atggggtttc gccatgtcgg ccaggctggt cttgaactcc tgacatcagg tgttcccaca 13800
atcccataaa gtgctgggat tgcaggcggg agccaccgca cccagccgat ttttttaaac 13860
attgaattta acagttgaaa cttaatttcc agaaaagctg cttttccatg tgattattta 13920
ccagcttttg tttctgtcga gttgcttctt ctgatgttca ctcgccaaac gtttaataaa 13980
gcaaggggga cacgcactcc ctctccagga gctcgcatac catggaagaa ataatttccg 14040
catccaaaca actccactac cagatggaag gtgatcaatg ccactgaaaa aaaggttcag 14100
atgctttttt ctaaaaaaaa ctttattttt tttctggagc acttttaggt tcacagcaaa 14160
actgagtgga tggtacagag atttctcatt tatgtcctgt gcccacacat gtacagctgc 14220
ccccgttatc aacatcccgc caccagagtg gtgcatttgc tatgattgat gagcctacat 14280
gacacatcat tatcacctga agtccatggt ttacatcaca gcactagtgt tgtacatcct 14340
atggctttgg acaaatgtat aatgacatac atctaccatt atagtatcat acagatgggc 14400
```

-continued

```
agtattttca ttgtccaaaa aaactatctg ctctgcctat tcatccctcc ccgactttcc  14460
ccaacccctg gcaaccactg atctttttac tgtaccttta tttttgcctt ttccaggatg  14520
tcatatagag ttggaatata cccatacata gtcttttcag attggcttct ttcagttagt  14580
aatattcatt tggggttcct ccatgtcttt tcatggcatg aacagcttat tttttttttt  14640
agcactgagt aatactccat cgtcttgatg tatcacggtt tatctagtca cctactgtca  14700
tctactgaag gacatcttgg ttgctttcaa gctctggcaa ttattaatag aggtggtata  14760
aacattttgt acaggttttt tgttttgttt tgtcttaaga cggagtctta ctctgtctcc  14820
caggctgggg tgcagtgccg tgatctcagc tcactgcaac ctccgcctcc tgggttcaag  14880
tgattctcct ggctcagcct cccgagtagg tgggattaca ggtgagcacc accacacctg  14940
gctaattttt gtatttttag tagagaaggg gtttccccat gttggccagt atggtctcaa  15000
actcctaacc tcaagtgatc tgcccacctc agcctcccaa agtgctggga ttacaggcat  15060
gagccaccat gcccagctgt gtgcaggttt ttatacgaac gttaagtttt caaatcattt  15120
gaataaatac caaggagcat gactgctgga ttgtgcaata aaagtatgtg tagttttgca  15180
agaaactaaa ctgcaaactg tcctccaaag tggctgtacc atttgcattt ccccactgaa  15240
acaaagagtt cctgttgttc cacatcctca ccagatgcat tttttcaaaa ggacaatttt  15300
cttatgggcc ttcaaaggag agaacaatct ctttcccctg gggaggatct gggatcctta  15360
tggtaagatg tggcatttgg accagacttt gaatgacagg ccaaatttgg aaagtatatt  15420
atgctccttt gactccttgg gatcatagaa tctttgatct ggaaggactc tcaaaggtca  15480
tccggtttca ttctctactt ggttctggag gaggccccta tctctaatta atggaaactg  15540
aggattctcc ttattggctg cattttaaaa cagattttgc tcccacttgt aggtggtaaa  15600
aaggaaatat ctggattagg agggcaaact tctgctttta ggcagtaccc tgcattgagg  15660
gatgtccaaa tcaccttgtc tttatttaca catccataca caatggaatg ctatgtagct  15720
gttaagatga agggggtaga gcaataaaaa caataaccat aatataagct aagcaaaaca  15780
aacaacaaag cagagatatc tctgtatata cacacgtatg cacatatgtg tgcttatata  15840
tgcttgacat tttcctttaa ggatatgatg cttatgggga gagagattga aggagcaagt  15900
gactcacttt tccgtataag ccttttgcat tgtttaagtg tattactatg tacatatagt  15960
attattttta atgaaaaatt ttttaaaaat tatacttaaa aacttttacc tgttttatat  16020
tttagtgctc tgccttaaga ttttgtgtag aaccataaag attacattgt cagagtcttg  16080
acaaatagga agcgagtcca attgcttcat gtgatagagg gaatgggaac ctcgagaggc  16140
tttctctgcc cagacttctg tctgggagga aaaggcacct actttctcta aggtttttta  16200
ttcaaaggaa catagcacca atagtggaat ttaaggcatc tgggggaagg ggatatgttt  16260
agggactgtt catttgcagg atcactcaaa tctcaaaatg tcacccagtc atcacgtgag  16320
gctaccttga gatgaacacc ctagtcccct gctttcttag aagcacaaac cttacctcct  16380
tcattcagga ccattatggc cattctacct aagaatattc ctaccagaac atttctggta  16440
ctggaaaggt gttcatcaat atctactgca taaacagtgc catcatggaa cctataacta  16500
gctcagaacg gctatgtttt agatgattat ttttaaaaag ttagaaatcg caaatataaa  16560
agctaagccc aaacaaaaaa agctaagcat aaaaacgtaa aagaatacca actgtgataa  16620
gaaggacaaa aaaacaatac ctttgtaatg taagacattt attttggcta aagttctggt  16680
gttttaacac tgatttgtga tacaacggac attaaacttc cttttaaaaa gaaaaaaaca  16740
```

-continued

```
atttggtagc tctccctttt ctgtccagaa aaattcactc tttcataatc aaattaccct  16800
aaaatttggt ggcgttaaga ggcaacaaaa gttaagcttc caacgaatct gttctctcaa  16860
ccggaaatgt cttctatttc caatcaggat aaaaccttga cttacttgca aggactatca  16920
cggttagccc ttcagtgatt cctgacacca gttctgtgaa aaagaaaatt tcctgcgaga  16980
aaagctcatg tcttcatatt gaagatcagt actttttttt ttttttttcc tttaaaacag  17040
tagcatctta acttgtggca caaaaggcac caacattccc tttccaaacc atccatcacc  17100
atgggtggaa ggcagcgcca cctgctggcc atcatattat ggctcacata cccataattt  17160
ccttgcggtg ctgaattcca agtggggatt attagagacc cctcagagcc aaaaggggac  17220
cttagaggtc ttctagatga gtcccctcat ttgtaggtgg tggtttctgg ataactcaga  17280
gtggcaggga cacagacgag cctgtggaaa ggtatactgc tttaagattg agaagaaaac  17340
catttggcgc tctaattttg cctggatggt gctctgtcag tcaaagaaag ggaacaggtc  17400
tggggagggg gtaagggcac cctgagttcc tgttccatca cttcccaggc agtagaaggc  17460
tgtccaggaa cagctcccat ccgcagctgg gcatgtgttg gctcttacac aagagacttt  17520
aattttactt gaagaactaa gagctaaatc ttgttaagta aatacggggt ttcaggggtg  17580
aaggactatc aagaaatccc aagttatcag cataaaagta gtcccaaagt aaaggcagta  17640
attctcccaa tggccttttc tccctcatgc ccccacagag actttcgaga ggtcctagtt  17700
agccagccac accaacctgc tgtgttcgcg taagtagctg tgcctgtccc atggggtgac  17760
cactgcctgg tcatgggagg ggagccccag ccccagctcc ctagcctttt ccaggagcag  17820
agcagaaagc tctactttgg ggtgctacat cccacctgga gaaagagctg cacattctag  17880
cctatgaggg acccaccctt ttcacttgct tctccggggc tggattgagg gtaagtgcag  17940
tacacctgga gatcccaggg agcccccttc ttgagaaaga gtatcgtatg aaagaatcca  18000
gcttcaggga gcagcaaacc caaaatcttg cccagctcca ccttatggag ctggacaacc  18060
ctgggggcca ggcccttaat cattctgaac ctcagttcct tttttttaaa aaaggtcaca  18120
atacaagaac aagctctact aactttacag ggttactgtg aggctcaagt tagattaagt  18180
tggaaggcta cctagaagct gtgcagtgag gtacccagtt tagaggatgg ccatttcact  18240
taggtgggtt tatctggaca cctttttcac tatctggaga agaagacaca tactggttgt  18300
tcagggctgc tgtggtcaca gagaaaagcg gacagcaaat gaccaggctg ggcagggctg  18360
cttctgtgtg atcagagacc ttcacagccg ggagtgaggc cttacgccac acctgcctct  18420
ccgtgtccca gccaggagct cctggccaac tctgaaaaag gcacattccc taccttggca  18480
tattaacact gcctgaattt aaatgtaaaa ctgagttgta aatagtcaac aaaagtccct  18540
gatatttctt ttgttttagg taagactcct tcacaaggcc ttgcgagtga tcctaccata  18600
aattcagtct tctgggagcg tgacacaccc accagaacaa tgccctatat atatttggtg  18660
ctcaaaaagt gtttaatttc ttaaactttt atcagacacc tatgtgcaag gtgctggggg  18720
catggctgag gaccttctct ttgcccagag tgaccctgaa gataaatagc atcacaatca  18780
ctttccataa taacaataac gtaaaatcct aacaagactg tatttaaaac aaaactctta  18840
tattctggca aatgtgcata cacatgtgag ggctggtgca ttccaatatc atccttagaa  18900
agtcttttga aaggtttatc gtgtttgggt ttttttgctc taccaccaat aaaggatcca  18960
tttggacact ccgccatgtc tcatgtctgc ctggctgagt cacttcaggg atcccgtgct  19020
ggcaccagag agctgtaaga gccacctgca atgggcaggg tgtgtgcctg ggacctttca  19080
cttccctgct tgtcttctgg ccgcgtttct gagaggcacg ccccccacac acatccatgc  19140
```

-continued

```
acacacgctg taattggcca acttcctcct tctgttcttg gaatagcaac cgagacaaaa  19200
agcagttagc acgagtggct tggcttgcc aacactacaa ttcaggacaa aacccttgta  19260
attctccaaa tggtggggtt tttaaatagg ttggacttca actccctgtt ttctaaaaaa  19320
gaaaaaaaaa aaagcatgcc caaggcatca ctcttctcaa aaacgaagtg actgagataa  19380
gatcgaaggg aaatattcca gagcagcaga ttctgaactc aaggcttcca aagattcaca  19440
ttttgaaaac tctatggatt taggagggtt ctccaggttt gcccacaagg cctctttgtg  19500
tagggaccat tcatcctaag gaaatcattc aaatgcagcc ttgctgtggg aatctccatc  19560
cactaataac tgacggacac ccccacccca gcttcggacc tcaagacgtg agagggctgc  19620
ctatgcacag ggtgtggaag gctgtgggga cagtgcgggg cacagacgtg gtggggagag  19680
tggcctgcat ttgcatagtt cctttactag ggctcaaggt gttgaggtcc acactcaaga  19740
gaggattcgg gagttgggga agggaggtca tgagggacct ctgtgagcat cttaggcctt  19800
acacttccac acacctcctg ccgtgggcca tcgggaagca tgcaggccac aggccttccc  19860
cctctgagcc cccatctcag ggaaaagaca tcataagtta cagaaacagg acaactgggg  19920
agcaaggacg ccccccttgg caagcttctt tatgtgctcc ccagggtggg gaaagtggcc  19980
caggactgtg ttgggacaca cttgtagaca agtgccttgt gatgctggga gcagggtaca  20040
gtgtgtttcc taaacatggc agctcgggac acctttgccc acggcctccc ccacggacct  20100
ctcgagcaga ggcggtgggg gtgccctagg gtttcaactt cccctccttg gctagtctgt  20160
cattgagctg gcagagctgg gccaggaagc catcgttggg gccgatctca cggttctgcc  20220
tcacgatgct cagggcagac ttgacgtcca tcttctgccg catcatgagg taggcgataa  20280
ctagcgttgg ggagcggcta taaccttccc ggcagtggac gagcacccgg cctgtaagaa  20340
acaggggaga cgtggtgagc tgggggcgtc ccatcacacc atggcgttgg tcaagactct  20400
tccgtgaagt gccacttaaa agcacaatgt cacgccactg tgtgcctgtc agaatggcta  20460
aaatgaaaag gatggaaaac ccaaagtgct ggtgaagata tggggcaact ggaactcttc  20520
tgcgtggctg ggggaggtga ggcgtgaatt ggcacaacca ctttggaaag ctgtgcggca  20580
cggcggtatc tcctcaagct gaacacgtgc atcccctctg gcccagcaat cccactccca  20640
ggcccaggtc caatagagat acgcattcac attcacgaac atgggccaga atgttcacag  20700
gcaacactgc acatcatggc ccacagttag aaacccccaa aggcccatcc acagtagaaa  20760
ggacaaatac aaagaatgac cagactgcca cttagcagaa gcaacacgga ggcagcacac  20820
acatatgagg tggatgagcc cacagagtag gaaagcgggc aaaaccatct gtgctgtcag  20880
aagcctgcaa ggggctgggc acagtggctc acgcctgtaa tcccagcact ttgggaggcc  20940
aaggcaactg gatcacaagg tcaggagttc gagaccagac tggccaacat agtgaaatcc  21000
cgtctttact aaagatacaa aaaaatagct gggtgtggtg gcgcgagcct ataatcccag  21060
ctactcagga ggctgaggcc agagaattgc ttgaacccag gaggcagagg ttgcggtgag  21120
gtgagattgt gctgagattg tgctccagcc tgggtgacag agcgagactc tgtctcaaaa  21180
aaaaaaagaa gcccgcgtgg cagaggccct gggagctggg gatgggggtg gtggagcata  21240
gagactgggg gtgctttcca gggtgctggt agtgttttgt ttcttttttt ttgagatgga  21300
gtttccttct tgttgcccag gctggagtgc agtggcgcga tctcggctca cttcagcctc  21360
cgcctcccgg gttcaagcaa ttctcctgcc tcagcctcct gagtagctgg gactacaggc  21420
gcatgccacc atgcccagct aatttttttg tatcttttag tagagatggg gttattttaa  21480
```

-continued

```
tatagtgtgt gtgtgcgtgt atatatatgt gtgtgtgtgt gtgtgtgtgt gtatgtgtgt  21540
gtatatatat atatataaat agacaccatc tctcaatatc cacagggcag attggctcca  21600
ggacctcctg ccgataccca aatccacaga tgctcaagtc cctgattata aaatgacatc  21660
atatatgcaa ataacctctg cacagcacat cctcccctat actttaaatc atctccagat  21720
gacttatgat acccaagaca atgtaaacat ttattagatt atatcatcta gagaataatg  21780
acaagaaaaa aaatctgtac atgttcagta cagacataac atctttttat gttgttttta  21840
atatttttca gactgaggtt agttgaatcc acagatgtgg aacccacgga tatggaggac  21900
cgactgtata ttctattggt tctgtttttt ctagagaatc ctgaccaata cactggttat  21960
taactcatga tccacctaac ctcaaggtgc ctcagttttc ttatctggcc aatagtaccc  22020
attgcacaag gtggttagat taaaggagag gacacatgaa tcctctaggt tagcacctgg  22080
catccatgtg cactcaataa atgttaccca atactgggca tcctctggta gcacctagta  22140
caccctcaac tacagcagcc ctggtcctgt gtcattgcca gacatgcgca gattgacttt  22200
tctctcccag aggacgaatt ctttaagagc aagaaatggc cggacacggt ggctcacacc  22260
tataatccca acactttggg aggtcgaggt gggcggatcc cctgaagtca ggagttcgag  22320
accatcctgg ccaacatggc gaaaccccgt ttctactaaa aatacaaaaa attagctggg  22380
catggtggca catgcctgta atcccagcta ctcagaaagc tgaggcagga gaatcacttg  22440
aacctgggag gtggagggtg cagtgagctg agattgagcc actgtactcc agcctgggtg  22500
acaagagcga gactccgtct caaaaaaaaa aaaaaaaaaa ggcaagaaat gtgggggcatt  22560
gatttttgga tgcgttacaa tctctagcat acactatgtg ctcaataaat atttgctgac  22620
tagctgagtg aattattacc tactaacacc tctataaggc cattgtttgg caaggaatct  22680
gctagcccag agtccaacag agtctcttct gctcctatca ccctaccccc aaaacaccac  22740
tctattttcc caatgccttc caaatcagga agcaggagtc ctccactttc ttgcccattc  22800
accctccggc ctgtatgccc gaaatattca gagtggggct tcccctgccc caccctagga  22860
atgagaccct ctgcagagca gccaccttac catctagaac atactctgca tgcccagtgc  22920
acacagagcc tactgggaaa ggggccagtt caacctccca ttcctctagg ctcagcccag  22980
atgccacctc ctccatgaag ctgttttccc agctagaagt gactgctccc tcttgagtac  23040
cctcagccat cccacccagc tctcagtgat gggtccctgg gccccacaca ctgttggagg  23100
ccagcatgtt tctgttgact cacttcgcca ctcattctta gaagcattta tacttggcat  23160
tagagcccat ggaattcttc atcacttgct cattcatcat ttgcagtgta cctactatgt  23220
gcctgatgct acatcaggtg ctaaggagac agacaaggaa caaagtagac ccagcctgag  23280
ggcaggcttc atggaagaga ggacaccatg ccaaggacaa ggtggagttt gccagaggaa  23340
ggggtaggga gaggcagaga gaacttttca gactaaagac ccagcacacc tggactgaga  23400
caggtcaaaa aaagggcgtg ttcctagttg tttggaaaga ggaaacaaag tcagagagct  23460
tgaaattccc tgaatgaata accaattgct attatacgag aacaacaaaa tccttcccct  23520
tcgcccagcc tatgtttaca cagggtgagg aactcagtac agctggagtg gaggaggtga  23580
gcagggttgg ggggtgacag tgaccaggaa ggaccatgag gggcctgtca gcaaagtctg  23640
cagatactcc acagtaaagc ttctctctga gccctgagcg ttcactgtcc agtggtctag  23700
aaaattctgt ttactggaaa tcattcagac agtgagcctg ctgggcccaa gagtcatcag  23760
tgtagtacag ccaaggctgt tcacacctca tgggggtccc ctccgctggg agggtttggg  23820
gtggggagag acgaagaggt aaagggagga gctgagagaa acagctaaaa gcagaaaggg  23880
```

-continued agaaagggca agtggcccag cctgctcagc tgatgtctgc tttgtggcct tctagggttt 23940
cttgctggaa tgccttggtg actgccagcg ccttggtagt tctccttcag tcttatctta 24000
tatttggggg ctgcaggaag tgtttcgtaa gtggctggaa gatttggcca ggggggctgt 24060
ggtttgctga ctgccaacct aagctgaccg cagctacccc ttttctcctt gccaggcaat 24120
cacgtgaatc tctagccaat gagatgtgag gggtatttct gggaaatgtt ttacttgttc 24180
ttaaagagag agactgggca tggtggcacg tgcttgtagt cccagctact caggaggctg 24240
aggtgagagg actgcttgag cccaggagtt ggagaccagt ctagacaaca tagcaagacc 24300
ctgtctcttt aaaaaagaga gagagagtgg ccaggcgcgg tggctcatgc ctgtaatccc 24360
agcactttgg gaggcagagg gaggcggatc acctgaggtc aggagttgga gaccagcctg 24420
accaacatgg tgaaacccca tctctactaa aaatacaaaa ttagccaggc gtgggggcgc 24480
atgcctgtaa tcccagctac ttgggaggct gaggcgggag gctgaggcag gagaatcgct 24540
tgaacctggg aggtggaggt tgcggtgagc caagatcgcg ccattgctct tcagcctggg 24600
caacaagagt gaaactccat ctaaaaaaaa aaaaaaaaaa aaaaaaggag agagagaaga 24660
ggaaaaaaaa gagtgggaag agatggctgc agggcctcat ctgctgtact ttgtcctgct 24720
tggatgtggt gactggatcc catcttggga ccatgacggg agcacccaac actgaggtgg 24780
cagaagagag aaagggaaag ggcctggtcc agaggccacc atggagctgc tgaatcaagc 24840
agccccttaa tcaaccagcc cccatgctcc ttcacctcag gacttcttgc catgcacatt 24900
aacacattaa cacatcttcc tcatcgttac agctgtttga atgggggacg tgtaagcaac 24960
tggaaaccaa cctccagcca aagtgcagtc aaacgcgagg accctggggc tgccatggtg 25020
tgaatgagtt gcacatcctg tgacacacgg ggccacttga cagccagcca ggtgagcaga 25080
gagagaccta cagctctgtc gttcacccca gaagatggga aacaagggag tttctaagaa 25140
gagacctgtt gtgggcctgt tttccagagg gacagtccag tcagagctgc ctcccatctt 25200
ttcctggtgg gaggtccctt accattcttt tgagccaaag cctggtcaat gaagtcggca 25260
gccctttcaa agtaagcgct gaggttgaac tcctgtgtgt cgttggcctt gatgcccagg 25320
tatgtgatgc cggagtcctt gtagaagttg gcattggtgt tgacgtgcat gaaggacctg 25380
ccctcagccg cgttcagcac atgggtgatg cctagtttct gcagcttggg gatgtcctga 25440
gccacagacc tggacaggag acagtggtgg ggatgattaa ccaaccaaat ggcagcccca 25500
gggggaggaa gatggagaag gatttaagcc tcttagcaaa gcaaggaaac cctccatgct 25560
ctggcccctg ccagcttctc ctgcctcatc ttatgacctc ttccctcact ctggccatat 25620
cgaattgcca gcagcttccc caaatagact ggtggtttca tagccatgct gtcccctctg 25680
tctggaatgc tctttcccac cttctctgga gaaatgcgcc ctctcatctt tcacaccctc 25740
cgcagtgttt gtctcccctc cattccattt ggccccatgc tccctaagct gtggtggggg 25800
tgtacatagc caactggtta cagatgggct ctggaaccag actaactggg tctgcatcct 25860
gcccaggtac tagccaggca accttaagca agccatttaa cctttctgtg cctcagtttc 25920
cctctctgta aaatggggat aacagtgcct tctccttgag gttgttatga gtattaaatg 25980
ggctattcca ttgacagagc tggacacggt agtgagcact atgattctaa tgcttgattg 26040
tgcttctgtg tttagacatc cagactgtga gctccttgag agaggaacca tgtctgcttt 26100
aagtctgttt ccccaccatc tgctatagta cctgctacat agtaggtgct gaataaataa 26160
gcggtgaatg agtgcaaaag aataaatttg tcacgtacca ggcagccccc tccctgcccc 26220

-continued

```
cagagggatc ctacctgcca cattccactg gctacgtttc caaagctctt ttgggtgatt  26280
tagtacttgg ggagtaagtg gccccaacag aactatggga ggttacaaaa taatttatct  26340
aaggtcgggt gcagtggctc acacctgtaa tcccagcact ctgggaagcc gaggcaggtg  26400
gatcacctgt caggagttcg ggaccagcct ggccaacatg gtgaaacccc gtctctacta  26460
aaaatacaaa agtgagccgg gtgtggtggt acatgcctgt aatcccagct actctgggat  26520
tacagaggct gagacaggag aatcacttga acccgggagg tggaggttgc agtgtgctga  26580
gattgtgcta ttgcactcta gcctgggtga cagagtgaga ctccgtctcg aaaaataaaa  26640
taaaataaaa taaaaataat aattggtctg aatggtgaaa aggccccttt atttcatctc  26700
acaaaacatc ccagtccaaa tagcagttta tactttataa aatgccacct cctgtgtgat  26760
cttgcttgcc cactgcgagc agccctgtga ggaacaagga tggcaatatc cctgcttaac  26820
agagcttgaa ctcaggccca acaggatgag cagagggatg ggcacaggcc ccgtgtgctg  26880
ctggtggcag atctgggaga agacctcctt tctcccgaca tccagccctg ctctatcttc  26940
cacctcactc tgcccctcat gcccacatct gctgcaaaac ccccaaggcc tggcacatgt  27000
ggctcacaca ggctctggct ctgccttgtg aggacgtggc tgcggccctg attttgttaa  27060
gggaatggag cccaaatcct cttggtgctt ggtgctcact gatcctccct gttgaggaac  27120
ccccacaccc ctggccaagt caaggtcaga ggtgcttaga gggcaaggga tgtattttct  27180
acagtggcca tcagcaattg ccactctggc tacaccagac gtgtacaacc ttggtttcca  27240
cttgggaagt gatgacagct gaatggccaa cctgcccaag caagcgggat tcctgaggct  27300
aacaaggcct gcttgctgct tggtgcaaga ggaagggtgt ctctagagct ttccaattcc  27360
tgaagccttt ggctgacact gtgggactct gtttattcct gcttaggaca ccgcgcaaga  27420
ctgtgaagca gtggctgata gaaaaaaaca ctttgaagag tcactcccat tcatctccct  27480
tctctaatac ttttttttt tgagatggag tttcgctctt gttgcccagt tggagtgcaa  27540
cggtacgatc ttggctcact gtaacctcca cctcccgtgt tcaaacgatt ctcctgcctc  27600
agcctccgga gtagctggga tcacaggcgc caggcaccat gcccagctaa tttttgtatt  27660
tttagtagag acagggtttc accatgttgg tcaggctggt ctcgaactgc tgacctcagg  27720
tgacccaccc gcctcggcct cccaaagtgc tgggattaca ggcgtgagcc atcgtgccag  27780
gcctctaata ctattaataa ttcaacattc aaaaaattta caattatcat tattactatc  27840
tctactatga atgaacattg tacagtgcct gacataaagc aggtgctcag actggtgaat  27900
gaatgatgga atggatgaga actgtcccca tgaggctggg gcctgatgga ccccttctag  27960
ttccatgatg acccccattt ccgtggcagt ccttggcagg ctaaacagca ggtcatagcg  28020
gaggtcagga aatacataca tgaacaagac attgaccctg tccttgtagt ccctcacaca  28080
ctctgagcca ccatttcctc ctctgtaaaa tgggaggagg gttagttttg agttttcaac  28140
atgccatcct tgggctgagc catgaagctt aggattttgg taactgggtc ctcagagtat  28200
cgtgaaaatc caacttgagg ctttccaagg ctgtacaggc atgctaatat attctttctt  28260
gaggctccta tttcacatct cagaatgtta acactggttc tttcctgctg attagacatt  28320
cttactagaa aaaaaattta aaatttaaat taaaaaaaat ctcttactgt ccgggtgcgg  28380
tggctcacgc ctgtaatccc agcacttttg gaggccgagg tgggcggatc atgaggtcag  28440
gagtttgaga ccagcctggc caagagacca gcctggccaa tatggtgaaa ccccgtctct  28500
actaaaaata caaaaagtag ccaggcgtgg tggcgggcgc ctgtaatccc agctactcgg  28560
gaggctgagg caggagaatt gcttgaaccc aggaggcaga ggttgcagtg agccgagatc  28620
```

-continued

```
tcgccattgc actccagcct gggtgacaga gcctgggggt gaaaggtcaa gagccttttc  28680
taggtggtgg ctcaggtcct tagggggggtt atcactggac cgttctagaa tctcctgtaa  28740
atcaaatcac atctggaagg tgggggcctg gaaatcccgg cccagctccc cggactcgct  28800
catttggggt gtttaggttc cctgatccgg gactgccggg ccgggaaaat tccatgcccg  28860
aattgtgacg tcggcccgtt gccatggcgg cgaaggcaga cattccgcgg tgacctcact  28920
gcagaaccag gcagctgtca catgacgcgc gggcaggaga ccggccgggc gaccgagggt  28980
cacctgttaa gtgaacatgg tagccccgac cccgcccaag gccaagcccc aagcgggtgg  29040
cggctgggac ccgggcaggc gccacccggg ctccgtgcac cccgccacgg ggaagggccg  29100
cgcccggcca ggcagggttc cagttccttg gccccacgcg cgggggtagg cgtcgactcc  29160
aggcccctcc caagccccg ctgtggctcc cggaggggcc atcgcgcccg ggctcccca  29220
acccaagact cgcgacaccc cgaccccagc ctcgggtggg cggggcgtcc cgagagggac  29280
ggcggggccg ggctcgcgaa agggactcac gcgttgccca cgtagatccg cggggtgacc  29340
tcgttgcagg gctggctcgg gaggctgtag cagccgctgc cgtccgagag caggtcgttg  29400
agatcctgca ccgagagctc gaacgagccc gacatggcgg cggcggggcc ctgcacgccc  29460
ggcaggagca agcgaggcgg agagcggcgg atcagctggg cgggggctcg cgccgggagc  29520
cgccccgtcc cgcccctggg gcgggcccgc cgggctccgg gagctgcgga gcgcgggcgc  29580
cgtgacgcgg gggccccgcg cgccactcct gggcgcgtcc cggggggaag acgccaccgc  29640
cctggagtct caggggtcct cgccccatcc cggtccaggc cgtttgtgta tctttgtaaa  29700
ctggcaagcg cggtaacttc cttccctgaa ttaaatgcag ggcccaataa acatttcgtg  29760
gcggaggtac acctaggggt cgcttcagtc tttcatgatt acagggaccg ccgggttcgg  29820
ctcgtgagcg gctccctgca gtggaggcac cacccgggcg cttgacagaa tccccgcccc  29880
agcccagccc tgctggatca gagtggacat tttacggacc ccaggaggtc cctacggtca  29940
aagtctgaga agccctactc tggggcgcat ctgctttcaa cattcattga gagtcatcgt  30000
cgtgcttaaa agcagtcagg tttggaattc tgaggaatta cttaacctga gcctgtttgc  30060
agggaaaaaa aaaaaaagcg ggatagtaat ggtacctaat tctagggttg ctggaagggt  30120
taaatgtgac attcaaagaa ggcacccagc actgcatggc gagcactcaa taggtgttag  30180
tccttcatca acaaatgcgt tgagcaccca gtgggtgcta taccctgtgc tggggtggag  30240
ataaatcaga ctcctgcagc ccttcctgga gcagatgcca gcccaccata agccactcag  30300
catttcctga actcccacta agtacaaaag atagtctctg tactggagga aagctgccct  30360
cccctactgc catgaaaaac tggcagtttc cttcctgcaa aagggcaaat ttggccttga  30420
attcaggaac cccacatcct gagcccagcc ctgccaccaa cttggttctt gagtaacgtt  30480
gctgctgctg tggtcttcag tttcctcatt tgcaaaagga attggatccg attatcatta  30540
gggtcaactt tctcctcctc caaaacttgt ggtcttgcac cttcagggga gctattgcag  30600
tggagactac ttagctgata gcccaagatg tgtaaccaag gctggaattt ctgtatccct  30660
caccccaccc cgtgcctgcc cacccctccc ggtgcaccac ttctttcctt ctggtgttgg  30720
ctggcagcat ctgcattcta agcagcgggg aaagctttcg agttccttga ccttcatctt  30780
gacttgagcc gaggttagca ttaaaaacac aagcccagag gcagccagcc atgctctgct  30840
gctcctactc ccttcccggg acctgtccct gatgtcataa ctgggtaact atgacagctt  30900
gtcatgggga cagctaggca cctcacagag gagtctgggt acctcatttc tgaagtgaga  30960
```

-continued

```
ctaggaagag aagatgaaca attccctgga ttatctggcc taccctgtta tcgtctctaa  31020
tcacaggcaa agcacaacct tcagaaagaa actggacttt ggccactacg tatctcacaa  31080
gaatagaata caaataggta tgtgggcagt ttgggctgga cactgctatt agggattttg  31140
gaatggtacc ccataaagag atcaacagga aaccagacca ggtcacagct ttgggatgat  31200
atggccttat ctgctgagtt tggggaagag ggcattagca ccaataacaa aatgtatctt  31260
ccaccaggga gttcactgga tggaaatact cctttaaact ccttaaagcc gaagtacgtt  31320
agaaagggga taagacttca gaagccaata gacaggctaa taatattgga aaaagattgg  31380
aagagaagct ctttcattgg attagaagga catttatctc tgtaaatttt attttcacta  31440
ttcttttgtt tctgctcaaa actctccaga gatgttcatt tgataaatca aaccaaactt  31500
cttgagtcgc attaaggtcc taattcgaaa ttgttcatta gtcaaggaca ttgtctagtg  31560
ctggttttct gaggccgcta ctggaattcc tgtgatgtaa cattgttccc ttttatcccc  31620
cttctctagc gaagcctact gttgatacca aacctccagt ggcgcacaca aatcacattt  31680
taaaattgag caaactacag gtatttgttc ttgctgcttg cagatgtgca gatgtatttt  31740
attgacttcc agtctgtttc ctaaagaggt tcaatttccc agagccttct aaatacccat  31800
ctactcaaag atttgttaat actcctcctc cccacgcgtc acccccagtc gttttttttcc  31860
cccctgatac ggagtctcgc tctgttgcct aggctggagt gcacaatctc ggctcactgc  31920
aacctccgcc tcccagattc aagcaattct cccgcctcag cctccagagt agctgggatt  31980
acaggcatgt ggcaccatgc ccagctaatt tttcatattt ttagtagaga caggggttca  32040
ccatgttggc caggatggtc ttagtctcat tacctcccgc ctgcctcggc ctcccaaagt  32100
gctgggatta caggcgtgag ccaccgtgcc cggccgccca gtcttttaag ttctgcttcc  32160
agtctccact gtggccctca atgcacccct ttcccacgat ctcagaggag gggaacacta  32220
agtcattgtg tgttggggca gtgcactgat ggtgtcacca tggtgaggtg tggtttctta  32280
ccagggtgaa caaaagaaaa tcaacaaaat cgagtatgaa aacaagcaac tgtgtcagaa  32340
aatcgcaaat gcccatcgcg gccctgccaa ggtggattgc tggaatgaat atttttccaa  32400
gaggtaatgt tctttgtctt catttcagtt ttgaaaagtc aaaattgact ttcctcttgg  32460
gttttagtgt gaggttttcc caagtcagag aagtacttaa gggaagttat cttgagggag  32520
aaccaaacag accatgttac acagaatgaa aactttaaaa atggggacct ttctctagca  32580
ttaaagagct tttatttcat cgaagagact tttcagagtc ctattcagtg tgtcacaaga  32640
atgcactgcg cacttttata aaatggtggc catgtgtctt agtccattat agggcgctat  32700
agcaaattgc tataaactgg tggcttataa acaacaaaaa tttctcatag ttctagaggc  32760
aaggaagtcc aaagatcaag gtgccagtaa attcggcatc tgaggagggc ctgcttcata  32820
gacaaccatc ttttcactgt aacctcacgg ggcagaagga gaaagaggct tctttcataa  32880
ggacactaat tccattaggg tgacctaatc agctctcaaa ggcccacccc ctaataccat  32940
caccttcatg gttaggattt gaacataaga attttggggg acacaggcat ctgttccata  33000
gcaccatggc tggggctatg atgtgacatt cttaaaatca gttccagaaa tctttcctga  33060
gcaactacta tgtgctaggt accaggaata ataaagatga aatgagatgt atatttcctt  33120
acctcaaaga actcaaggtc ttgtagggga gatatttatg gaaataatga caatgcagtg  33180
tgattaggga tacaaaagaa gctcatgcaa gagaaagaat ttgctggggg cgaggagatg  33240
gtcaagatgc cattctatat cctggtatat tctggtataa gttgaaagct gagaggagtg  33300
aggtgaccca aaacttgtcg ccagccgttt gtgatttatt cacagggaga ccttccccca  33360
```

-continued

```
accagaagtt ctcaatcctg gttttacatt ataatccttg gggaatttta agaaaatgcc  33420
agtgtgcacg gttcacctca gatcaatgaa gtagaatctt ctcatgggca acagggttga  33480
ggaccactga tataaacctg cgaatgcggt gcatgtttcc cggagtgcag tgcagaccaa  33540
caggctgtcc caggggcctg tgggctcagc aggacagttt actccctgca cttagacagt  33600
ctggcattta tgatctcatg acttcatctc ccccactcgt caagatgagc atttccttct  33660
tcacccattt cggggttttg tgtttttcag cttaaacaga gaaacaagga accgcgagct  33720
agtgagaatc accatggaaa accagggcat tctgaagagg cttgttgatc gcaaacccca  33780
ctatgaccgc agggcatctg agatagactg gcaggcacgt gggcactcat gttatactcc  33840
cagacacaca cagagtttgt cggtgttcag cctagagaga gtctcagaaa aatccctgaa  33900
cagctagagt cagatcacat gaaatgtaac aatcgttaaa agaaaaacca tccaaagcaa  33960
acaaagctaa caggcacaaa ccatcaaaca aacagctaaa acagcttggt agcaaagcca  34020
ttatgtgtca gtttcataac ataacaatta tgtgtcagtt tcagaaaaat aatctagtag  34080
cgtcttccct caccccttaa ttcattaaga aaggctgaat gtacagggat gaagggtata  34140
agattcagtc agtatgcggt tggtttgctt catttaggaa tgacccttaa aaaggccagg  34200
ggaggggaaa ccatctgtgg tgttttaaaa aacctccact taccgacttt ggtctttaaa  34260
tcttttctaa gtcatccctg ggatttagaa cttcagtaat agcaccaatg ccctggcatt  34320
gacataaacc aattttttc cttcaagaat tcaaggcgct atatcagaaa taccacgaga  34380
tatcttctct cccaaaatga ataggtatgt ctctcttact atcaaacact gtgaccacag  34440
ctgataccaa agccctgaga accccataaa tggcgaatga ggggcccagt taaggagacg  34500
gattttgctc ttctcatata atattgacta gtcttccatt cgggaaactt ggggctctct  34560
gactttattt cttctctcca tacaagaagg aaatgacatt gtcttttgtc atcatctttg  34620
aggctttgtg ggagtctgag gggaagtgat ttgttccaat aagacataaa ctggaagacc  34680
tgtggcttta aaattgtgcc aaagttacat tccaggtctc tgtcagtatt caaaagtacc  34740
agcatgttgt cattttgtat tatttaacat tattagtgat gactaagtgg tttcccccac  34800
ccaagggaga aagataaatg gacacttagg cgttccaaag aatagttctg tataattgat  34860
gtgtctcctt ctctcttctc cactgaatac aaggttactc accatggaaa agatacaaga  34920
gaaggcccta ggatttcttg gctgctcagg atctcaagac actcccgact ggctgaatgc  34980
tccatcttca gatgcttcaa taaagcttgg aacataaaat gcgtaagtta catttagggg  35040
acccaaaggc tttatgttct cattccaaaa tggggcaggc agaaggaaag atgcaatgag  35100
catttttatt tggggctatg aaaagaagtt ttaacgagag agagagagag aaatctgaga  35160
gaactcttta aaacatacac catcatcacc atcccgtgga agaagaaaag ctggggtgag  35220
atcatccagc cacaagtaca gcactgtcaa aatggaaaac gaaatcacat gacaacatca  35280
aggttcagaa aacacaagga acaaatgcca ttagttcctc tgtgaataca cacgatcgga  35340
aaagaatgcc tcattgaagt ttccatggac tctgttcatt tatagggagc agcagcagtg  35400
aaaatgtctc aaaacatacg gtgagacaat gttgcaggcc tgctatgatt ggtcatgcta  35460
gttttcagcc caactatatt agtcagcatt tgccaaagag acagactcaa taggagagag  35520
agagagagag agagagtgag agagatagat agagagtgag agagagagag aaagagagag  35580
agagaggaga ggatttattt ggggaattgg ctcacaagat catggaagct aaagaagtcc  35640
caccacaggc catctgcaag ctggagaccc tggtggagca gggcagacaa cccccaaagt  35700
```

-continued

```
ggggcttagc ctgcgagtgt tcttggcttc acccaggaaa gaatttaagg gtgagccagt  35760
ggtagggtag aagaagacag ttttattgaa gcagcagtgt tacagctcca tgactgctcc  35820
tgcagtacag ggctacccca aaggcagaga gttttgcagt catagttata cgtactttta  35880
attacatgta gattaagggg cggtttgtgc agaaattcta gggaaggagt agtaattttt  35940
tttttttttt ttgagatgaa atctcactct gtcgcccagg ctggagtgca gatggcgcga  36000
tctcagctca ctgcaacctc cgcctcctgg gttcaagcga ttctcctgcc tcagcctccc  36060
aagtagctga gactacaggc actcgccacc acgcccagct aatttttgta tttttagtag  36120
agacgaggtt tcaccatctt ggccaggctg gtcttgaact cctgacctcg tgatccgccc  36180
gcctcggcct ctcaaagtgc tgggattaca ggcgtgagcc accatgtccg gcctatagga  36240
aagggtagta atttttgggt ccttgggtca ttgccctgga aaggggtggt aactcctagg  36300
tgttgctacg gtaatggtaa actgacatgg cacactagtg ggagtgtctt atggaaagct  36360
gcttccaccc ctttcctgtt ttagctagtc ctcaattgga tcctgtgtcc aagccccgcc  36420
tctggagtca aggcctgcct cccacctcac tgggatgctg gtagcatggc ttggtccaag  36480
cccaaaaacc tcagaaccaa gaagaaggtg gtgtaactct cagttcgagg ccaaaggctg  36540
agaacccact agggggggaca agggtgctgg tgtgagtctt ggagtacaaa ggccaaggag  36600
cctagagttg ttgtcccagg acaggagagg aagagtgtat tccagttcca gcagatagat  36660
tgacatattc gcctcttgtc tgtttttgtt ctttctgaat ccacagcaag ttggatgatg  36720
cctctccaca ttgagagtgg atcttcccac atagttcact cagacttaca tgctaatctc  36780
ccctggaaac actcacagac acacccaaaa ataatgcttt accaggtttc tattcagtca  36840
agttggcacc ttaaattaac catcgcactg actttttaaa ctttctattt tgaaataatg  36900
aaaattcaca ggtagttgca cataaaggaa cagggaggcc tcctgcaccc tttacccagt  36960
ctccaccaat gttagcatct tgcgtaactg gagtacaata tcaaaaccag gaaactgaca  37020
ttggcatgat gcatggaacc tatgcaggtt tcatcagtta tacatgcact catttttgta  37080
catatatgta tagctctatg cggtttttgc cacatgtata gctttgtgta accacattcg  37140
agatacttaa aaccactatt atcaaaagac actcttattg ccaccctttt agccacagtc  37200
acctcagacc ctcaagccta actcttggca atcacaatct gttttccacc tctctgttag  37260
ttcatggtat tacgtaaatg gcgtcatgca atgtatgttc atccttttga gattggcttt  37320
tttcactcag gataatttcc ttgatgttca tccaagttgt gtgtgccttt ttattgctga  37380
gtagtattcc atggtatgga catgctacaa tatatttaac catacatcca tcaaaggaca  37440
ttggggtagt ttctagtttt tcaaacatta ttattattat tattattatt attttgagat  37500
ggagtctcat tctgttgccc aggctggagt gcagtggcac gatcttggct cactgcaacc  37560
tccacctctg ggttcaagc gattctcctg cctcagcctc ctgagtagct gggattacaa  37620
gcatgcatca ccaggcccgg ctaattttta tatttttagt agagacaggg tttcaccatg  37680
ttgacccggc tggtctcaaa ttcctgacct caggtgatcc acctgcctcg gcctcccaaa  37740
gtgctgggat tacagacatg agccaccaca cctggcctga ttttttaaat agcaaatttt  37800
gaaagttatt tacatattat aggaataagt cctttgcctg ctatgcgcct tgcatgtatt  37860
tttctcccag tctataattt gtcttttcat cctcagggtc tttgacagag taaaatattt  37920
ttatttggat gacatccaat atatcaatga tgaaactgtt ctatatcttg actctatcaa  37980
tgtcaatatc cttgttgtga tactgtacca tatagttttg cactatgcta ccactggggg  38040
aatctggtaa ggagtttaca ggatctctct gtattatttc ctacatgcat gtgaatatac  38100
```

-continued

```
aattatctca aaataaaaag cttaaaaaaa acaacatgcc taaatacaaa ttcattatta  38160
actggttcca gttaatctca gtttgaggaa caaccattct tctagacacc caggttaaaa  38220
acctgaggtc atcttttact tcattccttc tctttcctcc tatccccctc cctacatatc  38280
tttttttggt tttttgtttg tttgtttgtt taaagacaga gtcactctct tgcccaggct  38340
atggtctatg gaggtgatct taaagctaca agtcttatgt ctcaatctct gtatgagcta  38400
ctgccatatt tcaggcactt gtgatttgca acttgcatta ctaatgcaaa aatacgccca  38460
tatcactttc tagcttaatg gcttccgtga tttgccattc ttgcataatg ggctggagct  38520
ttatatagag catacaaggc ttttcatgat ccagcccatg aactgctcag gttatattag  38580
ttatagtttc aaatgtttgg agattttcca gttatctttc tgttattaat ttttaatttg  38640
atcccattat gtccagagaa tatactctat catttcaatt cttttaaatt tgttaaggtt  38700
tttttaaatc aaggtgaata ttttatggac atttgaaaag aatgtgtatt gcactgttat  38760
tgggcaaagt gttctataaa tatgttaggt cccgttggtt gatggtgttc agttcttcta  38820
catcctgatg attttctctc tagtagttct atcagttgct aagggtgggg tgttgaaatc  38880
cccaactcta attgtggatt tgtctatttc tctttttaac tctgtttttg cttcatatat  38940
tttgaagctc tggtgtttgg cacatacaca ttaaagattg ctatatattt ttggtggatt  39000
gatttattga tttttttttt ttttttgaga cagggtctca ctctgtcacc caggctggag  39060
tgcagcacac tgctgagtgt gatctcagtt cactgcaact tccatctcct aggctcaagc  39120
aatcctccca cctcagtctc ccaagtggct gggactatag gcacgcacca ctgtgcccag  39180
ctgatttttg tatttttttt agtagagatg gggtttcatc atattgccca ggctggtctc  39240
gaattcctgg gctcaagcga tccgcccacg ttggcctccc aaagtactga gattacagaa  39300
gtgagatctc tttattatta tataatgtcc ctctttgtcc ctagtaattt tctttctctg  39360
aacttacttt atctgatatt aacatactca gtactgcttt cttaaaatta gtgtttgcat  39420
gatgtattac cttttatcct ttcactttca gcctacctgt ctcattatgt ttgaaggaac  39480
atatacttgc agacagcaga tacagacagt ctctgactta caatggtttg acttaaatga  39540
tttttttttt ttttttgaga cggagtctcg ctctgtcgcc caggctggag tgcagtggcg  39600
caatctcggc tcactgcaag ctccgcctcc cgggttcacg ccattctcct gcctcagcct  39660
cccgagtagc tgggactata ggcgcccgcc accatgccca gctaattttt tgtagtttta  39720
gtagagacgg ggtttcacta tgttagccag gatggtctct atctcctgac ctcgtgatct  39780
gcccacctcg gcctcccaaa gtgctgggat tagaggcgtg agtcaccgcg cccggcatga  39840
tttttttttt tttaacctta tgatggttca aaagcaatat acattcagta gaaatcatac  39900
tttaagtacc catacaacca tttctattgt tcactttcag taccgtattc aacagataac  39960
atgacatatt caatacttta tcataaaata ggctttatgt taggtaattt tgcccaacta  40020
taggctaatg taagtgttct gagcacattt aagttaggcc tggctaagct ataatgtttg  40080
acaggttaga tgtattaaat gtatttttga ctttgaatgt ttttcaactt accatggatt  40140
tattgggaac ataacctcat cataagtcaa gaagcatctg tacgtctgtt ttttatgtatt  40200
gtgttgtttc tttctttccc tccctccttg ttcccttccc ttctctcctc ctcctcttcc  40260
ccctcccatt ccctcctctc ccctcccctc cccttccctt cccttccttc taccttcttt  40320
ccctttctta ggtcccagcc tccttctgtt aatttatttc tgtatggaga gcttccttta  40380
gccattcttt aagggtaggt ctcaacaaac tgtttctctt catctgagaa tgtcttcatt  40440
```

-continued

```
tttccctta ttcctgaagg ccaatttcac ctgataacag gattcaaggt tgacggtttt  40500
gttttcagca cttgataagt gttggaccac ttctagatgg cccccatcat ttcttttaca  40560
ggtagtgcaa aaatacagtt tgaattagca ttccttcctg gttgtttctc cctgactgtt  40620
ttaaagattt ctttttcttt aatctccagt ttttagaagg ttaattatga tgtgtcagta  40680
tggctttgga ctgttttctc tatttggagc tcaatcaact tcttgaatct gtaggtgttt  40740
gtcttccacc ggatttggga agttttcagc cattatttct ccgaatacgt tttagtctca  40800
cactttctcc tctcctgcaa agactctgat gatacaaatg tcagtagctc tatcacagga  40860
tccttagggt gtcacttcac cagccagaaa cctctgtggc tagtggcatc ttctgcctga  40920
gtattgcttg tgcccgctgg gcttgttctg cccactcagc ccagcaggct gcgctcagct  40980
cacactacag gcccagatcc cacacttgcc aggggtgagc caggcatgga gtggcaaggc  41040
gtgtgtgggc aagtgagcgc agggtctggc cactatgcac agccaggcat gctggctgct  41100
gtggtggggt ggggagctca ggtgctggca caggtgccag ctccatgcaa ggctgtggct  41160
ggaccagatg tactgcacac ggcttccact gcaggcatcc acgcctggat gaggggaacg  41220
cagtggcacc cggaagcttg gagacgccag aaatcgcaga gcccgaaaga gggtgtcaca  41280
gccctagctc agggagctgc agctcttctc tccttgtcac ccacaacatg gagagtgggg  41340
gtggcggcag gggggtgttt cagccctatt tgtgttacgg ctcttttagc cctgccattt  41400
gaagaggagg aaaaaatgat tctataccgt cttgttctga aaccataagc ctgatgttta  41460
aaggaagtag tggttggtgg ctgtattcaa agggcaggaa aaatggagta agaaactgat  41520
cagtggctgg gcactgtggc ccatacctgt aatcccagca ctttgggagg ccaaggcagg  41580
tggattgctt gaggtcagga gttcaagacc agcctgacca acatggtgaa accccgtctg  41640
tactaaaaat aaaaaaaatt agccaggcat ggtggtgggt gcctgtagtc ctagctactc  41700
aggaggctga ggcaggagaa tcgcttgaac ctgggaggca gaggttgcag tcagacgaaa  41760
tcatgccatt gcactctagc ctgggcgaca gacactccgt ctcaaaaaaa tagaaagaaa  41820
gaaagaaaga aatcgatcaa tattaactcc accaaataga gaaatgctgc tcattggttc  41880
ttaactatct gattaaaaat gggctttgtg catatgctga actctgcagt tattaaagaa  41940
atcatgaagt gttattgttt ggatgcatag tcctgtgatt ggtagcataa atgatgtgat  42000
actgggtaag tggatacaaa atttgattgg ccacatgttt taaagcatgt atttgaacat  42060
acaattggct aatatatctg agcactgcct gtaaatgaca gatggttcta actttcttga  42120
acccatcttc cacagggagt gaagtggata gcagggaagg ttacaaatca gtggattgag  42180
aatggcaaac aggaataact cactactgat tctgcccagc tgctactgaa cactgtcctg  42240
aaagagccaa agacattact aattgatcac agcactctcc tgttgagttt agttgatcac  42300
aataagagtg ctgtgatcac aataagagag tgctgtgatc aattagtaat gtcttccacc  42360
ggttcaggaa tgggcgttgg ctgcacatat gccacctatt taacacttcc gacctagaaa  42420
attcctctag agagcacatc ctctctggct gtagatacag gcagccaact tatctgtttg  42480
aagacccaag gattaaaaaa ggtccatctt gaggggtttg taataaggag atttattagt  42540
gttgggccca gagtaatgga tggagttttt ccaacatttt gcccaggggc tcagaacata  42600
tggactgcta gttgagatgg ggcttggaat tacatttaca cacattccac caataaatat  42660
ttgaacacag gtgcattttt taacaatagt tttctgcatg aactgcaaaa atgccttcca  42720
aatgacctct gtctctgggg tcctaccctt cctactccca taaatctggt agccaacaaa  42780
cagctgtaga cacagcttgt cttggggatt aggggctgcc ttgacaggaa ataaagcaag  42840
```

-continued

```
gatcactttt tttttttttt tgagacaggg tctcactttg ttgctcaggc tggagtgcag  42900
tggtgcaatc agagatcact gcagcctcca tctacctggg ctcaagcaat tctcccacct  42960
cagcttcccg agtagctggg accacagggg cacaccacca tgaccagcta attttttttt  43020
ttatacttta agttctaggg tacatgtgca caacgtggag gtttgttaca aaggtataca  43080
tgtgtcatgt tggtgtgctg cacccgttaa ctcgtcattt acattaggta tatctcctaa  43140
tgctatccct cctccctccc cccaccccac gacaggccct ggtgtgtgat gttccccacc  43200
ctgtgtccaa gtgttctcat tgttcaattc ccacctatga gtgagaacat gcagtgtttg  43260
gttttctgtc cttgcgatag tttgctcaga atgatggttt ccagcttcat ccatttccct  43320
acaaaggata tgaactcatc ctttttttacg gctgcatagt attccatggt gtaaatgtgt  43380
cacattttct taatccagtc tatcattgat ggacatttgg gttgttccaa gtctttgcta  43440
ctgtgaatag tgccgcaata aacatatgtg tgcatgtgtc tttataccag catgatttat  43500
aatcctttgg gtacatgccc agtgatggga tggctgggta aaatggtatt tctagttcta  43560
gatccttgag gaatcgccac actgtcttcc acaatggtgg aactagttta cagtcccacc  43620
aacagtgtaa aagtgttcct atttctccac atcctctcca gcacctgttg ttttctgact  43680
ttttaatgat cgccattcta actggtgtga gatggtatct catagtggtt ttgatgtgca  43740
tttctctgat ggccagtgat ggtgagcatt ttttcatgtg tctgttggct gcataaatgt  43800
cttcttctga gaagtgtctg tttatatcct ttgcccactt tttgatgggg ctgtttgatt  43860
tttgcttgta aatttaagtt ctttgtagat tttggatatt agcccattgt cagatgagta  43920
gattgcaaaa atttctccc attctgtagg ttgcctgttc actctgacgg tagtttcttt  43980
tgctgtgcag aagctcttta gtttaattag atcccatttg tcaattttgg cttttgttgc  44040
cattgctttt ggtgttttag tcatgaagtc ctcgcccgtg cctatggcct gaatggtatt  44100
gcctaggttt tcttctgggg tttttatcgt tttaagtcta acatttaagt ctttaatcca  44160
tcttcaatta atttttgtgt aagatataag gaagggatcc agtttcagct ttctacatat  44220
ggctagccag ttttcccagc accatttatt aaatagggaa tcatttcccc atttcttgtt  44280
tttgtcaggt ttctcaaaga tcagatggtt ttaggtgtgt gatattattt ccgggggctc  44340
tattctgttc cattggtcta tatctctgtt ttggtaccag taccattttg ttttggttac  44400
tgtaggcttg tagtatagtt tgaagtcagg tagcatgatg cctccagttt tgttcttttg  44460
gcttaggatt gtcttggcaa tgcgggctct tttttggttc catatgaact ttaaagtagt  44520
tttttccaat tctgtgaaga aagtcattgg tagcttgatg gggatggcat tgaatctata  44580
aattaccttg ggcagtatgg ccattttcac aatattgatt cttcctatcc atgagcatgg  44640
aatgttcttc catttgtttg tgtcctcttt tatttcgttg agcagtggtt tgtagttctc  44700
cttgaagagg tccttcacat cccttgtaag ttggattcct aggtatttta ttctctttga  44760
agcaattgtg aatgggagtt cactcatgat ttggctcttt gtttgtctgt tattggtgta  44820
taggaatgct tgcgattttt gcacattgat tttgtatcct gagactttgc tgaagttgct  44880
tatcagctta aggagatttt gggctgagat gatggggttt tctacatata caatcatgtt  44940
atctgcaaac agggacaatt tgacttcgtc ttttcctaat tgaataccct ctatttcttt  45000
ctcttgcctg actgccctgg ccagaacttc caacactacg ttgaatagga atagtgagag  45060
agagcatccc tgtcttgtgc cagttttcaa agggaatgct tccagttttt gcccattcag  45120
tatgatactg gctgtgggtt tatcatatat agctcttatt attttgagat acgtcccatc  45180
```

-continued

```
aatacctagt ttattgagag tttttagcat gaagggctgt tgaattttgt cgaaggcctt  45240
ttctgcatct attgagataa tcatgtggtt tttgtctttg gttctgttta tatgatggat  45300
tacgtttatt gatttgcata ggttgaacca gccttgcatc ccagagatga agccaacttg  45360
atcatgatag gtaagctttt tgatgtgctg ctggatttgg tttgccggta ttttattgag  45420
gatttttgca tcaatgttca tcagggatat tggtctaaaa ttctcttttt ttgtcgtgtc  45480
tctgtcaggc tttgatatca ggatgttggc ctcataaaat gaattaggga ggattctctc  45540
tttttctatt gattggaata gtttcagaag gaacggtacc agctcctctt tgtacctctg  45600
gtagaattcg gctgtgaatc tgtctggtcc tggacttttt ttggttggta ggctattaat  45660
tattgcctca atttcagaac ttgttattgg tctattcagg gattcaactt cttcctgttt  45720
tagtcttggg agggtgtatg tgtccaggaa tttatccatt tcttctaggt cttctagttt  45780
atttgcatag aggtgtttat agtattctct gatggtagtt tgtatttctg tgggatcagt  45840
ggtgatatcc cctttatcat tttttattgc gtctatttga ttcttctctc ttttcttcat  45900
tagtcttgct agcggtctat caattttgtt gatcttttca aaaaaccagc tcctggattc  45960
attgattttt tgaagggttt tttgtgtctc tatctccttc aattctgctc tgatcttagt  46020
tatctcttgc cttctgctag cttttgaatg tgtttgctct tgcttctcta gttcttttaa  46080
ttgtgatgtt agggtgtcaa ttttagatct ttcctgcttt ctcttgtggg catttagtgc  46140
tataaatttc cctctacaca ctgctttaaa tgtgtcccag agattctggt atgttgtgtc  46200
tttgttctca ttggtttcaa agaacatctt tatttctgcc ttcatttcgt tatgtaccca  46260
gtagtcattc aggatcaggt tgttcagttt ccatgtagtt gagcagtttt gagagagttt  46320
cttaatcctg agttctagtt tgattgcact gtggtctgag agacagtttg ttataatttc  46380
tgttctttta catttgctga ggagtgcttt acttccaact atgtggtcaa ttttggaata  46440
ggtgtgatgt gctgctgaga agaatgtata ttctgttgat ttagggtgca gagttctgta  46500
gatgtctatt aggtccgctt ggtgcagagc tgagttcaat tcctggatat ccttgttaac  46560
ttttttgtct cattgatctg tctaatgttg acagtggggg gttaaagtct cccattatta  46620
ttgtgtggga gtctaagtct ctttgtaggt ctctaaggac ttgctttatg aatctgggtg  46680
ctcctgtact gggagcatat atatttagga tagttagctc ttcttgttga tcactttacc  46740
attacgtaat ggcctttttt gtctcttttg atctttgttg gtttaaagtc tattttatca  46800
gagactagaa ttgcaacccc cgcttttttt ttgttttcca tttgcttggt agatcttcct  46860
ccatcccttt attttgagcc tatgtgtgtc tctgcacgtg agatgggtct cctgaataca  46920
gcacactgat gggttttgac tctatccaat ttgccagtct gtgtctttta attggagcat  46980
ttagcccatt tacttttaag gttaatattg ttatgtgtga atttgatcct gtcatcatga  47040
tgttagctgg ttattttgct cgttagttga tgcagtttct tcctagcatt gatggtcttt  47100
acaatttggc atgtttttgc agtggctggt accagttgtt cctttccagg tttagtgctt  47160
ccttcaggag ctcttgtaag gcaggcctgg tgatgacaaa atctcttagc atttgtttgt  47220
ctgtaaagga ttttatttct ccttcactta tgaagtttag tttggctgga tatgaaattc  47280
tgggttgaaa attctttcct ttaagaatgt tgaatattgg ctcccactct cttctggctt  47340
gtagagtttc tgccaagaga tccgctgtta gtctgatggg cttccctttg tgggtaaccc  47400
aacctttctc tctggctgcc cttaacattt tctccttcat ttcaactttg gtgaatctga  47460
taattatgtg tcttggggtt gctcttctcg aggagtatct ttgtggcatt ctctgtattt  47520
cctgaatttg aatgttggcc tgccttgctc gattggggaa gttctcccgc ataatatcct  47580
```

-continued

```
gaagagtgtt ttccaacttg gttccattct ccccatcact ttcgggtaca ccaatcagac  47640
gtaggtttgg tcttttcaca tagtcccata tttcttggag gctttgttca tttcttttta  47700
ctctttttc tctaaacttc ttttctcgct tcatttcctt catttgatct tcaatcactg  47760
ataccctttc tcccacttga tcaaatcagc tactgaagct tgtgcatgcg tcatgtagtt  47820
ctcatgccat ggttttcagc tccatcaggt catttaagga cttctctaca ctgtttattc  47880
tagttaccca ttcgtctaat cttttttcaa ggtttttagc tgctttgcga tgggtttgaa  47940
catcctcctt tagctcggag aagtctgtta ttaccgatca tctgaagcct tcttctctca  48000
actcatcgaa gtcattctct gtccagcttt gttccattgc tggcgaggag ctgcattcct  48060
ttggaggaga agaggcgctc tgatttttag aattttcagc ttttctgctc tggtttctcc  48120
ccatctttgt ggttttatct acctttggtc tttgatgatg gtgacgtaca ggtggggttt  48180
tggtgtggat gtcctttctg tttcttagtt ttccttctaa cagtcaggac cctcagctgc  48240
aggtctgttg gagtttgctg gaggtccact ccagaccctg tttgcctggg tatcaccagc  48300
ggaggctgca gaacagcaaa tattgcagaa cagcaaatga tgccatctga tccttcttct  48360
ggaagctttg tctcagaggg gcacccagct gtatgaggtg tcagtcggcc cctactggga  48420
ggtgtctccc agttaggcta ctcgggggtc agggacccac ttgaggaggc agtctgtccg  48480
ttctcagatc tcaaactcca tgctgggaga agcactactc tcttcaaagc tgtcagacag  48540
ggacgtttaa gtctgcagaa gtttctgctg ccttttgttc agctatgccc tgcccctgga  48600
ggtggagtct acagaggcag gcaggcctcc ttgagctgca gtgggctcca cccagttcca  48660
gcttccaggc tgctttgttt acctactcaa gcctcagcaa ttgtggacgc ccctccccca  48720
gcctcgctgc tgccttgcag ttctatctca gactgctgtg ctagcagtga gcgaggctca  48780
atgggcatgg gaccctctga gccaggcacg ggatataaac tcctggtgtg ccgtttgcta  48840
aggctgttgg aaaagtgcag tattagggtg ggagtgtccc gattttccag gtaccgtctg  48900
tcacggcttc cctttgctag gaaagggaat tccctgacct cttgcacttc cagggtgagg  48960
tgacgccctg ccctgctcca tgggctgcag ccactgtctg acaagcccca gtgagatgaa  49020
cctggtagct cagctggaaa tgcagaaatc acccatcttc tgcatcgctc atgctggcag  49080
ctgcagactg gagctattcc tatttggcca tcttggaacc taccccccca actaattttt  49140
aaatttttat tttattgttt ttatttattt aagacacagt cttgctctgt tgcccaggct  49200
ggagtgcagt ggcatgatct tggttcactg caacctctgc ctcccaggtt caagcaattc  49260
ttgtgcctca gcctctcgag tagctgggat tataggcgtg tgccaccatg cctggctaat  49320
ttttgtattt ttagtagaga cagggtttca ccatattggc cagactggtc tcaaactcct  49380
ggcctcaagt gatctgccta cttcagcctc ccaaagtgct gggattacaa gcgtgagcca  49440
atgctgctgg ctctaatttt atgtttaata gagacaaggt cttgctatgt tgcccaggct  49500
ggtcttgaac tcctgagccc aagtgatcct cctgcctcgg cctcccaaag tgctgggatt  49560
acaggcgtga gtcaccacac ttggctaagg atcacttttt aatactctgc ttcataatac  49620
atgtaaagag aattaccatc atttaatctg acaattgtgt aaaaatatta tgtaagcagc  49680
agaaaatgcc tgtggagtgg tataaaatgc agaaagaaca tcattgggtg cccaaccact  49740
gtgttcccac actggaggga aaaccaccta catggggctt tgagacttga ttaggatgtc  49800
caccatgatg cctcctgagg ggatcttcaa aagtaatttt taacgtatgt gggtttgttt  49860
tgcttttgcc tgtgagcaga cttcagatcc cagctctcct gcataacaac tttttttttg  49920
```

-continued

```
agacagagtc tcatttgtca cccaggctgg agtgcagtgg cacggtctcg gctcactgca  49980
acctctgcct cccaggttta agtgattctc ctgcctcagc ctcccaagta gctgggatta  50040
caggcacccg ccaccatgcc cagctaattt tttttttttt tttttttttt tttttagtag  50100
agacggggtt tcaccatttt ggccaggctg gtctcaaact cctgacctca agtgatccac  50160
tgcctcagcc tcccaaagtg ctaggattac aggcattatc ctgcataaca actttgcatg  50220
tgctggtcac acttcagggg cagctgccct ccctggcctg gctctctgta gatcagctca  50280
agaccaattt cacttgataa gaatccaata ctctctaagt gtaaagaagt ccccatcttt  50340
ttactagaaa gttctgaaga atgtgatcct gttacgtgga cctaccagtt catgagctag  50400
agcgttgcaa aggtatcctt gtgtagaagg taaaatggaa atttctaaat gggtggcaaa  50460
ccttctccct ggtgcttcac cttcaacttg gcctcctttt cctttcatga gtaaaagaag  50520
ttgaaaatgt acacgtgtat gtagcctctt ttcagtctta gaagttatgg tcacacttca  50580
tattataaat tctagctgta aacacattca tcatttataa gtgaattata ttagtgagta  50640
gcctcgatta tgggaccaca aaagaatgag gcagtatagt atagtggtta acgatcatct  50700
ctggtatttg ggcgatttag gctcaaatac catagctctg catttttaa tttttaaaat  50760
tttttgaggc agggtctcac tctgtcaccc aggctggagt gcagtggtgt aatcatggct  50820
cactgcagcc tcaacctcct cgttcatccc acctcagcct cctgagtagc tgggactaca  50880
agaacacacc accatgcccg gctagttttt gtatttttg tagaaatggg gttttgacac  50940
attgcccaga ctggtctcga actcctgaac tcaagcaatc cacccacctt ggcctcccaa  51000
agtgctagga ttataggcat gcactacagt gcctggcctg caattttttt tttaaatctg  51060
tgcaagcttg ggcacattat ttaaactgtc taagctttat tttttttctc gtttgtacaa  51120
tgagatgata agaatcctac cttattggct tggtgtattt atcagggtaa tgtatgtaaa  51180
ggccttagca tagcatccag cacagaataa agactgttgc tggctattaa taataaaaaa  51240
aaattctctg agcacctaag atatatcatg aatcctgggt gataatcatt tttgctcaga  51300
gacaacccat taggcccaca ctctgggtct acatactttt attcttgaca gaaatggttt  51360
acagtgacgt agccatagtt ttgacaggga gagtcatctg gtttcccaag atctagcaca  51420
atgggaaccc ctatgatctc atggcaggga ctggctagga ccaaggcaac tgtcagtaac  51480
aaaagggaca atggatggaa tagaacaaat caaacaaagc atgggctcga tgttaggaat  51540
ctgagggtat ttagaaaggg gaaaggcaac cttacattcc tcgagtccct gaaggcacca  51600
ctgcagtaca ggatagtaca gtaattcatg ttgatggtga agtgtgcctc agccttccag  51660
agaaaattta cgtatattca ctattttaaa ataggcagag aacccgtttt ctattaccag  51720
gcaagcactt caaaaaaaag gttaagatca acgttttagt gcttgaagac aggggaactt  51780
cagttacatg taaaatcccc ttggataaaa caagttagct tccaaaaaaa ctactaagcg  51840
tcactatgtt taaaaagctt aaacattctg cgaatcagta ctgtataaat taaccactac  51900
cacccacaaa agacagtggc tacttaactt tggtacaaag aatcagggtc agcttgcctg  51960
tgatacttta ataaatgaaa tgtgttgttt tctgatatgc cccttttcaaa tcatgatcca  52020
aagaggtgca gtgaaaaaca acagacaaaa accaacaaca aacaagactt cccacttata  52080
ctcttctcga tgatggaatt tgtggagaat tctctccctc tctgcgcttg agattccttg  52140
atggtaaaat gagggagtct ggactagatg atcttcaagg tcccgtccag cttggatgtt  52200
ctgggataaa gttacctgac ccaactaaca ggtacccagt gagtgtcctt gctcagcttc  52260
tctaagacca ctttgagctg gctgtaggca ccctggagat cctccttcac cagcacggcg  52320
```

-continued

```
tctaccaggt gcccgtaatg ccggtctatg aaggcggcag aagcggccat ctcttgctgc  52380
tgctcatcct gcaaggaaag gggtggtaaa aggagcaact gggttgttct cctataacaa  52440
acctataacc tttgtcttga gcaatgttcc aacctttaac ttttaagtga tgagtggatg  52500
actaggtccc actgataacc aactgtgtac acaagaacag agcataggga caacatcatg  52560
tcaaacttca aagaaagtta atgggcagta gacacaatca ctgttcagtc attcactcac  52620
agaatacctc ctgaggacct atgaactcaa agccacgata ggaagtgcat tggggatgct  52680
gattctataa ctgtgtatat atgctaatat cacacttcct gcctcagaag tacttccaaa  52740
gaagtagtag tattgtgccg catgacattc agtacacagg ttaaataatt ataagaaaga  52800
actataaata ataactatat aaaaacagag caaacatttc tgcaatcaac tggtggaaga  52860
aggagaagaa atcattctaa tgccctcctg aagactccta aattcacagt gcagaactca  52920
attcacttcc tcacaccaga gccaaacact agcacagcaa agtggagtta tttaagaaag  52980
cactggacaa ttctaatcaa attccccatt tccttagggc agctgatctc tttaatcaga  53040
ttgcttttct gacacttaac attaaggtat aggcaacaac tccatcttac acaatgtggg  53100
cactgtttgc atcttcattc aaaagaacct ctaataagta ttatttcaag tgagtagttg  53160
tctgacaatt agcctggttt tggaaaacag gaaagtggca ggcccattct aagtaaaatt  53220
acaaaataaa atttgtcgct ggcattcact cactgccctt tttagttctc tgttgctgtc  53280
tcccctctgc ttctaggggc tcagtgtttt catgctgcca cagggaaagg gtgagttctg  53340
ttctctccca aagagaccta cattccaaat attcccccct cttctctgtc accagtcaaa  53400
acccaattcc tacattagtg agagcatctg aaatttcagg attcgagtcc tcaagatcca  53460
ggaaaagggt ttggcatgct acttcaaaga tagtagaaat gtaagagaag gctgagataa  53520
tttcttctcc ttttctcctc caggagggaa aaaattcgat taaattggga gacacttctc  53580
aattctatat tctatataga atattcttgc agggctactt tcatactcag aagccctatc  53640
ccgtaactgc ccccggatct tcaaccccac cttccccact ccctgacaca cacccatcct  53700
atagacctgt ctgctgcttc cagtttcccc tcctccaggc acccacacgg ttcatcctgg  53760
aagcatttgg ctatttgaga aattacagaa ggaaaatttt tgccacaaag aaccacaatc  53820
tacctaataa atatctgcat ctggaaagaa cttaagtaaa tctctaatgg agtaaaaacg  53880
tgtgacattt gcttagcagt cataaatccc ctgaactcct ttcctggcct gtaacgatgg  53940
aactcgccca cctgtgtctt cagcaagagt cacagtcccg aagatcacat aggaaagatt  54000
cccctgtgct gtccgtcacc cccaggttgg atcagctttg ccgggtcaga agccagaagc  54060
cccattaact tgtggtcagc aaggaaacag aggatgtttt gggtccccta ccaggaactc  54120
aggtgccaga caatggacag atatttaaag ttacacaaaa cccatgcctt tgtgaggaat  54180
ttctccaaat gtcatctggg gtctgccaac atacatcaaa accacatgaa aggctgtgtg  54240
ttaaaaatgg agtgcctggg ccccactcca aaccccctag gtcggaatct ctgggagtag  54300
aaccggggac tctgtgttga acagcctcac tgtgaccctg ctgcctactc acagctgcag  54360
tgtggtggag catgaacggg ccagctgcat ttcatcatca gcccacctgc ttggaatgca  54420
gcattctggt gggcaataaa ggagatggga tagatgacaa aaccggccag gctggaagga  54480
cactgggaat agaatgcagc tgcttctctt gaaataacaa ccatgggcca gggagggttc  54540
tgaatcctag aaagctggca ctgcctgtgg acctgatgat ttggccttga gtcctaggaa  54600
gctgcctctt attctcccag tgacttcttg actctttgaa aaatgagcca tttcccccctg  54660
```

-continued

```
cttattcaat cctgaaatat ttgcaaaaca aaacaaagcc aatatagtaa aacaaatggg  54720
cagattgatc ctaaaattca tatggaaatg taaaggaccc agaatagcca aaacaagctt  54780
gaaaaacctg acttcaaaac ttactacaaa gctagtaatc aaagtaagac agtgtggtgc  54840
tggcctaaga atagacatgt agaccaatgg aatgggactg agactccaga aagaaaccct  54900
tacttttctt gccaattgat tctagacaag ggtgttaaaa taattaaatg agaaaatagt  54960
cttttcaacc agtgatgctg gggtaactgg ctatccacat gcaaagaatg aagttggacc  55020
cctacttcag acaatccaca gaaaataaca caaaatagat gacagatcca aatgtaactg  55080
ctacaactat aaatatctta aaagaaaaca aaggagtaaa tctttatggc cttggattcg  55140
acaatgattt cttagatatg acaccaaaaa tataaatgac aaaagaaaaa atagatacat  55200
tggactttat cacattttaa aatgttatgc ctcaaaggat gctatcaaga aagtaaggac  55260
caggcgtggt gcctcccagc actttgggag gccgaggcag gtggatcacc caggtcagga  55320
gttcgagacc agcctggcca acgtggtaaa accccatctc tactaaaaat acgaaggaaa  55380
ttagccgagc atgatggcat gcgcctgtaa tcccagctac ttggaggttg aggcaggaga  55440
atcactcgaa cctgggagct ggaggttgca gtgagccaac accgcaccat tgcgctccag  55500
cctgggcaac aagaacgaaa ctctgtctca aaaaaaaaga aagtgaaaag acaactcaga  55560
atgggaaaaa atatttgcaa atcatgcatc tgacaaggga cttgtatcca aatagataaa  55620
gaattcttac aactcaataa caaaaaatgg acatttaaaa atggacaaag tatttgaaca  55680
gacatttctc caagaaagat ataaaaatgg ccaataaaca catgaaaaga tgctcaactt  55740
cactgatgat tagagaaatg caaattaaaa ccacaatgag ataccacttc acacctacta  55800
gtagtgctat gattaaaaag acagacaata acaagggctg gtgaggatgt ggagaaatgg  55860
gaactcttga acactgctgc tgggaatgta aaatggtaca gctgccatgg tagagttaaa  55920
catagaacta ccctatgacc cagcaattcc ataccaaggt atacacccaa gagaaatgaa  55980
aacatatgtt cacacaaaaa cttgtatatg aacattcata acatgattca taatagctga  56040
aaaggtagaa acaatctaaa tgtccattaa tcgataaatg ggtaaacaaa atgtggtact  56100
ctatacaatg gaatgttatt cagccataaa aaaagaatga agtattgata catgaatgaa  56160
ctttaaaaac attatattaa gtgaaaaaag ccagatacaa aaggtcttac attgcatgaa  56220
tccatttata tgaaatgttt agaatagaca aatttatagt gacagtagat tagcagttgc  56280
ctgtggctag gaaggggctg gaggaaaaca gataatggga aattctaatg ggctcaaggt  56340
ttctttttga agtgatgaaa atactcttaa attgactgtg gtagttgcaa caactctgtg  56400
aatacatcat tgaattgtat gctttaaatg tgtgaattgt acagtatgta aattttatct  56460
cagtaaagct gttaactccc cctccaaaaa acacacagaa aacaaaacaa aatttagtca  56520
tgagcccact attcagggag aattgccttt agcgttttag tgtattttgt gtgtaacaca  56580
aaattagaat cctgattttt tattttgatt tattttttct tgtatttagc tatgtcatca  56640
aatattcctc caacacatgg cttttattta tttatttaat taatttattt ttttgagaca  56700
gagtcttgct ctgtcgccca ggctgaagta cagtggtgca atctcagctc actgaaaact  56760
ctgcctccca ggttcaagtg attttcctgc ctcagcctcc cgagtagctg ggattacaga  56820
tgcctgccac cacgcccagc taatttttgt atttttagta gagacggggt ttcaccatgt  56880
tggccaggct gatctcgaac tcctgacctc tgatgatcca cccacctcag cctcccaaag  56940
tgctgggatt acaggcgtga gccaccactc ccggccccaa catatggctt ttaactggct  57000
ataatacttc aatacatcct gtaagtgtca cataatggag tatattgaac tgagtcctga  57060
```

-continued

```
cagtgaacat tatttaggtt gtctctgatt tttttgttat atgatgggca tactgtatgt  57120
ttcttttttt tgtttttgag atggagtttt gctcttgctg cccaggctat agtgcgatgg  57180
cgcaatctcg gctcattgca acctctgcct ccaagttcaa gcaattctcc tgcctcagcc  57240
tcccaaatag ctgggattac aggcgcgtgc caccacaccc agctaatttt ttgtatttag  57300
tagagatggg gtttcaccat gttggtcagg ttggtcttga actcctgacc tcaggtgatc  57360
cacccgcctt ggccctccaa agtgttggga ttacaggtgt gagccactgc acccagccaa  57420
tattgtatgt ttctaaatga ttctagactt aagttgatat tcccctattc cccttagagt  57480
ttcttgtgtc tttttttttt tagatggagt cttgctctgt cacccaggct agagtgcagt  57540
ggcgtgattt tggctcactg caggctctgc ctcctgggtt caagtgtttc tcctgtctca  57600
gcctcccgag tagctgggat tacaggcatg caccaccaca cctggctaat ttttgtattt  57660
ttagtatgag acggggtttc accatgttgg cctggctggt ctcgaattcc tgacgtcagg  57720
tgatctgcct gcctcagcct cccaaagtgc tgggattata ggcgtgagcc accatgccag  57780
cctccccctt agagtttcta aaggagaaaa tttttctttt ttctacattt tttttttttt  57840
gagacagagt ctcactgtgt catgcaggct ggaatgcagt ggcatggtca tggctcactg  57900
cagccttgac ctattaggct caagtgatcc tcccactccc acctcagtct cccgagtagc  57960
taggactata ggtttgtgcc accacacctg gctaattttt gtaatttttt tgtagagatg  58020
gggtttcacc aagttgccca ggctggtctt gaattcctgg gctcaagcaa tctgcccgcc  58080
tcagcctccc aaagtgctga gacacaggtg tgagccaccg tacctggcca aggagagaat  58140
ttctaatgtt ccttgtatgt atgccattct aaataattta ctgagaccag atacggtggc  58200
tcacacctgt aatcccaaca ctttgggaag ctgaggcagg aggatcattt gaggccagga  58260
gtttgagacc ggcctggcca acacagagac accctgtctc tataaaaaaa ttttttttaa  58320
ttggctgggc attgatggta catgcctgta gtctcagcta cctaggaagc tgaggaagga  58380
agactgcttg agcccaggag ttcaaggctg cagtgagcca tgattgtacc actgcactcc  58440
agtctgggca atacagcaag atcctgtccc caaaaaaata aaaggctggg cacagtggct  58500
tacacctgta atcccagcac tttgggaggc caaggtggga gaatcacttg agcccaggag  58560
ttcaagacca gcctggacaa catagtgagt ccctgtcttt aaaaaaataa taataaaata  58620
aaaagtgtat caacgtggac agttaaaact gagaattagt atgaactagg attgcatcaa  58680
aatcttgact cagcgggagc ttcctgacca aggggaagga tccgagaagg cctccttcag  58740
atgaaaccag ctatatagga cagcaagtaa agtctattct gggactgagt tgcttctgac  58800
tgcccccacc acccacaaca acttccaact cattctgcta actgaccctg ttaagaacca  58860
aaaaagatga gtcaccaagc ccacacctcc tggaagaact ctgtcaaata tttaggtttt  58920
gggtgagggt ctcgccatcc tgacatagac tgggctgaac aaagaatcta tgacagtgaa  58980
acagaagttc atttaggaca catcagacga tctcatccac tagttttaga aatcccttca  59040
ttcactgatg attcaaactg gtttgatagc agtgataatg accttgttag ttggggtttc  59100
aatttaaaat acttggattt ggcctaggag tatagtttga tgagtacagt ctgtcacact  59160
cagatgaggt ccctgacagg tgtcacattt tgcgggaggg cgcttatgtg agggagtgga  59220
ggggcgtgag cccaggcaaa gccacctgcc tggtttggga ggcacttcca gctgttcacc  59280
ttgagccttc tggccatgta atcatcttct cttaagtttt tcaataggca aaatggaaag  59340
acaatcacat gtagaaggtg tgtcccgcat ccctcttcag ctgcaagcac ccttatgcag  59400
```

-continued ctagaagcgt tcctgtaaca gcctccctta ggccttcaga aaagaaacaa tcaactttaa 59460
acttacaaat ggggctgctg tgtcctcaca agctggggac ataggtggcg tttttctttt 59520
ttcctgaatt gcaggcttta caaatataat atagggttta aattctgagg tcctcagttg 59580
tttcagtgcc tgagaaagaa agttcaggaa tattatatac ttttgaagtg ttttgttgtg 59640
aaatagactt ttgaaagctc aataatcgtg tgcttcaata ccataacctc aacagcaaag 59700
gtcctggtta catgggtccc atgacaatgg acttcaactg ggcagaccaa ctgctccttt 59760
tctcatcctt cactttgacg ttgaactcag cggggccctg aagtcacact cactgccaac 59820
agaaggttcc taagcctcag ctcagagaca gttgctgtct ctcttagctc tgactcctcc 59880
ggctataatt aaccttctca ggctcctctc caccttccat ttctgatggg tgaggaagca 59940
ggagtcagtg tgtatctatt tagtcaaatg tcatcaatcg gactacatta ttacaaactt 60000
tgtgctatta catctcctct tggtattcaa agaagaaaag gtttgcaaag caaatgagat 60060
tactgaacag atcatttaaa actgtagact gtagaaactg cactcttggg ccaggtgcgg 60120
tggctcacac ctgtaatccc agcactttgg gaggccgagc cgggtggatc acgaggtcag 60180
gagatcaaga ccatcctggc taacatggtg aaaccccgtc tctactaaaa atacaaaaaa 60240
ttagccaggc gtggtggcgg gcacctgtag tcccagctac tcgggaggct gaggcaagag 60300
aatggcgtga acccgggagg cggagcttgc ggtgaaccaa gatcgcacca ctgcactcca 60360
gcctgggtga cagagcaaga atctgtctca aaaaaaaaga aaaagaaatt gtactcttga 60420
ttaatgcatt ttatctagaa gtaagggctc cacttggaaa cactagtatt aaactgctat 60480
atgcattatc tgcacccttg atcaataaag tgatcaataa aatcactttt caaagaaaat 60540
tttgaaactc agacttttaa ttttgatcac taactccctg taagtccaaa tgagtgtttt 60600
cctttatagg cataacgtgc tttttggaat atatttcaag caaacttctt taaaataaag 60660
cctacagttt atagcataaa atcagagatc tgtttctata gaggggaaaa aaaatcccca 60720
gattgagttc aaagcttgga agtttttcta aaagacaagg ttaaaaagat ggttaagccc 60780
ctgctgagtc cacagcatgc tgggtgtgca ggagtggaaa tgtttttgaa gcacttccca 60840
gggccgtgtc tccctccctc tttttcccct ttaaactgct ctcctcactg cctccctgag 60900
tggttctcta agccactgac tccacctgcc ctggttgggg agggggaggc ctggcaccga 60960
gagctcagcc ccagtttcac ctgggtactg acatctaatt ctctggcaca ttgcaatggc 61020
cagtcagcgc caccaactat tgcatgatct gttccacgca ggagttacta gcctgggtct 61080
gtgggccacc agagtgtcca caagctccct acaattaatg cagcatttgt ggatagaggg 61140
gcatgttttg gggtacaagg ctttcatttg attctcaaag gaagacccaa agaaattgaa 61200
cagccagtgt tctagactaa aaattcctta gactgaggtt aagtgttgtg taaaatgtac 61260
aatcccctag ttataaattc cgttaaccag aaatggccag caggcccagc aactcacttc 61320
tggctccaca tccaccaaac aaactttgtt tttggccata acagcctgaa tggcctccag 61380
gctggttcca tacagatttt ccttatattc accatgttcc aggaacctaa aacaccacca 61440
aaggggaaaa ggcctttagt tcctcagctt tcctaaatta gcaaagcaaa ggggacctcc 61500
caacatgact tctctcccgc ttccccc atc ctttccggga gtcctcccag gagctctagt 61560
ggaatacaga tacaaaaaca cacaactgcc tggagggcca actggcccat caagcaacgt 61620
acttgttgtg atgtaagtcg gcctcaaatg cttgcttaga cacaaagtga tattccactc 61680
cttccttctc atggctcttt cggggcctgg tggtatcttt taaagaaaga aggaaagctg 61740
ggcaaagaga tgtcacatca cagcacgcag ggacagcagc aggcttaggc actcatttgg 61800

-continued

```
gagttcactg ctgctgtgtc taaaccaggc acttccacct cattgcatgt ccctgtatca  61860
ggcactgtgc ctttccaggc aggcgtatca ctgattcaca caacaactct ttgatgtagg  61920
caaaaggagg cttttccttt tgcagctgag aaaactgagg cacggagagg ttcagcactg  61980
tgcacagtga cccacaacca gtagagagca cagccagaat cggtctctct gccaaatgcc  62040
cagcttatac ccttaaccac tctgctaact gactccctga tgctgtgttt tttttttgtt  62100
tgttttgttt tgttttttgt tttgagacgg agttttgctc gttccccagg ctacagcgca  62160
atggcatgat ttcggctcac tgcaacctct gccttctcgg ttcaagcgat tctcctgcct  62220
cagcctcccg agtagctgga attacaggca tgtaccacca cacccggcta attttgtatt  62280
tttagtagag atggggtttc tccatgttgg tcaggctggt ctcgaactcc cgacctcagg  62340
tgatccaccc gcctcagcct cccaaagtgc tgggattaca gacatgagcc accgcgccca  62400
gcatatgctg tggcttttaa agaatcactt aagggacccc tagtcctaac ttttaattct  62460
tcattgtttt ttatttttg agagcaaagg agccacacat acacttgacc ctgatgtatg  62520
cttttaattc tttagtcaat tagttctcat ctccagaaaa aggagacagg aagacagacc  62580
gtccctatat agatcggatg tgtttcagca aggctggctc tcaaacaaaa atgttgaaac  62640
acatggtgtt ttctcattga tttccataac agaattggga tgcacacttc tgaggaaaat  62700
caggtcttct gcagaacaag ggcacacaca aagccacaca cacagtattt tccaaaagat  62760
aaaatgggat cttgaggcac tgtgtcttct ggcccatggg aaccacccag ggtatgccct  62820
gtgttctttc tgtggcatct tagtccaacc tccggtagag gtgctagggt cacttttcca  62880
accatgtcat ccccctgctt aaaaacttgt atttatctat gggttacatt ctaaacaccc  62940
tagctgagta tctgagacct gcgtgatctg cccaacctct cagctccatt ttccagcaca  63000
ccatccacac taatctcccc ggtccccaac actgctccgt ccctttgcac atgttgtttc  63060
ctctgtaaag agaactattc ctttctcttc tgcctggaaa actcctattt actcttcaga  63120
acccagcata aaagtcactg cctctgggaa ggcttccctg actcccccag tttctaaaac  63180
aaaggaggaa agtctcctat ctgtggagtg cctagaagca ggtgggcctg accatccagg  63240
tacctcttct ccagggggtg gatccaaggg gttctgaacg atcagtgtgt gagcaacctc  63300
tgcatgtcct gtttcagtcc acctgaaact tggaaggccg tggctccctg aagccctcca  63360
ggtccatcac aggtgtgctg ccaggatggc ctccccaggg ccaccacctc ccccacatcc  63420
ctgccacttc agattgggct gtggaagaca gctctgacaa cccacagact agacgctggg  63480
cccaggggcc cagggagagc ggtgtgatca aagcaaggct tcatggttgc tctgccccag  63540
aacactctga ggaggcccca ttagggcccc cacagcaccc ctctcagtag ccaccaggca  63600
ttcacactgc atccctctga ggccaggggg actgagagtg agtcccagaa agaaaagggg  63660
cagccaaggg cacgaagtgg gaggcggcag gtgagaggcc attgtgcatc ctcgttaaga  63720
acatgactgg ggcaggctgc ctgggtatga atcctggctc caccacttac caactgtgtg  63780
acattggaca agttacttaa cctctctgac cctcactgtc ttcctctgcc acacaagatg  63840
ataacaatct ctcttctcag ggtactgggg agggctgacg cagggcacta cacataaaag  63900
ctcttggtgc attacctggc accttcattc tcctcctcct catcctcctt atcacattca  63960
gaaccaggat cctctgccca ctggagcttg acatcccagg gtgcccctgg cagcagtaag  64020
ccccaggaat tggcagggga ggcatcaccc aggaatgtac ccagctaccc tgacaaactg  64080
gaatctggct ataagggagt gccgagaaat accactcaca gggctctgtg gcttctctga  64140
```

-continued

```
cctgccctct catccaagca gagggcagcg gccacaggag tcaaaattca ctgtgatgag  64200
gaggaatgcc ccctactgtg ggggccccgt ggtgtcaggt tgaggctgcc actttgccta  64260
caatgtgctc tggactcatc tcccacccca ggcaggaacc aagcaagtgg tcctccaact  64320
tctgcctcag agggtctcag aggaccactg ggagtggatt tcttcccatc atgcctttgt  64380
cccacaattt gccaatagca ggcagtgcct ggtgatcctt taaacccaaa gtaaggattt  64440
ggatggatct ggggagttaa gtctccatgg aatatttgtg tgtgtgcaga caaacacaca  64500
ctcccacatg ggccctctta cgtggaacag cgacgccaaa gtgctgtggg ttctcagcca  64560
ccaccttttg cttcagctcg tgcagtcggg ctcccagaga ccctgggaaa caagaagaag  64620
gctgaccagg gtccctgctg agctccctcc ccacctgctc cagggaggaa accagatcac  64680
ttcctggaaa cccaggatgg cacctaccga tcagaaccac caggcggggc cgctctccgg  64740
gctggtgttg gtacctggcc acctcttcgt aagtcagcag ctccggagac tcagctccgg  64800
aggacatctt tccttcctgc gagccaccca gtctctccct acagcccagc cggaagctcc  64860
tccgaagacc agcttgggag gaggggcaga gggacaccat ggcatttgtc ccagttgtcc  64920
caggatctcc cagtagagac ttttcccacc tggccagacc tggagatggg actgagtccc  64980
actgacttct cccaacctcc tcctgctact ggaagaggtt gttcaggaaa tacaataata  65040
agatgaaagg gtgacccctg cattcacaaa ctagggctta aggtcactgt tttacttggc  65100
atgtgactga ccttggacaa gtcccttcat ctctctgagc ctcaatttcc ttacctgtga  65160
aatgaagata tgaatctaca actactatgt gtggtcctag attagatcct ggaccaaggg  65220
aaaatgtcat aaaggacatg atggggacaa ttgttaacat ttaaataaca gcatataaca  65280
gatttggata cattttaaat tctcagaatt tgatcactgc cctgagaaag tccttggcct  65340
taggaaatac atgctgagag atttagggtt aaagggacac gatgtctaca actaagtctc  65400
atatgactca ggaaaaaaaa attcagagat gtgggaaagg aaattgagca aacatggcaa  65460
aggagcaact ggtgaatctg ggtgtggagt atatgagagt tctttgtata attcttacac  65520
cttttcagta agtttgaaat tacttcagga caaaagttaa ggggctgggt gcagtggctc  65580
atgcctgtat cccagcactt tggtaggcca aggcaggcag atcacttgat ctcaggagtt  65640
caagaccagc tgggcaacat ggtgaaaccc tgtctctaca aaaaatacaa aaattagcca  65700
ggtatagtgg catgcacctg tagtcccagc tactagggag gctgagaggg aagaatcgct  65760
tgagcctggg aggctgaggc tgcagcgatt tgtgatcaca ccactgcact ccagtgtggg  65820
taacagagca agaccatatc tcaaaaaata agtttaaaaa aagtttaaaa actttttaga  65880
aaggaggatt gcttgaagcc aggagcttga aaccagctgg gcaacatagc gagaccccat  65940
ctctacaaaa aaaatttttt taatcagctg ggcatggtgt cagatgcctg cagtcccagc  66000
tactcaggag gctgaggtgg gaggattgtt tgagcctagg acattgaggc tgctgcaagc  66060
tgcaatgtca cacactactg cactccagcg tgagagacag ggcaaaaccc tgtctctaaa  66120
aaataaccaa aaaacaaaaa aaactttttg cctatctcta agacctttga aaaaactgac  66180
caaaacaagt gaaaaggggc tctggagagc cgcaaacacc cctcactgcg tggtagtggt  66240
gttaatattg aataaactcc aattgcaatg atggtgataa tagaattggt attaatgtag  66300
gggtgtgtgt gcctttcccg ccagggcagt gtgccccaca gctgggtaaa agctgggtgg  66360
gggcccaatg cctgggcagg ctcagctcct gcttgggttg agagaactga ggagagatgg  66420
gggtcccata ggctccactg ctccagaagg actcctgggg ctcagatcac cctgctttga  66480
cctctcccta actctggggc cttgggtggg gcaggtcgtg catgtgggtg tcagggggag  66540
```

-continued

```
ctacttaccc acatagtgcc ctttgaggta gccctcacag tcacaggtct ctgggaagca  66600
aacagaggga gggaagccag tgagtcccac cagacacatc cggcccaggg cacccagccc  66660
ctggatggcc aggcaggaag agccccctgg gatggtgtct cgtggggagc tcaggggaaa  66720
tcccatgtcc tggacacccc aagaaagcaa ggtcctctgt tttgctcagt tctccatgct  66780
taggccccta acagcctttc caggccctga gggggattct aggccagcag gcctccccag  66840
tccctgagtg tgagcagtgt gaatagggag ggattcactc cagcctgccc tgccctccca  66900
ccccttgtct cctatccagc cccatcacag cgtagccgag tcctggaaag gctgggccgc  66960
acgtgtcagg agggcaggga ggtgccccta aggccttgaa ccctgtcccc accagctttg  67020
cctgcctcaa ggaacagccc agtccagctg gcagagcagg aagaggtgcg cagacagtgg  67080
gaggggcaca gctgcccaga tagggaaaga acacgagccc ctcaggcccc agacgttcca  67140
cggaaaaggg gccacgcctg tggacagcgg atagatactg ggcctacctt tgtcacaagg  67200
ctgatcatct gcggtttgca caaaagacag atggaacagc attagtggag ggaagcgggg  67260
accctgcggc tgagggcagc cacggcccga gtgcctgagg agcccgccat ctggcctctt  67320
tccctttcct ccaacgaacc tgtgatctga gctgtggtac gttattaaac cccaagacct  67380
gctctaatta gtcttcttgt atgtgtctca ttagcaccag agaaagccag ctcatcagtg  67440
gcacagcagc ctcaaggcca ctgcccttct aacctgacag caagtctgga aaagtggcca  67500
ttgtcagggg cccagggagc agcttactct aggatcctgc ggtgggaata ggacccactc  67560
tctcttttct ggggttggag tctggccctg gaaaacgcag atgcctgagg atggagcggg  67620
gtggagcaga gctgcaggcc atctgtgttc tggtcacctg gcacctgctc aggccgctca  67680
ctcggttaca agtctgccct ctagtaccag agagaccatg ctctggaaaa gcttcctctc  67740
tgcacggggc cctaccctgg ggctctgatc acaggccttc agaaaatgtg accccaactc  67800
tgctcactta accttgtgac cctacatatt cccagcttag aaaagatagc tgactctacc  67860
gacttcacag ggttccaaga agtaggtgga catgttttct aaagtgtaaa gtgctacacg  67920
gtgtagagtt gccagataaa atgcaggaca cccacttaaa cttgaatttc aaataaacaa  67980
caagtaactt cttagtataa gtatgcctca aatattgcac aggacatact tatactataa  68040
taaaaactac ataaaaacat acttatacta gaaaccaatc tgtcatctat ctgaaattca  68100
agcttcaact gggcatcctt tatttgtatt tgcccagtct ggcaatctgg cagccctacc  68160
agaggcacca ggtcacacat ggccttctcc attcccttcc aacgccagtg cttcttccat  68220
tttcaaggtc agagagccct tgggaatcta acgaaagctg tggatcctca cacgcacatg  68280
cacacgcgtg tgaacacaca cacatctgca cattttggga aagctgttaa catacccccc  68340
agcatcatct atggactcca aatatacaag ctcctctcca gggactagct gccccccacc  68400
tcctacttcc cacccccctcc ttcctctgga gtccatgagc tcagacaaga cccctgatgc  68460
cccctccagc ccactgccta cttcttccca gcctgaatcc tccctcgccc taaccccggg  68520
ccctccctgg agtgccatcc ctgacaatct actcacaggg gggcttcctg aggctctggg  68580
ggctcggcag ggtgcccgcg gctctccggt agcttagtcg tctgcaggga cacaagggga  68640
tgggcgggcc cgtgagctgg gccagataac cacttgaaag gaaccttctg gaaaacttgg  68700
gaagccaagg cctggatccc acaggtgggc acacactgga cactctgagg gcctcctgct  68760
tagcactaag ttccaacgaa gggaacactt tcacagggct cactggctca ccaggaggaa  68820
gaaactgagt ctcttgctcc agaaatagct catccagctc aagatggcca cacaggatcc  68880
```

-continued

```
agcccggtgt acaatcctca gctggtcatt actctcctat ggccaatttc taaggagagg  68940
cagccccttc tctactcccc agcctcccca tctctgaggg agctgagaaa tagcagaatg  69000
actcccagga gaggccgagg acagaagtga ccctaattta acaccctccc ctcagcggaa  69060
ggctcagccc gggcagactg tccaatgtgg ccatgagtgg agaggtgggg ctctcagagg  69120
tcactagatt tccacattta aatgcagctg aagggccggg cgtggtggct cacacctgta  69180
atcccagtac tttaggaggc cgaggcggga ggatcacttg aggtcaggag ttcgagacca  69240
gcctggccaa cacggtgaaa ccccgtctct actaaaaaat acaaaaagta gctgggcatg  69300
gtggtgcacg tctgtaatcc cagctactcg ggaggctgag gcaggagaat ccaggagaat  69360
cacttgaacc cgggaggtgg aggttgcagt gagctgagat agcaccacta cactccagcc  69420
tgggcaagag tgaaaccatg tctcaaaaaa aaaaaaaaaa tgcagctgaa gagctgtccc  69480
ccacatcctc tggtaagatg ttgccaagac ctgtgaaccc taaaatggag atgggtctgg  69540
ggttcccgag gagacagagc ttcgttctca gacttcggca tctcagaatc gcctggaaca  69600
tttgttagaa tgtgagtttc tgggcaggac ccatggatct gcatttctaa caagtcccca  69660
ggtgacgctg aagcccccag ccaggggcc acaccttgag ggccactgaa atgggtgaac  69720
cccaaggtcc tgtccttacc acagtccaca caccaaaaga tgtgagggct acaacccaca  69780
gtggaagtca caactgccac cctctgaccc aagactgacc ttcctggaag tctaaagaaa  69840
taatttgaaa catgaggaac agtctatgtg caaagtaagt aagtactgca gccttataaa  69900
agtgaagaat tgggaacaac ctaatcgaag tgcagccaca ggaaagcagt gaaatcactt  69960
agctagttcc tctgagaagc cttccctgca ttcctggatg agggcgcagc ctcctaatat  70020
gaactcacac agcaccatgt cctcctccct tgcacccatc acgtttatat aaactgtgtg  70080
tttgaagagc gtctggcttt tccactgaac tataagctcc tccagggcag aaaccctgga  70140
ttcacagcag cccgcaagat gccagcacaa ggccagctca attcatccta aatacctgcc  70200
gcctaggaat gaatggcaca gctcctgatg agttagtata cagccactaa aatcacacta  70260
caaaaacgat gctataatat ggaaaatact cacgccaaaa atgtttaaaa aaaaaaaaag  70320
caagacccca aattctgtat gcaacactca cataaaaagc acagtaagga aacaaactat  70380
gcagtttaga taagggtgag acgtggggaa tttcctttca tagtcctcct cttcagtttt  70440
tttctgtttt tttgttttgt tttgttttgt tttttgagtc agggtctcac tcttactcag  70500
gctggagtgc agtggtgtga taacagctca ctgaagcctt gaccttttttg ggctcaactg  70560
atcctcccac cccagcctcc cgagtagctg ggactacagg tgtgtgcaac catgcccagc  70620
taattttttta ttttttgtag agacaaggtc ttactatgtt gcctaggctg gtcttgaact  70680
cctgggccca agggaacctt ctgcctcggc ttcccaaagt gctgggatta caggcgtgag  70740
tcatcaccat gcccagcctc tcttctgtat ttttatattt tgtttatcag cattctctga  70800
gcatgcatta taaaatatac attaacttag gctggatcca gtggctcatg cctgtaatcc  70860
tagcactttg ggaggtcaag gcaggtggat cacttgaggc caggagtttg agaccagcct  70920
ggccaaaccc tgtctctact aaaaatacaa aaattagcca ggcatggtgg tgcacgcctg  70980
taatctcagc tactcaggag gctgaggcgg gagaattgct tgaacccggg aggtggaggt  71040
tgcagtgagc taagattcgc cactgcactc cagcctgggt gacagaggga gactctgtct  71100
caaaaaaaaa aaaaatacac acacacacac acacacacac acacacacac attaacttaa  71160
taacataaat ttccatagat tcctttaaat ctcaaataac catcatcact agttatggga  71220
aaagaccaaa cacaagtgca actggtactt accttggggg aacaatgctc agcaggcccc  71280
```

-continued

```
tctggctgtg agggcagaga cttgggggtc tgccatgtac ctgtgcctct gccactctgg  71340
aaccagccct tcacaacata ccccagaccc acctctcctg gaaccccttg gaggggatga  71400
ggccggctcg aaggttggtg tccccgactc gcttggcctg ccaccacgtg gggtcgtcct  71460
ggctcaccac ctccaggacc tgcctgcgct ggaagggcag gcccgcctcc tggcaaggga  71520
tggcccggtc ctcccgaggg ttgtagtgga agagggcgcg catgaacacc tgcacaagga  71580
gggctctggt gaggcggccc ttccccaagt gagcacagac aggtcattgt cacatcaaag  71640
gccacatgac aacgaccatc cacacttagg aggaccaagt ggcctttcaa atagaaagct  71700
acttggaaat acactgcacg tatgttctta actgttcttc aaccatttgg gatactatag  71760
tcaggaagtc catcaagaat cagaaaatta ataagcccca tgactgaatg tctctttcct  71820
acctaaatat ttccttattt acttgaccag ctgtcctcat aacagcctct tagcatacac  71880
acagcaacaa ctaatcctgg gaacaaaaag taaaggcaag cacaatttct aactcaagtg  71940
ttatttttga tacgccaact gcgctgacgg aaggcagcag ccatctgtta tataagtaat  72000
ctagatgttt gggtaagaac acaaatatca acaaaactac tgttactgac tcctcaccat  72060
cacttttcag tgggtaattg acacccacag ctcttacggc tcaatcctgc ctcgtctgcc  72120
atagactcgg ccaagcccta attcccccct ctgctctaga gtcaccctct ctggagaaga  72180
tggtgtgagg acacagcatt tttcacactt ccttgttctc ttcgataatt tagtggcatg  72240
gattaacttt atttatttct attttcagac cattagggcc caatcacttc agtggcaaac  72300
aggaaaaaaa aagcaatcag gggtcttcct cagacagata caaactctat tcctttgtat  72360
gccaaccaga aaagattcca ctggacaaca gtaagaactt tctggcatat gttgtgggga  72420
cagatgccct taaccagcca cagatgttac cagggtccta agcactcaga agaatgtaat  72480
cttaagtggc cagcccaaat caagcatctg gatcaagaag aaatattcaa gaaggacagg  72540
ctgggggaca ggctactcat tttgtccttt aggaaaacca agttctcttc ctcaaagagg  72600
tttcctcaag tcagaaccct caaagttgca tgtgcggacc acattcgctt gtcctaggaa  72660
gaatcacttt ccaccaggta agaggaaata ttatgccctg ggatttaacc aaagagcaca  72720
aataagaaac agctatataa agattatttc ttcacttgct gtaaaaaact gtcattgaag  72780
acgtagtcca ttacaaatcc acattcttca aagtatcgac tgacatctcc tctgtgctag  72840
atgctgtaat gtttcttctt tcatgcatta agtactgaga ggcaggtatg ggaatgtctt  72900
gaaaaactgg catgcttcct tccattctct gctcaacagt atgtaattca ttatgctctc  72960
ctttttgcct tggctgccag gaaactctac tatgaaatca aagtgatgcc ctcctctcta  73020
tctcatcaac caccatctca cagttcaggt cttaacgtct cacctgggct tttacaagag  73080
ccttctacca ggcctccctg cctccaacct ctacccactc caccctcctc cccgtggctg  73140
cctcacggag ctttctaaaa cacaaatata actgcaccac tcccatccta aaaaaaaaaa  73200
aaaaagagct tattagaacc tatgggatta tctcttgggc tgtgggatgc cctcccatat  73260
gccccagggc tggaccattc agtgcagcct gggctgactt ccagctgcca gcacctgcat  73320
ctctttgcct aaggacttac tttctctggc cactggaacc tactcatctc tagtccagca  73380
ggcagaagtt gctaggaatt aatcccccgg gtgcagcctg gcaggagttg gtatatagat  73440
cgcccagctc ccagggcccc tgggtgggat gatggaggcg tgtgttctac aggggaagaa  73500
gtagttcccc aagttcccag caggactaag ctccagctgc ccatagtggt aacctgcttg  73560
ataacacacc cttagtcaga ttggctgtct tccctttccc agtcctgtac tggtatttcc  73620
```

-continued

```
tggggccact tcccaaataa accatttgca ttcaatcctt gtctcagggt cagcttctaa 73680
gaggccccac actaagcaag gattatgcca aaacccttaa caaggcattc gaggccattc 73740
agaacatagg cttaacccac ctccccagca aaacccacca ccatcctccc ctcaaagccc 73800
caccacatag cccttaacgt gctcctctcc agagtgccag ggagcctctg tatgggcaga 73860
ccccaccaag gtcctactcg tctttacctt cttcaggcct cagttccaac acccccattc 73920
tgtgacaccc tctagggtga ctgtaactct ttgtacagaa tcttggcaaa gcacttatca 73980
catagcaatg aaagacttgc tgcccttctg caccaggaag ccttgcagct accaagagtc 74040
cctgtctcca gcatctggca gagtgcctgg cacagagtag gtgaccaaat aaggcaggct 74100
cagcaacaat taaacaaatg gcagttgctt aattggttca gaattcagca cacttggtac 74160
cttctcctcc tcttcatggc cctgagtttc tatttcaatt aaaataacct tgtcttttat 74220
tagtaagcca cgtcaaatcc tgtttagaaa gaggcaggat acaaacaaat gcatcacttt 74280
gtgacggaat taaagtcctc cactgggcac agattactag gatcagatct atgatctgtt 74340
cgcaaatgac tgttacaaga gactggactg gatccagccc ccagccagcg agctgcatct 74400
ctcaagctga gagagggcac cgcggaccca cctccccata ccttgctctc ctttaagcga 74460
tcttcctcct gggtggctgg gatgattttt agggtgatgg atccctggga ctgggcctga 74520
aacgaaagag aacagaagct tctcgcctac caggtctaac cctccaagag ttcaactcct 74580
acttctcagg cctaaaaact gatgttcaga aagtcagact tgcagcctcc cctgaggccc 74640
actcttctag gatggtgccc tggttgaatg aactaaaaca aaactcagta accaagtaac 74700
tgtacatttt tgtatttttt agtattttta ttatttttaa gccagttcaa atttagcagt 74760
ggcgggttgg taactgtatt ttcaaaagtc aaagggacgg aagactttcc atgagaaccc 74820
aaggacacta cgtgttgaat tccaattctc catccctcct gaccgctacg gccccagagg 74880
gctcccttcc ttgcttttct cctgggtcat ctgaacaacc catttcggtt tcctttgcct 74940
ctttcctgcc tgatttgggg ctggtctctg attaatactt ccctctttgc ttccatctcc 75000
ccagtctcag gccatgccca gctttctagg agctcccttc accctcatct acagagaccc 75060
tgtagcccaa tgccaggggc ccaacaaagg aagaatgcag tcggaccagg acagcagggc 75120
ccaaaagatc acctcctggc ctctccacta cccagaaagc ccagaccctt gctctggagc 75180
acaagaaggt tggcacccaa agccacaaaa aagcaagctt gggcaaaagg actgaagggc 75240
ctgcctgcaa tccgcatcct ctacagagag ggctttattt tgttgttgtt tttttgtttt 75300
ttgagatgga gttttgctct cattgcccag gctggagtgc agtggcacga tctcgactcc 75360
ctgcaacctc cacctcctgg gttcaagcaa ttctcctgcc tcagcctccc aagcagctgg 75420
gattacaggg gcccacaacc acactcagct aattttttgt atttttagta gagacggggt 75480
ttcaccatgt tgcccaggct ggtctcgacc tgacctcagg tgacccacct gcctcggcct 75540
tccaaagtgc tgggattaca ggtgtgaact actgagccca gcccagagag ggctttaaac 75600
agtgggcctc ctcttttcag atctcatcct gtttctgccc ccaaaaccat cagaagttag 75660
cagagtgtca ggtcagggga ggaatcctga ggataaaggg gaccaagcta tgattggggc 75720
ttttcacaat ttcagttttg acttcaactc cccagaatgg accatggagg ttttcagcca 75780
agcattttat accttaaaat ccccttacac ttctgaaggg ctttaccctt ttccagatgt 75840
tagcatgcca atgataacca cacattggtt gagaaagaaa ctctatccca acgttaaagg 75900
aaaggaaatg gaaactcaga tgatctgatg gcttgtccaa ggttgcacag ctggaaggag 75960
gcagagccag gattcacacc caggacccag gacccaggag gggccttgtg aaagggaacc 76020
```

-continued

```
aggggaagga aggaaggctg tgctgaggag aaggtctaag agaggcagat ggaagggaag  76080
ttcccctcct cctgctgcca ccccataccc cgggcacact gttaggggca caccataagg  76140
ccactttgcc tgccacctcc tcaggacaac agcaaggcta agccagaatc tgtcctggct  76200
ccaggaagtg ccttgctctg ggtgtctgaa gacccagcac atccctagca ggcttgtagc  76260
acggaccaga atctggctga tctcgtcggg ccgcttgtgc aggactgcga tcccgttcac  76320
ttctcggagc tcatctccaa cgtggaccag gcctaggaga cacagggact gaccatcagc  76380
acaggaggag gacctgagca cccctcgctc agagctccaa gcaccacagg ggccggcctg  76440
agaagcccac tgcagggcca actcgaggtt taaagttgat gggtgggact ggggcgaact  76500
aagccctgct aagtgctggg cacctcactc ggcatgcagg gctcaaatca cccagtaaaa  76560
tctccaattt acaagttggc acctgagacc caggaagatt aagcagcttg cctaaggcca  76620
cattgctgag aaataatgaa gccagtattc aaacacagtt attatgatgt agaaagcctg  76680
tgttcttttt gctataatct ctgcttcttt aaaattatca ttaactctta gaatggcatt  76740
cttaagtctt aacaaggaaa gacaaaggca ccaatgaaga catcattaag agtgtaaaca  76800
cactatgagc ctctgcctga atgactaatg tctctgcata ttagggccct atatgctact  76860
caaagtgggc actggcccgg ctgcatcagc atcacctgga ggcaggttaa aagtgcagaa  76920
tcttcggcct agctcagacc tgctgaatca gtctgcattt taacaagatg ctcagggaat  76980
tcgtggactc gttaatgttt gcaaagtgct ggtctaggat tctctgcaac gatgaccccc  77040
cagactttgg gggtaacatc gccctatacc aggaggtttg tctcccagct tagtagctct  77100
tccacacacc ggtgattctc aacctttcta cccaaacgaa tctggggcac aaacactctc  77160
tttgtaatag tagcttgaca agacctggga tggtggggaa gggtgtcaac cctgtcccac  77220
agttagtaat cccgcaagcc catgctatat tcttaactgt cacagtcctt ggactaaacc  77280
aacgcatgag ctttttctca atcaccccaa agtactccat gactatttat atatatatat  77340
attttttttt tttttctttt ttttttgaga cggtctcact gcgtcgccca ctctagagtg  77400
tagtggtgta atcacggctc actgcaacct caaactcctg ggctcaaaca atcttcctgc  77460
ctgggcctcc cgaacagcta ggactacagg tgtgggccac ccgtgcatgg cctatatttt  77520
ctttttcttt ttttcttttt tttgagacgg aatttcactc ttgttgccca ggcgggagcg  77580
caatggcgcg atctcggctc actgcaacct ccacctccca gattcaagcg attctcttgc  77640
ctcagccttc ccaagtagct gtgattatag gcatgtgcca ccaagcctgg ctaattttgt  77700
atttttagta gagatggggt ttctctgtgt gggtcaggct ggtctcgaac tcccgacctc  77760
aggtgatccg cccacctcgg cctcccaaaa tgctgggatt acaggcgtga gccactgtgc  77820
ctggcttttt ttttttttc ttttttttt ttttttgaga cagagtctca ctctgttgcc  77880
cagactggag tgcagcagca tgatcttggc tcactgcaac ctccgcctcc caggtttgtg  77940
tgtttagtag aaatggggtt tcgccatgtt ggctaggctg gtctggaact cctggcttca  78000
agtgatccgc ctgcctcggc ctcttaaagt gctgggatta caggtgtgca ccaccatgcc  78060
cagctggcct atattttcta ttaaaatttc tactgacttg ggaaggagat gagaattcca  78120
gccacaaccc cagaaagcaa agcaaatccc aaacaggtga cctgatagga gggaggtaag  78180
gggacctatt agcaaaggtg gagggctctg gaacaatggc catgatcggg gctgggccag  78240
ctttgcactg ccgccactca ccgctcctgt ctgctgcgcc tcctcgcatg atcctggcca  78300
ccacaacagc ccctgagtgc tcgtcccgcc ggatggtggc accctgaacc cgagacagaa  78360
```

-continued

```
gagacaggtt cttaagcagc agctccaaac ctcagacccc tactctctgg acccaacaca  78420
gcctccccag tccctccctc tgacagtcca gagagatcag tggggacctt cccaatgctg  78480
aagacaaaac aaaaccaaca tcccccatta atatagccct gcactgtaca gtttacaagg  78540
cacaataatg ctgcaacatt ttagatgagg gactggggct cagagaagtt aaatatcctc  78600
aaggtcaccc agctggtaaa ggggaaagct ttttgtgatg ccaaatccag taagttctcc  78660
atcacatctc tctcatatca cagttcctac cacttgcaaa gacatttaat aatgaggatg  78720
acacgtgcca gctaattctc accctgcctc tacccaatca cagggttacc gggccttctg  78780
ctgctgctga gggaaaccaa ttatgcaccc cagccagggc ttcgggacca ggacttggcc  78840
catgaagcac agcagagatg acacttagga tgagaaaggc actaacgagc cctcgatttc  78900
ctgcaccaca caggccggac tgcagcagga cggcagaaag cttaagagct aagctctagg  78960
gctggacagc cttgggtgtg aacacagttc tgccgtttac aaaaagcatg tggacttaac  79020
aaggaaatct cttatcctct ccaagcctgt ttcctgtgag atgtgggaca gcatttaact  79080
cacagtgttg ttgcaaggat tccactcaag gcacttagta cacagtaagc actcaacata  79140
tgttaaccac ttattagtgg ctgtaactgc aaacacattt gcacacttat tgttaacatc  79200
atctgtgcca tctatttgaa gtacgtaaga taattattgc tagaaagaga ggccatcagc  79260
taagaacctc aggacttcta gccccccaga actgagaact ttccagcatc gctatccatc  79320
atttattcag ctctgaaccg ccagcaccca atacagagcc tggataggag ggctcacaat  79380
gtgtttgcta aatcaatgga tggccactcc attttacaag tgaggaaaca gaggcagagg  79440
agagatcctc gtctgtttgc agaagaggct cgtcggaggt catttgggga aagttggaaa  79500
tagagaatgc cagctgtggg atcctctgga gccaatctca attctctggg cttccaccac  79560
ttctgagcat ctcataaaca acgctgtccc tttgctcggt aaatcaatgc tgaaccagga  79620
ccaaagtgat agcagtctgt ctgctgggga gaggaatgcc ctgtgcttcc tcaacattca  79680
gagcaggcat tgtcacacgt tttctataag gggccacatg taaatatttg aggccagcca  79740
cacagtctct gtcacaacga ctcaactctg ccatcgcact ataaaggcag ccacagccaa  79800
tctgtaagtg aatgggcctg gttgtgctcc aaaaaagctt tattttaaaa aataagctgt  79860
gggctggttt tggcccttgg gctgtagttt gtccatttct ggcttaaagc atgatcaggg  79920
tcaccctgta caattgtgca ggttattaac tacacaaagg gtgttggcca cagttgagag  79980
gggctgtatc cacctagaga aaggggtgcc ctgcacacag aggcaccaca gggatgagca  80040
gcagcgcagg caaagctgcc gtcactcact ctgaagactt cggggaggat cttgtccagt  80100
gttctgggtg ggggtgagag gcaggggaag agtgggttag agaggggcag gcagcagcac  80160
ctaccagggg ttccttgttc ttcaccaagc ggacgatctt caccgattcc tcatcaaaat  80220
cctcatcgat attgtcaggc agaggcggga gaacggggtc aaaattcttc tgggcaaccg  80280
tgtcatgtac catgagcaca gcctgccggg aaagccagag aaaaggaagg ctggcccgcc  80340
gctcacaggg tcagcaggcc gcagctggcc ggtggtatgg agggtggcag acgccatgcc  80400
agagagacaa ctgcccagac actagtgctg aggatcgctc cctcagtctc cactcctcag  80460
cctcattagg agagctccct ccgcccccat cccaggagac ccagaggcat ggctgggcag  80520
gggctctgtg tgactaccct caggtgcggg gtggacagca gctggagcag ctccctctca  80580
tcactgtgca cggaggcggc ctgcaactcc tccatcacct gcagagaatg agacaggcgc  80640
cactgatggc tagaggtgcc cctgccccat atctgctggg tccttcctct ttggaagggc  80700
ccacccagct gcagccccca ggggcacacc agaccctcaa ccacccgacg acgatgatcc  80760
```

-continued

```
tgggaacatc acaccagggg tcaggagcag ctctatgggg ccatcctcca aggagccacc  80820
gttttaagcc ctacgtgctt tctgctttat gtggatcttc tcactgaacc ctcgcaacca  80880
acttgatgca gagggtcttg ttactttgcc attttacaga tgagaatcct gagactcaaa  80940
gagattaaac attttgcccg aagtcacaga gctcatatac agcacagcta ggatttgaac  81000
ctgggcttat ctggctctca gatgctattt tatgaatgag gaaatgggag ctcagagagg  81060
ttgagtggcc tacttaacat cacagagctg gtgggacagg cagcgctgag cctgggagcc  81120
aggcaatcta atgtgcccct aatcacattc cacagtggag aagggcccag ggctctgcac  81180
ccacaagctg cactcatccc tccccaggcc atctcctggg gttaggtgag tttattcagg  81240
aactgatctt agtaatcaac cagaatgggt tttccccaac cacgcaacat agacgactag  81300
gtccacaaga aattaagaag cgttccttta aaaaatgaga agcctgagcc agtatgcggg  81360
gacacactgt aggtcccttg acttcaggaa agcacagaca taatgtctta ttgacctatt  81420
caaatcacca gtcctcaggg cagtttggga actgctgagc caatccaatg ctctcattta  81480
cagcagagga agcagacttg ctaaagaaca cacagtaagt gggcagctcc atgtcacagt  81540
gtctcccagc ccagtccaag gctcacgggt tcctccctac ctttcgggga acccagagag  81600
aggaagagaa ggaggaggac aagggaagaa aacacctctt cacctttggg ctcctgattc  81660
ccggtgtccc cacactaagc aagcgaggca agatgaagga gccctacagg gtggggagtg  81720
gggcagacac tgtaaggaga aacctggggc ttacgtcctc agcgagggcc acagcgctgt  81780
gcagaactgg ggttggactt tgcctttcat aatagcgaag cttctcatga atctgcaaag  81840
acagagtatt tcagatgcac cctggacacc acacatccca cccacggctg tggggacatt  81900
tggggcagca gactgggcca ctgacagggc accataagag aaagtcctgt gtagtgggca  81960
agtgaaggcc ttcctggggc agggagatga ctaggatgac ctcagacggc cacagacagc  82020
tagaaagacc tctagacacc cttccacgca ggatgacgtg ggacttcacc ttcattaagt  82080
aactgaggct tttttcactg aaaacatccc tcaggaagcc catctcctcc ttgtggttgg  82140
agtcaggtct gagctgggag gtcagcaggg ccagggtttc atgcaaacct ggggagaggt  82200
gagaaaaaca aaggatagca aacgcagtgg gtgctccctg cccccgagga gcccgagtgg  82260
ggcctcaaac agcacttcag tcctgccgtg aggacattct ctccccaggc tctcactgcc  82320
agggcctgga ggctgccagg caggctcttg tcttcaggac tgtggcaggt ccagccgggg  82380
ggaggtactt accagagtcc tccgatagca ctggcatgct ggcgttgtca cctcccgacc  82440
tctccctgca gattctggga gaagggggtg gaggtgggta ttgaagctcc atcaagcata  82500
tttattgaac aaactgacta cacatctact gtgttctctg agaccaggct gtggacagag  82560
aggatgggaa caaataactc tgcttacttt tttcagagag gaaggaaata aagctaagat  82620
gtgctgagtg tcctcgatgt gccaagcatt gtgtggggtg atttctatga taaacttttt  82680
gtctgcacaa agtcctgaga aatgactgcg aatgttccca ttttattgat gaagaaacag  82740
cggcgtggaa gctttcagta agctgtgggt caaaatccat attcaagcag gctcttccag  82800
gctggccttg gaggtgccaa gtgaccctgc ctgacagtgt cagctgtcct ccgcagcgcg  82860
cccccctccac tgcaaccttc taagagccct ggctcaagtc tcctgctggg acacaccttc  82920
cacaactacc tggctgggcc tacaagcccc ctgtccccga ccccccaaga cccaacccaa  82980
agggagcctc cagactggag tgcagagagg aggggggaaa atgggagtcg ggcttccact  83040
atgcaggagg ggggacccct atctcatgag gccctccaaa ggtgctctgc agcacgtgga  83100
```

-continued

```
cctcaaaaag tcctccttag gaagaggaga aggagagtca tgactgattc attccgcaaa  83160
catggagcca gcccgcagcg ccgagccccg gtgccactaa gaggcgtaag agcggccccg  83220
ggccctccag cctccgcccc gccccgcccc gccacgccac gccggactca ccctcgggct  83280
gctccccgca ggaggccgag caccgactcc cgctcgctct ccgaaggaac ctgtgggaga  83340
acaaggagcg cactgggcgc aggagcagcg accccggggg acctcggagg gcggtcccgg  83400
aggacgcgga gcagcaggga gcggggggcg cgcggcgggg cgggcgcggg aagagggagg  83460
cgggggccga ggggcggggt tgagactccc gcggtgggct cggtgggccg cgaggctgtc  83520
cgggagcacg ggaggagggt ctcggcccgg cctcccgccc ctcccgccgc ggcgcccagc  83580
tccctcgtcc gttcccctcg cggcctccta cctcgtcgcg ccgggatgtg tgctccgcga  83640
acgggagccg cgcgagtgcc cagagcctgg gccgccgctg gctccgcctt cccggacccc  83700
tccctgcggc tgccgcgccg ggcgggggtg gcggagcctg aggaggcgcg gcgcggggag  83760
gaggcgcggc gcggggagga ggcgggggag gagcggaggc cgccctccgc gtctggcacc  83820
gccgcaccct ccgggccggg ctccgctagc cggcgtcgta cccgctcccg ctctcccgct  83880
ccctgagtcc cctgcctgtg tccccccgca ccctggcaca cagccagact tcccttccgc  83940
ccgcgcaacc caccctccgc gagtggaggg gtggacacct gctcaacaga gaattcgatt  84000
ttgcaaacat ttattgagcg ccctccaggt gccaggcgct gtgccagggg ccggggcttc  84060
aaagacgacc aaggcacaga tcctgggttt gaagatctcc agaggtgggg cggggggccg  84120
gtcggatgcg agggcaactc gctgtaacaa tgcaacgcgc tgggaaagat ttatcggtgc  84180
acgctgccct ggggacgcgg agcaggggag gagaagtcag gctggagagg agggggactc  84240
cattctgccc ggctgcaggg gagtgaggct acatagcaga ggcgagcagc atccaggggc  84300
tttactggaa aaagagctct gaaatggcca tgacgataac tgacttatat tgtgctgtct  84360
ccatgcccag gtactcctca gatcacttcc cttcacagta gttcctgata tcaagaccat  84420
tcttattttg gttctgcaat tgaggaaact gaggttcctg gtgaaagaat gtgtataggg  84480
gagagcatag gaactgctgg gtgagtgagc aggtggttgt gggtattaaa aggtgaggag  84540
tgggtgagtg agtgggcccc cttccctcaa tcccagcagc aaagaacggc acagcacatg  84600
tcaggagagg tggacccaga ggttaagtct ggaagtaaat ctagccctgc acagtaacca  84660
gggaaaatgg gttggcaggc cccacaggct gtagtgcatg gggaggctgt gagaggcagc  84720
aaatgtcatg atgatgtttc ccctcattcc tcaaaaatta tcctcattcc tcaagaaata  84780
tctacactat tgctcctcaa aatgtaacgt gcctgagact cactaggggg ttgtgtaatg  84840
ctggagtggt gccagattct gaatttctga caagctccca ggtgatgtga cgccactggt  84900
ctgcagacca cactttttga gtggagagag actgcatgag acacattctt agctgcaatg  84960
tttactgttg gaaaaataat gagaaccatc tgatccatct gatatgggtc aaatgatttt  85020
ggacaagaac accaggaagt ggtgttggaa caagtagata tttatgtgcc tgaagggacc  85080
caatccctac ctcacaccat attcaaaacg caatttaaga gagatcattg gcctaaacat  85140
aaagcaaatc gataaagcta ctagaataaa acaggagggt atcttttaaa tcttggggta  85200
tgcaaagatt tcctagaaag gatacaaaaa agccaggcat ggtggcatga gcctgtatcc  85260
cacatactca ggaggctgag gcaggcaaat tgcttgagcc caagagttca aggctgcagt  85320
gaactatgat cagtccactg cgcttcagct tgggtgacaa agagacaccg tttctaaaaa  85380
aagaaaaaat ttttaaaaaa agcatggacc ctgaaaacaa ttgataaatg gacctcatca  85440
aaatttaaaa ctcctgctca tcaaaaaaca ctattggcca ggtgcagtgg ctcatgcctg  85500
```

-continued

```
taatcccagc actttgggaa gccaaggtgg gtggatcatc tgaggtcagg atattgagac  85560
catcctggct aacacagtga aaccccatct ctactaaaaa tacaaaaaat tagccaggca  85620
tggtggcaca cacctgtgtc cgttccagct actcaggagg ctgaggcagg agaattgctt  85680
gaacccggga ggcagaggtt gcagtgagcc aagatcaggc cactgcactc cagcctgggt  85740
gacagagtga gactccatct caaaaaaaaa aaaaaaaaag accgggcgca gtggctcacg  85800
tctgtaatcc tagcactttg ggaggtcaag gcgggcagat cacgaggtca ggagatggag  85860
accattctgg ctaacatggt taaaccccgt ctctactaaa aataccaaaa attagccggg  85920
tgtggtggcg gaggttgcag ggagtggaga tcgcgccact gcactccagc ctgggccaca  85980
gggtgaggct ccgtctcaaa acaaaacaaa acaaaacaaa acaaaacaaa acaaaacaaa  86040
acactattaa gaaaatagga ccagggacca ggtgcagtgg cccacacctg taatcccttc  86100
aagcacttta agagttcaag gcgggtgaat ggcttgagcc caggagttcg agaccagcct  86160
gggcaacacg gcaaaaccca gtcggtatct actaaaatta caaaaactag ccaggcatgt  86220
tggcttgtgc cagtagtccc agctgctcag gagactgagg caggaggatc acttgagcct  86280
gggaagcaga ggttacagtg agccatgatt gtgacactgc actccaggct gggtgacaga  86340
gtaagaccct gtctcaaaaa aaaaaaaaga aaagaaaaga aaaaagaaag aaaaggaaag  86400
gaaaagaaaa gaggcaagcc acagactggg agactaggaa gaaatatatc tgacaaagag  86460
attgtattca gaataaagaa ctcctgtaac tcaataaaaa gacaaaccac ccaatcaaaa  86520
aacaggcaaa agatatgaac atgcacttca caaaagaaga tatacaaata accaataagc  86580
atatgagaaa gcactcatcc aacatcattt gtcatcaggg aaatgcaaat taaaacctgt  86640
catagtcagt tcctgctgct ataacaaaat accacagtaa tttataagaa gtaatagtaa  86700
tttattgctt acagttctag aggccggaaa gtccaagatc aaggggccag ctggttcagt  86760
gtctggtgag ggcctgttcc tcactgatgg cactggatag gtatcctcac atggtggaag  86820
agaaagacag gcataggcca ggcgcggtgg ctcacgcctg taatcccagc accttgggag  86880
gctgaggcag gtggatcaca aggtcaagag atcaagacca tcctggccag catggcaaaa  86940
ccccgtctct actaaaaata caaaaaaata gccaggcgtg gtggcaggca cctgtagtcc  87000
cagctacttg ggaggctgag gcaggagaat ggcgtgaacc cggaaggcag agcttgcagt  87060
gagctgagat cgcgccactg cactccagcc tgggcgacag agcgagactc catctcaaaa  87120
aaaaaaaaag aaagaaagaa agacgggcat aaagggatga acgctgtgtc ctcatgtggc  87180
agtaggggcc aaagggacta gggtgctccc ttcaagttct cttataaggg cattaatccc  87240
attcaagtgt ccatcaagaa gtgaatggat aaatattcat tcacttgtgg tatatccata  87300
caatggcata tttactcacc aataaaaaga aacaaattac aagaaagaaa tgatgaaaaa  87360
atttaagatg gcagagtata caattgatat taaaaattta tgactttccg gccaggcacg  87420
gtggctcacg cctgtaatcc cagcactttg ggaggccgag gcgggcagat cacaaggtca  87480
ggagatcgag accatcctgg ccaacatagt gaaactccgt ctctactaaa aatacaaaaa  87540
ttagctgggc ttggtggcac gtgcctgtaa tcccagctac tcaggaggct gaggcaggag  87600
aatagcttga accagggagt cagaggttgc agtgagccga gatcgcacca ctgcactcca  87660
gcctggtgac agagcgagac tctgtcttaa aaacaaacaa acaaacaaaa aaaacattat  87720
gactttcctg tggacaaaaa taattattaa gtataatgaa agaaaaaatc caaactaaga  87780
tatcaagaaa gattaaatac caatttataa acttaatagg aaaaatgaaa gacctattga  87840
```

-continued

```
tatttgggag aaaaaaactt taaaattcta gtgaaggaca taaaagataa aatgtacctc  87900
aaatggctag ggaaagaaca gttcaatagt gcaattatat taattcattc tgaaataatc  87960
tttataccca atgcaattcc aattaaaata taagaagtat ttttcacaga gaatttatta  88020
aatgctacca caattcatca ggaaaaataa acattggtga ataataggaa agttctggga  88080
aaaaaagagt tatgggacca agggaggtgg gatttaaaaa tatgaaaaca atttttaaag  88140
tttagtactg aggctatagt cccaggactc tgggaggccg aagcaggtag atcacttgag  88200
cccaggagtt caagaacagc ctgggcaaca tggcaaaacc ccatctctac aaaaaatgca  88260
aaaattatct gggtgtagtg gtgctcacct gtagtcccag atgctcagga ggctgaagca  88320
gaattgcctg aacccaggag ttcgaggctg cagtgagcca tgaccacacc actgcactca  88380
agtctgggtg acacagcaag accctgtctc aaaaaaaatg aattaataaa gtttagtact  88440
aaagaggcaa tcaacagcta gacaaataga acagaattga aagaacagaa atagtcctca  88500
tgtatactgt cttttaatat ttgagaaagg tgacatttaa gtggaaggag aggaattttt  88560
ttttttttt aatgtgggga caggccaggt gcagtggctc acacctgtaa tcgcagcagt  88620
ttgggaggct gaggcgggag gatctcttga gcccaggaat tcaagaccag cttgggcaac  88680
atagcaagac ctgtctctac taaaaataaa aaaattaaaa aaaattgatg catgtgcaag  88740
tagacccagc tactcaggag gctgaggtgg gaggattgct tgagctcagc agatagaggt  88800
tgcagtgagc cgtgatcatg ccactgcact ccagctcggg catcagagca agaccctgtc  88860
tcaaaataaa ataaggtatg gcgacaatta caatagctac tctttatggg aaaaaaaaag  88920
agagaggaaa aaaggctggg cgcagtggtt catgcctgta atcccagcac ttcggtaggt  88980
ggaggcgggc agatcacctg ccctcctctg caagattata aaaataaatt tactgagaaa  89040
atattttgat gtgagaagtg aggtagggat acagctttct ttcgcttttg ttttgagacg  89100
gggtcttgct ctgcggccag gcgggagtgc agtggcgaga tctcgtctca ctgcaagctc  89160
cgcctcccgg gttcaagtga ttctcctgcc tcagcctcct gagtagctag gattacaggc  89220
acccgccacc acacccagct aatgttgttg ttgttgttgt tgttgttgtt gttgttgttt  89280
gagacggagt ctcgctctgt cacccaggct ggagtgcagt ggtgcgatct cggctcactg  89340
caagctccgc ctcccgggtt cacgccattc tcctgcctca gcctcccgag tagctgggac  89400
tacaggtgcc tgccaccacg ccaggctaat tttttgtatt tttagtagag acgggatttc  89460
accgtgttag ccaggatggt ctcgatctct tgacctcgtg atccgcccgc tttggcctcc  89520
caaagtgctg ggattacaag catgagccac cgcgcccggc tgcagtgagg gaaacatttc  89580
taagtaaatt ccaaatccaa atctataaag gaaaaggtgg atatgtgtga tttaaaaaag  89640
ggtaaacatt tttataggta aaaatattat ttgcaacata tgatatcata tgcaatatga  89700
taaagttaaa ttcctcaatt taaaagagtt tacataaatg agaaaagatg aaaaaatttt  89760
aaacggtcaa agaaaatagt ctaatacaaa aaatacatag ccaataaaca cagaaaactg  89820
atgctagatc tcctgtttaa aaaaaaaaaa aaaggaaaaa aaatccaaaa gatgcacaac  89880
ctcactcata atcgaagaat tcttagccaa aataggaggc aatgtccctt gttaagacaa  89940
aaatgtttaa gtctgttgac atccagtgct atcaaggatg tggggaaaag acacatttac  90000
acatttggaa ggaatattat ttggtgcaaa ctttctggga cacgatctgg taatatttgt  90060
taaaatatta tatgtacatg tcctttagtc cagaggatat ttgggcaagc agaatggaag  90120
aaaagagaag cagagagaga tgtttaggtg gatgagagct tggagcagga gtgctgggag  90180
aggctgcatc ataggacagg gcaggtgcag ccagggcgga gttggcccag atggccggaa  90240
```

-continued

```
gctcagggca ggagtcgcct cacccagcca gggctcggtc aaggtgctcg tttagagcag  90300
ctgcacaggg aacaggaaga tgagctcaat gccagaggaa tgaatgactt tgggtccatc  90360
tggacaggga gaagagactt taccaagcat gctctggaaa aaaagagaat gccaacgatc  90420
cttgaagagg tgacagagag aatctgcttc aggctacagg tgtgcattgt cattgcattt  90480
ggcattcagc ccagacacca tagggaacca gaaataattc caagaggagc aatgggctag  90540
tgcccaggca tgcagcaaga gggcaagtca gaagcgggtg gagaaagggc aggctcagct  90600
ccatttactt ctcaatgaga agggaaatta ctgtactggg gttttggggt ttttttgttt  90660
tgttttgttt tttgagattt ctgataactt ttcctattgt ttgtggcttt tgttacctat  90720
ttctcttatt tttattttg ttttattttt ttgagacaga gtattgctct gtcacccagg  90780
ctggaatgca atggcacgat ctcagctcat tacaacctcc gcctcccggg ttcaagcgat  90840
cctccagcct cagcctccca agttgctggg actacaggca tgcgccacca ttcccagcca  90900
gtcctagaat tcttatgttg tgcttttttc aaatctgctg tcactttttg ttctttccag  90960
ttccctgcca aaaatgtcaa gcttgacttt tacctccttg agcacagtaa gaatagttgt  91020
gttaaggctg atcctgctat ttacagtata tggagtcccc acgggtctgt tttgttgttt  91080
ctgcatattc ttgcttattg agtcttctca tagatttggt tatctttgat tatatattag  91140
atggtatttg aaaaaactac ttgtaaaaat gatcagctta ggctgatgct attttcctcc  91200
agaaaggatt tttcactaat atctttaagg tacccgaggg tagggatggg gaaggtgctg  91260
ccagacaaga gccactttta attcaagttc aaagcttgaa gtttcctggg acacctaaat  91320
gacagaaagc tgggtggaag tccatggtgg cctggtttgt acagcctttt ggggtcccag  91380
cctaatgtga ccaaaaatat gccagattcc attccctgcc cccagagggc cctagactcc  91440
tagttcatcc tcttcgctgc tgctttggaa tcagtaaatg cccacaggga aaacaagcac  91500
atacactgag cttatctttc tggcttcctg tctacttgca tgcagactta tgcctgggaa  91560
cccccatgct ctttttagct tttcactgct tttttttttt ttttaagaca gtctcgctct  91620
gtcacccagg ctggagtgca gtgacatgct cacggctgac tgcagcctcg acccctcagg  91680
ctcaagtgat cctcccacct cagcctcccc agtatacttt cttttttctt aataaacttt  91740
atattttgga ataattttag atttacagaa aagttgcaaa gatagtacag agagttcctg  91800
aacacccttt cccctgtttt ctctaatgtt agcatcttac ataatcatga tacatttgtc  91860
aaaactaaga catgaacatt ggaatgttat tattaaggaa attccagact ttattaatct  91920
ttcactagtt tttccactaa tatcctttct ctgttctggg atccagtcca agataacaca  91980
ttgcagttag ccttcaaagt ttctgagaag atttgaaatt tacctatcag taaacgtggg  92040
catttactga ttgagctcct gaggcattac cagtctccca ttactgccct cctccatcat  92100
tttccctgtc attccccgaa gtaattggtt aacataaaaa atttgaaagg ggccgggtgc  92160
ggtggctcac acctgtaatc ccagcacttt gggagaccga agcaggcaga tcatttgagg  92220
tcaggagttt gagaccagct tggccaacat ggtgaaaccc tgtctctact aaaaatacca  92280
gaaaatgagc tgggcatggt ggcacgtgcc tgtaattcca gctactcagg aggctgaggc  92340
acgagaatcg cttggaccca ggaggtggag gttgcagtga gccgagatcg cgcctgctgt  92400
ctcaaaaaaa aaaaaaaaaa aaaaaaaaaa ttgaaaggga gttttcagat ttgtttgatg  92460
gagaaagttg aaaaatcgag tttgcaacca gctagggtag ggaagctgcg aggagactag  92520
aggatgaatg tatgacggaa aacaaaaagc atggtggtgg tctacactgt gctacagcaa  92580
```

-continued

```
ctagcaaact gcaagatctc cgtggctaaa cacagaaaag tctatctctt gctcattcca  92640
agtccgccgc acgcttggtg gctgtccagg gcagctgtct tccaagtggt agctcaggaa  92700
tccaaatctt cctgtcttgt ggctcatttg tctttgccgg ggacacgtct tccccactcc  92760
tgatgtttcc ttccatgagc agagaacccc actggcacaa aactcttagt ctctctccac  92820
gcctctctct acgcctctcc acacctctct ctacgcctct ccatgcctct ccacgcctct  92880
ctccacgcct ctccacgcct ctctccacgc ctctccacgc ctctctctac gcctctccac  92940
gcctctccac gcctctctcc acgcctctcc acgcctctcc acgcctctcc ccgcctctct  93000
ccacgcctct ccacgcctct ctctacgcct ctccacccct ctctccacgc ctctccacgc  93060
ctctctccac gcctctccac gcctctctcc acgcctctcc acgcctctct ccacgcctct  93120
ccacgcctct ccacgcctct ctccacgcct ctccacgcct ctctccacgc ctctccccgc  93180
ctctctccac gcctctccac gcctctctcc acgcctctcc acgcctctct ccacgcctct  93240
ctccacgcct ctccacgcct ctctccacgc ctctccacgc ctctctccac gcctctccac  93300
gcctctctcc acgcctctcc acgcctctct ccacgcctct ccacgcctct ctctacacct  93360
ctccacgcct ttctccatgc ctctgctgat ttgattgatg aatgttgaag gaggaacaag  93420
gcgtgtgtaa cccggctctc ttcttccttt tctctggtga gctggcccac ctgcaaaaag  93480
tgtgtgttct aaactgatac accacacctc accctgagta ttacgaggat ggcccagctc  93540
cactgaggaa agaaggacgc agttttacct gattctgggg ttcagcatta ggttctgccc  93600
actgtcctgt ttccaaaacc gtgttactat gcctgcatca agcttatcca cccgcggccc  93660
acgggctgca tgcagccagg atggctttaa atgaagcccc aaacaaactc gtaagctttc  93720
ttaaaacatt atgagattat ttttttaact catcagctat cactggtgtt actgtatttt  93780
atgtgtggtc caagacaatt cttcttcttg gcccagggaa gccaaaagat ggaacaccct  93840
gacctacata aacaataaac ataacttaca caaaagtgca cttatttgtt ccacagttat  93900
tcatcatcta agacagcagt tctcaaccca gggtattttt gcctctcagt gggatgtttg  93960
acaatgcctg gaggcttttt tttttttttt tttttgaga cagagtcttg ctctgtcacc  94020
caggctggag tgcagtggcg tgatctcagc tgactgcaag ctccacctcc cgggttcacg  94080
ccattctcct gcctcagcct cccgagtagc tgggactaca ggtgcccgcc accatgccca  94140
gctaattttt ttgtatttta tttttttaga gacggggttt caccgtgtta gccaggatgg  94200
tctcgatctc ctgaccttgt gatccgccca ccccggcctc ccaaagtgct gggattacag  94260
gcgtgagcca ctgcgcccgg ccttttttttt tttttttttt tttttgagac aaggtctcac  94320
tcccatcacc caggctggcg tgcagtgatg ggatctcgac tcactacagc ctcgacctcc  94380
catgctcagg tgattctgtc acctcagcct gtgtgtagct gggaccacag gtgcacactg  94440
ccatgcttgg ctaattttct gtatttttg cagagacggg gttttgtcat gttgcccagg  94500
ctggtctcaa actcctgggc tcaagtgatc cactcacctt ggcctcccaa agtgctggga  94560
ttataagcat gagccacctc acccagcctg gagacatttt tgattatcac aactgggaag  94620
ggactactgg catctagggg gtacagctgg agatgctgct aaacatccta taattcacag  94680
gacagtctcc cacaacaaag aattatctaa cttaaaatgt caacagtact gaggttgggg  94740
aaaccttgat cc                                                      94752
```

<210> SEQ ID NO 35
<211> LENGTH: 24
<212> TYPE: DNA
<213> ORGANISM: Artificial Sequence

```
<220> FEATURE:
<223> OTHER INFORMATION: Single base extension primer

<400> SEQUENCE: 35

ttttgaaggt agcgccacct gctg                                            24

<210> SEQ ID NO 36
<211> LENGTH: 30
<212> TYPE: DNA
<213> ORGANISM: Artificial Sequence
<220> FEATURE:
<223> OTHER INFORMATION: Single base extension primer

<400> SEQUENCE: 36

tttttttttt ttgtgagaag ctggccctcc                                      30

<210> SEQ ID NO 37
<211> LENGTH: 36
<212> TYPE: DNA
<213> ORGANISM: Artificial Sequence
<220> FEATURE:
<223> OTHER INFORMATION: Single base extension primer

<400> SEQUENCE: 37

tttttttttt tttttatga tggatgatgg aaagga                                36

<210> SEQ ID NO 38
<211> LENGTH: 43
<212> TYPE: DNA
<213> ORGANISM: Artificial Sequence
<220> FEATURE:
<223> OTHER INFORMATION: Single base extension primer

<400> SEQUENCE: 38

tttttttttt tttttttttt tttagtggta gttaaactga caa                       43

<210> SEQ ID NO 39
<211> LENGTH: 48
<212> TYPE: DNA
<213> ORGANISM: Artificial Sequence
<220> FEATURE:
<223> OTHER INFORMATION: Single base extension primer

<400> SEQUENCE: 39

tttttttttt tttttttttt ttttttttaa gttgcagtaa gccgagat                  48

<210> SEQ ID NO 40
<211> LENGTH: 54
<212> TYPE: DNA
<213> ORGANISM: Artificial Sequence
<220> FEATURE:
<223> OTHER INFORMATION: Single base extension primer

<400> SEQUENCE: 40

tttttttttt tttttttttt tttttttttt tttttttagt ataaagctg gctc            54

<210> SEQ ID NO 41
<211> LENGTH: 60
<212> TYPE: DNA
<213> ORGANISM: Artificial Sequence
<220> FEATURE:
<223> OTHER INFORMATION: Single base extension primer

<400> SEQUENCE: 41

tttttttttt tttttttttt tttttttttt tttttttttt tttatagttc tttcctagac     60
```

```
<210> SEQ ID NO 42
<211> LENGTH: 66
<212> TYPE: DNA
<213> ORGANISM: Artificial Sequence
<220> FEATURE:
<223> OTHER INFORMATION: Single base extension primer

<400> SEQUENCE: 42

tttttttttt tttttttttt tttttttttt tttttttttt tttttctgc tcagcaagca    60

gttcca                                                               66
```

ASSOCIATION OF POLYMORPHISMS IN THE *SOST* GENE REGION WITH BONE MINERAL DENSITY

CROSS-REFERENCE TO RELATED APPLICATION

This application claims the benefit of U.S. Provisional Patent Application No. 60/370,088, filed Apr. 3, 2002, which is incorporated herein by reference in its entirety.

BACKGROUND OF THE INVENTION

1. Field of the Invention

The present invention relates to the field of molecular biology, and more particularly, the detection of nucleotide polymorphisms including single nucleotide polymorphisms, and still more particularly nucleotide polymorphisms associated with osteoporosis.

2. Description of the Related Art

Two or three distinct phases of changes to bone mass occur over the life of an individual (see Riggs, *West J. Med.* 154: 63-77, 1991). The first phase occurs in both men and women, and proceeds to attainment of a peak bone mass. This first phase is achieved through linear growth of the endochondral growth plates, and radial growth due to a rate of periosteal apposition. The second phase begins around age 30 for trabecular bone (flat bones such as the vertebrae and pelvis) and about age 40 for cortical bone (e.g., long bones found in the limbs) and continues to old age. This phase is characterized by slow bone loss, and occurs in both men and women. In women, a third phase of bone loss also occurs, most likely due to postmenopausal estrogen deficiencies. During this phase alone, women may lose an additional 10% of bone mass from the cortical bone and 25% from the trabecular compartment (see Riggs, supra).

Loss of bone mineral content can be caused by a wide variety of conditions including, for instance, osteoporosis, osteopenia, bone dysplasia and bone fracture, and may result in significant medical problems. For example, osteoporosis is a debilitating disease in humans characterized by marked decreases in skeletal bone mass and mineral density, structural deterioration of bone including degradation of bone microarchitecture and corresponding increases in bone fragility and susceptibility to fracture in afflicted individuals. Osteoporosis in humans is preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). Osteoporosis is one of the most expensive diseases for the health care system, costing tens of billions of dollars annually in the United States. In addition to health care-related costs, long-term residential care and lost working days add to the financial and social costs of this disease. Worldwide approximately 75 million people are at risk for osteoporosis. See, e.g., Eisman, 1999 *Endocrine Rev.* 20:788; Giguere et al., 2000 *Clin. Genet.* 57:161; Zmuda et al., 1999 Genetic Epidemiol. 16:356; Uitterlinden, 1999 European Calcified Tissue Society on the World Wide Web at ectsoc.orq/reviews/005uitt.htm.

The frequency of osteoporosis in the human population increases with age, and among Caucasians is predominant in women (who comprise 80% of the osteoporosis patient pool in the United States). The increased fragility and susceptibility to fracture of skeletal bone in the aged is aggravated by the greater risk of accidental falls in this population. More than 1.5 million osteoporosis-related bone fractures are reported in the United States each year. Fractured hips, wrists, and vertebrae are among the most common injuries associated with osteoporosis. Hip fractures in particular are extremely uncomfortable and expensive for the patient, and for women correlate with high rates of mortality and morbidity.

Although osteoporosis has been defined as an increase in the risk of fracture due to decreased bone mass, none of the presently available treatments for skeletal disorders can substantially increase the bone density of adults. There is a strong perception among all physicians that drugs are needed which could increase bone density in adults, particularly in the bones of the wrist, spinal column and hip that are at risk in osteopenia and osteoporosis.

Current strategies for the prevention of osteoporosis may offer some benefit to individuals but cannot ensure resolution of the disease. These strategies include moderating physical activity (particularly in weight-bearing activities) with the onset of advanced age, including adequate calcium in the diet, and avoiding consumption of products containing alcohol or tobacco. For patients presenting with clinical osteopenia or osteoporosis, all current therapeutic drugs and strategies are directed to reducing further loss of bone mass by inhibiting the process of bone absorption, a natural component of the bone remodeling process that occurs constitutively.

For example, estrogen is now being prescribed to retard bone loss. There is, however, some controversy over whether there is any long term benefit to patients and whether there is any effect at all on patients over 75 years old. Moreover, use of estrogen is believed to increase the risk of breast and endometrial cancer.

High doses of dietary calcium, with or without vitamin D has also been suggested for postmenopausal women. However, high doses of calcium can often have unpleasant gastrointestinal side effects, and serum and urinary calcium levels must be continuously monitored (see Khosla and Rigss, *Mayo Clin. Proc.* 70:978-982, 1995).

Other therapeutics which have been suggested include calcitonin, bisphosphonates, anabolic steroids and sodium fluoride. Such therapeutics however, have undesirable side effects (e.g., calcitonin and steroids may cause nausea and provoke an immune reaction, bisphosphonates and sodium fluoride may inhibit repair of fractures, even though bone density increases modestly) that may prevent their usage (see Khosla and Rigss, supra).

No currently practiced therapeutic strategy involves a drug that stimulates or enhances the growth of new bone mass. Further the present invention provides methods for determining whether someone is susceptible to osteoporosis. Further, the present invention provides other, related advantages.

Summary of the Invention It is an aspect of the present invention to provide a method for determining a risk for or presence of altered bone mineral density in a subject, comprising determining a presence or absence of at least one sclerostin gene region nucleotide polymorphism in a biological sample from a subject, the sample comprising DNA having a sequence that corresponds to at least 50 consecutive nucleotides that are present in SEQ ID NO:1, wherein the presence of at least one sclerostin gene region nucleotide polymorphism at a position that corresponds to a non-coding region of SEQ ID NO:1 indicates an increased risk of altered bone mineral density. In one embodiment the invention provides a method for determining a risk for or presence of altered bone mineral density in a subject, comprising determining a presence or absence of at least one sclerostin gene region nucleotide polymorphism in a biological sample from a subject, said sample comprising DNA having a sequence that corresponds to at least 50 consecutive nucleotides that are present in SEQ ID NO:1; and determining gender of the subject, wherein the presence of at least one gender-associated sclerostin gene region nucleotide polymorphism indicates an increased risk of altered bone mineral density. In another embodiment the invention provides a method for determining a risk for or presence of altered bone mineral density in a subject, comprising determining a presence or absence of at least one sclerostin gene region nucleotide polymorphism in a biological sample from a subject, said sample comprising DNA having a sequence that corresponds to at least 50 consecutive nucleotides that are present in SEQ ID NO:1, wherein the presence of at least one sclerostin gene region nucleotide polymorphism in the sample indicates an increased risk of altered bone mineral density, and wherein the polymorphism is located at a nucleotide that corresponds to a nucleotide position of SEQ ID NO:1 that is selected from position 4103, 17966, 18293, 58083, 74235 and 91068.

In another embodiment there is provided a method for determining a risk for or presence of altered bone mineral density in a subject, comprising determining a presence or absence of at least one sclerostin gene region nucleotide polymorphism in a biological sample from a female subject, said sample comprising DNA having a sequence that corresponds to at least 50 consecutive nucleotides that are present in SEQ ID NO:1, wherein the presence of at least one sclerostin gene region nucleotide polymorphism in the sample indicates an increased risk of decreased bone mineral density, and wherein the polymorphism is located at a nucleotide that corresponds to a GGA trinucleotide insertion between positions 10565 and 10566 in SEQ ID NO:1. In another embodiment the invention provides a method for determining a risk for or presence of altered bone mineral density in a subject, comprising determining a presence or absence of at least one sclerostin gene region nucleotide polymorphism in a biological sample from a male subject, said sample comprising DNA having a sequence that corresponds to at least 50 consecutive nucleotides that are present in SEQ ID NO:1, wherein the presence of at least one sclerostin gene region nucleotide polymorphism in the sample indicates an increased risk of increased bone mineral density, and wherein the polymorphism is located at a nucleotide that corresponds to position 91068 in SEQ ID NO:1. In a further embodiment the polymorphism at position 91068 comprises an A91068G substitution.

Turning to another embodiment of the present invention, there is provided a method for determining a risk for or presence of altered bone mineral density in a subject, comprising determining a presence or absence of at least one sclerostin gene region nucleotide polymorphism in a biological sample from a subject, said sample comprising DNA having a sequence that corresponds to at least 50 consecutive nucleotides that are present in SEQ ID NO:1, wherein the presence of at least one sclerostin gene region nucleotide polymorphism in the sample indicates an increased risk of altered bone mineral density, and wherein the polymorphism is located at a nucleotide that corresponds to a nucleotide position of SEQ ID NO:1 that is not between positions 10354 and 16757.

In another embodiment the invention provides a method for determining a risk for or presence of altered bone mineral density in a subject, comprising determining a presence or absence of at least one sclerostin gene region nucleotide polymorphism in a biological sample from a subject, said sample comprising DNA having a sequence that corresponds to at least 50 consecutive nucleotides that are present in SEQ ID NO:1, wherein the presence of at least one sclerostin gene region nucleotide polymorphism in the sample indicates an increased risk of altered bone mineral density, and wherein the polymorphism is not located at a nucleotide that corresponds to a nucleotide position of SEQ ID NO:1 that is selected from the group consisting of position 10357 and a trinucleotide insertion between positions 10565 and 10566.

In still another embodiment the invention provides method for determining a risk for or presence of altered bone mineral density in a first subject suspected of having or being at risk for having altered bone mineral density, comprising determining a presence or absence of at least one sclerostin gene region nucleotide polymorphism that is associated with altered bone mineral density in each of a first and a second biological sample comprising DNA having a sequence that corresponds to at least 50 consecutive nucleotides that are present in SEQ ID NO:1, said first biological sample being obtained from said first subject and said second sample being obtained from a second subject known to be free of a risk or presence of altered bone mineral density, wherein the presence of at least one sclerostin gene region nucleotide polymorphism that is associated with altered bone mineral density in said first biological sample and the absence of said sclerostin gene region nucleotide polymorphism at a corresponding nucleotide in said second biological sample indicates an increased risk of altered bone mineral density, and wherein the polymorphism is not located at a nucleotide that corresponds to a nucleotide position of SEQ ID NO:1 that is selected from the group consisting of position 10357 and a trinucleotide insertion between positions 10565 and 10566.

According to another embodiment of the invention there is provided a method for determining a risk for or presence of altered bone mineral density in a first subject suspected of having or being at risk for having altered bone mineral density, comprising determining a presence or absence of at least one sclerostin gene region nucleotide polymorphism that is associated with altered bone mineral density in each of a first and a second biological sample comprising DNA having a sequence that corresponds to at least 50 consecutive nucleotides that are present in SEQ ID NO:1, said first biological sample being obtained from said first subject and said second sample being obtained from a second subject known to be free of a risk or presence of altered bone mineral density, wherein the presence of at least one sclerostin gene region nucleotide polymorphism that is associated with altered bone mineral density in said first biological sample and the absence of said sclerostin gene region nucleotide polymorphism at a corresponding nucleotide in said second biological sample indicates an increased risk of altered bone mineral density, and wherein the polymorphism is located at a nucleotide that corresponds to a nucleotide position of SEQ ID NO:1 that is not between positions 10354 and 16757. According to certain further embodiments of the above described methods, at least one sclerostin gene region nucleotide polymorphism is selected from a single nucleotide substitution at a nucleotide position in SEQ ID NO:1 that is selected from C4103G, C17966G, A18293G, T58083C, A74235G and A91068G In certain other further embodiments of the above described methods, the presence in a sample from a female subject of at least one sclerostin gene region nucleotide polymorphism that is a GGA trinucleotide insertion between nucleotide positions 10565 and 10566 in SEQ ID NO:1 indicates an increased risk of decreased bone mineral density. In certain other further embodiments of the above described methods the step of determining comprises contacting at least one biological sample with at least one oligonucleotide primer having a nucleotide sequence that is complementary to a portion of a nucleic acid molecule having the sequence set forth in SEQ ID NO:1, under conditions and for a time sufficient to allow hybridization of said primer to the DNA. In certain further embodiments the method comprises detecting hybridization and extension of the oligonucleotide primer to produce a product, and therefrom determining the presence or absence of at least one sclerostin gene region nucleotide polymorphism. In certain other further embodiments of methods described above, the step of determining comprises contacting each of said first and second biological samples with an oligonucleotide primer having a nucleotide sequence that is complementary to a sequence present in the DNA of said first sample and present in the DNA of said second sample, under conditions and for a time sufficient to allow hybridization of said primer to the DNA; and detecting hybridization and extension of the primer to the DNA of the first sample to produce a first product and hybridization and extension of the primer to the DNA of the second sample to produce a second product distinguishable from said first product, and therefrom determining the presence or absence of at least one sclerostin gene region nucleotide polymorphism. According to certain further embodiments the DNA in the sample is amplified. According to certain other further embodiments the DNA in the first sample is amplified and the DNA in the second sample is amplified. According to certain other further embodiments the oligonucleotide primer comprises a nucleic acid molecule which comprises a nucleotide sequence set forth in a sequence selected from SEQ ID NOS: 2, 3, 5, 6, 8, 9, 11, 12, 14, 15, 17, 18, 23, 24, 26, 27, 29 and 30.

Turning to another aspect, the present invention provides an isolated polynucleotide comprising a sclerostin gene region polymorphism, the polynucleotide comprising a nucleotide sequence selected from (a) the sequence set forth in SEQ ID NO:1 and containing at least one sclerostin gene region nucleotide polymorphism, wherein said polymorphism is located at a nucleotide that corresponds to a nucleotide position of SEQ ID NO:1 that is selected from position 4103, 10357, 10566, 17966, 18293, 58083, 74235 and 91068, (b) the sequence set forth in SEQ ID NO:1 and containing a single nucleotide substitution at a position corresponding to a nucleotide position in SEQ ID NO:1 that is selected from C4103G, C10357T, C17966G, A18293G, T58083C, A74235G and A91068G, (c) the sequence set forth in SEQ ID NO:1 and containing a GGA trinucleotide insertion between nucleotide positions 10565 and 10566 in SEQ ID NO:1, (d) the sequence set forth in any one of SEQ ID NOS:4, 7, 10, 13, 16, 19, 22, 25, 28, 31, 32 and 33, and (e) a sequence that is fully complementary to any sequence of (a)-(d).

In another embodiment the invention provides an isolated polynucleotide of at least 25 nucleotides comprising a polynucleotide sequence that corresponds to a portion of the nucleic acid sequence set forth in SEQ ID NO:1 in which at least one sclerostin gene region nucleotide polymorphism is present, wherein the polymorphism is located at a nucleotide that corresponds to a nucleotide position of SEQ ID NO:1 that is not between positions 10354 and 16757. In a further embodiment the sclerostin gene region nucleotide polymorphism is selected from (a) a single nucleotide substitution at a position corresponding to a nucleotide position in SEQ ID NO:1 that is selected from C4103G, C10357T, C17966G, A18293G, T58083C, A74235G and A91068G, and (b) a GGA trinucleotide insertion at a position corresponding to a nucleotide position in SEQ ID NO:1 that is between nucleotide positions 10565 and 10566. In another embodiment then invention provides an isolated polynucleotide comprising a nucleotide sequence selected from SEQ ID NOS:2, 3, 5, 6, 8, 9, 11, 12, 14, 15, 17, 18, 23, 24, 26, 27, 29 and 30. In certain embodiments the invention provides an immobilized polynucleotide, comprising any of the above described polynucleotides coupled to a solid support, and in certain other embodiments the invention provides a nucleic acid array comprising a plurality of such isolated nucleic acid molecules immobilized on a solid support. In another embodiment there is provided a kit for identifying a sclerostin gene region polymorphism, comprising any of the above-described isolated polynucleotides and an ancillary reagent.

In another embodiment the invention provides a method of stratifying human subjects according to sclerostin gene region polymorphisms, comprising determining presence or absence of at least one sclerostin gene region polymorphism in a biological sample obtained from each of a plurality of subjects, wherein (i) presence or absence of a sclerostin gene region polymorphism indicates altered bone mineral density, and (ii) the polymorphism is located at a nucleotide that corresponds to a nucleotide position of SEQ ID NO:1 that is not between positions 10354 and 16757, and therefrom stratifying said subjects. In a further embodiment the sclerostin gene region polymorphism is selected from (a) a single nucleotide substitution at a position corresponding to a nucleotide position in SEQ ID NO:1 that is selected from C4103G, C10357T, C17966G, A18293G, T58083C, A74235G and A91068G, and (b) a GGA trinucleotide insertion at a position corresponding to a nucleotide position in SEQ ID NO:1 that is between nucleotide positions 10565 and 10566. In certain further embodiments the method comprises determining gender of each subject, wherein the presence of at least one gender-associated sclerostin gene region nucleotide polymorphism indicates an increased risk of altered bone mineral density, and in certain still further embodiments the gender-associated sclerostin gene region nucleotide polymorphism is selected from (a) a GGA trinucleotide insertion at a position corresponding to a nucleotide position in SEQ ID NO:1 that is between nucleotide positions 10565 and 10566, presence of which in a female subject indicates an increased risk of decreased bone mineral density, and (b) an A-to-G substitution at a position corresponding to nucleotide position 91068 in SEQ ID NO:1, presence of which in a male subject indicates an increased risk of increased bone mineral density.

Accordingly, the present invention provides nucleotide sequences that are associated with polymorphisms in the SOST gene region. Sequences associated with these nucleotide polymorphisms include SEQ ID NOs: 4, 7, 10, 13, 16, 19, 22, 25, 28, 31, 32 and 33 as identified herein. As described in greater detail below, diseases and/or conditions associated with bone density can be detected and/or predicted by the methods of the current invention using nucleotide sequences disclosed herein. Exemplary diseases and/or conditions include without limitation, osteopenia, osteoporosis and gum diseases.

These and other aspects of the present invention will become evident upon reference to the following detailed description and attached drawings. In addition, various references are set forth herein which describe in more detail certain aspects of this invention, and are therefore incorporated by reference in their entireties as if fully set forth herein.

BRIEF DESCRIPTION OF THE SEVERAL VIEWS OF THE DRAWING(S)

FIG. 1 shows that the effect of the genotypes associated with bone density strongly increase with age.

BRIEF DESCRIPTION OF THE SEQUENCE IDENTIFIERS

SEQ ID NO:1 sets forth the DNA sequence of the SOST gene region, including the SOST gene body and extended flanking sequence.

SEQ ID NO:2 sets forth the DNA sequence for the forward primer used in the detection of the SRP1 polymorphism.

SEQ ID NO:3 sets forth the DNA sequence for the reverse primer used in the detection of the SRP1 polymorphism.

SEQ ID NO:4 sets forth the DNA sequence corresponding to the SRP1 polymorphism.

SEQ ID NO:5 sets forth the DNA sequence for the forward primer used in the detection of the SRP2 polymorphism.

SEQ ID NO:6 sets forth the DNA sequence for the reverse primer used in the detection of the SRP2 polymorphism.

SEQ ID NO:7 sets forth the DNA sequence corresponding to the SRP2 polymorphism.

SEQ ID NO:8 sets forth the DNA sequence for the forward primer used in the detection of the SRP3 polymorphism.

SEQ ID NO:9 sets forth the DNA sequence for the reverse primer used in the detection of the SRP3 polymorphism.

SEQ ID NO:10 sets forth the DNA sequence corresponding to the SRP3 polymorphism.

SEQ ID NO:11 sets forth the DNA sequence for the forward primer used in the detection of the alternative SRP2+SRP3 polymorphism.

SEQ ID NO:12 sets forth the DNA sequence for the reverse primer used in the detection of the alternative SRP2+SRP3 polymorphism.

SEQ ID NO:13 sets forth the DNA sequence corresponding to the alternative SRP2+SRP3 polymorphism.

SEQ ID NO:14 sets forth the DNA sequence for the forward primer used in the detection of the SRP5 polymorphism.

SEQ ID NO:15 sets forth the DNA sequence for the reverse primer used in the detection of the SRP5 polymorphism.

SEQ ID NO:16 sets forth the DNA sequence corresponding to the SRP5 polymorphism.

SEQ ID NO:17 sets forth the DNA sequence for the forward primer used in the detection of the SRP6 polymorphism.

SEQ ID NO:18 sets forth the DNA sequence for the reverse primer used in the detection of the SRP6 polymorphism.

SEQ ID NO:19 sets forth the DNA sequence corresponding to the SRP6 polymorphism.

SEQ ID NO:20 sets forth the DNA sequence for the forward primer used in the detection of the alternate SRP5+SRP6 polymorphism.

SEQ ID NO:21 sets forth the DNA sequence for the reverse primer used in the detection of the alternate SRP5+SRP6 polymorphism.

SEQ ID NO:22 sets forth the DNA sequence corresponding to the alternate SRP5+SRP6 polymorphism.

SEQ ID NO:23 sets forth the DNA sequence for the forward primer used in the detection of the SRP7 polymorphism.

SEQ ID NO:24 sets forth the DNA sequence for the reverse primer used in the detection of the SRP7 polymorphism.

SEQ ID NO:25 sets forth the DNA sequence corresponding to the SRP7 polymorphism.

SEQ ID NO:26 sets forth the DNA sequence for the forward primer used in the detection of the SRP8 polymorphism.

SEQ ID NO:27 sets forth the DNA sequence for the reverse primer used in the detection of the SRP8 polymorphism.

SEQ ID NO:28 sets forth the DNA sequence corresponding to the SRP8 polymorphism.

SEQ ID NO:29 sets forth the DNA sequence for the forward primer used in the detection of the SRP9 polymorphism.

SEQ ID NO:30 sets forth the DNA sequence for the reverse primer used in the detection of the SRP9 polymorphism.

SEQ ID NO:31 sets forth the DNA sequence corresponding to the SRP9 polymorphism.

SEQ ID NO:32 is an alternative sequence for the SRP3 polymorphism.

SEQ ID NO:33 is an alternative sequence for the SRP2+SRP3 polymorphism.

SEQ ID NO:34 presents the human chromosome 17 sequence set forth in EMBL Acc. No. AC003098.

DETAILED DESCRIPTION OF THE INVENTION

The present invention relates to the unexpected discovery of specific nucleotide polymorphisms in the sclerostin gene region of human chromosome 17. More specifically, the invention relates to the surprising determination of sclerostin gene region nucleotide polymorphisms (SRP) in non-protein coding regions of the sclerostin gene region, including SRP the presence of which in a DNA sample from a subject correlates with an increased likelihood that the subject has, or is at risk for having, altered (e.g., increased or decreased in a statistically significant manner relative to a control subject) bone mineral density. The invention is thus directed generally to compositions and methods for diagnosing the risk or presence of altered bone mineral density (BMD) in a subject, and to compositions and methods for the identification of agents that may be suitable for treating diseases, disorders or other conditions associated with altered BMD (i.e., BMD that is increased or decreased in a statistically significant manner relative to normal control BMD levels). The invention may be useful for pharmacogenomic purposes, for example to stratify patient populations according to the suitability of particular therapeutic agents for use in such populations.

As also discussed above, "altered bone mineral density" may refer to any condition or state, including those that accompany a disease, where any structure or activity that is directly or indirectly related to formation and/or maintenance of bone mass has been changed in a statistically significant manner. Altered BMD may have its origin in cells and tissues (or their products) that are proximately involved in bone formation and maintenance as well as in cells and tissues (or their products) acting from distal sites to regulate bone formation or maintenance, in direct interactions between genes and/or gene products of such cells and tissues, or in structural or functional changes that occur as the result of interactions between intermediates that may be formed as the result of such interactions, including metabolites, catabolites, substrates, precursors, cofactors and the like.

According to the present invention, determination or detection of one or more sclerostin gene region polymorphisms provide a novel and useful parameter for diagnosing the risk or presence of altered BMD in a subject, and for identifying agents that may be suitable for treating altered BMD. As discussed above and in, e.g., U.S. Pat. Nos. 6,395,511, 6,489,445, and 6,495,736, a number of conditions are associated with alterations in BMD. Further, detection of an appropriate parameter can provide preclinical evidence for a risk of or predisposition to a disease or disorder that is characterized by altered BMD. In particular, and according to non-limiting theory, in certain embodiments the invention contemplates determining in a subject at a relatively early age an increased risk, predisposition, likelihood or the like of the occurrence of altered BMD in the subject, even where such altered BMD may not manifest itself until the subject has attained a relatively advanced age, which may be an age greater than 30, 35, 40, 45, 50, 55, 60, 65 or more years.

A "sclerostin gene region" includes the area of human chromosome 17 that contains the polynucleotide sequence set forth in SEQ ID NO:1. According to the present invention there are provided compositions and methods that derive from the unexpected identification of nucleotide polymorphisms in the genomic DNA of the sclerostin gene region. In particular, there are provided a number of such sclerostin gene region nucleotide polymorphisms (SRPs), which include polymorphisms in non-coding regions of SEQ ID NO:1 (e.g., segments or portions of SEQ ID NO:1 that are comprised of polynucleotide sequences which do not encode the amino acid sequences that comprise a sclerostin polypeptide, such as the sclerostin polypeptides described in U.S. Pat. No. 6,489,445 and referred to therein as "Beer" proteins). As described in greater detail herein, the occurrence of certain SRPs in a sample from a subject can be correlated with (e.g., shown with statistical significance to indicate) an increased risk for altered BMD in the subject. Expressly excluded from certain preferred embodiments of the invention are sclerostin gene region nucleotide polymorphisms that are located at a nucleotide that corresponds to a nucleotide position that is between positions 10354 and 16757 of SEQ ID NO:1. Expressly excluded from certain other preferred embodiments of the invention are sclerostin gene region nucleotide polymorphisms that are located at a nucleotide that corresponds to nucleotide position 10357 of SEQ ID NO:1, or that corresponds to a trinucleotide insertion between positions 10565 and 10566 of SEQ ID NO:1. Also excluded from certain preferred embodiments of the invention are sclerostin gene region nucleotide polymorphisms that are located at a nucleotide that corresponds to position 6136, 6140 and/or 9047 of EMBL Accession No. AC003098 [SEQ ID NO:34] (see, e.g., WO 01/98491), and to nucleotide positions 15095, 15091 and 12184 of SEQ ID NO:1.

Determination of a sclerostin gene region polymorphism may involve strong but not necessarily absolute nucleotide sequence conservation when corresponding portions of sclerostin gene region DNA in a sample from a subject suspected of having or being at risk for having altered BMD, and sclerostin gene region DNA in a sample from a subject known to be free of such risk, are compared, as discussed herein. The invention provides compositions and methods that include the use of nucleic acid molecules, or portions thereof, having nucleotide sequences that are found in the human DNA sequence set forth in SEQ ID NO:1 and fragments of SEQ ID NO:1 that are suitable for use as oligonucleotide primers in nucleic acid primer extension or amplification techniques, as hybridization probes for the detection of complementary nucleotide sequences in a sample or for any number of additional uses that are well known to those familiar with the art. According to the various embodiments described herein, DNA may be nuclear DNA, including chromosomal and non-chromosomal DNA, which in preferred embodiments comprises all or a portion of a sclerostin gene region.

Nucleic acid sequences within the scope of the invention include isolated DNA and RNA sequences that specifically hybridize under conditions of moderate or high stringency to DNA nucleotide sequences such as those found in SEQ ID NO:1, including specific DNA sequences disclosed herein or fragments thereof, and their complements. As used herein, conditions of moderate stringency, as known to those having ordinary skill in the art, and as defined by Sambrook et al., *Molecular Cloning: A Laboratory Manual,* 2nd Ed. Vol. 1, pp. 1.101-104, Cold Spring Harbor Laboratory Press (1989), include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution), and washing conditions of about 50-60° C., 0.5×SSC, 0.1% SDS. Conditions of high stringency are defined as hybridization conditions as above, and with washing at 60-68° C., 0.2×SSC, 0.1% SDS. In other embodiments, hybridization to a DNA nucleotide sequence may be at normal stringency, which is approximately 25-30° C. below Tm of the native duplex (e.g., 5×SSPE, 0.5% SDS, 5×Denhardt's solution, 50% formamide, at 42° C. or equivalent conditions), at low stringency hybridizations, which utilize conditions approximately 40° C. below Tm, or at high stringency hybridizations, which utilize conditions approximately 10° C. below Tm. The skilled artisan will recognize that the temperature, salt concentration, and chaotrope composition of hybridization and wash solutions may be adjusted as necessary according to factors such as the length and nucleotide base composition of the probe. (See also, e.g., Ausubel et al., *Current Protocols in Molecular Biology*, Greene Publishing, 1987.) As also known to those having ordinary skill in the art, variations in stringency of hybridization conditions may be achieved by altering the time, temperature and/or concentration of the solutions used for pre-hybridization, hybridization and wash steps, and suitable conditions may also depend in part on the particular nucleotide sequences of the probe used, and of the blotted, proband nucleic acid sample. Accordingly, it will be appreciated that suitably stringent conditions can be readily selected without undue experimentation where a desired selectivity of the probe is identified, based on its ability to hybridize to one or more certain proband sequences while not hybridizing to certain other proband sequences.

An "isolated nucleic acid molecule" refers to a polynucleotide molecule in the form of a separate fragment or as a component of a larger nucleic acid construct, that has been separated from its source cell (including the chromosome it normally resides in) at least once, preferably in a substantially pure form. Isolated nucleic acids may be nucleic acids having particular disclosed nucleotide sequences or may be regions, portions or fragments thereof. Those having ordinary skill in the art are able to prepare isolated nucleic acids having the complete nucleotide sequence, or the sequence of any portion of a particular isolated nucleic acid molecule, when provided with the appropriate nucleic acid sequence information as disclosed herein. Nucleic acid molecules may be comprised of a wide variety of nucleotides, including DNA, RNA, nucleotide analogues such as phosphorothioates or peptide nucleic acids, or other analogues with which those skilled in the art will be familiar, or some combination of these.

In one embodiment, known DNA sequences derived from SEQ ID NO:1 may be utilized to design oligonucleotide primers or hybridization probes suitable for screening genomic libraries. Preferably, such oligonucleotide primers or probes are 18, 19, 20, 21, 22, 23, 24, 25, 26, 27, 28, 29, 30, 31-35, 36-40, 41-50, 51-60, 61-75 or more bases in length and have sequences that, under the hybridization conditions selected, hybridize to complementary DNA sequences lacking nucleotide substitutions, insertions, duplications or deletions ("polymorphisms" or "mutations") relative to the corresponding region of the DNA sequence of SEQ ID NO:1.

Portions of a polymorphic DNA sequence (or of an oligonucleotide primer or probe) and the DNA sequence of SEQ ID NO:1 are regarded as "corresponding" nucleic acid sequences, regions, fragments or the like, based on the convention for numbering DNA nucleic acid positions according to SEQ ID NO:1, wherein a candidate polymorphic DNA sequence (or primer or probe) is aligned with the DNA sequence of SEQ ID NO:1 such that at least 70%, preferably at least 80% and more preferably at least 90% of the nucleotides in a given sequence of at least 18-20 consecutive nucleotides of a sequence are identical. In certain preferred embodiments, a polymorphic DNA sequence is greater than 95% identical to a corresponding DNA sequence that is present in SEQ ID NO:1. In certain particularly preferred embodiments, an oligonucleotide primer or probe, or a region of a polymorphic DNA sequence that lacks any polymorphisms, is identical to a corresponding portion of SEQ ID NO:1. Those oligonucleotide probes having sequences that are identical in corresponding regions of SEQ ID NO:1 may be identified and selected following hybridization target DNA sequence analysis, to verify the absence of mutations in the target DNA sequence.

DNA containing one or more sclerostin gene region polymorphisms may be isolated from genomic DNA, typically by first generating an appropriate DNA library through techniques for constructing libraries that are known in the art (see Sambrook et al., *Molecular Cloning: A Laboratory Manual*, Cold Spring Harbor Press, 1989) or purchased from commercial sources (e.g., Clontech, Palo Alto, Calif.). Briefly, genomic DNA libraries can be constructed in chromosomal vectors, such as YACs (yeast artificial chromosomes), bacteriophage vectors, such as pBeloBAC11, λEMBL3, λgt10, cosmids, or plasmids. Alternatively, isolated DNA may be prepared by preferentially amplifying sclerostin gene region DNA sequences present in biological samples using, for example, DNA amplification methodologies such as PCR or other amplification techniques that are well known in the art, with suitable oligonucleotide primers complementary to such DNA sequences as disclosed herein. To facilitate hybridization detection, the oligonucleotide may be conveniently labeled, generally at the 5' end, with a reporter molecule, such as a radionuclide, e.g., $^{32}P$, enzymatic label, protein label, fluorescent label, biotin or other suitable labeling moieties known in the art.

Such libraries are then generally plated as phage or colonies, depending upon the vector used. Subsequently, a plate replica to which the colonies or phage have been transferred, such as a nitrocellulose or nylon membrane or the like, is probed to identify candidate clones that contain the polymorphic sclerostin gene region DNA sequence. Such candidates may be verified as containing such polymorphisms by any of various means including, for example, DNA sequence analysis or hybridization with a second, non-overlapping probe selected as described above to hybridize with target DNA sequences lacking nucleotide substitutions, deletions, duplications or insertions relative to the corresponding portion of the DNA sequence of SEQ ID NO:1.

Once a library is identified as containing DNA having at least one scleorstin gene region polymorphism, the polymorphic DNA can be isolated by amplification. Briefly, when using genomic library DNA as a template, amplification primers are designed based upon a DNA sequence that has been determined (e.g., SEQ ID NO:1) and primer "walking" is used to select primers that anneal to DNA regions within such sequences. The primers preferably have a GC content of about 50% and contain restriction sites to facilitate cloning. Primers typically do not have self-complementary sequences, nor do they contain complementary sequences at their 3' end (to prevent primer-dimer formation). The primers are annealed to genomic DNA and sufficient amplification cycles are performed to yield a product readily visualized by gel electrophoresis and staining. The amplified fragment is purified and inserted into a vector, such as λgt10 or pBS(M13+), and propagated. Confirmation of the nature of the fragment is obtained by DNA sequence analysis.

Oligonucleotide primers or probes as described above for use in isolating polymorphic sclerostin gene region DNA from genomic DNA may also be useful in the present invention for determining the presence of a sclerostin gene region nucleotide polymorphism by any of a variety of techniques well known in the art for determining the amount of specific nucleic acid target sequences present in a sample based on specific hybridization of a primer to the target sequence. Optionally, in certain of these techniques, hybridization precedes nucleotide polymerase catalyzed extension of the primer using the strand containing the target sequence as a template, and/or ligation of oligonucleotides hybridized to adjacent target sequences, and embodiments of the invention using primer extension are particularly preferred. For examples of references on such quantitative detection techniques, including those that may be used to detect nucleotide insertions, substitutions, duplications or deletions in a portion of a sclerostin gene region DNA sequence site near an oligonucleotide primer target hybridization site that corresponds to a portion of the DNA sequence of SEQ ID NO:1, and further including those that involve primer extension, see, for example, Kuppuswamy et al. (*Proc. Nat. Acad. Sci. USA* 88:1143, 1991), Botstein et al. (*Am. J. Hum. Gen.* 32:314, 1980), Gibbs et al. (*Nucl. Ac. Res.* 17:2437, 1989), Newton et al. (*Nucl. Ac. Res.* 17:2503, 1989), Syvanen et al., (*Genomics* 8:684, 1990), Grossman et al. (*Nucl. Ac. Res.* 22:4527, 1994), and Saiki et al. (*Proc. Nat. Acad. Sci.* 86:6230, 1989), all of which are hereby incorporated by reference.

A particularly useful method for this purpose is the primer extension assay disclosed by Krook et al. (*Hum. Molec. Genet.* 1:391, 1995) which teaches modification of primer extension reactions to detect multiple nucleotide substitutions, insertions, deletions or other mutations. Other examples of useful techniques for quantifying the presence of specific nucleic acid target sequences in a sample include but need not be limited to labeled probe hybridization to the target nucleic acid sequences with or without first partially separating target nucleic acids from other nucleic acids present in the sample.

Examples of other useful techniques for determining the amount of specific nucleic acid target sequences (e.g., a target sequence containing a polymorphism such as a sclerostin gene region polymorphism as provided herein) present in a sample based on specific hybridization of a primer to the target sequence include specific amplification of target nucleic acid sequences and quantification of amplification products, including but not limited to polymerase chain reaction (PCR, Gibbs et al., *Nucl. Ac. Res.* 17:2437, 1989), transcriptional amplification systems, strand displacement amplification and self-sustained sequence replication (3SR, Gingeras et al., *J. Infect. Dis.* 164:1066, 1991), the cited references for which are hereby incorporated in their entireties. Examples of other useful techniques include ligase chain reaction (e.g., Landegren et al., *Science* 241:1077, 1988; Nickerson et al., *Proc. Natl. Acad. Sci. USA* 87:8923 1990; Barany, *Proc. Natl. Acad. Sci. USA* 88:189, 1991; Wu et al., *Genomics* 4:560, 1989), single stranded conformational polymorphism analysis, Q-beta replicase assay, restriction fragment length polymorphism (RFLP, Botstein et al., *Am. J. Hum. Gen.* 32:314, 1980) analysis, cycled probe technology and solid-phase DNA-binding assays such as those disclosed in U.S. Pat. No. 6,340,566, as well as other suitable methods that will be known to those familiar with the art.

Sequence length or molecular mass of polynucleotides, for example, primer extension assay products containing sclerostin gene region polymorphisms, may be determined using any known method for characterizing the size of nucleic acid sequences with which those skilled in the art are familiar. In a preferred embodiment, such products are characterized by capillary electrophoresis. In another preferred embodiment, primer extension products are characterized by mass spectrometry (MS), which may further include matrix assisted laser desorption ionization/time of flight (MALDI-TOF) analysis or other MS techniques known to those having skill in the art. See, for example, U.S. Pat. No. 5,622,824, U.S. Pat. No. 5,605,798 and U.S. Pat. No. 5,547,835. In another preferred embodiment, primer extension products are characterized by liquid or gas chromatography, which may further include high performance liquid chromatography (HPLC), gas chromatography-mass spectrometry (GC-MS) or other well known chromatographic methodologies.

Also contemplated according to the compositions and methods of the present invention are uses of the isolated nucleic acid molecules described herein as immobilized polynucleotides, which may include a polynucleotide that is covalently or non-covalently coupled to a solid support. Coupling chemistries and selection of support materials are well known in the art, and such supports may include supports made of glass, silica, metal, plastic, fiber, resin, polymers and the like, including for example cellulose, nitrocellulose, polyacetate, polycarbonate, polystyrene, polyester, polyvinyldifluorobenzene, nylon, carbon fiber or any other suitable solid material for the intended use and with which those skilled in the art will be familiar. In certain related embodiments one or a plurality of the nucleic acid molecules described herein may be provided as an array immobilized on a solid support, which includes any of a number of well known configurations for spatially arranging such polynucleotides in an identifiable (e.g., addressable) fashion. The skilled artisan will be familiar with various compositions and methods for making and using arrays of such solid-phase immobilized nucleic acid arrays. In certain other related embodiments the invention contemplates a kit for identifying a scloerostin gene region polymorphism as provided herein, which kit comprises an isolated polynucleotide as described herein (including solid phase immobilized nucleic acid molecules) and an ancillary reagent such as appropriate buffers, wash solutions, indicators, detection media and the like, depending on the particular assay configuration to be practiced.

As used herein, DNA sequence variability refers to the DNA sequence variation between one DNA sequence and a second DNA sequence. Either the first or the second DNA sequence may be a reference or control sequence such as a wild type sequence. Thus, DNA sequence variability is, for example, the differences in the DNA sequence between the reference or control sequence and another sequence of interest. As used herein, differences between two DNA sequences of interest may be identified by hybridization under conditions which permit base pairing between the two strands. When the hybrid formed between the two strands contains mismatches, then the two DNA sequences contain one or more differences in their base sequences.

As referred to herein, a nucleotide polymorphism represents a change in the DNA sequence from a normal sequence or wild type sequence to a mutated or different sequence. Nucleotide polymorphisms of the current invention can include genetic mutations, single base pair mutations, DNA mismatches, DNA insertions, DNA deletions, DNA transversions, frameshift mutations, damaged DNA, DNA duplications and or other alterations in a normal or wild type DNA sequence. As referred to herein, a single nucleotide polymorphism (SNP) refers to a nucleotide polymorphism which is a single nucleotide variation in the genetic sequence of an organism relative to a standard sequence. It is estimated that the average human will have a SNP every 1000 base pairs (there are ca. 3 billion base pairs in the human genome). Many SNPs are nonconsequential; however, some may render the organism prone to disease.

In one embodiment, the present invention provides nucleotide sequences that are associated with SOST gene region polymorphisms (SRP). Sequences associated with these nucleotide polymorphisms include SEQ ID NOs: 4, 7, 10, 13, 16, 19, 22, 25, 28, 31, 32 and 33 as identified herein.

In another embodiment of the invention, diseases and/or conditions associated with bone density can be detected and/or predicted by the methods of the current invention using nucleotide sequences as identified herein. Exemplary diseases and/or conditions include without limitation, osteopenia, osteoporosis and gum diseases.

As described herein, the present invention provides compositions and methods related to novel polymorphic sclerostin gene region DNA sequences that may differ from known DNA sequences at one or more nucleotide positions as disclosed herein, for example, the SRPs 1-3 and 5-9 described in the Examples and Sequence Listing, and the DNA sequences of SEQ ID NOS:4, 7, 10, 13, 16, 19, 22, 25, 28, and 31-33. Details for obtaining SEQ ID NO:1 are provided below in the Examples. Those having ordinary skill in the art can also readily obtain other isolated sclerostin gene region DNA sequences using well known methodologies including those provided herein and in the cited references, and further including the use of the oligonucleotide primers provided in the Examples. Databases (e.g., GenBank, EMBL) and methods for nucleic acid sequence analysis are also well known in the art, for example, similarity between two sequences may be readily determined using well known computer programs such as the BLAST algorithm (Altschul, *J. Mol. Biol.* 219: 555-565, 1991; Henikoff and Henikoff, *Proc. Natl. Acad. Sci. USA* 89:10915-10919, 1992), which is available at the NCBI website (on the World Wide Web at ncbi.nlm.nih.gov/cgi-bin/BLAST). Default parameters may be used. Examples of other useful computer algorithms are those used in programs such as Align and FASTA, which may be accessed, for example, at the Genestream internet website of the Institut de Genetique Humaine, Montpellier, France (on the World Wide Web at igh.cnrs.fr/home.eng.html) and used with default parameters.

In another particularly preferred embodiment of the invention, sclerostin gene region DNA in a biological sample containing DNA is first amplified by methodologies well known in the art and described herein, such that the amplification products may be used as templates in a method for determining the presence or absence of at least one sclerostin gene region nucleotide in the sample.

Biological samples containing DNA which comprises a sclerostin gene region may comprise any tissue or cell preparation in which genomic DNA may be present. In preferred embodiments such samples comprise DNA having a nucleotide sequence that corresponds to at least 20, 30, 40, 50, 60, 70, 80, 90, 100, 101-200 or more consecutive nucleotides that are present in SEQ ID NO:1, and in other preferred embodiments such samples may comprise DNA having a nucleotide sequence that corresponds to at least 200-500, 501-1,000, 1,000-5,000, 5,001-10,000 or more consecutive nucleotides that are present in SEQ ID NO:1. Biological samples may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. In certain preferred embodiments of the invention, the subject or biological source may be suspected of having or being at risk for having altered BMD, and in certain preferred embodiments of the invention the subject or biological source may be known to be free of a risk or presence of such a condition.

In certain other preferred embodiments where it is desirable to determine whether or not a subject or biological source falls within clinical parameters indicative of altered BMD, signs and symptoms of altered BMD that are accepted by those skilled in the art may be used to so designate a subject or biological source, for example clinical signs referred to in Jouanny et al. (1995 *Arthritis Rheum.* 38:61), Melton (1997 *Fourth International Symposium: Osteoporosis*; National Osteoporosis Foundation, Washington, D.C., p. 23), Consensus Development Conference: Diagnosis, prophylaxis and treatment of osteoporosis (1993 *Am. J. Med.* 94:646-650), Eisman (2000 *Endocr. Rev.* 20:788) and references cited therein, or other means known in the art for diagnosing conditions, diseases or disorders associated with altered BMD such as those described herein.

The present invention also provides compositions and methods that are useful in pharmacogenomics, for the classification and/or stratification of a subject or a patient population, for instance correlation of one or more traits in a subject with indicators of the responsiveness to, or efficacy of, a particular therapeutic treatment. In certain embodiments of the invention, determination of the presence of at least one sclerostin gene region nucleotide polymorphism in a biological sample from a subject is combined with identification of the subject's gender to determine the risk for, or presence of, altered BMD in the subject. According to such embodiments, and without wishing to be bound by theory, certain sclerostin gene region nucleotide polymorphisms described herein can be correlated with an increased risk for altered BMD as a factor of the subject's gender, and may therefore be referred to as "gender-associated" sclerostin gene region nucleotide polymorphisms. For instance, and as described in greater detail in the Examples, the presence of the sclerostin gene region nucleotide polymorphism SRP3 in female subjects indicated a presence, or risk of having, increased BMD. As also described in the Examples, the presence of the sclerostin gene region nucleotide polymorphism SRP9 in male subjects indicated a presence, or risk of having, decreased BMD. Accordingly, and without wishing to be bound by theory, the invention contemplates gender-specific associations and/or correlations of particular sclerostin gene region nucleotide polymorphisms with altered BMD.

As described herein, determination of at least one sclerostin gene region nucleotide polymorphism may be used to stratify a patient population that includes individuals suspected of having or being at risk for having altered BMD. Accordingly, in another preferred embodiment of the invention, determination of one or more such polymorphisms in a biological sample containing DNA from such subjects may provide a useful correlative indicator for that subject. A subject so classified on the basis of one or more particular sclerostin gene region nucleotide polymorphisms may then be monitored using BMD clinical parameters referred to above, such that correlation between polymorphisms and any particular clinical score used to evaluate BMD may be monitored. For example, stratification of a patient population according to sclerostin gene region polymorphisms (SRPs) disclosed herein may provide a useful marker with which to correlate the efficacy of any candidate therapeutic agent being used in subjects having altered BMD. In a further preferred embodiment of this aspect of the invention, determination of one or more SRPs in concert with determination of a subject's gender may also be useful, as discussed in greater detail herein. These and related advantages will be appreciated by those familiar with the art.

The following Examples are provided by way of illustration and not limitation.

EXAMPLES

Example 1

Method for Identifying Individuals Susceptible to Developing Osteoporosis

Natural variants in the human SOST gene region were identified by sequencing ~90 kb of genomic DNA from a panel of 90 ethnically diverse individuals from the NIGMS Human Variation Collection, panel HD01-HD09. Eight polymorphisms (SRP1-3 and SRP5-9) spanning a total of ~87 kb were chosen to genotype 1,927 men and women aged 55-80 years from a large population-based prospective cohort study of elderly Dutch Caucasians (*Eur. J. Epidem.*, 1991, 7:403-422). Genomic DNA was obtained from peripheral blood of each individual by conventional methods. For each polymorphism genotyping assay, 10 ng of genomic DNA were used in a polymerase chain reaction (PCR) with oligonucleotide primers located on either side of the polymorphism.

Genomic DNA was extracted from samples of peripheral venous blood according to standard procedures. Polymorphism-containing regions were amplified from genomic DNA with the polymerase chain reaction (PCR). Each PCR was carried out in a 10 μl reaction volume containing 5 ng of genomic-DNA, 1.5 mM magnesium chloride, 0.2 mM deoxy-NTP, 2 pmol of each primer (see below), 0.2 units of Taq polymerase (Promega) and 10×PCR buffer (Promega) containing 20 mM Tris-HCl (pH 8.0), 100 mM KCl, 0.1 mM EDTA, 1 mM DDT, 50% glycerol, 0.5% Nonidet®-P40 and 0.5% Tween®20. The reactions were performed in a 384-wells thermocycler (MJ Research Tetrad) with different cycling protocols for each amplicon (37 cycles, Tm=53° C. for SRPs 8 and 9, Tm=55° C. for SRPs 1, 2-3 and 7, Tm=60° C. for SRPs 5-6). The genotypes were detected by the Single Base Extension (SBE) procedure using SBE primers of different lengths (Table 1). The SBE reactions were performed according to details provided by the manufacturer (ABI Prism® SNaPsho™ Multiplex Kit) with slight modifications. The genotypes thus generated were analyzed with the software program called Genotyper 3.7 (Applied Biosystems) and also checked by eye. To confirm the accuracy of the genotyping, 150 randomly selected samples were genotyped for a second time with the same method. No discrepancies were found.

TABLE 1

SOST REGION POLYMORPHISMS (SRP) AND PRIMERS FOR SBE GENOTYPING

| SRP# | Position No. SEQ ID NO: 1 | PCR primers (5'-3') | SBE primers (5'-3') |
|---|---|---|---|
| SRP1 | C4103G[a] (SEQ ID NO: 2) | Fd CTTTCCACAGGCTCGTCT (SEQ ID NO: 35)<br>Rv CTCTCAACCGGAAATGTCT (SEQ ID NO: 3) | $(T)_{4}$GAAGGTAGCGCCACCTGCTG |
| SRP2 | C10357T[a] | Fd AGGTGGGGCTATAAGCATCCATCC (SEQ ID NO: 11)<br>Rv GTCCTTTCCCACCTGCCTCAACTT (SEQ ID NO: 12) | $(T)_{10}$TTGTGAGAAGCTGGCCCTCC (SEQ ID NO: 36) |
| SRP3 | 10565insGGA[a] | | $(T)_{16}$ATGATGGATGATGGAAAGGA (SEQ ID NO: 37) |
| SRP5 | C17966G[a] | Fd TAAGGTGGGATGCTCAACTCG (SEQ ID NO: 20)<br>Rv CAGGAGAATCACTTGAATCCG (SEQ ID NO: 21) | $(T)_{22}$TAGTGGTAGTTAAACTGACAA (SEQ ID NO: 38) |
| SRP6 | A18293G[a] (SEQ ID NO: 39) | | $(T)_{28}$AAGTTGCAGTAAGCCGAGAT |
| SRP7 | T58083C[b] | Fd CCCTACCTTACTGTCCGCCTCTCA (SEQ ID NO: 23)<br>Rv GTGCTACCTCTCGGGAAAACATAA (SEQ ID NO: 24) | $(T)_{34}$TTTAGTATAAAAGCTGGCTC (SEQ ID NO: 40) |
| SRP8 | A74235G[b] | Fd GAGCAACCGGCGTATCC (SEQ ID NO: 26)<br>Rv GGGGTTTCTTTCTGGCTCTCA (SEQ ID NO: 27) | $(T)_{40}$TTTATAGTTCTTTCCTAGAC (SEQ ID NO: 41) |
| SRP9 | A91068G[b] | Fd CCAGCAATGTTGAGGAAT (SEQ ID NO: 29)<br>Rv CGCAGGAAGGTGTGGAGA (SEQ ID NO: 30) | $(T)_{46}$CTGCTCAGCAAGCAGTTCCA (SEQ ID NO: 42) |

In the case of SRP2 and 3, and SRP5 and 6, the polymorphisms were close enough together that the primary PCR could be performed using primers flanking the pair of polymorphisms. In general, primers were designed to amplify fragments of 150-500 base pairs (bp) in length. Specific alleles at each site were determined by a single-base extension (SBE) assay, using the Applied Biosystems (ABI, Foster City, Calif.) SNAPshot™ kit reagents and oligonucleotide design protocol according to the supplier's recommendations. Products of the SBE were pooled, then resolved and detected on a capillary electrophoresis instrument (ABI 3100). Standard statistical methods were used to determine whether particular alleles were associated with high or low bone density.

The SRP1 polymorphism was identified using the SRP1 forward and reverse primer pair (SEQ ID NOs:2 and 3). The amplicon generated using this primer pair is disclosed in SEQ ID NO:4. This sequence identifies the SRP1 polymorphism at nucleotide position 4103 of SEQ ID NO:1. This specific polymorpism involves the substitution of a C to a G.

The SRP2 polymorphism was identified using the SRP2 forward and reverse primer pair (SEQ ID NOs:5 and 6). The amplicon generated using this primer pair is disclosed in SEQ ID NO:7. This sequence identifies the SRP2 polymorphism at nucleotide position 10357 of SEQ ID NO:1. This specific polymorpism involves the substitution of a C to a T.

The SRP3 polymorphism was identified using the SRP3 forward and reverse primer pair (SEQ ID NOs:8 and 9). The amplicon generated using this primer pair is disclosed in SEQ ID NOs:10 and 32. This sequence identifies the SRP3 polymorphism at nucleotide position 10566 of SEQ ID NO:1. This specific polymorpism involves either the inclusion (or deletion) of nucleotides GGA as a trinucleotide insertion (or deletion) between positions 10565 and 10566 of SEQ ID NO:1.

The SRP5 polymorphism was identified using the SRP5 forward and reverse primer pair (SEQ ID NOs:14 and 15). The amplicon generated using this primer pair is disclosed in SEQ ID NO:16. This sequence identifies the SRP5 polymorphism at nucleotide position 17966 of SEQ ID NO:1. This specific polymorpism involves the substitution of a C to a G.

The SRP6 polymorphism was identified using the SRP6 forward and reverse primer pair (SEQ ID NOs:17 and 18). The amplicon generated using this primer pair is disclosed in SEQ ID NO:19. This sequence identifies the SRP6 polymorphism at nucleotide position 18293 of SEQ ID NO:1. This specific polymorpism involves the substitution of an A to a G.

The SRP7 polymorphism was identified using the SRP7 forward and reverse primer pair (SEQ ID NOs:23 and 24). The amplicon generated using this primer pair is disclosed in SEQ ID NO:25. This sequence identifies the SRP7 polymorphism at nucleotide position 58083 of SEQ ID NO:1. This specific polymorpism involves the substitution of a T to a C.

The SRP8 polymorphism was identified using the SRP8 forward and reverse primer pair (SEQ ID NOs:26 and 27). The amplicon generated using this primer pair is disclosed in SEQ ID NO:28. This sequence identifies the SRP8 polymorphism at nucleotide position 74235 of SEQ ID NO:1. This specific polymorpism involves the substitution of an A to a G.

The SRP9 polymorphism was identified using the SRP9 forward and reverse primer pair (SEQ ID NOs:29 and 30). The amplicon generated using this primer pair is disclosed in SEQ ID NO:31. This sequence identifies the SRP9 polymorphism at nucleotide position 91068 of SEQ ID NO:1. This specific polymorpism involves the substitution of an A to a G.

Example 2

Assoclation of Polymorphisms in the SOST Gene Region with Bone Mineral Density in Elderly Subjects Osteoporosis has a strong genetic component but the genes involved are poorly defined. The association between the gene encoding sclerostin (SOST) and bone mineral density (BMD) was examined in order to ascertain whether SOST can be considered an osteoporosis candidate gene. Sclerostin is an important regulator of bone density, and mutations in SOST result in sclerosteosis (see, e.g., NCBI Online Mendelian Inheritance in Man database of human genes and genetic disorders, on the World Wide Web at ncbi.nlm.nih.gov/omim, MIM 269500; 17q12-q21), a rare recessive sclerosing bone dysplasia. As described in Example 1, >90 kb of the SOST gene region in 90 ethnically diverse individuals was sequenced, and a set of 8 polymorphisms thus found was used to genotype 1927 men and women (55-80 years) from a large population-based prospective cohort study of elderly Dutch Caucasians. Subjects were participants of the Rotterdam Study, a population based cohort study of 7983 subjects aged 55 years and over and who live in the Ommoort district of Rotterdam, The Netherlands. The study was designed to document the occurrence of diseases in the elderly in relation to several potential determinants (Hofman et al., 1991 *Eur. J. Epidemiol.* 7:403). Genotype effects on BMD and on risk of vertebral and non-vertebral fractures (n=270) were analyzed during 7 years of follow-up.

Height and weight were measured at the initial examination, with the subject in a standing position with indoor clothing without shoes. BMD (in grams per square centimeter) was determined by dual-energy x-ray absorptiometry (DPX-L densitometer, Lunar, Madison, Wis.) at the femoral neck (FN) and lumbar spine (LS) (vertebrae L2, L3, L4), as described by Burger et al., 1994 *Bone Miner.* 25:1-13. Dietary intake of calcium (in milligrams per day) during the preceding year was assessed by a food frequency questionnaire and adjusted for energy intake. Age at menopause and current use of cigarettes were assessed by a questionnaire.

Non-vertebral fractures, including hip, wrist and other fractures were recorded by general practitioners (GPs), who covered 80% of the population. Research physicians confirmed follow-up information by checking GPs' patient records and collected the data for the remaining 20% of the population. For 600 women and 519 men, lateral radiographs of the spine from the fourth thoracic to the fifth lumbar vertebra were measured at follow-up and examined for the presence of prevalent vertebral fractures by morphometric analysis, as described by Burger et al., 1997 *J. Bone Miner. Res.* 12:152.

Subjects were grouped according to genotype for each polymorphism separately. Allele frequencies and Hardy-Weinberg equilibrium (HWE) were analyzed with a chi-square test. BMD and other relevant clinical variables of the three genotype groups were compared according to an allele dose effect. Allele dose was defined as the number of copies of a certain allele in the genotype. In case of a consistent trend reflected as an allele-dose effect, linear regression analysis was performed to quantify the association. In case of a dominant or a recessive effect of the test allele, analysis of (co) variance AN(C)OVA was performed to test for differences between two genotype groups. For dominant alleles test-allele carriers were compared to non-carriers, while for recessive effects homozygous subjects for the test allele were compared to heterozygous carriers combined with non-carriers. Multiple linear regression was used to adjust bone-density values for possible confounding factors such as age and anthropometric variables. To estimate the risk of non-vertebral and vertebral fractures, odds ratios (with 95 percent confidence intervals) were calculated by multivariate logistic regression analysis.

No SOST gene coding polymorphisms were found, but 3 variants within 8 kb upstream of the coding sequence were identified, in addition to 3 variants within a far downstream 52 kb interval recently found to be deleted in van Buchem disease, a monogenic bone disorder very similar to sclerosteosis. A 3 bp GGA-insertion in the SCL promoter region (SRP3; allele frequency 39%) was shown to be associated with decreased BMD in women at the femoral neck (p=0.05) and at the lumbar spine (p=0.01) with evidence for an allele-dose effect. Genotype differences were found to strongly increase with age (FIG. 1). In addition, a G-substitution in the van Buchem deletion region (SRP9; allele frequency 41%) was found to be associated with increased BMD in men at femoral neck (p=0.006) and at lumbar spine (p=0.01) with evidence for an allele-dose effect. In both cases differences between extreme genotypes amounted to 0.2 SD and no genotype effects on fracture risk were observed. Variants in the SOST gene region were thus shown to be associated with BMD differences and were found to be modified as a function of gender (SRP3 and 9) and of age (SRP3).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for determining an increased risk for decreased bone mineral density in a human female subject aged 71-80 years, comprising:

detecting the presence of a sclerostin gene region nucleotide polymorphism in a biological sample from a female subject, said sample comprising DNA comprising at least 50 consecutive nucleotides that are present in SEQ ID NO: 1, wherein the polymorphism is a GGA trinucleotide insertion between positions 10565 and 10566 in SEQ ID NO: 1 or the complement thereof, wherein the presence of said polymorphism indicates an increased risk of decreased bone mineral density in female subjects aged 71-80 years.

2. The method of claim 1, wherein the detecting step comprises:

contacting the biological sample with at least one oligonucleotide primer selected from the group consisting of SEQ ID NO: 8 and SEQ ID NO: 9, under conditions and for a time sufficient to allow hybridization of said primer to the DNA.

3. The method of claim 1, wherein the biological sample is selected from the group consisting of blood, biopsy specimen, tissue explant, organ culture and tissue sample.

4. The method of claim 2, further comprising:

detecting hybridization and extension of the oligonucleotide primer to produce a product, and therefrom determining the presence the polymorphism.

5. The method of 1, wherein the DNA in the sample is amplified.

6. The method of claim 1, further comprising diagnosing the subject as having an increased risk of osteoporosis.

7. The method of claim 1, further comprising monitoring bone mineral density clinical parameters of the subject.

8. The method of claim 1, further comprising treating said female subject with an agent for treating decreased bone mineral density.

9. The method of claim 8 wherein the agent is selected from the group consisting of estrogen, calcium, vitamin D, calcitonin, bisphosphonates, anabolic steroids and sodium fluoride.

* * * * *